United States Patent
Ricci et al.

(10) Patent No.: US 9,235,941 B2
(45) Date of Patent: Jan. 12, 2016

(54) SIMULTANEOUS VIDEO STREAMING ACROSS MULTIPLE CHANNELS

(71) Applicant: AutoConnect Holdings LLC, Wellesley, MA (US)

(72) Inventors: Christopher P. Ricci, Saratoga, CA (US); Octavian Chincisan, Richmond Hill (CA); Alisher I. Yusupov, Richmond Hill (CA)

(73) Assignee: AutoConnect Holdings LLC, Wellesley, MA (US)

( * ) Notice: Subject to any disclaimer, the term of this patent is extended or adjusted under 35 U.S.C. 154(b) by 0 days.

(21) Appl. No.: 14/253,334

(22) Filed: Apr. 15, 2014

(65) Prior Publication Data

US 2014/0310739 A1 Oct. 16, 2014

Related U.S. Application Data

(60) Provisional application No. 61/811,981, filed on Apr. 15, 2013, provisional application No. 61/865,954, filed on Aug. 14, 2013, provisional application No. 61/870,698, filed on Aug. 27, 2013, provisional application No. 61/891,217, filed on Oct. 15, 2013, provisional application No. 61/904,205, filed on Nov. 14, 2013, provisional application No. 61/924,572, filed on Jan. 7, 2014, provisional application No. 61/926,749, filed on Jan. 13, 2014.

(51) Int. Cl.
*H04N 7/16* (2011.01)
*G07C 9/00* (2006.01)
(Continued)

(52) U.S. Cl.
CPC ............. *G07C 9/00158* (2013.01); *B60Q 1/00* (2013.01); *B60R 16/037* (2013.01); *B60R 16/0373* (2013.01); *B60R 25/00* (2013.01); *B60R 25/1004* (2013.01); *B60W 40/09* (2013.01); *B60W 50/08* (2013.01); *G01C 21/00* (2013.01); *G01C 21/26* (2013.01); *G01C 21/34* (2013.01); *G01C 21/36* (2013.01); *G01C 21/3647* (2013.01); *G05D 1/0027* (2013.01);
(Continued)

(58) Field of Classification Search
CPC ..................... H04N 21/4532; H04N 21/4542
USPC ........................................ 725/28, 46
See application file for complete search history.

(56) References Cited

U.S. PATENT DOCUMENTS 4,754,255 A   6/1988   Sanders et al.
5,204,817 A   4/1993   Yoshida (Continued)

FOREIGN PATENT DOCUMENTS

| EP | 1909069 | 12/2010 |
|---|---|---|
| KR | 2006-0128484 | 12/2006 |
| WO | WO 2012/102879 | 8/2012 |

OTHER PUBLICATIONS

International Search Report and Written Opinion for International (PCT) Patent Application No. PCT/US2014/034088, mailed Dec. 24, 2014 9 pages.

(Continued)

*Primary Examiner* — Jivka Rabovianski
(74) *Attorney, Agent, or Firm* — Sheridan Ross P.C.

(57) ABSTRACT

Methods and systems for a media controller subsystem that can provide video streaming using a distributed network control server, media server, and virtual network console on a common processing or circuit board and filter and apply restrictions to media content based on one or more of the identity of the vehicle occupant requesting media content, the identity of a portable computational device associated with the vehicle occupant, and the spatial location of the vehicle occupant and/or remote computational device.

30 Claims, 51 Drawing Sheets

(51) Int. Cl.

| | |
|---|---|
| G08B 25/01 | (2006.01) |
| G08G 1/0965 | (2006.01) |
| H04W 76/02 | (2009.01) |
| H04W 48/02 | (2009.01) |
| H04W 4/12 | (2009.01) |
| H04W 4/20 | (2009.01) |
| G05D 23/19 | (2006.01) |
| G05D 1/00 | (2006.01) |
| G05D 1/02 | (2006.01) |
| B60W 40/09 | (2012.01) |
| B60W 50/08 | (2012.01) |
| G06F 3/01 | (2006.01) |
| H04W 4/04 | (2009.01) |
| H04W 36/32 | (2009.01) |
| G08G 1/16 | (2006.01) |
| G01C 21/36 | (2006.01) |
| G01C 21/26 | (2006.01) |
| H04N 21/414 | (2011.01) |
| G08B 13/196 | (2006.01) |
| B60R 25/10 | (2013.01) |
| G06F 21/31 | (2013.01) |
| G06F 21/32 | (2013.01) |
| H04W 4/00 | (2009.01) |
| H04L 29/08 | (2006.01) |
| B60Q 1/00 | (2006.01) |
| B60R 16/037 | (2006.01) |
| G01C 21/00 | (2006.01) |
| G01C 21/34 | (2006.01) |
| G06F 3/0481 | (2013.01) |
| G06F 3/0484 | (2013.01) |
| G06F 9/445 | (2006.01) |
| G06F 17/28 | (2006.01) |
| G06F 17/30 | (2006.01) |
| G06F 21/00 | (2013.01) |
| G06K 9/00 | (2006.01) |
| G06Q 10/02 | (2012.01) |
| G06Q 10/00 | (2012.01) |
| G06Q 20/14 | (2012.01) |
| G06Q 30/00 | (2012.01) |
| G06Q 30/02 | (2012.01) |
| G06Q 30/06 | (2012.01) |
| G06Q 50/30 | (2012.01) |
| G07C 5/00 | (2006.01) |
| G07C 5/08 | (2006.01) |
| G08B 21/02 | (2006.01) |
| H04L 29/06 | (2006.01) |
| H04N 21/214 | (2011.01) |
| H04N 21/218 | (2011.01) |
| H04N 21/258 | (2011.01) |
| H04N 21/454 | (2011.01) |
| H04N 21/475 | (2011.01) |
| B60R 25/00 | (2013.01) |
| H04W 84/00 | (2009.01) |
| G08G 1/0967 | (2006.01) |
| H04N 7/18 | (2006.01) |
| H04W 12/06 | (2009.01) |
| H04W 12/08 | (2009.01) |
| G08B 21/06 | (2006.01) |
| G08B 29/18 | (2006.01) |
| G06F 3/0488 | (2013.01) |
| B60Q 1/52 | (2006.01) |

(52) U.S. Cl.
CPC .......... *G05D1/0212* (2013.01); *G05D 23/1917* (2013.01); *G06F 3/016* (2013.01); *G06F 3/017* (2013.01); *G06F 3/0481* (2013.01); *G06F 3/04842* (2013.01); *G06F 8/65* (2013.01); *G06F 17/28* (2013.01); *G06F 17/30247* (2013.01); *G06F 17/30557* (2013.01); *G06F 17/30864* (2013.01); *G06F 21/00* (2013.01); *G06F 21/31* (2013.01); *G06F 21/32* (2013.01); *G06K 9/00255* (2013.01); *G06K 9/00268* (2013.01); *G06Q 10/02* (2013.01); *G06Q 10/20* (2013.01); *G06Q 20/145* (2013.01); *G06Q 30/00* (2013.01); *G06Q 30/012* (2013.01); *G06Q 30/0265* (2013.01); *G06Q 30/0633* (2013.01); *G06Q 30/0639* (2013.01); *G06Q 30/0645* (2013.01); *G06Q 50/30* (2013.01); *G07C 5/00* (2013.01); *G07C 5/008* (2013.01); *G07C 5/085* (2013.01); *G07C 5/0808* (2013.01); *G07C 9/00126* (2013.01); *G08B 13/19647* (2013.01); *G08B 21/0205* (2013.01); *G08B 25/016* (2013.01); *G08G 1/0965* (2013.01); *G08G 1/166* (2013.01); *H04L 63/08* (2013.01); *H04L 67/10* (2013.01); *H04L 67/12* (2013.01); *H04N 21/214* (2013.01); *H04N 21/2181* (2013.01); *H04N 21/25841* (2013.01); *H04N 21/41422* (2013.01); *H04N 21/4542* (2013.01); *H04N 21/4751* (2013.01); *H04W 4/003* (2013.01); *H04W 4/046* (2013.01); *H04W 4/12* (2013.01); *H04W 4/206* (2013.01); *H04W 36/32* (2013.01); *H04W 48/02* (2013.01); *H04W 76/021* (2013.01); *B60Q 1/52* (2013.01); *G06F 3/0488* (2013.01); *G08B 21/06* (2013.01); *G08B 29/188* (2013.01); *G08G 1/096725* (2013.01); *G08G 1/096741* (2013.01); *G08G 1/096775* (2013.01); *H04N 7/181* (2013.01); *H04W 12/06* (2013.01); *H04W 12/08* (2013.01); *H04W 84/005* (2013.01)

(56) References Cited

U.S. PATENT DOCUMENTS

| | | | |
|---|---|---|---|
| 5,296,840 | A | 3/1994 | Gieffers |
| 5,529,138 | A | 6/1996 | Shaw et al. |
| 5,531,122 | A | 7/1996 | Chatham et al. |
| 5,572,450 | A | 11/1996 | Worthy |
| 5,825,283 | A | 10/1998 | Camhi |
| 5,986,575 | A | 11/1999 | Jones et al. |
| 6,148,261 | A | 11/2000 | Obradovich et al. |
| 6,356,838 | B1 | 3/2002 | Paul |
| 6,557,752 | B1 | 5/2003 | Yacoob |
| 6,563,910 | B2 | 5/2003 | Menard et al. |
| 6,587,739 | B1 | 7/2003 | Abrams et al. |
| 6,607,212 | B1 | 8/2003 | Reimer et al. |
| 6,617,981 | B2 | 9/2003 | Basinger |
| 6,675,081 | B2 | 1/2004 | Shuman et al. |
| 6,757,593 | B2 | 6/2004 | Mori et al. |
| 6,778,888 | B2 | 8/2004 | Cataldo et al. |
| 6,892,131 | B2 | 5/2005 | Coffee et al. |
| 6,944,533 | B2 | 9/2005 | Kozak et al. |
| 7,020,544 | B2 | 3/2006 | Shinada et al. |
| 7,047,129 | B2 | 5/2006 | Uotani |
| 7,058,898 | B2 | 6/2006 | McWalter et al. |
| 7,096,431 | B2 | 8/2006 | Tambata et al. |
| 7,142,696 | B1 | 11/2006 | Engelsberg et al. |
| 7,233,861 | B2 | 6/2007 | Van Buaer et al. |
| 7,239,960 | B2 | 7/2007 | Yokota et al. |
| 7,295,904 | B2 | 11/2007 | Kanevsky et al. |
| 7,313,547 | B2 | 12/2007 | Mocek et al. |
| 7,333,012 | B1 | 2/2008 | Nguyen |
| 7,346,435 | B2 | 3/2008 | Amendola et al. |
| 7,526,539 | B1 | 4/2009 | Hsu |
| 7,667,618 | B2 | 2/2010 | Chitor et al. |
| 7,748,021 | B2 | 6/2010 | Obradovich et al. |
| 7,796,190 | B2 | 9/2010 | Basso et al. |

(56) References Cited

U.S. PATENT DOCUMENTS

| | | |
|---|---|---|
| 7,832,762 B2 | 11/2010 | Breed |
| 7,864,073 B2 | 1/2011 | Lee et al. |
| 7,873,471 B2 | 1/2011 | Gieseke |
| 7,969,324 B2 | 6/2011 | Chevion et al. |
| 8,060,631 B2 | 11/2011 | Collart et al. |
| 8,233,919 B2 | 7/2012 | Haag et al. |
| 8,245,609 B1 | 8/2012 | Greenwald et al. |
| 8,334,847 B2 | 12/2012 | Tomkins |
| 8,346,233 B2 | 1/2013 | Aaron et al. |
| 8,350,721 B2 | 1/2013 | Carr |
| 8,417,449 B1 | 4/2013 | Denise |
| 8,442,389 B2 | 5/2013 | Kashima et al. |
| 8,442,758 B1 | 5/2013 | Rovik et al. |
| 8,497,842 B2 | 7/2013 | Tomkins et al. |
| 8,509,982 B2 | 8/2013 | Montemerlo et al. |
| 8,521,410 B2 | 8/2013 | Mizuno et al. |
| 8,543,330 B2 | 9/2013 | Taylor et al. |
| 8,547,340 B2 | 10/2013 | Sizelove et al. |
| 8,548,669 B2 | 10/2013 | Naylor |
| 8,552,886 B2 | 10/2013 | Bensoussan |
| 8,578,279 B2 | 11/2013 | Chen et al. |
| 8,600,611 B2 | 12/2013 | Seize |
| 8,613,385 B1 * | 12/2013 | Hulet et al. ............ 235/375 |
| 8,634,984 B2 | 1/2014 | Sumizawa |
| 8,660,735 B2 | 2/2014 | Tengler et al. |
| 8,671,068 B2 | 3/2014 | Harber et al. |
| 8,718,797 B1 | 5/2014 | Addepalli et al. |
| 8,730,033 B2 | 5/2014 | Yarnold et al. |
| 8,782,262 B2 | 7/2014 | Collart et al. |
| 8,788,220 B2 | 7/2014 | Soles et al. |
| 8,793,034 B2 | 7/2014 | Ricci |
| 8,793,065 B2 | 7/2014 | Seltzer et al. |
| 8,798,918 B2 | 8/2014 | Onishi et al. |
| 8,812,171 B2 | 8/2014 | Fillev et al. |
| 8,818,725 B2 | 8/2014 | Ricci |
| 8,825,031 B2 | 9/2014 | Aaron et al. |
| 8,825,277 B2 | 9/2014 | McClellan et al. |
| 8,825,362 B2 | 9/2014 | Kirsch |
| 8,825,382 B2 | 9/2014 | Liu |
| 8,831,826 B2 | 9/2014 | Ricci |
| 8,838,095 B2 | 9/2014 | Jouin |
| 8,862,299 B2 | 10/2014 | Ricci |
| 8,862,317 B2 | 10/2014 | Shin et al. |
| 2002/0009978 A1 | 1/2002 | Dukach et al. |
| 2002/0026278 A1 | 2/2002 | Feldman et al. |
| 2002/0065046 A1 | 5/2002 | Mankins et al. |
| 2002/0077985 A1 | 6/2002 | Kobata et al. |
| 2002/0103622 A1 | 8/2002 | Burge |
| 2002/0126876 A1 | 9/2002 | Paul et al. |
| 2002/0128774 A1 | 9/2002 | Takezaki et al. |
| 2002/0143461 A1 | 10/2002 | Burns et al. |
| 2002/0143643 A1 | 10/2002 | Catan |
| 2002/0174021 A1 | 11/2002 | Chu et al. |
| 2003/0004624 A1 | 1/2003 | Wilson et al. |
| 2003/0060937 A1 | 3/2003 | Shinada et al. |
| 2003/0065432 A1 | 4/2003 | Shuman et al. |
| 2003/0101451 A1 | 5/2003 | Bentolila et al. |
| 2003/0204290 A1 | 10/2003 | Sadler et al. |
| 2004/0036622 A1 | 2/2004 | Dukach et al. |
| 2004/0039504 A1 | 2/2004 | Coffee et al. |
| 2004/0093155 A1 | 5/2004 | Simonds et al. |
| 2004/0153356 A1 | 8/2004 | Lockwood et al. |
| 2004/0204837 A1 | 10/2004 | Singleton |
| 2004/0217850 A1 | 11/2004 | Perttunen et al. |
| 2004/0225557 A1 | 11/2004 | Phelan et al. |
| 2004/0260470 A1 | 12/2004 | Rast |
| 2005/0038598 A1 | 2/2005 | Oesterling et al. |
| 2005/0065716 A1 | 3/2005 | Timko et al. |
| 2005/0097541 A1 | 5/2005 | Holland |
| 2005/0122235 A1 | 6/2005 | Teffer et al. |
| 2005/0159853 A1 | 7/2005 | Takahashi et al. |
| 2005/0197748 A1 | 9/2005 | Holst et al. |
| 2005/0261815 A1 | 11/2005 | Cowelchuk et al. |
| 2005/0283284 A1 | 12/2005 | Grenier et al. |
| 2006/0036358 A1 | 2/2006 | Hale et al. |
| 2006/0058948 A1 | 3/2006 | Blass et al. |
| 2006/0130033 A1 | 6/2006 | Stoffels et al. |
| 2006/0173841 A1 | 8/2006 | Bill |
| 2006/0175403 A1 | 8/2006 | McConnell et al. |
| 2006/0243056 A1 | 11/2006 | Sundermeyer et al. |
| 2006/0287807 A1 | 12/2006 | Teffer |
| 2007/0032225 A1 | 2/2007 | Konicek et al. |
| 2007/0061057 A1 | 3/2007 | Huang et al. |
| 2007/0118301 A1 | 5/2007 | Andarawis et al. |
| 2007/0135995 A1 | 6/2007 | Kikuchi et al. |
| 2007/0182625 A1 | 8/2007 | Kerai et al. |
| 2007/0192486 A1 | 8/2007 | Wilson et al. |
| 2007/0194944 A1 | 8/2007 | Galera et al. |
| 2007/0200663 A1 | 8/2007 | White et al. |
| 2008/0033635 A1 | 2/2008 | Obradovich et al. |
| 2008/0082237 A1 | 4/2008 | Breed |
| 2008/0086455 A1 | 4/2008 | Meisels et al. |
| 2008/0104227 A1 | 5/2008 | Birnie et al. |
| 2008/0129475 A1 | 6/2008 | Breed et al. |
| 2008/0147280 A1 | 6/2008 | Breed |
| 2008/0161986 A1 | 7/2008 | Breed |
| 2008/0169940 A1 | 7/2008 | Lee et al. |
| 2008/0255721 A1 | 10/2008 | Yamada |
| 2008/0300778 A1 | 12/2008 | Kuznetsov |
| 2009/0006525 A1 | 1/2009 | Moore |
| 2009/0119657 A1 | 5/2009 | Link, II |
| 2009/0125174 A1 | 5/2009 | Delean |
| 2009/0138336 A1 | 5/2009 | Ashley et al. |
| 2009/0157312 A1 | 6/2009 | Black et al. |
| 2009/0222200 A1 | 9/2009 | Link et al. |
| 2009/0234578 A1 | 9/2009 | Newby et al. |
| 2009/0254446 A1 | 10/2009 | Chernyak |
| 2009/0284359 A1 | 11/2009 | Huang et al. |
| 2009/0287405 A1 | 11/2009 | Liu et al. |
| 2009/0299572 A1 | 12/2009 | Fujikawa et al. |
| 2009/0312998 A1 | 12/2009 | Berckmans et al. |
| 2010/0023204 A1 | 1/2010 | Basir et al. |
| 2010/0036560 A1 | 2/2010 | Wright et al. |
| 2010/0057337 A1 | 3/2010 | Fuchs |
| 2010/0066498 A1 | 3/2010 | Fenton |
| 2010/0070338 A1 | 3/2010 | Siotia et al. |
| 2010/0087984 A1 | 4/2010 | Joseph |
| 2010/0087987 A1 | 4/2010 | Huang et al. |
| 2010/0106344 A1 | 4/2010 | Edwards et al. |
| 2010/0106418 A1 | 4/2010 | Kindo et al. |
| 2010/0125387 A1 | 5/2010 | Sehyun et al. |
| 2010/0125405 A1 | 5/2010 | Chae et al. |
| 2010/0125811 A1 | 5/2010 | Moore et al. |
| 2010/0136944 A1 | 6/2010 | Taylor et al. |
| 2010/0137037 A1 | 6/2010 | Basir |
| 2010/0145700 A1 | 6/2010 | Kennewick et al. |
| 2010/0145987 A1 | 6/2010 | Harper et al. |
| 2010/0152976 A1 | 6/2010 | White et al. |
| 2010/0169432 A1 | 7/2010 | Santori et al. |
| 2010/0174474 A1 | 7/2010 | Nagase |
| 2010/0179712 A1 | 7/2010 | Pepitone et al. |
| 2010/0211300 A1 | 8/2010 | Jaffe et al. |
| 2010/0211304 A1 | 8/2010 | Hwang et al. |
| 2010/0211441 A1 | 8/2010 | Sprigg et al. |
| 2010/0222939 A1 | 9/2010 | Namburu et al. |
| 2010/0235891 A1 | 9/2010 | Oglesbee et al. |
| 2010/0274410 A1 | 10/2010 | Tsien et al. |
| 2010/0289643 A1 | 11/2010 | Trundle et al. |
| 2010/0304640 A1 | 12/2010 | Sofman et al. |
| 2010/0305807 A1 | 12/2010 | Basir et al. |
| 2010/0306080 A1 | 12/2010 | Trandal et al. |
| 2010/0306309 A1 | 12/2010 | Santori et al. |
| 2010/0321151 A1 | 12/2010 | Matsuura et al. |
| 2010/0332130 A1 | 12/2010 | Shimizu et al. |
| 2011/0040438 A1 | 2/2011 | Kluge et al. |
| 2011/0077808 A1 | 3/2011 | Hyde et al. |
| 2011/0078024 A1 | 3/2011 | Messier et al. |
| 2011/0090078 A1 | 4/2011 | Kim et al. |
| 2011/0093438 A1 | 4/2011 | Poulsen |
| 2011/0093846 A1 | 4/2011 | Moinzadeh et al. |
| 2011/0112717 A1 | 5/2011 | Resner |
| 2011/0130915 A1 | 6/2011 | Wright et al. |
| 2011/0137520 A1 | 6/2011 | Rector et al. |
| 2011/0184642 A1 | 7/2011 | Rotz et al. |

(56) References Cited

U.S. PATENT DOCUMENTS

| | | |
|---|---|---|
| 2011/0197187 A1 | 8/2011 | Roh |
| 2011/0210867 A1 | 9/2011 | Benedikt |
| 2011/0224865 A1 | 9/2011 | Gordon et al. |
| 2011/0231091 A1 | 9/2011 | Gourlay et al. |
| 2011/0245999 A1 | 10/2011 | Kordonowy |
| 2011/0246210 A1 | 10/2011 | Matsur |
| 2011/0247013 A1 | 10/2011 | Feller et al. |
| 2011/0257973 A1 | 10/2011 | Chutorash et al. |
| 2011/0291926 A1 | 12/2011 | Gokturk et al. |
| 2011/0301844 A1 | 12/2011 | Aono |
| 2011/0309926 A1 | 12/2011 | Eikelenberg et al. |
| 2011/0309953 A1 | 12/2011 | Petite et al. |
| 2011/0313653 A1 | 12/2011 | Lindner |
| 2011/0320089 A1 | 12/2011 | Lewis |
| 2012/0010807 A1 | 1/2012 | Zhou |
| 2012/0030512 A1 | 2/2012 | Wadhwa et al. |
| 2012/0046822 A1 | 2/2012 | Anderson |
| 2012/0047530 A1 | 2/2012 | Shkedi |
| 2012/0053793 A1 | 3/2012 | Sala et al. |
| 2012/0053888 A1 | 3/2012 | Stahlin et al. |
| 2012/0059789 A1 | 3/2012 | Sakai et al. |
| 2012/0065815 A1 | 3/2012 | Hess |
| 2012/0101876 A1 | 4/2012 | Truvey et al. |
| 2012/0101914 A1 | 4/2012 | Kumar et al. |
| 2012/0105613 A1 | 5/2012 | Weng et al. |
| 2012/0109451 A1 | 5/2012 | Tan |
| 2012/0179547 A1 | 7/2012 | Besore et al. |
| 2012/0188876 A1 | 7/2012 | Chow et al. |
| 2012/0197523 A1 | 8/2012 | Kirsch |
| 2012/0204166 A1 | 8/2012 | Ichihara |
| 2012/0254763 A1 | 10/2012 | Protopapas et al. |
| 2012/0254804 A1 | 10/2012 | Shema et al. |
| 2012/0289253 A1 | 11/2012 | Haag et al. |
| 2012/0316720 A1 | 12/2012 | Hyde et al. |
| 2012/0323413 A1 | 12/2012 | Kedar-Dongarkar et al. |
| 2012/0327231 A1 | 12/2012 | Cochran et al. |
| 2013/0019252 A1 | 1/2013 | Haase et al. |
| 2013/0024060 A1 | 1/2013 | Sukkarie et al. |
| 2013/0030645 A1 | 1/2013 | Divine et al. |
| 2013/0031540 A1 | 1/2013 | Throop et al. |
| 2013/0055096 A1 * | 2/2013 | Kim et al. .................... 715/738 |
| 2013/0059607 A1 | 3/2013 | Herz et al. |
| 2013/0066512 A1 | 3/2013 | Willard et al. |
| 2013/0079964 A1 | 3/2013 | Sukkarie et al. |
| 2013/0083805 A1 | 4/2013 | Lu et al. |
| 2013/0099915 A1 | 4/2013 | Prasad et al. |
| 2013/0103196 A1 | 4/2013 | Monceaux et al. |
| 2013/0116882 A1 | 5/2013 | Link et al. |
| 2013/0116915 A1 | 5/2013 | Ferreira et al. |
| 2013/0134730 A1 | 5/2013 | Ricci |
| 2013/0135118 A1 | 5/2013 | Ricci |
| 2013/0138591 A1 | 5/2013 | Ricci |
| 2013/0138714 A1 | 5/2013 | Ricci |
| 2013/0139140 A1 | 5/2013 | Rao et al. |
| 2013/0141247 A1 | 6/2013 | Ricci |
| 2013/0141252 A1 | 6/2013 | Ricci |
| 2013/0143495 A1 | 6/2013 | Ricci |
| 2013/0143546 A1 | 6/2013 | Ricci |
| 2013/0143601 A1 | 6/2013 | Ricci |
| 2013/0144459 A1 | 6/2013 | Ricci |
| 2013/0144460 A1 | 6/2013 | Ricci |
| 2013/0144461 A1 | 6/2013 | Ricci |
| 2013/0144463 A1 | 6/2013 | Ricci et al. |
| 2013/0144470 A1 | 6/2013 | Ricci |
| 2013/0144486 A1 | 6/2013 | Ricci |
| 2013/0144520 A1 | 6/2013 | Ricci |
| 2013/0144657 A1 | 6/2013 | Ricci |
| 2013/0145065 A1 | 6/2013 | Ricci |
| 2013/0145279 A1 | 6/2013 | Ricci |
| 2013/0145297 A1 | 6/2013 | Ricci et al. |
| 2013/0145360 A1 | 6/2013 | Ricci |
| 2013/0145401 A1 | 6/2013 | Ricci |
| 2013/0145482 A1 | 6/2013 | Ricci et al. |
| 2013/0147638 A1 | 6/2013 | Ricci |
| 2013/0151065 A1 | 6/2013 | Ricci |
| 2013/0151088 A1 | 6/2013 | Ricci |
| 2013/0152003 A1 | 6/2013 | Ricci et al. |
| 2013/0154298 A1 | 6/2013 | Ricci |
| 2013/0158821 A1 | 6/2013 | Ricci |
| 2013/0166096 A1 | 6/2013 | Jotanovic |
| 2013/0166097 A1 | 6/2013 | Ricci |
| 2013/0166208 A1 | 6/2013 | Forstall et al. |
| 2013/0167159 A1 | 6/2013 | Ricci et al. |
| 2013/0197796 A1 | 8/2013 | Obradovich et al. |
| 2013/0198031 A1 | 8/2013 | Mitchell et al. |
| 2013/0204455 A1 | 8/2013 | Chia et al. |
| 2013/0207794 A1 | 8/2013 | Patel et al. |
| 2013/0212065 A1 | 8/2013 | Rahnama |
| 2013/0215116 A1 | 8/2013 | Siddique et al. |
| 2013/0218445 A1 | 8/2013 | Basir |
| 2013/0219039 A1 | 8/2013 | Ricci |
| 2013/0226365 A1 | 8/2013 | Brozovich |
| 2013/0226371 A1 | 8/2013 | Rovik et al. |
| 2013/0226449 A1 | 8/2013 | Rovik et al. |
| 2013/0231784 A1 | 9/2013 | Rovik et al. |
| 2013/0241720 A1 | 9/2013 | Ricci et al. |
| 2013/0245882 A1 | 9/2013 | Ricci |
| 2013/0261966 A1 | 10/2013 | Wang et al. |
| 2013/0282946 A1 | 10/2013 | Ricci |
| 2013/0293364 A1 | 11/2013 | Ricci et al. |
| 2013/0293452 A1 | 11/2013 | Ricci et al. |
| 2013/0295913 A1 | 11/2013 | Matthews et al. |
| 2013/0300554 A1 | 11/2013 | Braden |
| 2013/0304371 A1 | 11/2013 | Kitatani et al. |
| 2013/0325568 A1 | 12/2013 | Mangalvedkar et al. |
| 2013/0332023 A1 | 12/2013 | Bertosa et al. |
| 2013/0338914 A1 | 12/2013 | Weiss |
| 2013/0345929 A1 | 12/2013 | Bowden et al. |
| 2014/0028542 A1 | 1/2014 | Lovitt et al. |
| 2014/0058672 A1 | 2/2014 | Wansley et al. |
| 2014/0067201 A1 | 3/2014 | Visintainer et al. |
| 2014/0067564 A1 | 3/2014 | Yuan |
| 2014/0109075 A1 | 4/2014 | Hoffman et al. |
| 2014/0164611 A1 | 6/2014 | Molettiere et al. |
| 2014/0169621 A1 | 6/2014 | Burr |
| 2014/0207328 A1 | 7/2014 | Wolf et al. |
| 2014/0220966 A1 | 8/2014 | Muetzel et al. |
| 2014/0244111 A1 | 8/2014 | Gross et al. |
| 2014/0244156 A1 | 8/2014 | Magnusson et al. |
| 2014/0245278 A1 | 8/2014 | Zellen |
| 2014/0245284 A1 | 8/2014 | Alrabady et al. |
| 2014/0252091 A1 | 9/2014 | Morse et al. |
| 2014/0257627 A1 | 9/2014 | Hagan, Jr. |
| 2014/0278070 A1 | 9/2014 | McGavran et al. |
| 2014/0278071 A1 | 9/2014 | San Filippo et al. |
| 2014/0281971 A1 | 9/2014 | Isbell, III et al. |
| 2014/0282470 A1 | 9/2014 | Buga et al. |
| 2014/0292545 A1 | 10/2014 | Nemoto |
| 2014/0306799 A1 | 10/2014 | Ricci |
| 2014/0306814 A1 | 10/2014 | Ricci |
| 2014/0306817 A1 | 10/2014 | Ricci |
| 2014/0306826 A1 | 10/2014 | Ricci |
| 2014/0306833 A1 | 10/2014 | Ricci |
| 2014/0306834 A1 | 10/2014 | Ricci |
| 2014/0306835 A1 | 10/2014 | Ricci |
| 2014/0307655 A1 | 10/2014 | Ricci |
| 2014/0307724 A1 | 10/2014 | Ricci |
| 2014/0308902 A1 | 10/2014 | Ricci |
| 2014/0309789 A1 | 10/2014 | Ricci |
| 2014/0309790 A1 | 10/2014 | Ricci |
| 2014/0309804 A1 | 10/2014 | Ricci |
| 2014/0309805 A1 | 10/2014 | Ricci |
| 2014/0309806 A1 | 10/2014 | Ricci |
| 2014/0309813 A1 | 10/2014 | Ricci |
| 2014/0309814 A1 | 10/2014 | Ricci et al. |
| 2014/0309815 A1 | 10/2014 | Ricci et al. |
| 2014/0309838 A1 | 10/2014 | Ricci |
| 2014/0309839 A1 | 10/2014 | Ricci et al. |
| 2014/0309847 A1 | 10/2014 | Ricci |
| 2014/0309849 A1 | 10/2014 | Ricci |
| 2014/0309852 A1 | 10/2014 | Ricci |
| 2014/0309853 A1 | 10/2014 | Ricci |
| 2014/0309862 A1 | 10/2014 | Ricci |
| 2014/0309863 A1 | 10/2014 | Ricci |

(56) References Cited

U.S. PATENT DOCUMENTS

| | | |
|---|---|---|
| 2014/0309864 A1 | 10/2014 | Ricci |
| 2014/0309865 A1 | 10/2014 | Ricci |
| 2014/0309866 A1 | 10/2014 | Ricci |
| 2014/0309867 A1 | 10/2014 | Ricci |
| 2014/0309868 A1 | 10/2014 | Ricci |
| 2014/0309869 A1 | 10/2014 | Ricci |
| 2014/0309870 A1 | 10/2014 | Ricci et al. |
| 2014/0309871 A1 | 10/2014 | Ricci |
| 2014/0309872 A1 | 10/2014 | Ricci |
| 2014/0309873 A1 | 10/2014 | Ricci |
| 2014/0309874 A1 | 10/2014 | Ricci |
| 2014/0309875 A1 | 10/2014 | Ricci |
| 2014/0309876 A1 | 10/2014 | Ricci |
| 2014/0309877 A1 | 10/2014 | Ricci |
| 2014/0309878 A1 | 10/2014 | Ricci |
| 2014/0309879 A1 | 10/2014 | Ricci |
| 2014/0309880 A1 | 10/2014 | Ricci |
| 2014/0309885 A1 | 10/2014 | Ricci |
| 2014/0309886 A1 | 10/2014 | Ricci |
| 2014/0309891 A1 | 10/2014 | Ricci |
| 2014/0309892 A1 | 10/2014 | Ricci |
| 2014/0309893 A1 | 10/2014 | Ricci |
| 2014/0309913 A1 | 10/2014 | Ricci et al. |
| 2014/0309919 A1 | 10/2014 | Ricci |
| 2014/0309920 A1 | 10/2014 | Ricci |
| 2014/0309921 A1 | 10/2014 | Ricci et al. |
| 2014/0309922 A1 | 10/2014 | Ricci |
| 2014/0309923 A1 | 10/2014 | Ricci |
| 2014/0309927 A1 | 10/2014 | Ricci |
| 2014/0309929 A1 | 10/2014 | Ricci |
| 2014/0309930 A1 | 10/2014 | Ricci |
| 2014/0309934 A1 | 10/2014 | Ricci |
| 2014/0309935 A1 | 10/2014 | Ricci |
| 2014/0309982 A1 | 10/2014 | Ricci |
| 2014/0310031 A1 | 10/2014 | Ricci |
| 2014/0310075 A1 | 10/2014 | Ricci |
| 2014/0310103 A1 | 10/2014 | Ricci |
| 2014/0310186 A1 | 10/2014 | Ricci |
| 2014/0310277 A1 | 10/2014 | Ricci |
| 2014/0310379 A1 | 10/2014 | Ricci et al. |
| 2014/0310594 A1 | 10/2014 | Ricci et al. |
| 2014/0310610 A1 | 10/2014 | Ricci |
| 2014/0310702 A1 | 10/2014 | Ricci et al. |
| 2014/0310788 A1 | 10/2014 | Ricci |
| 2015/0007155 A1 | 1/2015 | Hoffman et al. |

OTHER PUBLICATIONS

International Search Report and Written Opinion for International (PCT) Patent Application No. PCT/US14/034194, mailed Dec. 31, 2014 11 pages.
Official Action for U.S. Appl. No. 14/253,836, mailed Feb. 24, 2015 12 pages.
Official Action for U.S. Appl. No. 14/253,706, mailed Jan. 29, 2015 8 pages.
Official Action for U.S. Appl. No. 14/253,729, mailed Mar. 6, 2015 7 pages.
Official Action for U.S. Appl. No. 14/252,871, mailed Mar. 27, 2015 10 pages.
Official Action for U.S. Appl. No. 14/253,2014, mailed Jan. 26, 2015 6 pages.
Official Action for U.S. Appl. No. 14/253,330, mailed Apr. 13, 2015 11 pages.
Official Action for U.S. Appl. No. 14/252,858, mailed Jan. 26, 2015 8 pages.
Official Action for U.S. Appl. No. 14/253,034, mailed Jan. 26, 2015 12 pages.
Notice of Allowance for U.S. Appl. No. 14/253,405, mailed Mar. 5, 2015 5 pages.
Official Action for U.S. Appl. No. 14/252,876, mailed Jan. 30, 2015 9 pages.
Official Action for U.S. Appl. No. 14/253,838, mailed Mar. 12, 2015 32 pages.
Notice of Allowance for U.S. Appl. No. 14/253,312, mailed Dec. 19, 2014 8 pages.
Official Action for U.S. Appl. No. 14/253,371, mailed Dec. 16, 2014 7 pages.
Notice of Allowance for U.S. Appl. No. 14/253,371, mailed Apr. 15, 2015 6 pages.
Official Action for U.S. Appl. No. 14/253,416, mailed Dec. 1, 2014 8 pages.
Notice of Allowance for U.S. Appl. No. 14/253,416, mailed Mar. 18, 2015 6 pages.
Notice of Allowance for U.S. Appl. No. 14/253,058, mailed Jan. 28, 2015 9 pages.
Official Action for U.S. Appl. No. 14/253,022, mailed Feb. 20, 2015 13 pages.
Official Action for U.S. Appl. No. 14/253,251, mailed Dec. 29, 2014 8 pages.
Notice of Allowance for U.S. Appl. No. 14/253,251, mailed Apr. 10, 2015 5 pages.
Official Action for U.S. Appl. No. 14/253,388, mailed Jan. 30, 2015 8 pages.
Official Action for U.S. Appl. No. 14/253,406, mailed Dec. 11, 2014 6 pages.
Notice of Allowance for U.S. Appl. No. 14/253,406, mailed Apr. 6, 2015 6 pages.
Official Action for U.S. Appl. No. 14/253,464, mailed Jan. 28, 2015 9 pages.
Official Action for U.S. Appl. No. 14/253,755, mailed Apr. 24, 2015 13 pages.
Official Action for U.S. Appl. No. 14/253,727, mailed Jan. 6, 2015 8 pages.
Official Action for U.S. Appl. No. 14/253,743, mailed Feb. 12, 2015 8 pages.
Official Action for U.S. Appl. No. 14/253,766, mailed Dec. 12, 2014 7 pages.
Notice of Allowance for U.S. Appl. No. 14/253,766, mailed Apr. 10, 2015 5 pages.
Notice of Allowance for U.S. Appl. No. 14/253,506, mailed Mar. 6, 2015 5 pages.
U.S. Appl. No. 14/543,535, filed Nov. 17, 2014, Ricci.
"Accessibility a guide for Businesses and Organizations," Microsoft, 2011, 53 pages.
"Accessibility Guide for Educators," Microsoft, 2014, 1 page [retrieved from www.microsoft.com/enable/education/].
"Guide for Individuals with Language and Communication Impairments," Microsoft, 2014, 9 pages [retrieved from www.microsoft.com/enable/guides/language.aspx].
"Guide for Individuals with Vision Impairments," Microsoft, 2014, 8 pages [retrieved from www.microsoft/com/enable/guides/vision.aspx].
"Guide for Individuals with Age-related Impairments," Microsoft, 2014, 1 page [retrieved from www.icrosoft.com/enable/aging].
"Guide for Individuals with Learning Impairments," Microsoft, 2014, 1 page [retrieved from www.microsoft.com/enable/guides/learning.aspx].
"Guide for Individuals with Dexterity and Mobility Impairments," Microsoft, 2014, 6 pages [retrieved from www.microsoft.com/enable/guides/dexterity.aspx].
"Guide for Individuals with Hearing Impairments," Microsoft, 2014, 5 pages [retrieved from www.microsoft.com/enable/guides/hearing.aspx].
Bennett "Meet Samsung's Version of Apple AirPlay," CNET.com, Oct. 10, 2012, 11 pages [retrieved from the internet on Aug. 14, 2014 from www.cnet.com/products/samsung-allshare-cast-hub-eadt10jdegsta/].
International Search Report and Written Opinion for International (PCT) Patent Application No. PCT/US2014/034092, mailed Aug. 22, 2014 8 pages.
International Search Report and Written Opinion for International (PCT) Patent Application No. PCT/US2014/034099, mailed Aug. 25, 2014 8 pages.
International Search Report and Written Opinion for International (PCT) Patent Application No. PCT/US2014/034087, mailed Aug. 22, 2014 7 pages.

(56) References Cited

OTHER PUBLICATIONS

International Search Report and Written Opinion for International (PCT) Patent Application No. PCT/US14/34232, mailed Sep. 15, 2014 8 pages.
International Search Report and Written Opinion for International (PCT) Patent Application No. PCT/US14/34098, mailed Sep. 15, 2014 10 pages.
International Search Report and Written Opinion for International (PCT) Patent Application No. PCT/US14/34108, mailed Sep. 15, 2014 7 pages.
International Search Report and Written Opinion for International (PCT) Patent Application No. PCT/US2014/034101, mailed Aug. 22, 2014 7 pages.
International Search Report and Written Opinion for International (PCT) Patent Application No. PCT/US2014/034103, mailed Sep. 3, 2014 7 pages.
International Search Report and Written Opinion for International (PCT) Patent Application No. PCT/US14/34114, mailed Sep. 15, 2014 9 pages.
International Search Report and Written Opinion for International (PCT) Patent Application No. PCT/US14/34125, mailed Sep. 15, 2014 8 pages.
International Search Report and Written Opinion for International (PCT) Patent Application No. PCT/US14/34254, mailed Sep. 15, 2014 10 pages.
Official Action for U.S. Appl. No. 14/253,729, mailed Nov. 19, 2014 8 pages.
Official Action for U.S. Appl. No. 14/253,405, mailed Nov. 18, 2014 6 pages.
Official Action for U.S. Appl. No. 14/253,838, mailed Nov. 20, 2014 31 pages.
Official Action for U.S. Appl. No. 14/253,506, mailed Nov. 14, 2014 9 pages.

* cited by examiner

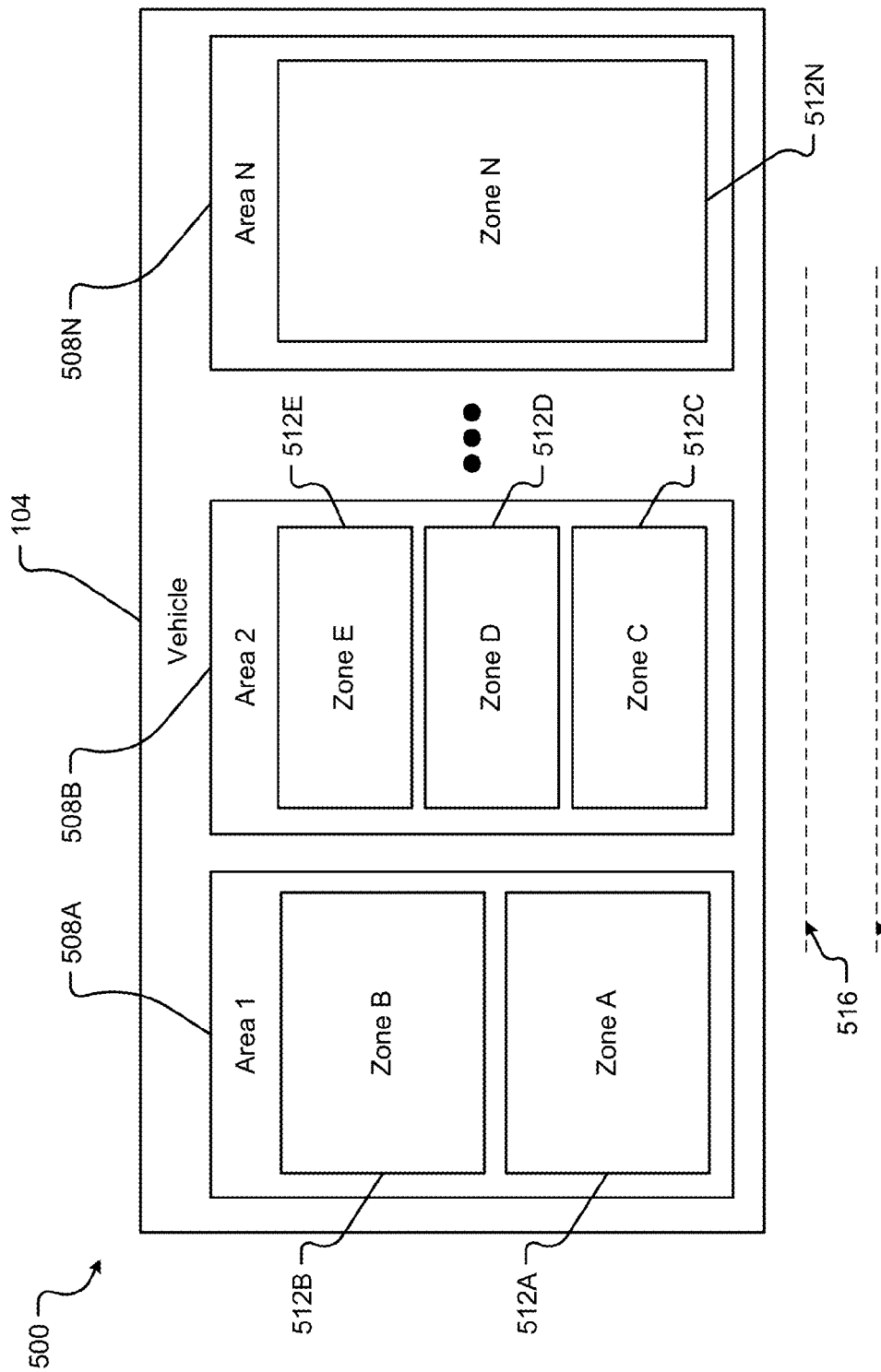

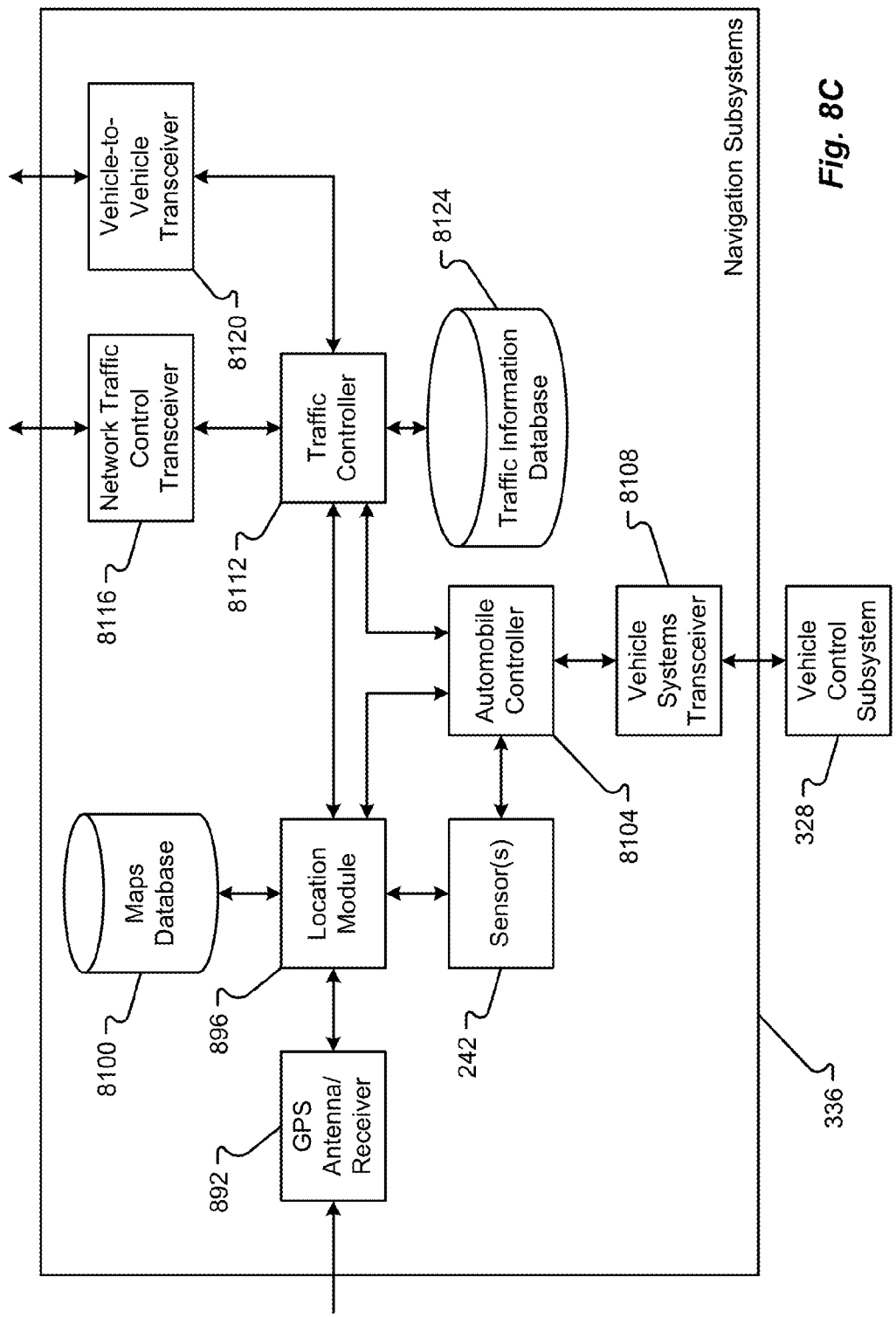

Tap

Long Press

Drag

Flick

Pinch

Spread

SIMULTANEOUS VIDEO STREAMING ACROSS MULTIPLE CHANNELS

CROSS REFERENCE TO RELATED APPLICATIONS

The present application claims the benefits of and priority, under 35 U.S.C. §119(e), to U.S. Provisional Application Ser. Nos. 61/811,981, filed on Apr. 15, 2013, entitled "Functional Specification for a Next Generation Automobile"; 61/865,954, filed on Aug. 14, 2013, entitled "Gesture Control of Vehicle Features"; 61/870,698, filed on Aug. 27, 2013, entitled "Gesture Control and User Profiles Associated with Vehicle Features"; 61/891,217, filed on Oct. 15, 2013, entitled "Gesture Control and User Profiles Associated with Vehicle Features"; 61/904,205, filed on Nov. 14, 2013, entitled "Gesture Control and User Profiles Associated with Vehicle Features"; 61/924,572, filed on Jan. 7, 2014, entitled "Gesture Control and User Profiles Associated with Vehicle Features"; and 61/926,749, filed on Jan. 13, 2014, entitled "Method and System for Providing Infotainment in a Vehicle." The entire disclosures of the applications listed above are hereby incorporated by reference, in their entirety, for all that they teach and for all purposes.

This application is also related to U.S. patent application Ser. No. 13/420,236, filed on Mar. 14, 2012, entitled, "Configurable Vehicle Console"; Ser. No. 13/420,240, filed on Mar. 14, 2012, entitled "Removable, Configurable Vehicle Console"; Ser. No. 13/462,593, filed on May 2, 2012, entitled "Configurable Dash Display"; Ser. No. 13/462,596, filed on May 2, 2012, entitled "Configurable Heads-Up Dash Display"; Ser. No. 13/679,459, filed on Nov. 16, 2012, entitled "Vehicle Comprising Multi-Operating System"; Ser. No. 13/679,234, filed on Nov. 16, 2012, entitled "Gesture Recognition for On-Board Display"; Ser. No. 13/679,412, filed on Nov. 16, 2012, entitled "Vehicle Application Store for Console"; Ser. No. 13/679,857, filed on Nov. 16, 2012, entitled "Sharing Applications/Media Between Car and Phone (Hydroid)"; Ser. No. 13/679,878, filed on Nov. 16, 2012, entitled "In-Cloud Connection for Car Multimedia"; Ser. No. 13/679,875, filed on Nov. 16, 2012, entitled "Music Streaming"; Ser. No. 13/679,676, filed on Nov. 16, 2012, entitled "Control of Device Features Based on Vehicle State"; Ser. No. 13/678,673, filed on Nov. 16, 2012, entitled "Insurance Tracking"; Ser. No. 13/678,691, filed on Nov. 16, 2012, entitled "Law Breaking/Behavior Sensor"; Ser. No. 13/678,699, filed on Nov. 16, 2012, entitled "Etiquette Suggestion"; Ser. No. 13/678,710, filed on Nov. 16, 2012, entitled "Parking Space Finder Based on Parking Meter Data"; Ser. No. 13/678,722, filed on Nov. 16, 2012, entitled "Parking Meter Expired Alert"; Ser. No. 13/678,726, filed on Nov. 16, 2012, entitled "Object Sensing (Pedestrian Avoidance/Accident Avoidance)"; Ser. No. 13/678,735, filed on Nov. 16, 2012, entitled "Proximity Warning Relative to Other Cars"; Ser. No. 13/678,745, filed on Nov. 16, 2012, entitled "Street Side Sensors"; Ser. No. 13/678,753, filed on Nov. 16, 2012, entitled "Car Location"; Ser. No. 13/679,441, filed on Nov. 16, 2012, entitled "Universal Bus in the Car"; Ser. No. 13/679,864, filed on Nov. 16, 2012, entitled "Mobile Hot Spot/Router/Application Share Site or Network"; Ser. No. 13/679,815, filed on Nov. 16, 2012, entitled "Universal Console Chassis for the Car"; Ser. No. 13/679,476, filed on Nov. 16, 2012, entitled "Vehicle Middleware"; Ser. No. 13/679,306, filed on Nov. 16, 2012, entitled "Method and System for Vehicle Data Collection Regarding Traffic"; Ser. No. 13/679,369, filed on Nov. 16, 2012, entitled "Method and System for Vehicle Data Collection"; Ser. No. 13/679,680, filed on Nov. 16, 2012, entitled "Communications Based on Vehicle Diagnostics and Indications"; Ser. No. 13/679,443, filed on Nov. 16, 2012, entitled "Method and System for Maintaining and Reporting Vehicle Occupant Information"; Ser. No. 13/678,762, filed on Nov. 16, 2012, entitled "Behavioral Tracking and Vehicle Applications"; Ser. No. 13/679,292, filed Nov. 16, 2012, entitled "Branding of Electrically Propelled Vehicles Via the Generation of Specific Operating Output"; Ser. No. 13/679,400, filed Nov. 16, 2012, entitled "Vehicle Climate Control"; Ser. No. 13/840,240, filed on Mar. 15, 2013, entitled "Controller Area Network Bus"; Ser. No. 13/678,773, filed on Nov. 16, 2012, entitled "Location Information Exchange Between Vehicle and Device"; Ser. No. 13/679,887, filed on Nov. 16, 2012, entitled "In Car Communication Between Devices"; Ser. No. 13/679,842, filed on Nov. 16, 2012, entitled "Configurable Hardware Unit for Car Systems"; Ser. No. 13/679,204, filed on Nov. 16, 2012, entitled "Feature Recognition for Configuring a Vehicle Console and Associated Devices"; Ser. No. 13/679,350, filed on Nov. 16, 2012, entitled "Configurable Vehicle Console"; Ser. No. 13/679,358, filed on Nov. 16, 2012, entitled "Configurable Dash Display"; Ser. No. 13/679,363, filed on Nov. 16, 2012, entitled "Configurable Heads-Up Dash Display"; and Ser. No. 13/679,368, filed on Nov. 16, 2012, entitled "Removable, Configurable Vehicle Console". The entire disclosures of the applications listed above are hereby incorporated by reference, in their entirety, for all that they teach and for all purposes.

BACKGROUND

Whether using private, commercial, or public transport, the movement of people and/or cargo has become a major industry. In today's interconnected world, daily travel is essential to engaging in commerce. Commuting to and from work can account for a significant portion of a traveler's day. As a result, vehicle manufacturers have begun to focus on making this commute, and other journeys, more enjoyable.

Currently, vehicle manufacturers attempt to entice travelers to use a specific conveyance based on any number of features. Most of these features focus on vehicle safety or efficiency. From the addition of safety-restraints, air-bags, and warning systems to more efficient engines, motors, and designs, the vehicle industry has worked to appease the supposed needs of the traveler. Recently, however, vehicle manufactures have shifted their focus to user and passenger comfort as a primary concern. Making an individual more comfortable while traveling instills confidence and pleasure in using a given vehicle, increasing an individual's preference for a given manufacturer and/or vehicle type.

One way to instill comfort in a vehicle is to create an environment within the vehicle similar to that of an individual's home. Integrating features in a vehicle that are associated with comfort found in an individual's home can ease a traveler's transition from home to vehicle. Several manufacturers have added comfort features in vehicles such as the following: leather seats, adaptive and/or personal climate control systems, music and media players, ergonomic controls, and, in some cases, Internet connectivity. However, because these manufacturers have added features to a conveyance, they have built comfort around a vehicle and failed to build a vehicle around comfort.

SUMMARY

There is a need for a vehicle ecosystem, which can integrate both physical and mental comforts, while seamlessly communicating with current electronic devices to result in a totally intuitive and immersive user experience. These and other needs are addressed by the various aspects, embodiments, and/or configurations of the present disclosure. Also, while the disclosure is presented in terms of exemplary and optional embodiments, it should be appreciated that individual aspects of the disclosure can be separately claimed.

A method can be provided by the present disclosure that includes the steps of:

providing, in a vehicle, first and second operating systems executing on a common microprocessor, wherein the first operating system comprises one or more applications performing a critical vehicle task, function, and/or operation and the second operating system comprises one or more applications performing an infotainment task, function, and/or operation;

collecting, by a computer control module, one or more metrics regarding an operation of the first and/or second operating system and/or computer and/or a network in communication with the computer;

determining, by the computer control module, whether the collected one or metrics are normal and/or abnormal; and when the collected one or metrics is not normal or abnormal, shutting down the second operating system but not the first operating system.

In a vehicle, first and second operating systems can execute on a common microprocessor, the first operating system can comprise one or more applications performing a critical vehicle task, function, and/or operation and the second operating system can comprise one or more applications performing an infotainment task, function, and/or operation, and a tangible and non-transient computer readable medium in the vehicle can include microprocessor executable and readable instructions that, when executed by the microprocessor, can perform operations including:

collecting, by a computer control module, one or more metrics regarding an operation of the first and/or second operating system and/or a network in communication with the computer;

determining, by the computer control module, whether the collected one or metrics of one or more of the first and/or second operating system and/or a network in communication with the computer are normal and/or abnormal; and applying one or more of the following rules:

when the collected one or metrics associated with the first operating system is not normal or abnormal, shutting down the first and second operating systems;

when the collected one or metrics associated with the second operating system is not normal or abnormal, shutting down the second, but not the first, operating system; and when the collected one or metrics associated with the network is not normal or abnormal, shutting down the second, but not the first, operating system.

A vehicle can include:

a first computer having a first operating system executing one or more applications performing a critical vehicle task, function, and/or operation; and a second computer having a different second operating system executing one or more applications performing at least one of an infotainment task, function, and/or operation and less critical task, function, and/or operation, wherein at least one of the following can be true:

(a) a computer control module collects one or more metrics regarding an operation of the first and/or second computers and/or a network in communication with the first and/or second computer, determines whether the collected one or metrics regarding an operation of the first and/or second computers and/or network are normal and/or abnormal, and apply one or more of the following rules:

when the collected one or metrics associated with the first operating system is not normal or abnormal, shutting down the first and second operating systems;

when the collected one or metrics associated with the second operating system is not normal or abnormal, shutting down the second, but not the first, operating system; and when the collected one or metrics associated with the network is not normal or abnormal, shutting down the second, but not the first, operating system; and (b) the first and second computers are configured to be incapable of communicating with each other.

Each member of the set of critical vehicle tasks, functions, and/or operations can be different from each member of the set of infotainment tasks, functions, and/or operations, whereby the union of the two sets is null.

The critical task, function or operation can be one or more of monitoring, controlling, and/or operating the ECU, TCU, door settings, window settings, and/or blind spot monitor, monitoring, controlling, and/or operating the safety equipment, monitoring and/or controlling certain critical sensors such as the power source controller and energy output sensor, engine temperature, oil pressure sensing, hydraulic pressure sensors, sensors for headlight and other lights, vehicle control system sensors, and/or steering/torque sensor, controlling the operation of the engine, head light control unit, power steering, display panel, switch state control unit, power control unit, and/or brake control unit, and/or issuing alerts to a user and/or remote monitoring entity of potential problems with a vehicle operation.

The infotainment task, function or operation can be one or more of receiving, processing, and/or providing media and/or multimedia content.

The first operating system can be simulated by a first virtual machine and the second operating system by a second virtual machine and the computer control module can be in or configured as a hypervisor module.

The first and second operating systems can concurrently and independently run on a common kernel.

A first requirement applied to the first operating system to determine abnormal operation can be different from a second requirement applied to the second operating system to determine abnormal operation.

The present disclosure can include a method, vehicle, and/or tangible and non-transient computer readable medium comprising the steps, operations, and/or functions of:

(a) determining, by a microprocessor executable device discovery daemon, that a computational device is connected to or attempting to connect to a network and/or communication subsystem of a vehicle;

(b) in response, determining, by the device discovery daemon, whether the computational device is located within a predetermined area and/or zone of the vehicle; and (c) applying, by the device discovery daemon, at least the following rules:

(C1) when the computational device is located within the predetermined area and/or zone of the vehicle, permitting the computational device to access or attempt to access the vehicle network and/or communication subsystem; and (C2) when the computational device is not located within the predetermined area and/or zone of the vehicle, not permitting the computational device to access or attempt to access the vehicle network and/or communication subsystem.

A type of the computational device can determine a specific predetermined area and/or zone of the vehicle, from among a plurality of predetermined areas and/or zones, to be used in applying the rules.

The computational device can be one or more of a tablet computer, laptop, smart phone, and personal digital assistant.

The specific predetermined area and/or zone of the vehicle can be at least part of the passenger compartment.

The device discovery daemon can perform sub-steps of step (a) including:

receiving, by the device discovery daemon, information from an on board vehicle sensor that a new occupant has entered the vehicle;

in response to the receipt of the information, emitting, by the device discovery daemon, a ping to discover the computational device; and when a responsive signal is received from the computational device, determining, by the device discovery daemon, that the computational device is attempting to connect to a network and/or communication subsystem of a vehicle.

The determining step/operation/function (b) can base the determination on whether the computational device is located within the predetermined area and/or zone of the vehicle on one or more of signal strength of a signal from the computational device as received by an access point of the vehicle, a received satellite-based position of the computational device, triangulation based on relative received signal strengths of a signal from the computational device as received by multiple access points of the vehicle, image processing of images of the predetermined area and/or zone, occupant presence and/or location information received by an on board vehicle sensor, whether the computational device is attempting to connect to the network and/or communication subsystem wirelessly or by hard wire connection, whether the computational device has moved relative to a selected access point during a defined time interval, whether the received signal strength of signaling from the computational device at a selected access point varies temporally, a type or service of the computational device, and input received from a user of the computational device.

When the computational device is determined to be located within the predetermined area and/or zone of the vehicle and is permitted to access or attempt to access the vehicle network and/or communication subsystem and wherein the device discovery daemon can determine a set of tasks, functions, and/or operations that can be performed and a set of tasks, functions, and/or operations that cannot be performed based on the determined location of the computational device.

The device discovery daemon can determine a level of confidence that the computational device is located within the predetermined area and/or zone and wherein the device discovery daemon determines that the computational device is located within the predetermined area and/or zone when the level of confidence has at least a threshold value.

A method, vehicle, and/or computer executable instructions can be provided that perform at least the following steps, operations, and functions:

(a) determining, by a microprocessor executable media controller subsystem, that a user is driving a vehicle; and (b) in response, the microprocessor executable media controller subsystem performing one or more of the following steps:

(i) removing a video channel but not an audio channel from media content to be displayed on a screen associated with the user;

(ii) applying screen magnification to content displayed on the screen associated with the user;

(iii) reconfiguring the screen and/or content to provide a large font and/or icon size for the displayed content compared to the displayed content when the user is not driving the vehicle;

(iv) removing unnecessary animations from the content to be displayed on the screen;

(v) removing background images from, while leaving at least one foreground image in, the content to be displayed on the screen;

(vi) compared to the displayed content when the user is not driving the vehicle, reconfiguring the screen and/or content to provide higher contrast to make the displayed content more visible to the user;

(vii) initiating a screen reader to audibly describe currently displayed content to the user;

(viii) compared to the period for notification dialog boxes to remain open on the screen when the user is not driving the vehicle, enabling a longer period for notification dialog boxes to remain open on the screen;

(ix) changing the color and/or transparency of window borders on the displayed content;

(x) changing the thickness of a focus rectangle around a currently selected object in a dialog box displayed on the screen;

(xi) changing the color, size and/or thickness of an on-screen mouse pointer displayed on the screen;

(xii) changing a keyboard setting of a keyboard displayed on the screen;

(xiii) formatting a web page, in the content to be displayed, differently from the web page format received from a web server;

(xiv) compared to the size of a mouse-selectable screen object when the user is not driving the vehicle, increasing a size of a mouse-selectable screen object to provide a larger target;

(xv) enabling mouse keys to move the mouse cursor on the screen;

(xvi) enabling one or more of sticky keys, toggle keys, and filter keys; and (xvii) enabling the screen to receive input written by the user's finger as an inputted command or request.

The user can be determined to be driving the vehicle when the user is determined to be in a driver's seat of the vehicle.

The user can be determined to be driving the vehicle when the vehicle is at least one of in gear and in motion.

The method/vehicle/instructions can further perform the following steps, operations, and functions:

(c) determining, by the media controller subsystem, that the user is no longer driving the vehicle; and (d) in response to step (c), the media controller subsystem performing one or more of the following steps:

(i) no longer removing a video channel from media content to be displayed;

(ii) no longer applying screen magnification to content to be displayed;

(iii) reconfiguring the display to provide a smaller font and/or icon size for the content to be displayed compared to the font and/or icon size used when the user is driving the vehicle;

(iv) no longer removing unnecessary animations from the content to be displayed;

(v) no longer removing background images from the content to be displayed;

(vi) reconfiguring the screen to provide lower contrast compared to the contrast used when the user is driving the vehicle;

(vii) disabling the screen reader;

(viii) compared to the period for notification dialog boxes to remain open on the screen when the user is driving the vehicle, enabling a shorter period for notification dialog boxes to remain open on the screen;

(ix) compared to the color and/or transparency of window borders on the displayed content when the user is driving the vehicle changing the color and/or transparency of window borders on the displayed content;

(x) compared to the thickness of a focus rectangle around a currently selected object in a dialog box displayed on the screen color and/or transparency of window borders on the displayed content when the user is driving the vehicle, changing the thickness of a focus rectangle around a currently selected object in a dialog box displayed on the screen;

(xi) compared to the color, size and/or thickness of an on-screen mouse pointer displayed on the screen when the user is driving the vehicle, changing the color, size and/or thickness of an on-screen mouse pointer displayed on the screen;

(xii) compared to the keyboard setting of a keyboard displayed on the screen when the user is driving the vehicle, changing a keyboard setting of a keyboard displayed on the screen;

(xiii) no longer formatting a web page, in the content to be displayed, differently from the web page format received from a web server;

(xiv) compared to the size of a mouse-selectable screen object when the user is driving the vehicle, decreasing a size of a mouse-selectable screen object to provide a larger target;

(xv) disabling mouse keys to move the mouse cursor on the screen;

(xvi) disabling the one or more of sticky keys, toggle keys, and filter keys; and (xvii) disabling the screen to receive input written by the user's finger as an inputted command or request.

The user can be determined not to be driving the vehicle when the vehicle is at least one of not in gear, parked, and not in motion.

The user can be determined to be in a driver's seat of the vehicle when the user is located within a predetermined area and/or zone.

The determining step (a) can base the determination on whether the user is located within the predetermined area and/or zone of the vehicle on one or more of signal strength of a signal from a computational device associated with the user as received by an access point of the vehicle, a received satellite-based position of the computational device, triangulation based on relative received signal strengths of a signal from the computational device as received by multiple access points of the vehicle, image processing of images of the predetermined area and/or zone, user presence and/or location information received by an on board vehicle sensor, and input received from a user of the computational device.

A media controller subsystem can include:

a microprocessor executable distributed network control server operable to access selected content on a public network external to a vehicle comprising the media controller subsystem, the distributed network control server having at least one of an assigned Internet Protocol address and global unicast address;

a microprocessor executable media server operable to receive requests for content from a vehicle occupant and provide requested content to a portable computational device associated with the vehicle occupant, the media server having a contactable electronic address on a local area network maintained by the vehicle;

a microprocessor readable memory to store content; and a microprocessor executable virtual network console operable to provide the computational device with remote access to the media server.

The distributed network control server, media server, and virtual network console can be on a common media processing board mounted on the vehicle.

The portable computational device can be discrete from, remote from, and in wireless communication with the media processing board.

The virtual network console can operate in accordance with the Remote Frame Buffer protocol on top of the TCP/IP suite of protocols, thereby causing the remote computational device to appear to a computer mounted in the vehicle as if the remote computational device is part of the on board vehicle control system comprising the computer.

The vehicle occupant, through the remote computational device, can control one or more of the following media presentation features of a screen and sound system mounted on the vehicle: volume, contrast, resolution, and channel selection.

A method, vehicle, and instructions can perform at least the following steps, operations, and functions:

(a) determining, by a microprocessor executable media server, at least one of an identity of a vehicle occupant requesting media content, an identity of a portable computational device associated with the vehicle occupant, and a spatial location of the vehicle occupant and/or remote computational device;

(b) based on the at least one of the identity of the vehicle occupant requesting media content, the identity of a portable computational device associated with the vehicle occupant, and the spatial location of the vehicle occupant and/or remote computational device, applying, by the microprocessor executable media server, at least one of a filter and restriction to the requested media content to form filtered and/or permitted media content to be provided to the portable computational device; and (c) providing, by a microprocessor executable media server, the filtered and/or permitted media content to the portable computational device.

The portable computational device can be discrete from, remote from, and in wireless communication with the media processing board.

The filter and/or restriction can be applied to a media request of the vehicle occupant before and/or after the requested media content is accessed.

The filter and/or restriction can be one or more of an age-related content filter and/or restriction, a vehicle occupant seating location filter and/or restriction, and a privacy filter and/or restriction.

A method, vehicle, and tangible and non-transient computer readable medium can be provided to perform steps, operations, and functions, including:

(a) receiving a request from a vehicle occupant to perform a vehicle task, function and/or operation;

(b) determining that the vehicle occupant has been authenticated successfully;

(c) accessing an account for the vehicle occupant, the account defining rights and privileges of the user with respect to controlling a vehicle task, function and/or operation;

(d) determining at least one of an area and/or zone occupied by the vehicle occupant and an operating state of the vehicle; and (e) based upon the account corresponding to the vehicle occupant and the at least one of an area and/or zone occupied by the vehicle occupant and an operating state of the vehicle, applying the following rules:

(i) when the account permits the vehicle occupant to perform the requested vehicle task, function and/or operation, performing or causing to be performed the vehicle task, function, and/or operation; and (ii) when the account does not permit the vehicle occupant to perform the requested vehicle task, function and/or operation, not performing or causing to be performed the vehicle task, function, and/or operation.

In step, operation, or function (e), a microprocessor executable vehicle control system can apply the rules based on the account corresponding to the vehicle occupant and the area and/or zone occupied by the vehicle occupant. Then vehicle occupant can perform a first set of vehicle tasks, functions and operations when in a first area and/or zone and a different set of vehicle tasks, functions, and operations when in a different second area and/or zone.

In step, operation, or function (e), the microprocessor executable vehicle control system can apply the rules based on the account corresponding to the vehicle occupant and the operating state of the vehicle. The vehicle occupant can perform a first set of vehicle tasks, functions and operations when the vehicle is in a first operating state and a different set of vehicle tasks, functions, and operations when the vehicle is in a second operating state.

When rule (i) applies, the vehicle occupant can control the requested vehicle task, function and/or operation using one or more of a cell phone, laptop, tablet computer, and personal digital assistant.

A different authentication procedure can be used for the vehicle occupant when requesting a first set of vehicle tasks, operations, and functions than when requesting a second set of vehicle tasks, operations, and functions.

The account can include rights and privileges for the vehicle occupant with respect to a vehicle task, function or operation, security and/or authentication requirements and/or credentials for the vehicle occupant, and personal settings of the vehicle occupant.

The personal settings of the vehicle occupant can include a plurality of a seat setting, climate control setting, lighting setting, configuration of an instrument cluster on a screen, rear view mirror setting, driving mode, media channel setting or preset, media delivery preference, music genre preference, scheduled program, playlist, synchronization with cloud-based data associated with the vehicle occupant, application-specific personalization and selections, and a display setting and configuration.

A method/vehicle/computer readable instructions can perform at least the following steps/operations/functions:

(a) detecting, by a microprocessor executable media controller subsystem, a change in state of a vehicle, a driver of the vehicle having a graphical user interface on board and/or in communication with a computer network controlled by computer on board the vehicle;

(b) in response, reconfiguring, by the media controller subsystem, the graphical user interface by at least one of the following actions to reduce driver distraction and/or make content displayed by the graphical user interface more visible to the driver:

apply screen magnification to at least part of the content displayed on the graphical user interface;

render at least part of the displayed content in a larger font and/or icon size;

initiate a screen reader to audibly provide and/or describe at least part of the displayed content to the driver;

initiate haptic feedback to provide and/or describe at least part of the displayed content to the driver;

disable unnecessary animation effects from at least a part of the displayed content;

remove a background image from while leaving a foreground image in at least part of the displayed content;

enable a longer period for notification dialog boxes to remain open in the displayed content;

enable a longer contact period of a digit of the driver to select a selectable object in the displayed content;

disable automatic arrangement of windows when a mouse cursor is moved to an edge of the displayed content;

enable activate a window in at least part of the displayed content by hovering over the window with a mouse cursor;

enable keyboard web page navigation in the displayed content;

enable a high contrast between text and a background color in at least part of the displayed content;

change a color and transparency of a border of a window in at least part of the displayed content;

change a thickness of a focus rectangle around a currently selected item in a dialog box in the displayed content;

change a color, size, and/or thickness of an on-screen mouse pointer in the displayed content;

change a keyboard setting displayed in the displayed content and/or in communication with the displayed content;

ignore a color, font style, font size, and/or format of a web page of the displayed content in accordance with a predetermined style sheet;

increase a size of a selectable object in at least part of the displayed content;

enable blind typing on the graphical user interface; and remove one or more selectable objects from the displayed content.

A method/vehicle/computer readable instructions can perform at least the following steps/operations/functions:

(a) mapping, by a microprocessor executable media controller subsystem, a graphical user interface on board and/or in communication with a computer network controlled by computer on board the vehicle with a segmented control surface, whereby each segment corresponds to an item of content displayed on the graphical user interface;

(b) tracking, by a microprocessor executable media controller subsystem, a position of a body part of a user on the control surface relative to the control surface segments;

(c) determining, by a microprocessor executable media controller subsystem, that the body part of the user is located on a first segment; and (d) in response, at least one of providing displayed content corresponding to the first segment and selecting a selectable object corresponding to the first segment.

The control surface can be electrically, magnetically, and electromagnetically nonresponsive to contact of the user's body part.

The control surface can be optically nonresponsive to contact of the user's body part.

The control surface can be part of an arm rest and/or dashboard and wherein the graphical user interface is virtual and not displayed to the user.

The control surface can be part of an arm rest and/or dashboard and wherein the graphical user interface is displayed to the user on a screen on board the vehicle.

A method/vehicle/computer readable instructions can perform at least the following steps/operations/functions:

(a) determining, by a vehicle control system, that a vehicle occupant has an impairment; and (b) in response, altering a communication interface of the vehicle to accommodate the impairment.

The impairment can be one or more of a vision impairment, hearing impairment, dexterity impairment, mobility impairment, language impairment, and communication impairment.

The communication interface can be a screen on board the vehicle.

The location of the vehicle occupant and the screen corresponding to the determined occupant location can be determined.

The alteration can be one or more of:

apply screen magnification to at least part of the content displayed on the screen;

render at least part of the displayed content in a larger font and/or icon size;

initiate a screen reader to audibly provide and/or describe at least part of the displayed content to the occupant;

initiate haptic feedback to provide and/or describe at least part of the displayed content to the occupant;

disable unnecessary animation effects from at least a part of the displayed content;

remove a background image from while leaving a foreground image in at least part of the displayed content;

enable a longer period for notification dialog boxes to remain open in the displayed content;

enable a longer contact period of a digit of the occupant to select a selectable object in the displayed content;

disable automatic arrangement of windows when a mouse cursor is moved to an edge of the displayed content;

enable activate a window in at least part of the displayed content by hovering over the window with a mouse cursor;

enable keyboard web page navigation in the displayed content;

enable a high contrast between text and a background color in at least part of the displayed content;

change a color and transparency of a border of a window in at least part of the displayed content;

change a thickness of a focus rectangle around a currently selected item in a dialog box in the displayed content;

change a color, size, and/or thickness of an on-screen mouse pointer in the displayed content;

change a keyboard setting displayed in the displayed content and/or in communication with the displayed content;

ignore a color, font style, font size, and/or format of a web page of the displayed content in accordance with a predetermined style sheet;

increase a size of a selectable object in at least part of the displayed content;

enable blind typing on the graphical user interface;

enable text and/or a visual alternative to an audio channel associated with the displayed content;

increase a volume setting of the audio channel;

change a sound provided by the audio channel;

enable sign language interpretation;

enable a text phone application;

change a setting of a mouse associated with the displayed content; and remove one or more selectable objects from the displayed content.

A method/vehicle/computer readable instructions can perform at least the following steps/operations/functions:

(a) sensing, by a vehicle control system, a sound from a source external to a vehicle;

(b) identifying, by the vehicle control system, a type and/or source of the sound;

(c) based on the identifying step, notifying a driver of the vehicle of the type and/or source of the sound.

The notification can be one or more of a visual notification, an audible notification, and a haptic notification.

The notification can be an audible notification.

The audible notification can be one or more of a portion of the frequency range of the received sound, a frequency shifted portion of the received sound, and a phase shifted portion of the sound.

A method/vehicle/computer readable instructions can perform at least the following step/operation/function:

altering, by a vehicle control system, an interface of a vehicle based on one or more of a user impairment, user medical condition, user age, user physical condition, user driving characteristic and driving history.

The interface can be one or more of a steering wheel, pedal, a graphical user interface, and a setting and/or configuration of an automated vehicle response system.

The automated vehicle response system can be a collision avoidance system.

A method/vehicle/computer readable instructions can perform at least the following step/operation/function:

maintaining a persona of a vehicle occupant; and based on the persona of the vehicle occupant and vehicle-related information, perform an action assisting the vehicle occupant.

the vehicle-related information comprises at least one of a current and/or future vehicle location and path of vehicle travel.

The action performed can depend on a seating position of the vehicle occupant.

The persona can include one or more of bioinformatics, medical information, driving history, personal information, private information, travel information, and Internet browsing history and/or browsed content.

The vehicle related information can include one or more of vehicle context, state, external surroundings, location, past, current, and/or intended path of travel, waypoint, and destination.

The action can be one or more of making an appointment, making a reservation, purchasing an item on line, adding a waypoint or destination to path of travel on a navigation system of the vehicle, adding an entry into the occupant's electronic calendar, changing a destination or path of travel on the navigation system, warning the occupant, notifying the occupant, and sending a message to a person at a waypoint or destination of the vehicle regarding an arrival time.

The steps/functions/operations can determine relevant information other than the persona of the vehicle occupant and the vehicle-related information.

The relevant information can include one or more of a persona of a selected person not currently in the vehicle, a message from a friend or family member of the vehicle occupant, a current activity of the friend and/or family member, a location, hours of operation, and/or descriptive information about a point and/or location of interest near the vehicle and/or the vehicle's path of travel, a location, hours of operation, and/or descriptive information about a vehicle service facility near the vehicle and/or the vehicle's path of travel, a location, hours of operation, and/or descriptive information about a hotel and/or motel near the vehicle and/or the vehicle's path of travel, a current location of the friend or family member near the vehicle and/or the vehicle's path of travel, and a road condition along a path of travel of the vehicle.

The vehicle can obtain the persona from one or more of a different vehicle driven by the occupant and a home computer.

The vehicle can synchronize with the different vehicle and/or home computer when the vehicle is parked in proximity thereto and an ignition of the vehicle is turned off.

The maintaining of the persona can include collecting information from one or more vehicle sensors and/or from a remote information source.

A type of information collected can depend on a seating position of the occupant.

The type of information collected can depend on one or more of an identity of the occupant, an age of the occupant, and an association of the occupant with the vehicle.

The persona can be defined in a format (e.g., grammar, syntax, and/or semantics) that can be processed by vehicles of different manufacturers.

A vehicle backplane assembly can include at least the following components:

A plurality of blade processors in a vehicle that includes a first set of blade processors installed prior to vehicle sale and not modifiable and/or replaceable by the vehicle owner and a second set of blade processors installable after vehicle sale and is modifiable and/or replaceable by the vehicle owner. Each blade processor includes a microprocessor, a memory, and a network interface and each of the blade processors performing a different set of functions.

The restricted access by the customer to the first set of blade processors can be done through restrictions on software rights and privileges (e.g., read only rights and privileges to machine code with no right or privilege to modify same) and physical access to the first set of blade processors (e.g., through a locked housing containing one or more components of the blade processors).

The assembly can include a third set of blade processors that interfaces with the first and second set of blade processors to provide input to and/or receive output from a corresponding one of the first and second blade processors.

A satellite receiving system can be a member of the third set of blade processors and a navigation system a member of one of the first and second set of blade processors.

Each of the first and second sets of blade processors can include a corresponding Universal Serial Bus ("USB") hub, the USB hub comprising a plurality of ports to permit devices to connect to the USB hub.

The first set of blades can include a master blade processor operable to inventory hardware and/or software in communication with the backplane assembly, assign blade processors to applications attempting to execute, and/or determine a health state of a selected the blade processor.

A vehicle can include a plurality of blade processors, each blade processor performing a function that is at least one of a vehicle task, function, or operation and an infotainment task, function, or operation.

The blade processors can have a backplane.

The backplane can have a first communication zone defining a trusted network within the vehicle to connect with trusted computational devices and/or module provided or certified by the vehicle manufacturer but not untrusted computational devices and/or modules provided by vehicle occupants. Whether or not a computational device and/or module is certified by a manufacturer can be determined using known license check procedures, such as a unique identifier, a unique credential (e.g., password or encrypted or unencrypted key), and the like. When the check is completed satisfactorily (e.g., the unique identifier or a unique credential (e.g., password or encrypted or unencrypted key) provided by the device and/or module matches a stored identifier in the memory of the vehicle control system (or master blade processor)), the computational device and/or module is deemed to be certified by the manufacturer. When the check is not completed satisfactorily, the computational device and/or module is not deemed to be certified by the manufacturer.

The backplane can have a second communication zone defining an untrusted network to connect with the untrusted computational devices.

The backplane can have a third communication zone providing power and data transmission to the plurality of blade processors.

The first and second communication zones can be connected logically on opposing sides of a firewall blade processor.

A master blade processor can enable a connection to a computational device connected to the first communication zone upon verification that the connected computational device is certified by a vehicle manufacturer.

The first and second communication zones can be configured as separate Ethernet switches. The first and second communication zones are typically not in signal communication with one another.

A firewall can have a dedicated slot that bridges the first and second communication zones and uses the third communication zone for power connections.

An output of each of the plurality of blade processors can be an IP message framed into an Ethernet packet.

A sensor and/or controller of the vehicle can communicate by a Car Area Network ("CAN") protocol. An Ethernet bus controller can terminate a CAN bus to the sensor and/or controller and a CAN Ethernet controller subsystem can translate an Ethernet message from a blade processor to a CAN protocol-based message.

The plurality of blade processors can be configured as a crate having the backplane connector and on-backplane Ethernet interfaces enabling the blade processors to communicate with one another using Ethernet messages.

A vehicle can include a plurality of blade processors, each blade processor performing a function that is at least one of a vehicle task, function, or operation and an infotainment task, function, or operation. The plurality of blade processors can include a master blade processor operable to assign a component and/or module requiring a blade processor for execution to a selected blade processor.

The master blade processor can inventory hardware and software capabilities of components and/or modules in communication with the master blade processor to provide an application resource table comprising component and/or module identity, functional description, and/or computational resource requirements and/or capabilities needed for execution of the component and/or module.

A blade processor can be assigned to execute the component and/or module when the blade processor satisfies the corresponding computational resource requirements and/or capabilities.

The master blade processor can assign a network address to each blade processor and communication device in communication with the master blade processor.

The master blade processor can assign a component and/or module to a selected blade processor when the selected blade processor is available or, though unavailable, is executing a component and/or module having a lower priority than the component and/or module to be assigned to the selected blade processor.

The present disclosure can provide a number of advantages depending on the particular aspect, embodiment, and/or configuration. For example, operating multiple operating systems on a common on board computer platform for vehicle control and infotainment tasks, functions and operations can provide a high level of vehicle security and block successfully intrusive attacks. The network security configurations can enable both infotainment and critical vehicle tasks, functions, and operations to performed automatically and concurrently in a vehicle without increasing driver danger from computer-targeted attacks by an outside source. Using a common computer to run safely both the first and second operating systems can not only reduce vehicle manufacturing costs but also provide a simpler computational architecture. The device discovery daemon, by locating the portable device seeking access to the vehicle network, can not only provide higher levels of security from intrusive attacks via a computational device external to the vehicle but also protect the privacy and resources of the vehicle network. The application of accessibility technologies to the driver's screen can successfully reduce driver distractions while enabling the driver to perform permissible computational tasks. The availability of accessibility technologies in the vehicle can not only comply with prevailing legal requirements but also enhance passenger enjoyment. The use of network control and media servers and virtual network console functionality on a common processing board can provide a simple yet effective way to stream media to devices within the vehicle network. The use of media filters and restrictions based on one or more of the identity of the vehicle occupant requesting media content, the identity of a portable computational device associated with the vehicle occupant, and the spatial location of the vehicle occupant and/or remote computational device can enable compliance with prevailing laws regarding driver distractions while providing the vehicle owner with the ability to control media access by one or more selected vehicle occupants. The use of user accounts to control passenger access to vehicle tasks, functions, and operations can prevent a non-driving passenger, for instance, from controlling a critical vehicle task, function or operation and confusing or frustrating the driver. The inactive control surface can enable a vehicle occupant to perform tasks, functions and operations without viewing his or her screen. This provides yet another convenient method for driver control of vehicle and non-vehicle tasks, functions, and operations without distraction while driving the vehicle. The blade processor architecture can take advantage of the pervasiveness of TCP/IP and the large volume of components and/or modules made for IP-based distributed systems, such as the Ethernet. The architecture can be a modular distributed system that can be upgraded and/or extended over time, without changing the basic processing architecture. Because the various subsystems can communicate with one another by protocol-based messages, there is not requirement that all software be written in any specific language or execute on any specific operating system. This can allow developers to use the most appropriate run time environment for the subsystem being developed. For instance, when a real time operating system ("RTOS") is required because of the timing constraints of the run time environment (i.e., real time control of a function), a subsystem can be developed using RTOS, without constraining the runtime environment of less demanding systems (e.g., a console subsystem).

These and other advantages will be apparent from the disclosure.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

"Accessible technology" refers to any computer technology that users can adjust and/or employ to accommodate his or her vision, dexterity, hearing, cognitive, language, learning, and/or speech needs. Accessibility technology can be in the form of accessibility features or settings built into software programs and specialty hardware devices or software programs.

"Assistive technology" refers to any technology that users can adjust and/or employ to accommodate his or her vision, dexterity, hearing, cognitive, language, learning, and/or speech needs. Examples of assistive technology include accessible technology, adjuncts, peripherals, plug-ins, and add-ins.

The term "disability" refers to the consequence of an impairment that may be physical, cognitive, intellectual, mental, sensory, emotional, developmental, or some combination of these. By way of illustration, Section 503 defines "disability" as an impairment that substantially limits a major life activity, even if it were not to limit any other major life activity, or an impairment that is episodically active or in remission and would substantially limit a major life activity when active.

The term "automatic" and variations thereof, as used herein, refer to any process or operation done without material human input when the process or operation is performed. However, a process or operation can be automatic, even though performance of the process or operation uses material or immaterial human input, if the input is received before the performance of the process or operation. Human input is deemed to be material if such input influences how the process or operation will be performed. Human input that consents to the performance of the process or operation is not deemed to be "material."

The term "automotive navigation system" can refer to a satellite navigation system designed for use in vehicles. It typically uses a GPS navigation device to acquire position data to locate the user on a road in the unit's map database. Using the road database, the unit can give directions to other locations along roads also in its database. Dead reckoning using distance data from sensors attached to the drivetrain, a gyroscope and an accelerometer can be used for greater reliability, as GPS signal loss and/or multipath can occur due to urban canyons or tunnels.

The term "bus" and variations thereof, as used herein, can refer to a subsystem that transfers information and/or data between various components. A bus generally refers to the collection communication hardware interface, interconnects, bus architecture, standard, and/or protocol defining the communication scheme for a communication system and/or communication network. A bus may also refer to a part of a communication hardware that interfaces the communication hardware with the interconnects that connect to other components of the corresponding communication network. The bus may be for a wired network, such as a physical bus, or wireless network, such as part of an antenna or hardware that couples the communication hardware with the antenna. A bus architecture supports a defined format in which information and/or data is arranged when sent and received through a communication network. A protocol may define the format and rules of communication of a bus architecture.

The terms "communication device," "smartphone," and "mobile device," and variations thereof, as used herein, can be used interchangeably and may include any type of device capable of communicating with one or more of another device and/or across a communications network, via a communications protocol, and the like. Exemplary communication devices may include but are not limited to smartphones, handheld computers, laptops, netbooks, notebook computers, sub-notebooks, tablet computers, scanners, portable gaming devices, phones, pagers, GPS modules, portable music players, and other Internet-enabled and/or network-connected devices.

A "communication modality" can refer to any protocol- or standard defined or specific communication session or interaction, such as Voice-Over-Internet-Protocol ("VoIP"), cellular communications (e.g., IS-95, 1G, 2G, 3G, 3.5G, 4G, 4G/IMT-Advanced standards, 3GPP, WIMAX™, GSM, CDMA, CDMA2000, EDGE, 1xEVDO, iDEN, GPRS, HSPDA, TDMA, UMA, UMTS, ITU-R, and 5G), Bluetooth™, text or instant messaging (e.g., AIM, Blauk, eBuddy, Gadu-Gadu, IBM Lotus Sametime, ICQ, iMessage, IMVU, Lync, MXit, Paltalk, Skype, Tencent QQ, Windows Live Messenger™ or MSN Messenger™, Wireclub, Xfire, and Yahoo! Messenger™), email, Twitter (e.g., tweeting), Digital Service Protocol (DSP), and the like.

The term "communication system" or "communication network" and variations thereof, as used herein, can refer to a collection of communication components capable of one or more of transmission, relay, interconnect, control, or otherwise manipulate information or data from at least one transmitter to at least one receiver. As such, the communication may include a range of systems supporting point-to-point or broadcasting of the information or data. A communication system may refer to the collection individual communication hardware as well as the interconnects associated with and connecting the individual communication hardware. Communication hardware may refer to dedicated communication hardware or may refer a processor coupled with a communication means (i.e., an antenna) and running software capable of using the communication means to send and/or receive a signal within the communication system. Interconnect refers some type of wired or wireless communication link that connects various components, such as communication hardware, within a communication system. A communication network may refer to a specific setup of a communication system with the collection of individual communication hardware and interconnects having some definable network topography. A communication network may include wired and/or wireless network having a pre-set to an ad hoc network structure.

The term "computer-readable medium," as used herein refers to any tangible storage and/or transmission medium that participates in providing instructions to a processor for execution. Such a medium may take many forms, including but not limited to, non-volatile media, volatile media, and transmission media. Non-volatile media includes, for example, non-volatile random access memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a compact disc read only memory (CD-ROM), any other optical medium, punch cards, paper tape, any other physical medium with patterns of holes, a random access memory (RAM), a programmable read only memory (PROM), and erasable programmable read only memory EPROM, a FLASH-EPROM, a solid state medium like a memory card, any other memory chip or cartridge, a carrier wave as described hereinafter, or any other medium from which a computer can read. A digital file attachment to an e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. It should be noted that any computer readable medium that is not a signal transmission may be considered non-transitory.

The terms dash and dashboard and variations thereof, as used herein, may be used interchangeably and can be any panel and/or area of a vehicle disposed adjacent to an operator, user, and/or passenger. Dashboards may include, but are not limited to, one or more control panel(s), instrument housing(s), head unit(s), indicator(s), gauge(s), meter(s), light(s), audio equipment, computer(s), screen(s), display(s), HUD unit(s), and graphical user interface(s).

The term "module" as used herein refers to any known or later developed hardware, software, firmware, artificial intelligence, fuzzy logic, or combination of hardware and software that is capable of performing the functionality associated with that element.

The term "desktop" refers to a metaphor used to portray systems. A desktop is generally considered a "surface" that may include pictures, called icons, widgets, folders, etc. that can activate and/or show applications, windows, cabinets, files, folders, documents, and other graphical items. The icons are generally selectable to initiate a task through user interface interaction to allow a user to execute applications and/or conduct other operations.

The term "display" refers to a portion of a physical screen used to display the output of a computer to a user.

The term "displayed image" refers to an image produced on the display. A typical displayed image is a window or desktop. The displayed image may occupy all or a portion of the display.

The term "display orientation" refers to the way in which a rectangular display is oriented for viewing. The two most common types of display orientations are portrait and landscape. In landscape mode, the display is oriented such that the width of the display is greater than the height of the display (such as a 4:3 ratio, which is 4 units wide and 3 units tall, or a 16:9 ratio, which is 16 units wide and 9 units tall). Stated differently, the longer dimension of the display is oriented substantially horizontal in landscape mode while the shorter dimension of the display is oriented substantially vertical. In the portrait mode, by contrast, the display is oriented such that the width of the display is less than the height of the display. Stated differently, the shorter dimension of the display is oriented substantially horizontal in the portrait mode while the longer dimension of the display is oriented substantially vertical. A multi-screen display can have one composite display that encompasses all the screens. The composite display can have different display characteristics based on the various orientations of the device.

The term "electronic address" can refer to any contactable address, including a telephone number, instant message handle, e-mail address, Uniform Resource Locator ("URL"), Global Universal Identifier ("GUID"), Universal Resource Identifier ("URI"), Address of Record ("AOR"), electronic alias in a database, etc., combinations thereof.

The term "gesture" refers to a user action that expresses an intended idea, action, meaning, result, and/or outcome. The user action can include manipulating a device (e.g., opening or closing a device, changing a device orientation, moving a trackball or wheel, etc.), movement of a body part in relation to the device, movement of an implement or tool in relation to the device, audio inputs, etc. A gesture may be made on a device (such as on the screen) or with the device to interact with the device.

The term "gesture capture" refers to a sense or otherwise a detection of an instance and/or type of user gesture. The gesture capture can be received by sensors in three-dimensional space. Further, the gesture capture can occur in one or more areas of a screen, for example, on a touch-sensitive display or a gesture capture region. A gesture region can be on the display, where it may be referred to as a touch sensitive display, or off the display, where it may be referred to as a gesture capture area.

The terms "infotainment" and "infotainment system" may be used interchangeably and can refer to the hardware/software products, data, content, information, and/or systems, which can be built into or added to vehicles to enhance driver and/or passenger experience. Infotainment may provide media and/or multimedia content. An example is information-based media content or programming that also includes entertainment content.

A "multi-screen application" refers to an application that is capable of producing one or more windows that may simultaneously occupy one or more screens. A multi-screen application commonly can operate in single-screen mode in which one or more windows of the application are displayed only on one screen or in multi-screen mode in which one or more windows are displayed simultaneously on multiple screens.

A "single-screen application" refers to an application that is capable of producing one or more windows that may occupy only a single screen at a time.

The terms "online community," "e-community," or "virtual community" can mean a group of people that interact via a computer network, for social, professional, educational, and/or other purposes. The interaction can use a variety of media formats, including wikis, blogs, chat rooms, Internet forums, instant messaging, email, and other forms of electronic media. Many media formats may be used in social software separately and/or in combination, including text-based chat rooms and forums that use voice, video text or avatars.

The term "satellite positioning system receiver" can refer to a wireless receiver or transceiver to receive and/or send location signals from and/or to a satellite positioning system (SPS), such as the Global Positioning System ("GPS") (US), GLONASS (Russia), Galileo positioning system (EU), Compass navigation system (China), and Regional Navigational Satellite System (India).

The term "social network service" may include a service provider that builds online communities of people, who share interests and/or activities, or who are interested in exploring the interests and/or activities of others. Social network services can be network-based and may provide a variety of ways for users to interact, such as e-mail and instant messaging services.

The term "social network" can refer to a network-based social network.

The term "screen," "touch screen," "touchscreen," or "touch-sensitive display" refers to a physical structure that enables the user to interact with the computer by touching areas on the screen and provides information to a user through a display. The touch screen may sense user contact in a number of different ways, such as by a change in an electrical parameter (e.g., resistance or capacitance), acoustic wave variations, infrared radiation proximity detection, light variation detection, and the like. In a resistive touch screen, for example, normally separated conductive and resistive metallic layers in the screen pass an electrical current. When a user touches the screen, the two layers make contact in the contacted location, whereby a change in electrical field is noted and the coordinates of the contacted location calculated. In a capacitive touch screen, a capacitive layer stores electrical charge, which is discharged to the user upon contact with the touch screen, causing a decrease in the charge of the capacitive layer. The decrease is measured, and the contacted location coordinates determined. In a surface acoustic wave touch screen, an acoustic wave is transmitted through the screen, and the acoustic wave is disturbed by user contact. A receiving transducer detects the user contact instance and determines the contacted location coordinates.

The term "window" refers to a, typically rectangular, displayed image on at least part of a display that contains or provides content different from the rest of the screen. The window may obscure the desktop. The dimensions and orientation of the window may be configurable either by another module or by a user. When the window is expanded, the window can occupy substantially all of the display space on a screen or screens.

The terms "determine," "calculate," and "compute," and variations thereof, as used herein, are used interchangeably and include any type of methodology, process, mathematical operation, or technique.

It shall be understood that the term "means," as used herein, shall be given its broadest possible interpretation in accordance with 35 U.S.C., Section 112, Paragraph 6 or other applicable law. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The terms "vehicle," "car," "automobile," and variations thereof may be used interchangeably herein and can refer to a device or structure for transporting animate and/or inanimate or tangible objects (e.g., persons and/or things), such as a self-propelled conveyance. A vehicle as used herein can include any conveyance or model of a conveyance, where the conveyance was originally designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

The term "profile," as used herein, can refer to any data structure, data store, and/or database that includes one or more items of information associated with a vehicle, a vehicle system, a device (e.g., a mobile device, laptop, mobile phone, etc.), or a person.

The term "in communication with," as used herein, refers to any coupling, connection, or interaction using electrical signals to exchange information or data, using any system, hardware, software, protocol, or format, regardless of whether the exchange occurs wirelessly or over a wired connection.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible utilizing, alone or in combination, one or more of the features set forth above or described in detail below.

BRIEF DESCRIPTION OF THE DRAWINGS

FIG. 5A is a first block diagram of an embodiment of a vehicle interior environment separated into areas and/or zones;

FIG. 8C is a block diagram of an embodiment of a Navigation subsystem for a vehicle;

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference letter or label.

DETAILED DESCRIPTION

Presented herein are embodiments of systems, devices, processes, data structures, user interfaces, etc. The embodiments may relate to an automobile and/or an automobile environment. The automobile environment can include systems associated with the automobile and devices or other systems in communication with the automobile and/or automobile systems. Furthermore, the systems can relate to communications systems and/or devices and may be capable of communicating with other devices and/or to an individual or group of individuals. Further, the systems can receive user input in unique ways. The overall design and functionality of the systems provide for an enhanced user experience making the automobile more useful and more efficient. As described herein, the automobile systems may be electrical, mechanical, electro-mechanical, software-based, and/or combinations thereof.

Figure 1:
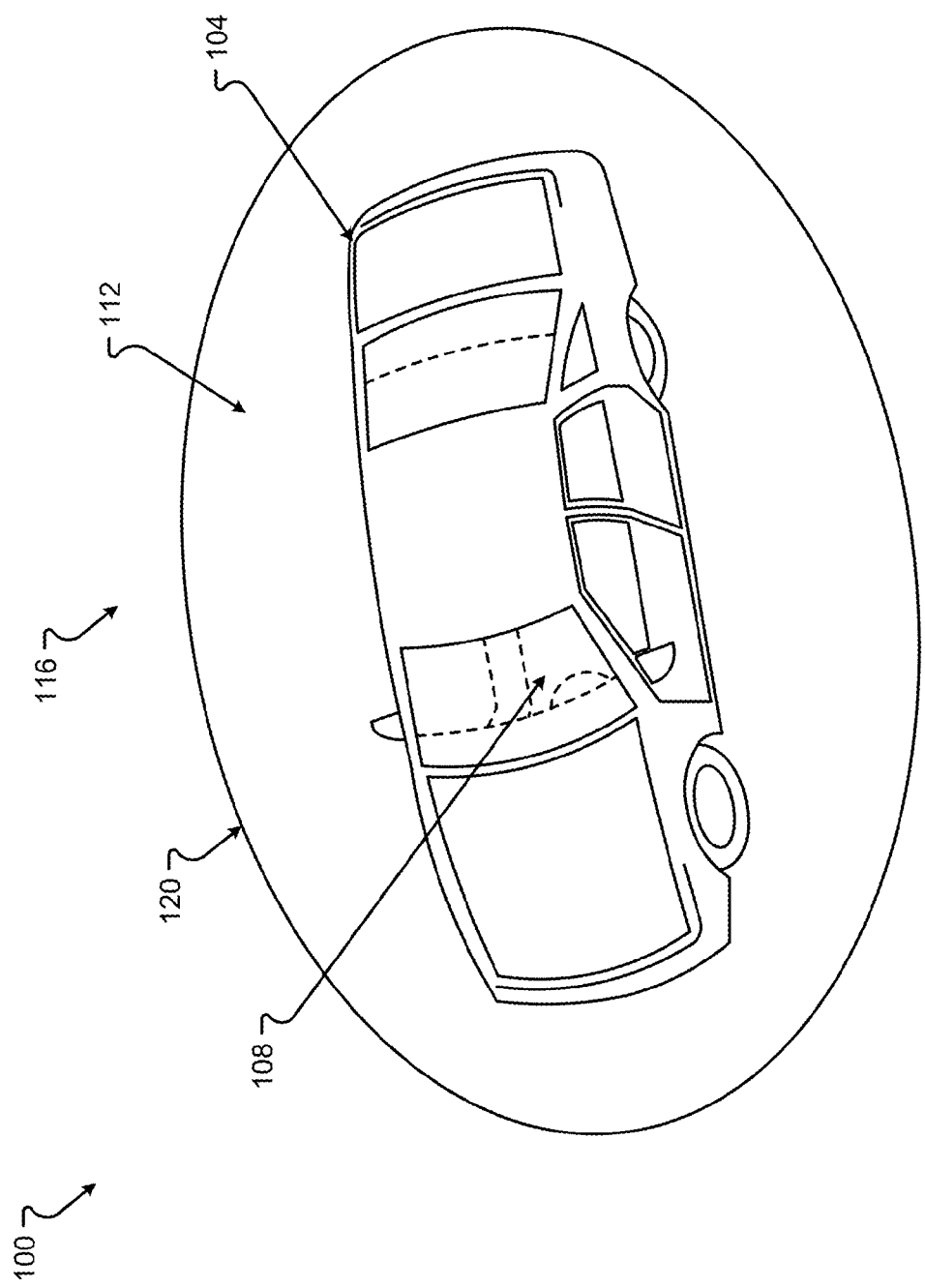
FIG. 1 depicts an embodiment of a vehicle operating environment.

A vehicle environment 100 that may contain a vehicle ecosystem is shown in FIG. 1. The vehicle environment 100 can contain areas associated with a vehicle or conveyance 104. The vehicle 104 is shown as a car but can be any type of conveyance. The environment 100 can include at least three zones. A first zone 108 may be inside a vehicle 104. The zone 108 includes any interior space, trunk space, engine compartment, or other associated space within or associated with the vehicle 104. The interior zone 108 can be defined by one or more techniques, for example, geo-fencing.

A second zone 112 may be delineated by line 120. The zone 112 is created by a range of one or more sensors associated with the vehicle 104. Thus, the area 112 is exemplary of the range of those sensors and what can be detected by those sensors associated with the vehicle 104. Although sensor range is shown as a fixed and continuous oval, the sensor range may be dynamic and/or discontinuous. For example, a ranging sensor (e.g., radar, lidar, ladar, etc.) may provide a variable range depending on output power, signal characteristics, or environmental conditions (e.g., rain, fog, clear, etc.). The rest of the environment includes all space beyond the range of the sensors and is represented by space 116. Thus, the environment 100 may have an area 116 that includes all areas beyond the sensor range 112. The area 116 may include locations of travel that the vehicle 104 may proceed to in the future.

Figure 2:
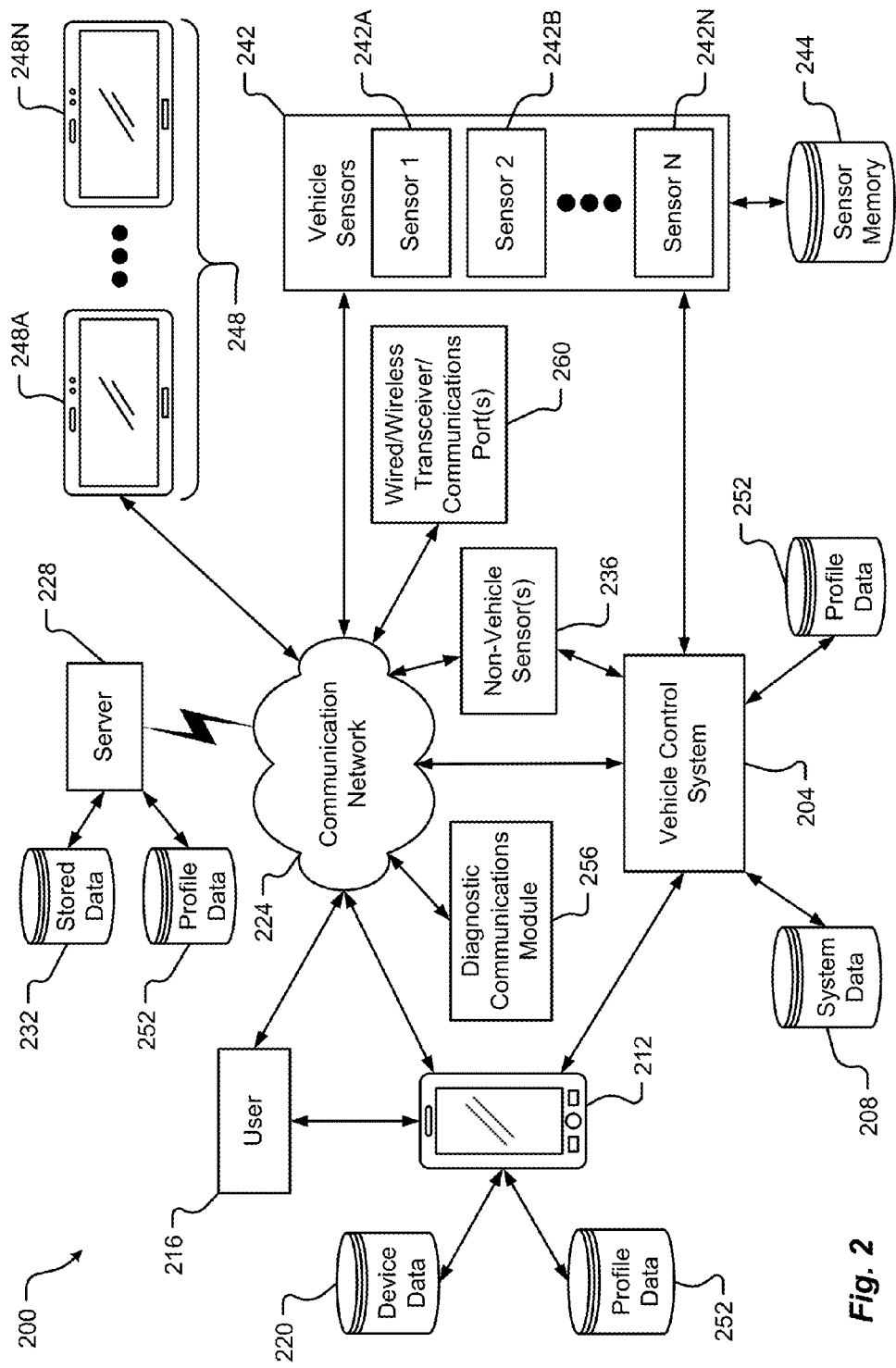
FIG. 2 is a block diagram of an embodiment of a vehicle system.

An embodiment of a vehicle system 200 is shown in FIG. 2. The vehicle system 200 may comprise hardware and/or software that conduct various operations for or with the vehicle 104. The operations can include, but are not limited to, providing information to the user 216, receiving input from the user 216, and controlling the functions or operation of the vehicle 104, etc. The vehicle system 200 can include a vehicle control system 204. The vehicle control system 204 can be any type of computing system operable to conduct the operations as described herein. An example of a vehicle control system may be as described in conjunction with FIG. 3.

The vehicle control system 204 may interact with a memory or storage system 208 that stores system data. System data 208 may be any type of data needed for the vehicle control system 204 to control effectively the vehicle 104. The system data 208 can represent any type of database or other storage system. Thus, the system data 208 can be a flat file data system, an object-oriented data system, or some other data system that may interface with the vehicle control system 204.

The vehicle control system 204 may communicate with a device or user interface 212, 248. The user interface 212, 248 may be operable to receive user input either through touch input, on one or more user interface buttons, via voice command, via one or more image sensors, or through a graphical user interface that may include a gesture capture region, as described in conjunction with the other figures provided herein. Further, the symbol 212, 248 can represent a device that is located or associated with the vehicle 104. The device 212, 248 can be a mobile device, including, but not limited to, a mobile telephone, a mobile computer, or other type of computing system or device that is either permanently located in or temporarily associated with, but not necessarily connected to, the vehicle 104. Thus, the vehicle control system 204 can interface with the device 212, 248 and leverage the device's computing capability to provide one or more of the features or functions as described herein.

The device or user interface 212, 248 can receive input or provide information to a user 216. The user 216 may thus interact with the vehicle control system 204 through the interface or device 212, 248. Further, the device 212, 248 may include or have access to device data 220 and/or profile data 252. The device data 220 can be any type of data that is used in conjunction with the device 212, 248 including, but not limited to, multimedia data, preferences data, device identification information, or other types of data. The profile data 252 can be any type of data associated with at least one user 216 including, but in no way limited to, bioinformatics, medical information, driving history, personal information (e.g., home physical address, business physical address, contact addresses, likes, dislikes, hobbies, size, weight, occupation, business contacts—including physical and/or electronic addresses, personal contacts—including physical and/or electronic addresses, family members, and personal information related thereto, etc.), other user characteristics, advertising information, user settings and feature preferences, travel information, associated vehicle preferences, communication preferences, historical information (e.g., including historical, current, and/or future travel destinations), Internet browsing history, or other types of data. In any event, the data may be stored as device data 220 and/or profile data 252 in a storage system similar to that described in conjunction with FIGS. 12A through 12D.

As an example, the profile data 252 may include one or more user profiles. User profiles may be generated based on data gathered from one or more of vehicle preferences (e.g., seat settings, HVAC settings, dash configurations, and the like), recorded settings, geographic location information (e.g., provided by a satellite positioning system (e.g., GPS), Wi-Fi hotspot, cell tower data, etc.), mobile device information (such as mobile device electronic addresses, Internet browsing history and content, application store selections, user settings and enabled and disabled features, and the like), private information (such as user information from a social network, user presence information, user business account, and the like), secure data, biometric information, audio information from on board microphones, video information from on board cameras, Internet browsing history and browsed content using an on board computer and/or the local area network enabled by the vehicle 104, geographic location information (e.g., a vendor storefront, roadway name, city name, etc.), and the like.

The profile data 252 may include one or more user accounts. User accounts may include access and permissions to one or more settings and/or feature preferences associated with the vehicle 104, communications, infotainment, content, etc. In one example, a user account may allow access to certain settings for a particular user, while another user account may deny access to the settings for another user, and vice versa. The access controlled by the user account may be based on at least one of a user account priority, role, permission, age, family status, a group priority (e.g., the user account priority of one or more users, etc.), a group age (e.g., the average age of users in the group, a minimum age of the users in the group, a maximum age of the users in the group, and/or combinations thereof, etc.).

For example, a user 216 may be allowed to purchase applications (e.g., software, etc.) for the vehicle 104 and/or a device associated with the vehicle 104 based on information associated with the user account. This user account information may include a preferred payment method, permissions, and/or other account information. As provided herein, the user account information may be part of the user profile and/or other data stored in the profile data 252.

As another example, an adult user (e.g., a user with an age of 18 years old and/or over, etc.) may be located in an area of a vehicle 104, such as a rear passenger area. Continuing this example a child user (e.g., a user with an age of 17 years old and/or less, etc.) may be located in the same, or close, area. In this example, the user account information in the profile data 252 associated with both the adult user and the child user may be used by the vehicle 104 in determining whether content is appropriate for the area given the age of the child user. For instance, a graphic movie containing violence (e.g., a movie associated with a mature rating, such as a Motion Picture Association of America (MPAA) rating of "R," "NC-17," etc.) may be suitable to present to a display device associated with the adult user but may not be acceptable to present to the display device if a 12-year old child user may see and/or hear the content of the movie.

The vehicle control system 204 may also communicate with or through a communication network 224. The communication network 224 can represent any type of wireless and/or wired communication system that may be included within the vehicle 104 or operable to communicate outside the vehicle 104. Thus, the communication network 224 can include a local area communication capability and a wide area communication capability. For example, the communication network 224 can include a Bluetooth® wireless system, an 802.11x (e.g., 802.11G/802.11N/802.11AC, or the like, wireless system), a CAN bus, an Ethernet network within the vehicle 104, or other types of communication networks that may function with or be associated with the vehicle 104. Further, the communication network 224 can also include wide area communication capabilities, including one or more of, but not limited to, a cellular communication capability, satellite telephone communication capability, a wireless wide area network communication capability, or other types of communication capabilities that allow for the vehicle control system 204 to communicate outside the vehicle 104.

The vehicle control system 204 may communicate through the communication network 224 to a server 228 that may be located in a facility that is not within physical proximity to the vehicle 104. Thus, the server 228 may represent a cloud computing system or cloud storage that allows the vehicle control system 204 to either gain access to further computing capabilities or to storage at a location outside of the vehicle 104. The server 228 can include a computer processor and memory and be similar to any computing system as understood to one skilled in the art.

Further, the server 228 may be associated with stored data 232. The stored data 232 may be stored in any system or by any method, as described in conjunction with system data 208, device data 220, and/or profile data 252. The stored data 232 can include information that may be associated with one or more users 216 or associated with one or more vehicles 104. The stored data 232, being stored in a cloud or in a distant facility, may be exchanged among vehicles 104 or may be used by a user 216 in different locations or with different vehicles 104. Additionally or alternatively, the server may be associated with profile data 252 as provided herein. It is anticipated that the profile data 252 may be accessed across the communication network 224 by one or more components of the system 200. Similar to the stored data 232, the profile data 252, being stored in a cloud or in a distant facility, may be exchanged among vehicles 104 or may be used by a user 216 in different locations or with different vehicles 104.

The vehicle control system 204 may also communicate with one or more sensors 236, 242, which are either associated with the vehicle 104 or communicate with the vehicle 104. Vehicle sensors 242 may include one or more sensors for providing information to the vehicle control system 204 that determine or provide information about the environment 100 in which the vehicle 104 is operating. Embodiments of these sensors may be as described in conjunction with FIGS. 6A-7B. Non-vehicle sensor 236 can be any type of sensor that is not currently associated with the vehicle 104. For example, non-vehicle sensor 236 can be sensors in a traffic system operated by a third party that provides data to the vehicle control system 204. Further, the non-vehicle sensor(s) 236 can be other types of sensors which provide information about the distant environment 116 or other information about the vehicle 104 or the environment 100. These non-vehicle sensors 236 may be operated by third parties but provide information to the vehicle control system 204. Examples of information provided by the sensors 236 and that may be used by the vehicle control system 204 may include weather tracking data, traffic data, user health tracking data, vehicle maintenance data, or other types of data, which may provide environmental or other data to the vehicle control system 204. The vehicle control system 204 may also perform signal processing of signals received from one or more sensors 236, 242. Such signal processing may include estimation of a measured parameter from a single sensor, such as multiple measurements of a range state parameter from the vehicle 104 to an obstacle, and/or the estimation, blending, or fusion of a measured state parameter from multiple sensors such as multiple radar sensors or a combination of a ladar/lidar range sensor and a radar sensor. Signal processing of such sensor signal measurements may comprise stochastic signal processing, adaptive signal processing, and/or other signal processing techniques known to those skilled in the art.

The various sensors 236, 242 may include one or more sensor memory 244. Embodiments of the sensor memory 244 may be configured to store data collected by the sensors 236, 242. For example, a temperature sensor may collect temperature data associated with a vehicle 104, user 216, and/or environment, over time. The temperature data may be collected incrementally, in response to a condition, or at specific time periods. In this example, as the temperature data is collected, it may be stored in the sensor memory 244. In some cases, the data may be stored along with an identification of the sensor and a collection time associated with the data. Among other things, this stored data may include multiple data points and may be used to track changes in sensor measurements over time. As can be appreciated, the sensor memory 244 can represent any type of database or other storage system.

The diagnostic communications module 256 may be configured to receive and transmit diagnostic signals and information associated with the vehicle 104. Examples of diagnostics signals and information may include, but is in no way limited to, vehicle system warnings, sensor data, vehicle component status, service information, component health, maintenance alerts, recall notifications, predictive analysis, and the like. Embodiments of the diagnostic communications module 256 may handle warning/error signals in a predetermined manner. The signals, for instance, can be presented to one or more of a third party, occupant, vehicle control system 204, and a service provider (e.g., manufacturer, repair facility, etc.).

Optionally, the diagnostic communications module 256 may be utilized by a third party (i.e., a party other than the user 216, etc.) in communicating vehicle diagnostic information. For instance, a manufacturer may send a signal to a vehicle 104 to determine a status associated with one or more components associated with the vehicle 104. In response to receiving the signal, the diagnostic communications module 256 may communicate with the vehicle control system 204 to initiate a diagnostic status check. Once the diagnostic status check is performed, the information may be sent via the diagnostic communications module 256 to the manufacturer. This example may be especially useful in determining whether a component recall should be issued based on the status check responses returned from a certain number of vehicles.

Wired/wireless transceiver/communications ports 260 may be included. The wired/wireless transceiver/communications ports 260 may be included to support communications over wired networks or links, for example with other communication devices, server devices, and/or peripheral devices. Examples of wired/wireless transceiver/communications ports 260 include Ethernet ports, Universal Serial Bus (USB) ports, Institute of Electrical and Electronics Engineers (IEEE) 1594, or other interface ports.

Figure 3:
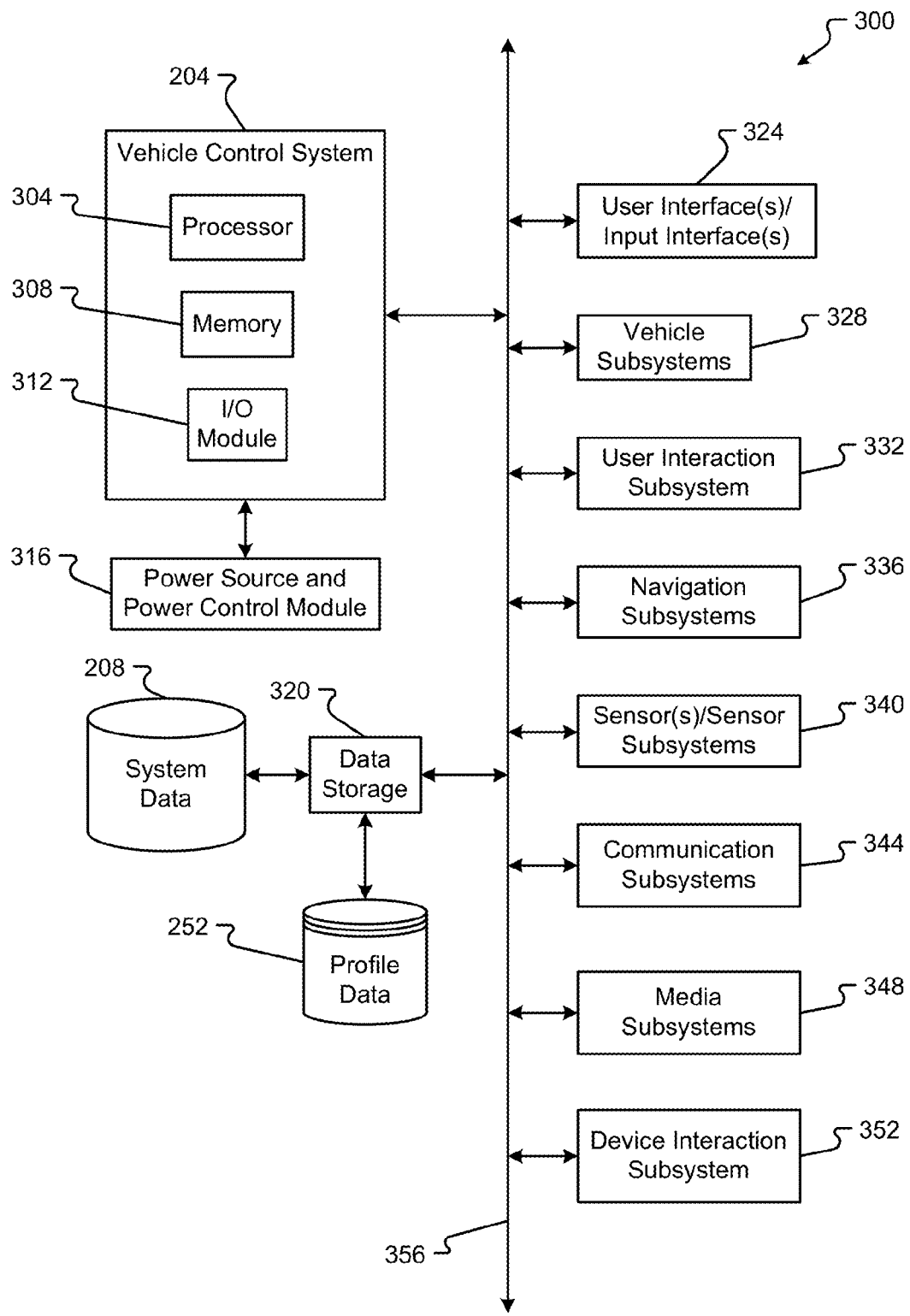
FIG. 3 is a block diagram of an embodiment of a vehicle control system environment.

An embodiment of a vehicle control environment 300 including a vehicle control system 204 may be as shown in FIG. 3. Beyond the vehicle control system 204, the vehicle control environment 300 can include one or more of, but is not limited to, a power source and/or power control module 316, a data storage module 320, user interface(s)/input interface(s) 324, vehicle subsystems 328, user interaction subsystems 332, Global Positioning System (GPS)/Navigation subsystems 336, sensor(s) and/or sensor subsystems 340, communication subsystems 344, media subsystems 348, and/or device interaction subsystems 352. The subsystems, modules, components, etc. 316-352 may include hardware, software, firmware, computer readable media, displays, input devices, output devices, etc. or combinations thereof. The system, subsystems, modules, components, etc. 204, 316-352 may communicate over a network or bus 356. This communication bus 356 may be bidirectional and perform data communications using any known or future-developed standard or protocol. An example of the communication bus 356 may be as described in conjunction with FIG. 4.

The vehicle control system 204 can include a processor 304, memory 308, and/or an input/output (I/O) module 312. Thus, the vehicle control system 204 may be a computer system, which can comprise hardware elements that may be electrically coupled. The hardware elements may include one or more central processing units (CPUs) 304; one or more components of the I/O module 312 including input devices (e.g., a mouse, a keyboard, etc.) and/or one or more output devices (e.g., a display device, a printer, etc.).

The processor 304 may comprise a general purpose programmable processor or controller for executing application programming or instructions. The processor 304 may, optionally, include multiple processor cores, and/or implement multiple virtual processors. Additionally or alternatively, the processor 304 may include multiple physical processors. As a particular example, the processor 304 may comprise a specially configured application specific integrated circuit (ASIC) or other integrated circuit, a digital signal processor, a controller, a hardwired electronic or logic circuit, a programmable logic device or gate array, a special purpose computer, or the like. The processor 304 generally functions to run programming code or instructions implementing various functions of the vehicle control system 204.

The input/output module 312 and associated ports may be included to support communications over wired or wireless networks or links, for example with other communication devices, server devices, and/or peripheral devices. Examples of an input/output module 312 include an Ethernet port, a Universal Serial Bus (USB) port, Institute of Electrical and Electronics Engineers (IEEE) 1594, or other interface.

The vehicle control system 204 may also include one or more storage devices 308. By way of example, storage devices 308 may be disk drives, optical storage devices, solid-state storage devices such as a random access memory ("RAM") and/or a read-only memory ("ROM"), which can be programmable, flash-updateable and/or the like. The vehicle control system 204 may additionally include a computer-readable storage media reader; a communications system (e.g., a modem, a network card (wireless or wired), an infra-red communication device, etc.); and working memory 308, which may include RAM and ROM devices as described above. The vehicle control system 204 may also include a processing acceleration unit, which can include a digital signal processor (DSP), a special-purpose processor, and/or the like.

The computer-readable storage media reader can further be connected to a computer-readable storage medium, together (and, optionally, in combination with storage device(s)) comprehensively representing remote, local, fixed, and/or removable storage devices plus storage media for temporarily and/or more permanently containing computer-readable information. The communications system may permit data to be exchanged with an external or internal network and/or any other computer or device described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices, and/or other machine readable mediums for storing information.

Figure 10:
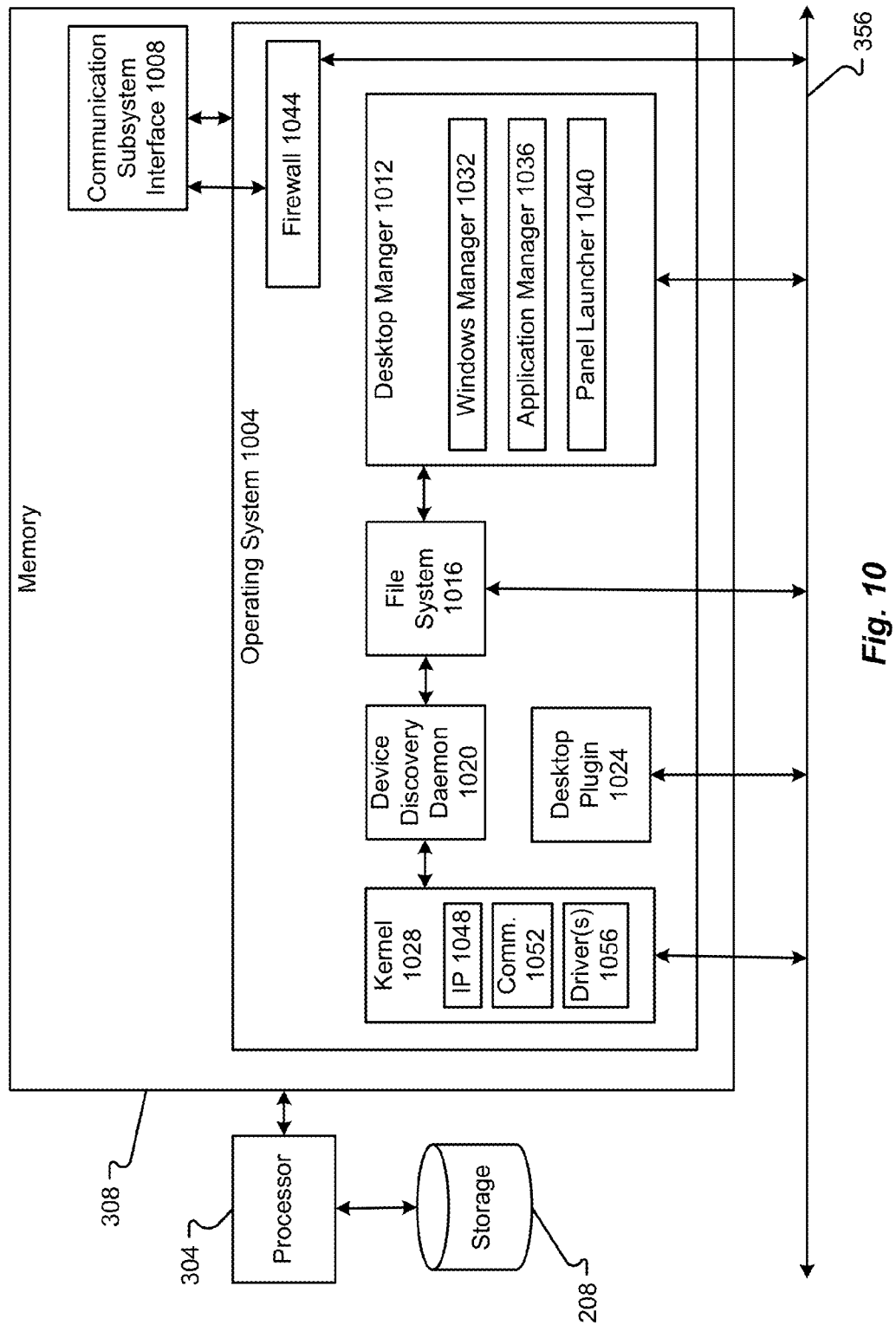
FIG. 10 is a block diagram of an embodiment of a software architecture for the vehicle control system.

The vehicle control system 204 may also comprise software elements including an operating system and/or other code, as described in conjunction with FIG. 10. It should be appreciated that alternates to the vehicle control system 204 may have numerous variations from that described herein.

For example, customized hardware might also be used and/or particular elements might be implemented in hardware, software (including portable software, such as applets), or both. Further, connection to other computing devices such as network input/output devices may be employed.

The power source and/or power control module 316 can include any type of power source, including, but not limited to, batteries, alternating current sources (from connections to a building power system or power line), solar cell arrays, etc. One or more components or modules may also be included to control the power source or change the characteristics of the provided power signal. Such modules can include one or more of, but is not limited to, power regulators, power filters, alternating current (AC) to direct current (DC) converters, DC to AC converters, receptacles, wiring, other converters, etc. The power source and/or power control module 316 functions to provide the vehicle control system 204 and any other system with power.

The data storage 320 can include any module for storing, retrieving, and/or managing data in one or more data stores and/or databases. The database or data stores may reside on a storage medium local to (and/or resident in) the vehicle control system 204 or in the vehicle 104. Alternatively, some of the data storage capability may be remote from the vehicle control system 204 or automobile, and in communication (e.g., via a network) to the vehicle control system 204. The database or data stores may reside in a storage-area network ("SAN") familiar to those skilled in the art. Similarly, any necessary files for performing the functions attributed to the vehicle control system 204 may be stored locally on the respective vehicle control system 204 and/or remotely, as appropriate. The databases or data stores may be a relational database, and the data storage module 320 may be adapted to store, update, and retrieve data in response to specifically-formatted commands. The data storage module 320 may also perform data management functions for any flat file, object oriented, or other type of database or data store.

A first data store that may be part of the vehicle control environment 300 is a profile data store 252 for storing data about user profiles and data associated with the users. A system data store 208 can include data used by the vehicle control system 204 and/or one or more of the components 324-352 to facilitate the functionality described herein. The data stores 208 and/or 252 may be as described in conjunction with FIGS. 1 and/or 12A-12D.

The user interface/input interfaces 324 may be as described herein for providing information or data and/or for receiving input or data from a user. Vehicle systems 328 can include any of the mechanical, electrical, electromechanical, computer, or other systems associated with the function of the vehicle 100. For example, vehicle systems 328 can include one or more of, but is not limited to, the steering system, the braking system, the engine and engine control systems, the electrical system, the suspension, the drive train, the cruise control system, the radio, the heating, ventilation, air conditioning (HVAC) system, the windows and/or doors, etc. These systems are well known in the art and will not be described further.

Examples of the other systems and subsystems 324-352 may be as described further herein. For example, the user interface(s)/input interface(s) 324 may be as described in FIGS. 2 and 8B; the vehicle subsystems 328 may be as described in FIG. 6a et. seq.; the user interaction subsystem 332 may be as described in conjunction with the user/device interaction subsystem 817 of FIG. 8B; the Navigation subsystem 336 may be as described in FIGS. 6A and 8C; the sensor(s)/sensor subsystem 340 may be as described in FIGS. 7A and 7B; the communication subsystem 344 may be as described in FIGS. 2, 4, 5B, 5C, and 9; the media subsystem 348 may be as described in FIG. 8A; and, the device interaction subsystem 352 may be as described in FIG. 2 and in conjunction with the user/device interaction subsystem 817 of FIG. 8B.

Figure 4:
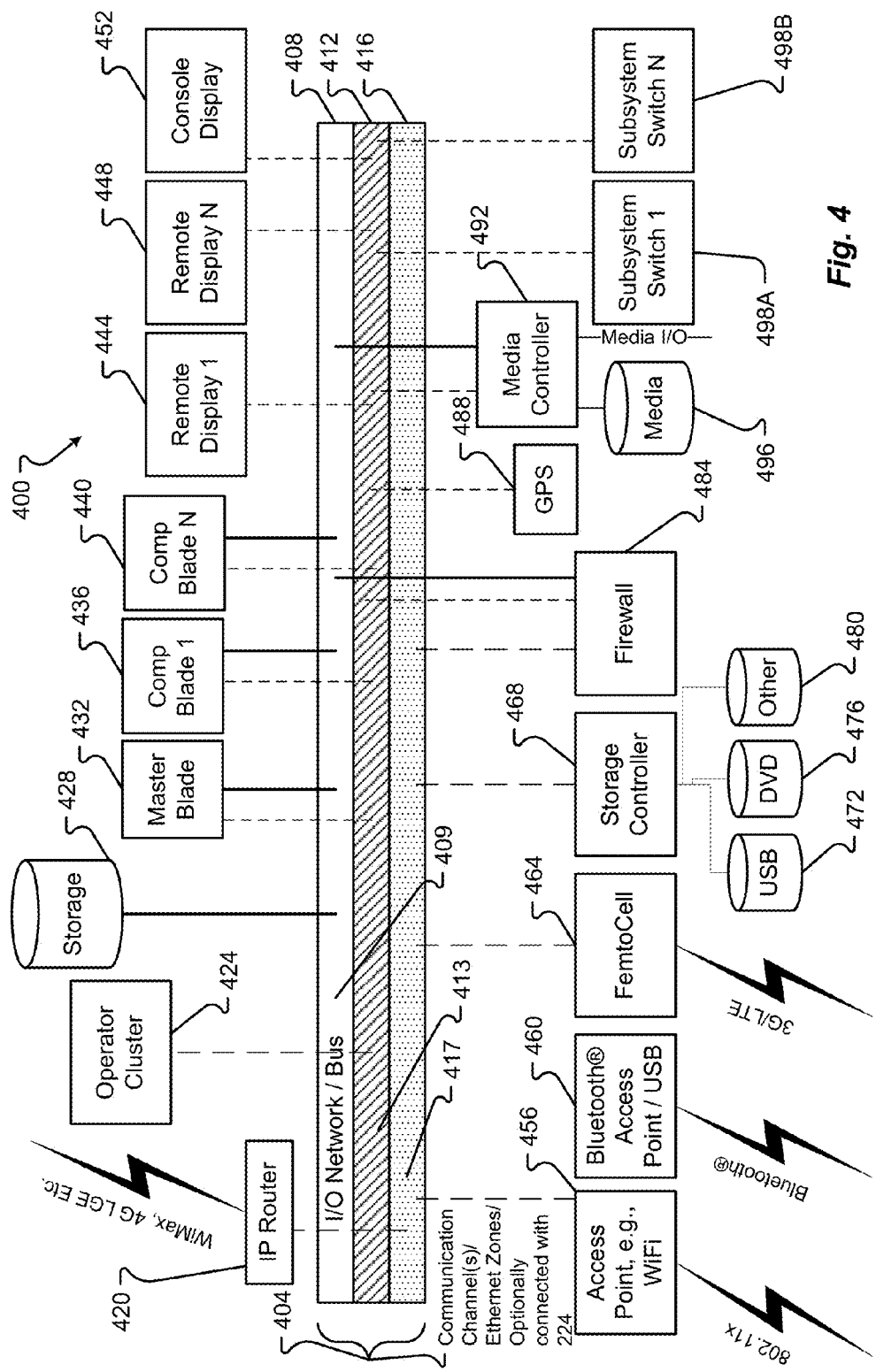
FIG. 4 is a block diagram of an embodiment of a vehicle communications subsystem.

FIG. 4 illustrates an optional communications channel architecture 400 and associated communications components. FIG. 4 illustrates some of the optional components that can be interconnected via the communication channels/zones 404. Communication channels/zones 404 can carry information on one or more of a wired and/or wireless communications link with, in the illustrated example, there being three communications channels/zones, 408, 412, and 416.

This optional environment 400 can also include an IP router 420, an operator cluster 424, one or more storage devices 428, one or more blades, such as master blade 432, and computational blades 436 and 440. Additionally, the communications channels/zones 404 can interconnect one or more displays, such as, remote display 1 444, remote display N 448, and console display 452. The communications channels/zones 404 also interconnect an access point 456, a Bluetooth® access point/USB hub 460, a Femtocell 464, a storage controller 468, that is connected to one or more of USB devices 472, DVDs 476, or other storage devices 480. To assist with managing communications within the communication channel, the environment 400 optionally includes a firewall 484 which will be discussed hereinafter in greater detail. Other components that could also share the communications channel/zones 404 include GPS 488, media controller 492, which is connected to one or more media sources 496, and one or more subsystems, such as subsystem switches 498.

Optionally, the communications channels/zones 404 can be viewed as an I/O network or bus where the communications channels are carried on the same physical media. Optionally, the communication channels 404 can be split amongst one or more physical media and/or combined with one or more wireless communications protocols. Optionally, the communications channels 404 can be based on wireless protocols with no physical media interconnecting the various elements described herein.

The environment 400 shown in FIG. 4 can include a collection of blade processors that are housed in a "crate." The crate can have a PC-style backplane connector 408 and a backplane Ethernet 408 that allows the various blades to communicate with one another using, for example, an Ethernet.

Various other functional elements illustrated in FIG. 4 can be integrated into this crate architecture with, as discussed hereinafter, various zones utilized for security. Optionally, as illustrated in FIG. 4, the backplane 404/408 can have two separate Ethernet zones that may or may not be on the same communications channel. Optionally, the zones exist on a single communications channel on the I/O network/bus 408. Optionally, the zones are actually on different communications channels, e.g., 412, 416; however, the implementation is not restricted to any particular type of configuration. Rather, as illustrated in FIG. 4, there can be a red zone 417 and a green zone 413, and the I/O backplane on the network/bus 408 that enables standard I/O operations. This backplane or I/O network/bus 408 also optionally can provide power distribution to the various modules and blades illustrated in FIG. 4. The red and green Ethernet zones, 417 and 413 respectively, can be implemented as Ethernet switches, with one on each side of the firewall 484. Two Ethernets (untrusted and trusted) are not connected in accordance with an optional embodiment.

Optionally, the connector geometry for the firewall can be different for the Ethernet zones than for the blades that are a part of the system.

The red zone 417 only needs to go from the modular connector to the input side of the backplane connector of the firewall 484. While FIG. 4 indicates that there are five external red zone connectors to the firewall 484, provisions can be made for any number of ports with the connections being made at the access point 456, the Bluetooth® access point (combo controller) 460, Femtocell 464, storage controller 468, and/or firewall 484. Optionally, the external port connections can be made through a manufacturer configurable modular connector panel, and one or more of the red zone Ethernet ports could be available through a customer supplied crate which allows, for example, wired Ethernet connections from a bring-your-own-device (BYOD) to the firewall 484.

The green zone 413 goes from the output side of the firewall 484 and generally defines the trusted Ethernet. The Ethernet on the backplane 408 essentially implements an Ethernet switch for the entire system, defining the Ethernet backbone of the vehicle 104. All other modules, e.g., blades, etc., can connect to a standard backplane bus and the trusted Ethernet. Some number of switch ports can be reserved to connect to an output modular connector panel to distribute the Ethernet throughout the vehicle 104, e.g., connecting such elements as the console display 452, remote displays 444, 448, GPS 488, etc. Optionally, only trusted components, either provided or approved by the manufacturer after testing, can be attached to the green zone 413, which is by definition in the trusted Ethernet environment.

Optionally, the environment 400, shown in FIG. 4, utilizes IPv6 over Ethernet connections wherever possible. Using, for example, the Broadcom single-twisted pair Ethernet technology, wiring harnesses are simplified and data transmission speeds are maximized. However, while the Broadcom single-twisted pair Ethernet technology can be used, in general, systems and methods can work comparably well with any type of well-known Ethernet technology or other comparable communications technology.

As illustrated in FIG. 4 the I/O network/bus 408 is a split-bus concept that contains three independent bus structures:

The red zone 417—the untrusted Ethernet environment. This zone 417 may be used to connect network devices and customer provided devices to the vehicle information system with these devices being on the untrusted side of the firewall 484.

The green zone 413—the trusted Ethernet environment, this zone 413 can be used to connect manufacturer certified devices such as GPS units, remote displays, subsystem switches, and the like, to the vehicle network 404. Manufacturer certified devices can be implemented by vendors that allow the vehicle software system to validate whether or not a device is certified to operate with the vehicle 100. Optionally, only certified devices are allowed to connect to the trusted side of the network.

The I/O bus 409—the I/O bus may be used to provide power and data transmission to bus-based devices such as the vehicle solid state drive, the media controller blade 492, the computational blades 436, 440, and the like.

As an example, the split-bus structure can have the following minimum configuration:

Two slots for the red zone Ethernet;

One slot for built-in LTE/WiMax access 420 from the car to other network resources such as the cloud/Internet;

One slot for user devices or bring-your-own device access, this slot can implement, for example, WiFi, Bluetooth®, and/or USB connectivity 456, which can be provided in, for example, the customer crate;

One slot for combined red zone and green zone Ethernet, this slot can be reserved for the firewall controller;

Two slots for computational blades. Here the two computation blades are illustratively as shown the optional master blade and the multimedia blade or controller 492 which can be provided as standard equipment; and The expansion controller that allows the I/O bus to be extended and provides additional Ethernet switch ports for one or more of the red or green zones, which may require that the basic green zone Ethernet switch implementation will support additional ports beyond the initial three that are needed for the basic exemplary system.

It should be possible to build 8 or 16 or more Ethernet switches that allow for the expansion with existing component(s) in a straight-forward manner.

The red zone 417 can be implemented as an 8-port Ethernet switch that has three actual bus ports within the crate with the remaining five ports being available on the customer crate. The crate implements red zone slots for the firewall controller 484, the combo controller which includes WiFi, Bluetooth®, USB hub (456, 460) and the IP router 420.

The firewall controller 484 can have a dedicated slot that bridges the red zone 417, green zone 413, and uses the I/O bus for power connections. In accordance with an optional low cost implementation, the firewall 484 can be implemented by a dummy module that simply bridges the red zone 417 and the green zone 413 without necessarily providing any firewall functionality. The combo controller 460 that includes the WiFi, Bluetooth®, and USB hub can be provided for consumer device connections. This controller can also implement the IPv6 (un-routable) protocol to insure that all information is packetized for transmission via IP over the Ethernet in the I/O network/bus 408.

The combo controller 460 with the USB hub can have ports in the customer crate. The combo controller 460 can implement USB discovery functions and packetizes the information for transmission via IP over Ethernet. The combo controller 460 can also facilitate installation of the correct USB driver for the discovered device, such as a BYOD from the user. The combo controller 460 and USB hub can then map the USB address to a "local" IPv6 address for interaction with one or more of the computational blades which is generally going to be the media controller 492.

The IP router 420 can implement Internet access through a manufacturer provided service. This service can allow, for example, a manufacturer to offer value-added services to be integrated into the vehicle information systems. The existence of the manufacturer provided Internet access can also allow the "e-Call" function and other vehicle data recorder functions to be implemented. IP router 420 also allows, for example, WiMax, 4G LTE, and other connections to the Internet through a service provider that can be, for example, contracted by the manufacturer. Internally, the IP router 420 can allow cellular handset connections to the Internet through a Femtocell 464 that is part of the IP router implementation. The IP router 420, with the Femtocell 464, can also allow a cone of silence functionality to be implemented. The IP router 420 can be an optional component for a vehicle provided by, for example, the manufacturer, a dealer, or installed by a user. In the absence of the IP router 420, it is possible to connect a consumer handheld device to the I/O network/bus 408 using, for example, either WiFi or Bluetooth® 456, 460. While functionality may be somewhat reduced when using a handheld device instead of a built-in Ethernet connection, systems and methods of this invention can also work utilizing this consumer handheld device which then connects to the Internet via, for example, WiMax, 4G, 4G LTE, or the like.

Figure 5B:
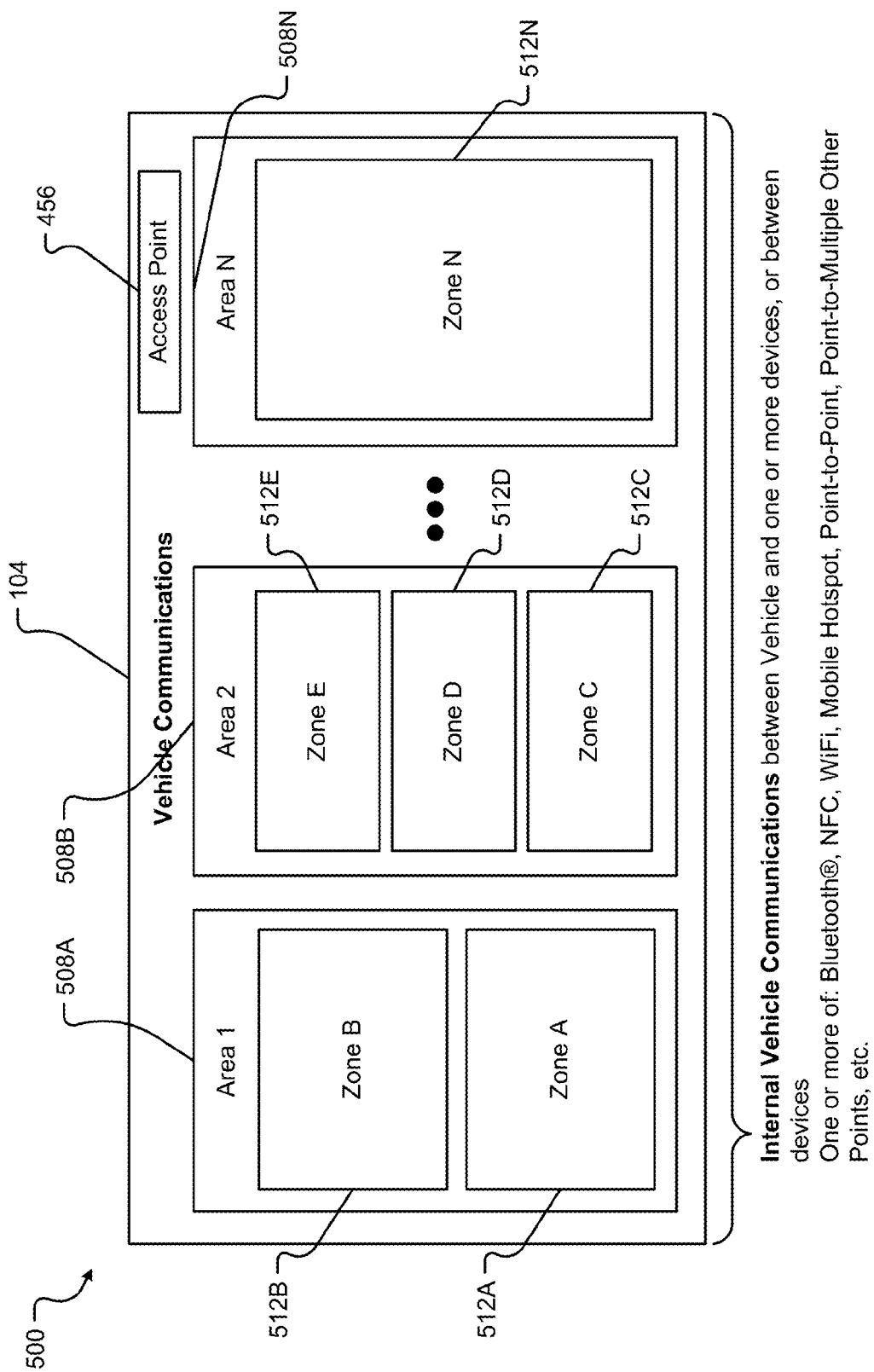
FIG. 5B is a second block diagram of an embodiment of a vehicle interior environment separated into areas and/or zones.
Figure 5C:
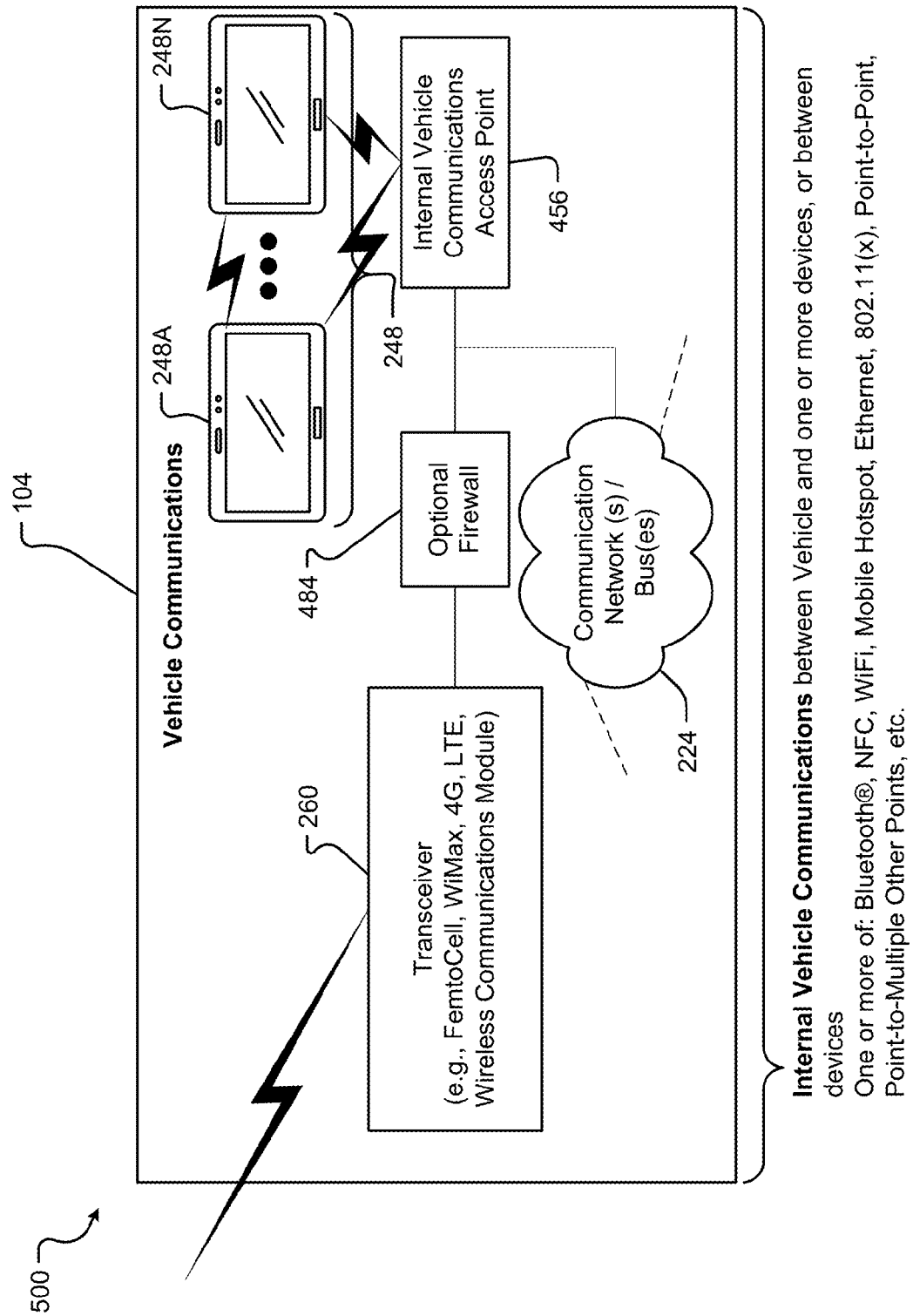
FIG. 5C is a third block diagram of an embodiment of a vehicle interior environment separated into areas and/or zones.

FIGS. 5A-5C show configurations of a vehicle 104. In general, a vehicle 104 may provide functionality based at least partially on one or more areas, zones, and distances, associated with the vehicle 104. Non-limiting examples of this functionality are provided herein below.

An arrangement or configuration for sensors within a vehicle 104 is as shown in FIG. 5A. The sensor arrangement 500 can include one or more areas 508 within the vehicle. An area can be a larger part of the environment inside or outside of the vehicle 104. Thus, area one 508A may include the area within the trunk space or engine space of the vehicle 104 and/or the front passenger compartment. Area two 508B may include a portion of the interior space 108 (e.g., a passenger compartment, etc.) of the vehicle 104. The area N, 508N, may include the trunk space or rear compartment area, when included within the vehicle 104. The interior space 108 may also be divided into other areas. Thus, one area may be associated with the front passenger's and driver's seats, a second area may be associated with the middle passengers' seats, and a third area may be associated with a rear passenger's seat. Each area 508 may include one or more sensors that are positioned or operate to provide environmental information about that area 508.

Each area 508 may be further separated into one or more zones 512 within the area 508. For example, area 1 508A may be separated into zone A 512A, and zone B 512B. Each zone 512 may be associated with a particular portion of the interior occupied by a passenger. For example, zone A 512A may be associated with a driver. Zone B 512B, may be associated with a front passenger. Each zone 512 may include one or more sensors that are positioned or configured to collect information about the environment or ecosystem associated with that zone or person.

A passenger area 508B may include more than two zones as described in conjunction with area 508A. For example, area 508B may include three zones, 512C, 512D, and 512E. These three separate zones 512C, 512D, and 512E may be associated with three passenger seats typically found in the rear passenger area of a vehicle 104. An area 508N and may include a single zone 512N as there may be no separate passenger areas but may include a single trunk area within the vehicle 104. The number of zones 512 is unlimited within the areas as the areas are also unlimited inside the vehicle 104. Further, it should be noted that there may be one or areas 508 or zones 512 that may be located outside the vehicle 104 that may have a specific set of sensors associated therewith.

Optionally, each area/access point 508, 456, 516, 520, and/or zone 512, associated with a vehicle 104, may comprise one or more sensors to determine a presence of a user 216 and/or device 212, 248 in and/or adjacent to each area 508, 456, 516, 520, and/or zone 512. The sensors may include vehicle sensors 242 and/or non-vehicle sensors 236 as described herein. It is anticipated that the sensors may be configured to communicate with a vehicle control system 204 and/or the diagnostic communications module 256. Additionally or alternatively, the sensors may communicate with a device 212, 248. The communication of sensors with the vehicle 104 may initiate and/or terminate the control of device 212, 248 features. For example, a vehicle operator may be located in a second outside area 520 associated with a vehicle 104. As the operator approaches the first outside area 516, associated with the vehicle 104, the vehicle control system 204 may determine to control features associated with one or more device 212, 248 and diagnostic communications module 256.

Optionally, the location of the device 212, 248 relative to the vehicle 104 may determine vehicle functionality and/or features to be provided and/or restricted to a user 216. By way of example, a device 212, 248 associated with a user 216 may be located at a second outside area 520 from the vehicle 104. In this case, and based at least partially on the distance of the device 212, 248 from the vehicle 104 (e.g., provided by detecting the device 212, 248 at or beyond the second outside area 520) the vehicle 104 may lock one or more features (e.g., ignition access, vehicle access, communications ability, etc.) associated with the vehicle 104. Optionally, the vehicle 104 may provide an alert based on the distance of the device 212, 248 from the vehicle 104. Continuing the example above, once the device 212, 248 reaches the first outside area 516 of the vehicle 104 at least one of the vehicle features may be unlocked. For instance, by reaching the first outside area 516, the vehicle 104 may unlock a door of the vehicle 104. In some cases, when the device is detected to be inside the vehicle 104, the various sensors 236, 242 may determine that the user 216 is in an area 508 and/or zone 512. As is further described herein, features of the vehicle 104, device 212, 248, and/or other components may be controlled based on rules stored in a memory.

FIG. 5B illustrates optional internal vehicle communications between one or more of the vehicle and one or more devices or between devices. Various communications can occur utilizing one or more Bluetooth®, NFC, WiFi, mobile hot spot, point-to-point communications, point-to-multipoint other point communications, an ad hoc network, or in general any known communications protocol over any known communications media or media-types.

Optionally, various types of internal vehicle communications can be facilitated using an access point 456 that utilizes one or more of Bluetooth®, NFC, WiFi, wireless Ethernet, mobile hot spot technology, or the like. Upon being connected with, and optionally authenticated to the access point 456, the connected device is able to communicate with one or more of the vehicle and one or more other devices that are connected to the access point 456. The type of connection to the access point 456 can be based on, for example, the zone 512, in which the device is located.

The user may identify their zone 512 in conjunction with an authentication procedure to the access point 456. For example, a driver in zone A 512A, upon authenticating to the access point 456, can cause the access point 456 to send a query to the device asking the device user in which zone 512 they are located. As discussed hereinafter, the zone 512 the user device is located in may have an impact on the type of communications, available bandwidth, the types of other devices or vehicle systems or subsystems the device could communicate with, and the like. As a brief introduction, internal communications with zone A 512A may be given preferential treatment over those communications originating from area 2 508B, which could have in itself, preferential treatment over communications originating within area N 508N.

Moreover, the device in zone A 512A can include profile information that governs the other devices that are allowed to connect to the access point 456 and what those devices have access to, how they can communicate, how much bandwidth they are allocated, and the like. While, optionally, the device associated with zone A 512A will be considered the "master" controller of the profile that governs the internal vehicle communications, it should be appreciated that this was arbitrarily chosen since it is assumed that there will always be a driver in a car that is present in zone A 512A. However, it should be appreciated the driver in zone A 512A, for example, may not have a communications device in which case a device associated with one of the other areas or zones, such as zone B 512B, area 2 508B, or area N 508N could also be associated with or control this master profile.

Optionally, various devices located within the various zones 512 can connect using, for example, ports provided by access point 456 or Bluetooth® access point/USB hub 460 as illustrated in FIG. 4. Similarly, the device(s) could connect utilizing the Femtocell 464 and optionally be directly connected via, for example, a standard Ethernet port.

As discussed, each one of the areas, area 1 508A, area 2 508B, and area N 508N, can each have associated therewith a profile that governs, for example, how many and what types of devices can connect from that area 508, bandwidth allocated to that area 508, the types of media or content available to device(s) within that area 508, the interconnection of devices within that area 508 or between areas 508, or, in general, can control any aspect of communication of an associated device with any one or more other associated devices/vehicle systems within the vehicle 104.

Optionally, area 2 508B devices can be provided with full access to multimedia and infotainment available within the vehicle 104, however, devices in area 2 508B may be restricted from any access to vehicle functions. Only devices in area 1 508A may be able to access vehicle control functions such as when "parents" are located in area 1 508A and the children are located in area 2 508B. Optionally, devices found in zone E 512E of area 2 508B may be able to access limited vehicle control functionality such as climate control within area 2. Similarly, devices in area N 508N may be able to control climate features within zone N 512N.

As will be appreciated, profiles can be established that allow management of communications within each of the areas 508, and further optionally within each of the zones 512. The profile can be granular in nature controlling not only what type of devices can connect within each zone 512, but how those devices can communicate with other devices and/or the vehicle and types of information that can be communicated.

To assist with identifying a location of a device within a zone 512, a number of different techniques can be utilized. One optional technique involves one or more of the vehicle sensors detecting the presence of an individual within one of the zones 512. Upon detection of an individual in a zone 512, communications subsystems 344 and the access point 456 can cooperate to not only associate the device within the zone 512 with the access point 456 but to also determine the location of the device within an area, and optionally within a zone 512. Once the device is established within a zone 512, a profile associated with the vehicle 104 can store information identifying that device and/or a person and optionally associating it with a particular zone 512 as a default. As discussed, there can be a master profile optionally associated with the device in zone A 512A, this master profile can govern communications with the communications subsystems 340 and where communications within vehicle 104 are to occur.

Some optional profiles are illustrated below where the Master Profile governs other device connectivity:
Master Profile:

| Area 1 508A | Area 2 508B | Area N 508N | Other |
| --- | --- | --- | --- |
| All Communications | Allow Access to Infotainment | No Access | Master Profile acts as Firewall and Router |
| All Vehicle Controls | Allow Area 2 Climate Control | | |

Secondary Profile (e.g., device in Zone B 512B, Area 1 508A)

| Area 1 508A | Area 2 508B | Area N 508N | Other |
| --- | --- | --- | --- |
| All Communications | Allow Access to Infotainment | Allow Access to Infotainment | Master Profile acts as Firewall and Router |
| All Vehicle Controls | Allow Area 2 Climate Control | Allow Area 2 Climate Control | |

Secondary Profile, Option 2

| Area 1 508A | Area 2 508B | Area N 508N | Other |
| --- | --- | --- | --- |
| All Communications | Allow Access to Infotainment, Internet | Allow Access to Infotainment | |
| All Vehicle Controls Except Driver-centric Controls | Allow Area 2 Climate Control | Allow Area 2 Climate Control | |

Some optional profiles are illustrated below where the Area/Zone governs device connectivity:
Area 2 508B Profile:

| Area 1 508A | Area 2 508B | Area N 508N | Other |
| --- | --- | --- | --- |
| No Communications with Area 1 Devices | Allow Access to Infotainment, Allow Access to Other Area 2 or Zone N Devices, Internet | | |
| No Vehicle Controls | Allow Area 2 Climate Control | | |

Area N 508N Profile:

| Area 1 508A | Area 2 508B | Area N 508N | Other |
| --- | --- | --- | --- |
| Communications with Area 1, Zone B Device | | Allow Access to Infotainment, Allow Access to Other Area N or Zone N Devices | |
| No Vehicle Controls | | Allow Area N Climate Control | |

Area 2 508B Profile:

| Area 1 508A | Area 2 508B | Area N 508N | Other |
| --- | --- | --- | --- |
| Media Sharing with Area 1, Zone B and Vehicle | Allow Access to Infotainment, Allow Access to Other Area 2 or Zone N Devices, Internet and Femtocell | | |
| No Vehicle Controls | | | |

Optionally, a user's device, such as a SmartPhone, can store in, for example a profile, with which zone 512 the user's device is associated. Then, assuming the user sits in the same zone 512 and area 508 as previously, the user's device can re-establish the same communications protocols with the access point 456 as were previously established.

In addition or in the alternative, the areas 508 and zones 512 can have associated therewith restrictions as to which one or more other user's devices with which users' devices can connect. For example, a first user's device can connect with any other user device in area 2 508B or area N 508N, however is restricted from connecting with a user device in area 1 508A, zone A 512A. However, the first user device may be able to communicate with another user's device that is located in area 1 508A, zone B 512B. These communications can include any type of standard communications such as sharing content, exchanging messages, forwarding or sharing multimedia or infotainment, or in general can include any communications that would ordinarily be available between two devices and/or the vehicle and vehicle systems. As discussed, there may be restrictions on the type of communications that can be sent to the device in area 1 508A, zone A 512A. For example, the user's device in area 1 508A, zone A 512A may be restricted from receiving one or more of text messages, multimedia, infotainment, or in general anything that can be envisioned as a potential distraction to the driver. Moreover, it should be appreciated that the communications between the various devices and the various zones 512 need not necessarily occur with the assistance of access point 456, but the communications could also occur directly between the device(s).

FIG. 5C outlines optional internal vehicle communications between one or more of the vehicle and one or more devices. More specifically, FIG. 5C illustrates an example of vehicle communications where the vehicle 104 is equipped with the necessary transceivers to provide a mobile hot spot functionality to any user device(s) therein, such as user devices 248A and 248N.

Optionally, and as discussed above, one or more user devices can connect to the access point 456. This access point 456 is equipped to handle communications routing to not only the communication network/buses 224 for intra-vehicle communications, but optionally can also communicate with, for example, the Internet or the cloud, in cooperation with transceiver 260. Optionally included is a firewall 484 that has the capability of not only blocking certain types of content, such as a malicious content, but can also operate to exclude certain type of communications from emanating from the vehicle 104 and transceiver 260. As will be appreciated, various profiles could be established in the firewall 484 that controls not only the type of communications that can be received at the vehicle 104, but the type of communications that can be sent from the vehicle 104.

The transceiver 260 can be any type of well-known wireless transceiver that communicates using a known communications protocol such as WiMax, 4G, 4G LTE, 3G, or the like. The user devices can communicate via, for example, WiFi link 248 with the access point 456, with the transceiver 260 providing Internet connectivity to the various user devices. As will be appreciated, there may need to be an account associated with transceiver 260 with a wireless carrier to provide data and/or voice connectivity to enable the user devices to communicate with the Internet. Typically, the account is established on a month-to-month basis with an associated fee but could also be performed based on the amount of data to be transmitted, received, or in any other manner.

Moreover, one or more of the user's devices and access point 456 can maintain profile information that governs how the user's devices are able to communicate with other devices, and optionally the Internet. Optionally, a profile can exist that only allows the user's devices to communicate with other user's devices and/or the vehicle, multimedia and/or the vehicle infotainment system, and may not be allowed access to the Internet via transceiver 260. The profile can stipulate that the user's device could connect to the Internet via transceiver 260 for a specified period of time and/or up to a certain amount of data usage. The user's device can have full access to the Internet via transceiver 260 with no limit on time or data usage which would reduce the data usage of the user's device since it is connected via WiFi to the access point 456, but however, would increase the data usage by transceiver 260, and therefore, shift the billing for that data usage to the transceiver 260 instead of the user's device. Still further, and as previously discussed, the various profiles may stipulate which user's device has priority for use of the bandwidth provided by the transceiver 260. For example, a user's device located area 1 508A, zone A 512A may be given preferential routing treatment of data above that of a user's device in zone N 512N. In this manner, for example, a driver would be given priority for Internet access above that of the passengers. This could become important, for example, when the driver is trying to obtain traffic or direction information or, for example, when the vehicle is performing a download to update various software features.

As will be appreciated, the optional firewall 484 can cooperate with the access point 456 and the various profiles that area 508 associated with the various devices within the vehicle 104 and can fully implement communications restrictions, control bandwidth limits, Internet accessibility, malicious software blocking, and the like. Moreover, the optional firewall 484 can be accessed by an administrator with one or more of these configuration settings edited through an administrator's control panel. For example, in a scenario where parents are always in area 1 508A, it may be appropriate to give all of the user's devices in area 1 508A full access to the Internet utilizing transceiver 260, however, while restricting access and/or bandwidth to any other user devices within the vehicle 104. As the user's device and profile would be known by the firewall 484, upon the user's device being associated with the access point 456, the firewall 484 and transceiver 260 can be configured to allow communications in accordance with the stored profile.

Figure 6A:
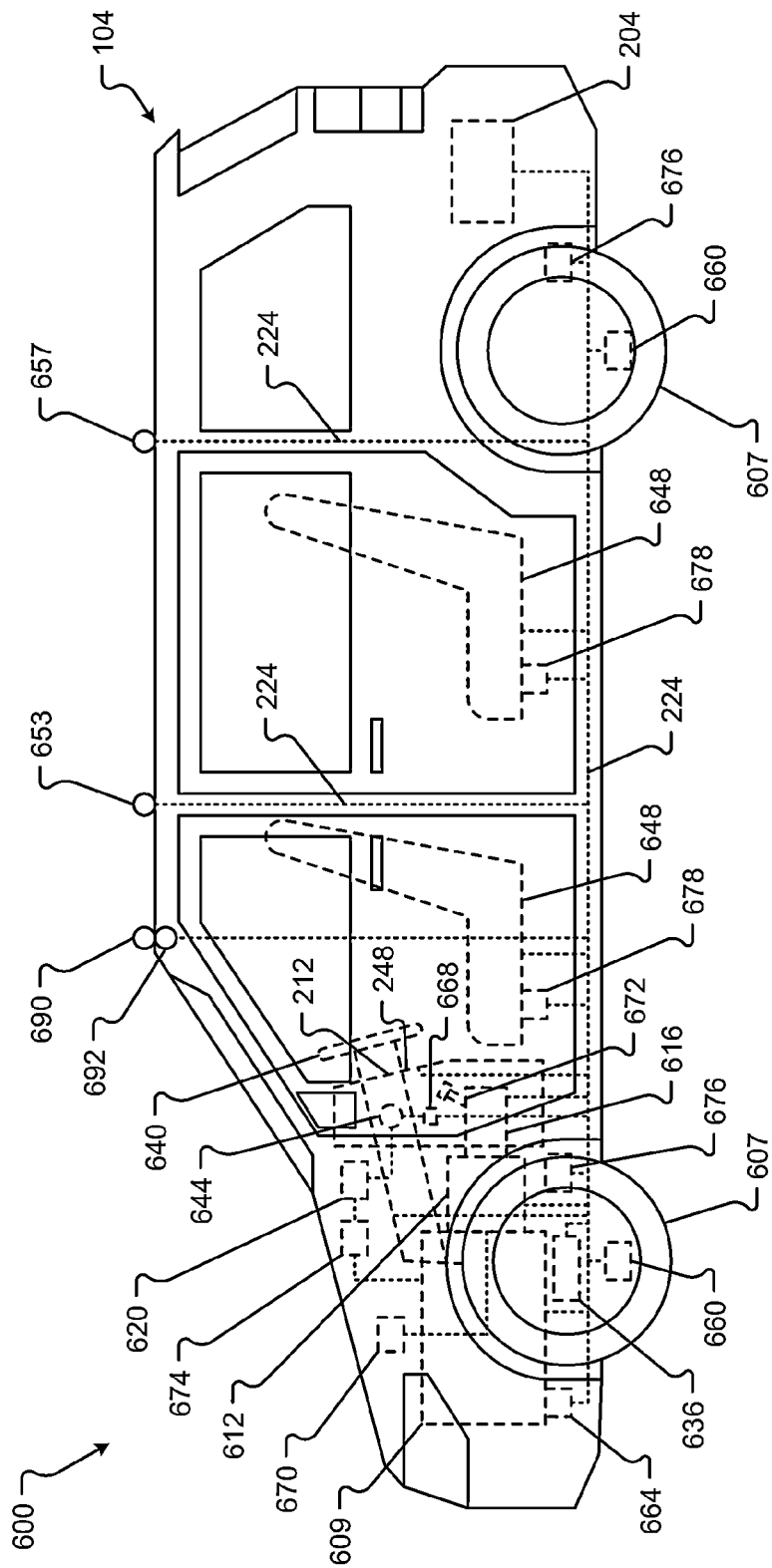
FIG. 6A depicts an embodiment of a sensor configuration for a vehicle.

A set of sensors or vehicle components 600 associated with the vehicle 104 may be as shown in FIG. 6A. The vehicle 104 can include, among many other components common to vehicles, wheels 607, a power source 609 (such as an engine, motor, or energy storage system (e.g., battery or capacitive energy storage system)), a manual or automatic transmission 612, a manual or automatic transmission gear controller 616, a power controller 620 (such as a throttle), a vehicle control system 204, the display device 212, a braking system 636, a steering wheel 640, a power source activation/deactivation switch 644 (e.g., an ignition), an occupant seating system 648, a wireless signal receiver 653 to receive wireless signals from signal sources such as roadside beacons and other electronic roadside devices, and a satellite positioning system receiver 657 (e.g., a Global Positioning System ("GPS") (US), GLONASS (Russia), Galileo positioning system (EU), Compass navigation system (China), and Regional Navigational Satellite System (India) receiver), driverless systems (e.g., cruise control systems, automatic steering systems, automatic braking systems, etc.).

The vehicle 104 can include a number of sensors in wireless or wired communication with the vehicle control system 204 and/or display device 212, 248 to collect sensed information regarding the vehicle state, configuration, and/or operation. Exemplary sensors may include one or more of, but are not limited to, wheel state sensor 660 to sense one or more of vehicle speed, acceleration, deceleration, wheel rotation, wheel speed (e.g., wheel revolutions-per-minute), wheel slip, and the like, a power source energy output sensor 664 to sense a power output of the power source 609 by measuring one or more of current engine speed (e.g., revolutions-per-minute), energy input and/or output (e.g., voltage, current, fuel consumption, and torque) (e.g., turbine speed sensor, input speed sensor, crankshaft position sensor, manifold absolute pressure sensor, mass flow sensor, and the like), and the like, a switch state sensor 668 to determine a current activation or deactivation state of the power source activation/deactivation switch 644, a transmission setting sensor 670 to determine a current setting of the transmission (e.g., gear selection or setting), a gear controller sensor 672 to determine a current setting of the gear controller 616, a power controller sensor 674 to determine a current setting of the power controller 620, a brake sensor 676 to determine a current state (braking or non-braking) of the braking system 636, a seating system sensor 678 to determine a seat setting and current weight of seated occupant, if any) in a selected seat of the seating system 648, exterior and interior sound receivers 690 and 692 (e.g., a microphone, sonar, and other type of acoustic-to-electric transducer or sensor) to receive and convert sound waves into an equivalent analog or digital signal. Examples of other sensors (not shown) that may be employed include safety system state sensors to determine a current state of a vehicular safety system (e.g., air bag setting (deployed or undeployed) and/or seat belt setting (engaged or not engaged)), light setting sensor (e.g., current headlight, emergency light, brake light, parking light, fog light, interior or passenger compartment light, and/or tail light state (on or off)), brake control (e.g., pedal) setting sensor, accelerator pedal setting or angle sensor, clutch pedal setting sensor, emergency brake pedal setting sensor, door setting (e.g., open, closed, locked or unlocked) sensor, engine temperature sensor, passenger compartment or cabin temperature sensor, window setting (open or closed) sensor, one or more interior-facing or exterior-facing cameras or other imaging sensors (which commonly convert an optical image into an electronic signal but may include other devices for detection objects such as an electromagnetic radiation emitter/receiver that emits electromagnetic radiation and receives electromagnetic waves reflected by the object) to sense objects, such as other vehicles and pedestrians and optionally determine the distance, trajectory and speed of such objects, in the vicinity or path of the vehicle, odometer reading sensor, trip mileage reading sensor, wind speed sensor, radar transmitter/receiver output, brake wear sensor, steering/torque sensor, oxygen sensor, ambient lighting sensor, vision system sensor, ranging sensor, parking sensor, heating, venting, and air conditioning (HVAC) sensor, water sensor, air-fuel ratio meter, blind spot monitor, hall effect sensor, microphone, radio frequency (RF) sensor, infrared (IR) sensor, vehicle control system sensors, wireless network sensor (e.g., Wi-Fi and/or Bluetooth® sensor), cellular data sensor, and other sensors either future-developed or known to those of skill in the vehicle art.

In the depicted vehicle embodiment, the various sensors can be in communication with the display device 212, 248 and vehicle control system 204 via signal carrier network 224. As noted, the signal carrier network 224 can be a network of signal conductors, a wireless network (e.g., a radio frequency, microwave, or infrared communication system using a communications protocol, such as Wi-Fi), or a combination thereof. The vehicle control system 204 may also provide signal processing of one or more sensors, sensor fusion of similar and/or dissimilar sensors, signal smoothing in the case of erroneous "wild point" signals, and/or sensor fault detection. For example, ranging measurements provided by one or more RF sensors may be combined with ranging measurements from one or more IR sensors to determine one fused estimate of vehicle range to an obstacle target.

The control system 204 may receive and read sensor signals, such as wheel and engine speed signals, as a digital input comprising, for example, a pulse width modulated (PWM) signal. The processor 304 can be configured, for example, to read each of the signals into a port configured as a counter or configured to generate an interrupt on receipt of a pulse, such that the processor 304 can determine, for example, the engine speed in revolutions per minute (RPM) and the speed of the vehicle in miles per hour (MPH) and/or kilometers per hour (KPH). One skilled in the art will recognize that the two signals can be received from existing sensors in a vehicle comprising a tachometer and a speedometer, respectively. Alternatively, the current engine speed and vehicle speed can be received in a communication packet as numeric values from a conventional dashboard subsystem comprising a tachometer and a speedometer. The transmission speed sensor signal can be similarly received as a digital input comprising a signal coupled to a counter or interrupt signal of the processor 304 or received as a value in a communication packet on a network or port interface from an existing subsystem of the vehicle 104. The ignition sensor signal can be configured as a digital input, wherein a HIGH value represents that the ignition is on and a LOW value represents that the ignition is OFF. Three bits of the port interface can be configured as a digital input to receive the gear shift position signal, representing eight possible gear shift positions. Alternatively, the gear shift position signal can be received in a communication packet as a numeric value on the port interface. The throttle position signal can be received as an analog input value, typically in the range 0-5 volts. Alternatively, the throttle position signal can be received in a communication packet as a numeric value on the port interface. The output of other sensors can be processed in a similar fashion.

Other sensors may be included and positioned in the interior space 108 of the vehicle 104. Generally, these interior sensors obtain data about the health of the driver and/or passenger(s), data about the safety of the driver and/or passenger(s), and/or data about the comfort of the driver and/or passenger(s). The health data sensors can include sensors in the steering wheel that can measure various health telemetry for the person (e.g., heart rate, temperature, blood pressure, blood presence, blood composition, etc.). Sensors in the seats may also provide for health telemetry (e.g., presence of liquid, weight, weight shifts, etc.). Infrared sensors could detect a person's temperature; optical sensors can determine a person's position and whether the person has become unconscious. Other health sensors are possible and included herein.

Safety sensors can measure whether the person is acting safely. Optical sensors can determine a person's position and focus. If the person stops looking at the road ahead, the optical sensor can detect the lack of focus. Sensors in the seats may detect if a person is leaning forward or may be injured by a seat belt in a collision. Other sensors can detect that the driver has at least one hand on a steering wheel. Other safety sensors are possible and contemplated as if included herein.

Comfort sensors can collect information about a person's comfort. Temperature sensors may detect a temperature of the interior cabin. Moisture sensors can determine a relative humidity. Audio sensors can detect loud sounds or other distractions. Audio sensors may also receive input from a person through voice data. Other comfort sensors are possible and contemplated as if included herein.

Figure 6B:
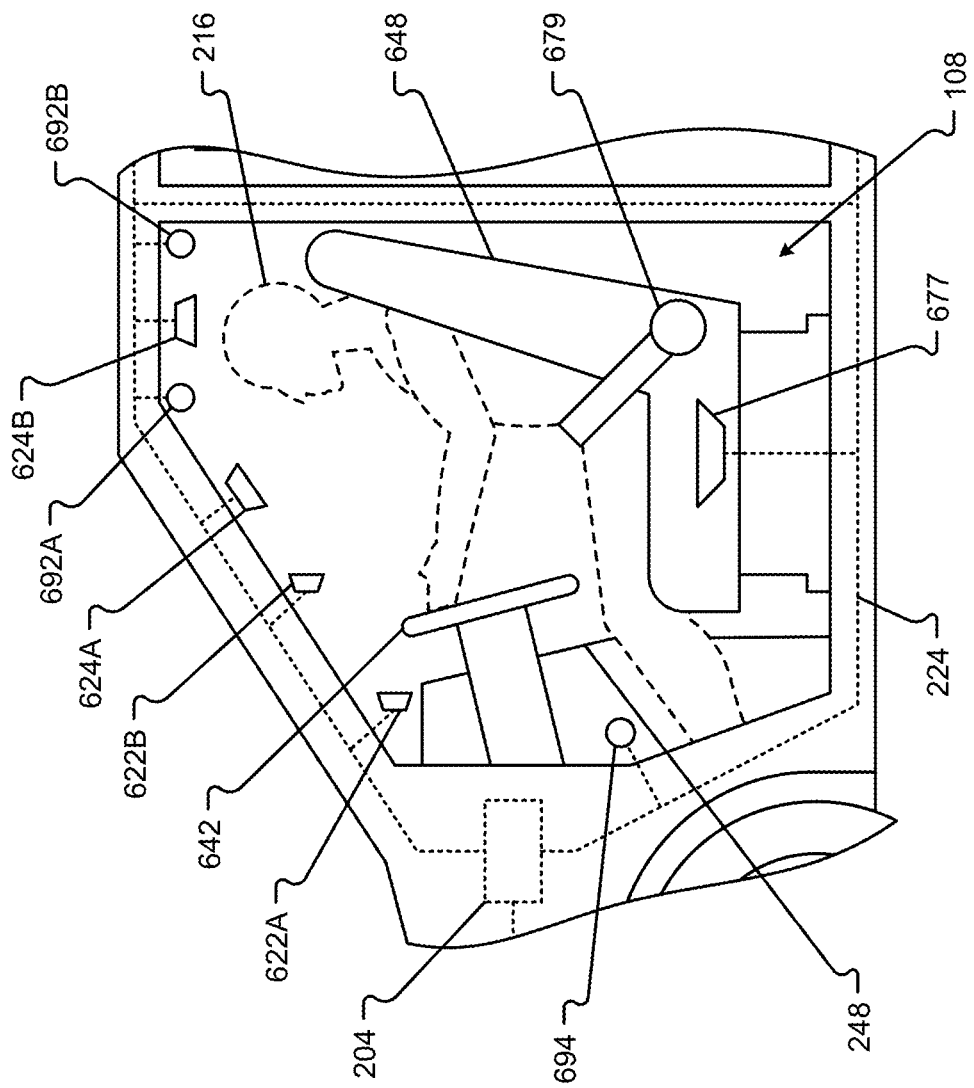
FIG. 6B depicts an embodiment of a sensor configuration for a zone of a vehicle.

FIG. 6B shows an interior sensor configuration for one or more zones 512 of a vehicle 104 optionally. Optionally, the areas 508 and/or zones 512 of a vehicle 104 may include sensors that are configured to collect information associated with the interior 108 of a vehicle 104. In particular, the various sensors may collect environmental information, user information, and safety information, to name a few. Embodiments of these sensors may be as described in conjunction with FIGS. 7A-8B.

Optionally, the sensors may include one or more of optical, or image, sensors 622A-B (e.g., cameras, etc.), motion sensors 624A-B (e.g., utilizing RF, IR, and/or other sound/image sensing, etc.), steering wheel user sensors 642 (e.g., heart rate, temperature, blood pressure, sweat, health, etc.), seat sensors 677 (e.g., weight, load cell, moisture, electrical, force transducer, etc.), safety restraint sensors 679 (e.g., seatbelt, airbag, load cell, force transducer, etc.), interior sound receivers 692A-B, environmental sensors 694 (e.g., temperature, humidity, air, oxygen, etc.), and the like.

The image sensors 622A-B may be used alone or in combination to identify objects, users 216, and/or other features, inside the vehicle 104. Optionally, a first image sensor 622A may be located in a different position within a vehicle 104 from a second image sensor 622B. When used in combination, the image sensors 622A-B may combine captured images to form, among other things, stereo and/or three-dimensional (3D) images. The stereo images can be recorded and/or used to determine depth associated with objects and/or users 216 in a vehicle 104. Optionally, the image sensors 622A-B used in combination may determine the complex geometry associated with identifying characteristics of a user 216. For instance, the image sensors 622A-B may be used to determine dimensions between various features of a user's face (e.g., the depth/distance from a user's nose to a user's cheeks, a linear distance between the center of a user's eyes, and more). These dimensions may be used to verify, record, and even modify characteristics that serve to identify a user 216. As can be appreciated, utilizing stereo images can allow for a user 216 to provide complex gestures in a 3D space of the vehicle 104. These gestures may be interpreted via one or more of the subsystems as disclosed herein. Optionally, the image sensors 622A-B may be used to determine movement associated with objects and/or users 216 within the vehicle 104. It should be appreciated that the number of image sensors used in a vehicle 104 may be increased to provide greater dimensional accuracy and/or views of a detected image in the vehicle 104.

The vehicle 104 may include one or more motion sensors 624A-B. These motion sensors 624A-B may detect motion and/or movement of objects inside the vehicle 104. Optionally, the motion sensors 624A-B may be used alone or in combination to detect movement. For example, a user 216 may be operating a vehicle 104 (e.g., while driving, etc.) when a passenger in the rear of the vehicle 104 unbuckles a safety belt and proceeds to move about the vehicle 104. In this example, the movement of the passenger could be detected by the motion sensors 624A-B. Optionally, the user 216 could be alerted of this movement by one or more of the devices 212, 248 in the vehicle 104. In another example, a passenger may attempt to reach for one of the vehicle control features (e.g., the steering wheel 640, the console, icons displayed on the head unit and/or device 212, 248, etc.). In this case, the movement (i.e., reaching) of the passenger may be detected by the motion sensors 624A-B. Optionally, the path, trajectory, anticipated path, and/or some other direction of movement/motion may be determined using the motion sensors 624A-B. In response to detecting the movement and/or the direction associated with the movement, the passenger may be prevented from interfacing with and/or accessing at least some of the vehicle control features (e.g., the features represented by icons may be hidden from a user interface, the features may be locked from use by the passenger, combinations thereof, etc.). As can be appreciated, the user 216 may be alerted of the movement/motion such that the user 216 can act to prevent the passenger from interfering with the vehicle 104 controls. Optionally, the number of motion sensors in a vehicle 104, or areas of a vehicle 104, may be increased to increase an accuracy associated with motion detected in the vehicle 104.

The interior sound receivers 692A-B may include, but are not limited to, microphones and other types of acoustic-to-electric transducers or sensors. Optionally, the interior sound receivers 692A-B may be configured to receive and convert sound waves into an equivalent analog or digital signal. The interior sound receivers 692A-B may serve to determine one or more locations associated with various sounds in the vehicle 104. The location of the sounds may be determined based on a comparison of volume levels, intensity, and the like, between sounds detected by two or more interior sound receivers 692A-B. For instance, a first interior sound receiver 692A may be located in a first area of the vehicle 104 and a second interior sound receiver 692B may be located in a second area of the vehicle 104. If a sound is detected at a first volume level by the first interior sound receiver 692A and a second, higher, volume level by the second interior sound receiver 692B in the second area of the vehicle 104, the sound may be determined to be closer to the second area of the vehicle 104. As can be appreciated, the number of sound receivers used in a vehicle 104 may be increased (e.g., more than two, etc.) to increase measurement accuracy surrounding sound detection and location, or source, of the sound (e.g., via triangulation, etc.).

Seat sensors 677 may be included in the vehicle 104. The seat sensors 677 may be associated with each seat and/or zone 512 in the vehicle 104. Optionally, the seat sensors 677 may provide health telemetry and/or identification via one or more of load cells, force transducers, weight sensors, moisture detection sensor, electrical conductivity/resistance sensor, and the like. For example, the seat sensors 677 may determine that a user 216 weighs 180 lbs. This value may be compared to user data stored in memory to determine whether a match exists between the detected weight and a user 216 associated with the vehicle 104. In another example, if the seat sensors 677 detect that a user 216 is fidgeting, or moving, in a seemingly uncontrollable manner, the system may determine that the user 216 has suffered a nervous and/or muscular system issue (e.g., seizure, etc.). The vehicle control system 204 may then cause the vehicle 104 to slow down and in addition or alternatively the automobile controller 8104 (described below) can safely take control of the vehicle 104 and bring the vehicle 104 to a stop in a safe location (e.g., out of traffic, off a freeway, etc).

Health telemetry and other data may be collected via the steering wheel user sensors 642. Optionally, the steering wheel user sensors 642 may collect heart rate, temperature, blood pressure, and the like, associated with a user 216 via at least one contact disposed on or about the steering wheel 640.

The safety restraint sensors 679 may be employed to determine a state associated with one or more safety restraint devices in a vehicle 104. The state associated with one or more safety restraint devices may serve to indicate a force observed at the safety restraint device, a state of activity (e.g., retracted, extended, various ranges of extension and/or retraction, deployment, buckled, unbuckled, etc.), damage to the safety restraint device, and more.

Environmental sensors 694, including one or more of temperature, humidity, air, oxygen, carbon monoxide, smoke, and other environmental condition sensors may be used in a vehicle 104. These environmental sensors 694 may be used to collect data relating to the safety, comfort, and/or condition of the interior space 108 of the vehicle 104. Among other things, the data collected by the environmental sensors 694 may be used by the vehicle control system 204 to alter functions of a vehicle. The environment may correspond to an interior space 108 of a vehicle 104 and/or specific areas 508 and/or zones 512 of the vehicle 104. It should be appreciate that an environment may correspond to a user 216. For example, a low oxygen environment may be detected by the environmental sensors 694 and associated with a user 216 who is operating the vehicle 104 in a particular zone 512. In response to detecting the low oxygen environment, at least one of the subsystems of the vehicle 104, as provided herein, may alter the environment, especially in the particular zone 512, to increase the amount of oxygen in the zone 512. Additionally or alternatively, the environmental sensors 694 may be used to report conditions associated with a vehicle (e.g., fire detected, low oxygen, low humidity, high carbon monoxide, etc.). The conditions may be reported to a user 216 and/or a third party via at least one communications module as provided herein.

Among other things, the sensors as disclosed herein may communicate with each other, with devices 212, 248, and/or with the vehicle control system 204 via the signal carrier network 224. Additionally or alternatively, the sensors disclosed herein may serve to provide data relevant to more than one category of sensor information including, but not limited to, combinations of environmental information, user information, and safety information to name a few.

Figure 7A:
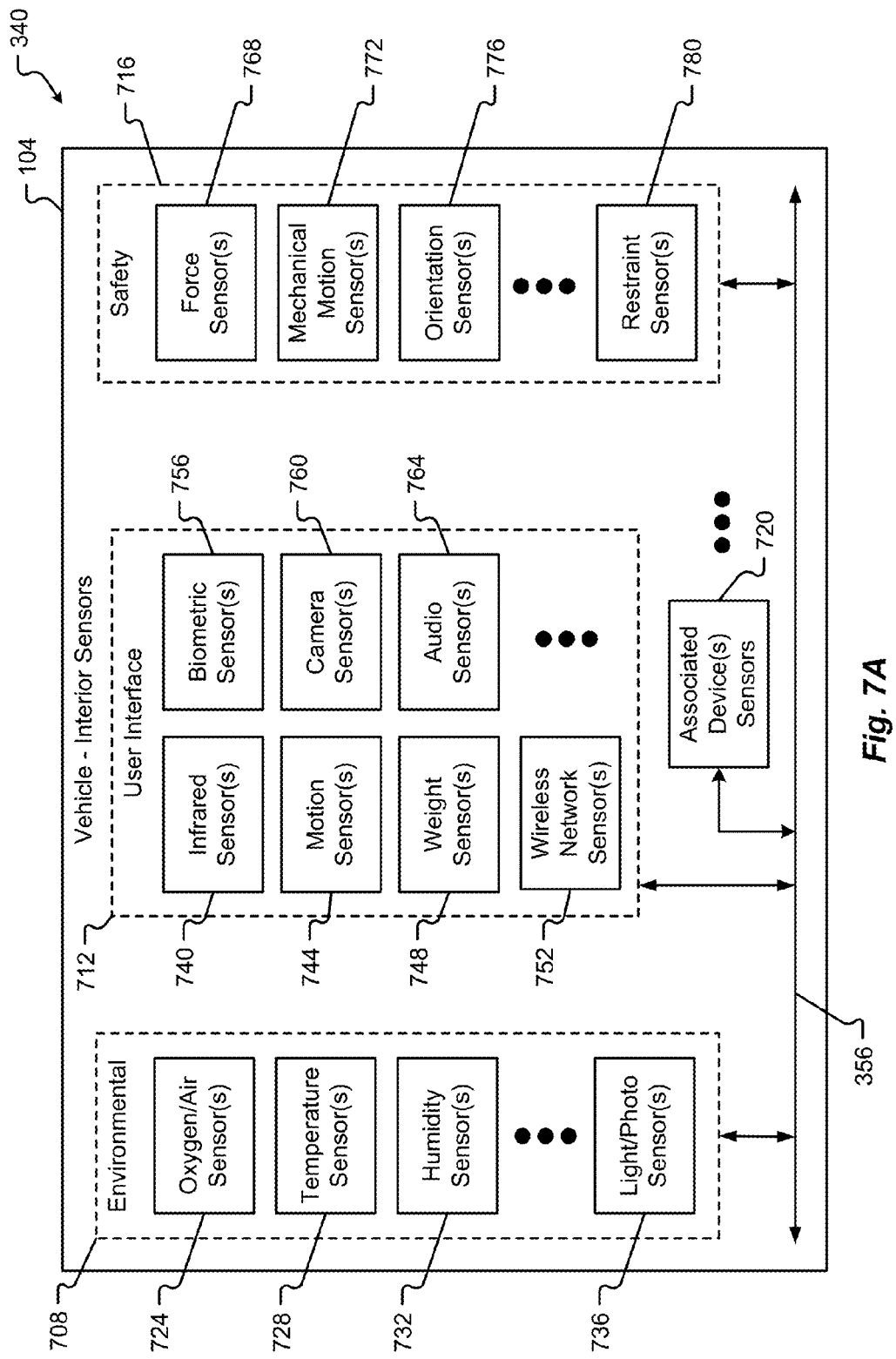
FIG. 7A is a block diagram of an embodiment of interior sensors for a vehicle.
Figure 7B:
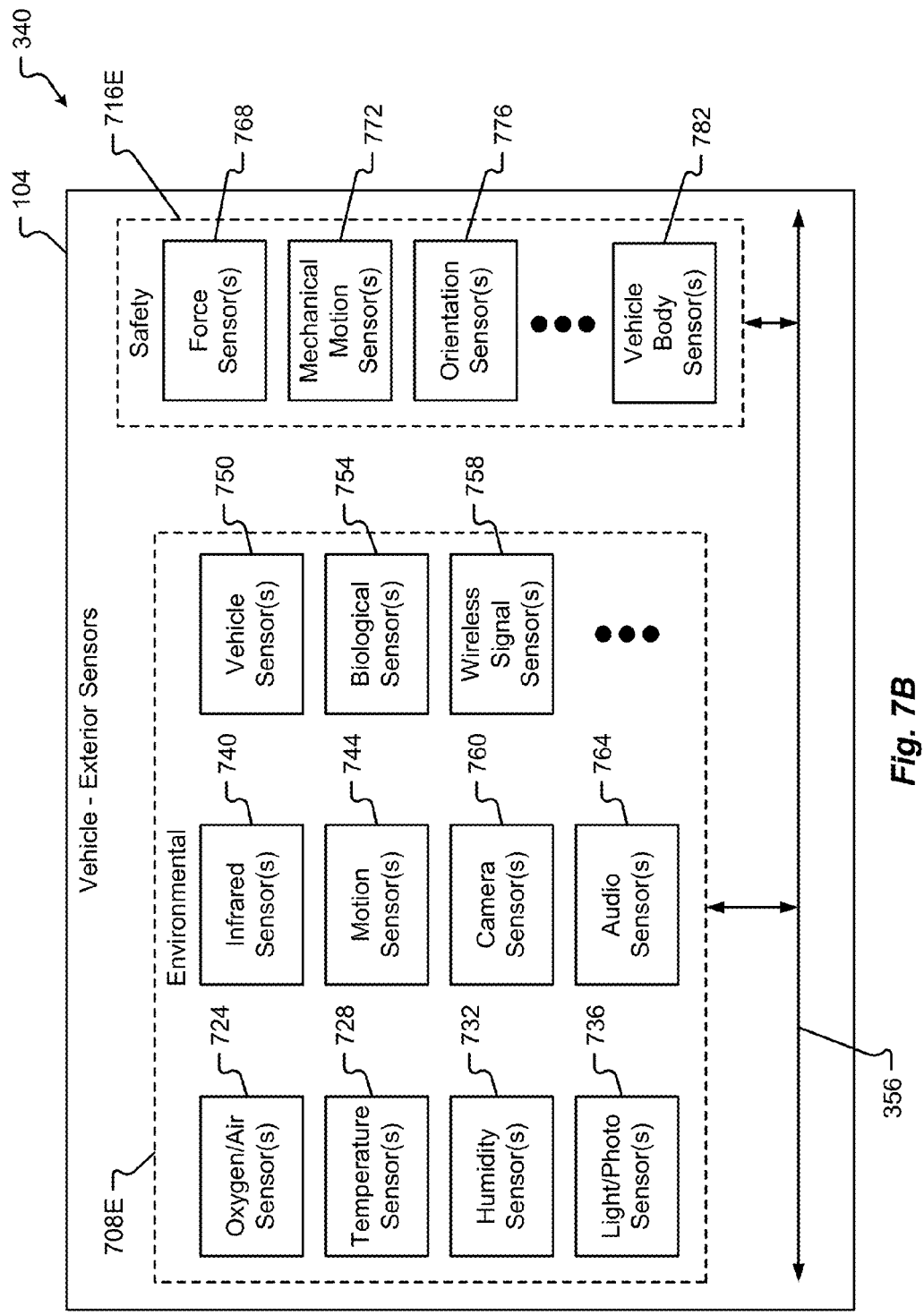
FIG. 7B is a block diagram of an embodiment of exterior sensors for a vehicle.

FIGS. 7A-7B show block diagrams of various sensors that may be associated with a vehicle 104. Although depicted as interior and exterior sensors, it should be appreciated that any of the one or more of the sensors shown may be used in both the interior space 108 and the exterior space of the vehicle 104. Moreover, sensors having the same symbol or name may include the same, or substantially the same, functionality as those sensors described elsewhere in the present disclosure. Further, although the various sensors are depicted in conjunction with specific groups (e.g., environmental 708, 708E, user interface 712, safety 716, 716E, etc.) the sensors should not be limited to the groups in which they appear. In other words, the sensors may be associated with other groups or combinations of groups and/or disassociated from one or more of the groups shown. The sensors as disclosed herein may communicate with each other, the devices 212, 248, and/or the vehicle control system 204 via one or more communications channel(s) 356.

FIG. 7A is a block diagram of an embodiment of interior sensors 340 for a vehicle 104 is provided. The interior sensors 340 may be arranged into one or more groups, based at least partially on the function of the interior sensors 340. The interior space 108 of a vehicle 104 may include an environmental group 708, a user interface group 712, and a safety group 716. Additionally or alternatively, there may be sensors associated with various devices inside the vehicle (e.g., devices 212, 248, smart phones, tablets, mobile computers, etc.)

The environmental group 708 may comprise sensors configured to collect data relating to the internal environment of a vehicle 104. It is anticipated that the environment of the vehicle 104 may be subdivided into areas 508 and zones 512 in an interior space 108 of a vehicle 104. In this case, each area 508 and/or zone 512 may include one or more of the environmental sensors. Examples of environmental sensors associated with the environmental group 708 may include, but are not limited to, oxygen/air sensors 724, temperature sensors 728, humidity sensors 732, light/photo sensors 736, and more. The oxygen/air sensors 724 may be configured to detect a quality of the air in the interior space 108 of the vehicle 104 (e.g., ratios and/or types of gasses comprising the air inside the vehicle 104, dangerous gas levels, safe gas levels, etc.). Temperature sensors 728 may be configured to detect temperature readings of one or more objects, users 216, and/or areas 508 of a vehicle 104. Humidity sensors 732 may detect an amount of water vapor present in the air inside the vehicle 104. The light/photo sensors 736 can detect an amount of light present in the vehicle 104. Further, the light/photo sensors 736 may be configured to detect various levels of light intensity associated with light in the vehicle 104.

The user interface group 712 may comprise sensors configured to collect data relating to one or more users 216 in a vehicle 104. As can be appreciated, the user interface group 712 may include sensors that are configured to collect data from users 216 in one or more areas 508 and zones 512 of the vehicle 104. For example, each area 508 and/or zone 512 of the vehicle 104 may include one or more of the sensors in the user interface group 712. Examples of user interface sensors associated with the user interface group 712 may include, but are not limited to, infrared sensors 740, motion sensors 744, weight sensors 748, wireless network sensors 752, biometric sensors 756, camera (or image) sensors 760, audio sensors 764, and more.

Infrared sensors 740 may be used to measure IR light irradiating from at least one surface, user 216, or other object in the vehicle 104. Among other things, the Infrared sensors 740 may be used to measure temperatures, form images (especially in low light conditions), identify users 216, and even detect motion in the vehicle 104.

The motion sensors 744 may be similar to the motion detectors 624A-B, as described in conjunction with FIG. 6B. Weight sensors 748 may be employed to collect data relating to objects and/or users 216 in various areas 508 of the vehicle 104. In some cases, the weight sensors 748 may be included in the seats and/or floor of a vehicle 104.

Optionally, the vehicle 104 may include a wireless network sensor 752. This sensor 752 may be configured to detect one or more wireless network(s) inside the vehicle 104. Examples of wireless networks may include, but are not limited to, wireless communications utilizing Bluetooth®, Wi-Fi™, ZigBee, IEEE 802.11, and other wireless technology standards. For example, a mobile hotspot may be detected inside the vehicle 104 via the wireless network sensor 752. In this case, the vehicle 104 may determine to utilize and/or share the mobile hotspot detected via/with one or more other devices 212, 248 and/or components associated with the vehicle 104.

Biometric sensors 756 may be employed to identify and/or record characteristics associated with a user 216. It is anticipated that biometric sensors 756 can include at least one of image sensors, IR sensors, fingerprint readers, weight sensors, load cells, force transducers, heart rate monitors, blood pressure monitors, and the like as provided herein.

The camera sensors 760 may be similar to image sensors 622A-B, as described in conjunction with FIG. 6B. Optionally, the camera sensors may record still images, video, and/or combinations thereof. The audio sensors 764 may be similar to the interior sound receivers 692A-B, as described in conjunction with FIGS. 6A-6B. The audio sensors may be configured to receive audio input from a user 216 of the vehicle 104. The audio input from a user 216 may correspond to voice commands, conversations detected in the vehicle 104, phone calls made in the vehicle 104, and/or other audible expressions made in the vehicle 104.

The safety group 716 may comprise sensors configured to collect data relating to the safety of a user 216 and/or one or more components of a vehicle 104. The vehicle 104 may be subdivided into areas 508 and/or zones 512 in an interior space 108 of a vehicle 104 where each area 508 and/or zone 512 may include one or more of the safety sensors provided herein. Examples of safety sensors associated with the safety group 716 may include, but are not limited to, force sensors 768, mechanical motion sensors 772, orientation sensors 776, restraint sensors 780, and more.

The force sensors 768 may include one or more sensors inside the vehicle 104 configured to detect a force observed in the vehicle 104. One example of a force sensor 768 may include a force transducer that converts measured forces (e.g., force, weight, pressure, etc.) into output signals.

Mechanical motion sensors 772 may correspond to encoders, accelerometers, damped masses, and the like. Optionally, the mechanical motion sensors 772 may be adapted to measure the force of gravity (i.e., G-force) as observed inside the vehicle 104. Measuring the G-force observed inside a vehicle 104 can provide valuable information related to a vehicle's acceleration, deceleration, collisions, and/or forces that may have been suffered by one or more users 216 in the vehicle 104. As can be appreciated, the mechanical motion sensors 772 can be located in an interior space 108 or an exterior of the vehicle 104.

Orientation sensors 776 can include accelerometers, gyroscopes, magnetic sensors, and the like that are configured to detect an orientation associated with the vehicle 104. Similar to the mechanical motion sensors 772, the orientation sensors 776 can be located in an interior space 108 or an exterior of the vehicle 104.

The restraint sensors 780 may be similar to the safety restraint sensors 679 as described in conjunction with FIGS. 6A-6B. These sensors 780 may correspond to sensors associated with one or more restraint devices and/or systems in a vehicle 104. Seatbelts and airbags are examples of restraint devices and/or systems. As can be appreciated, the restraint devices and/or systems may be associated with one or more sensors that are configured to detect a state of the device/system. The state may include extension, engagement, retraction, disengagement, deployment, and/or other electrical or mechanical conditions associated with the device/system.

The associated device sensors 720 can include any sensors that are associated with a device 212, 248 in the vehicle 104. As previously stated, typical devices 212, 248 may include smart phones, tablets, laptops, mobile computers, and the like. It is anticipated that the various sensors associated with these devices 212, 248 can be employed by the vehicle control system 204. For example, a typical smart phone can include, an image sensor, an IR sensor, audio sensor, gyroscope, accelerometer, wireless network sensor, fingerprint reader, and more. It is an aspect of the present disclosure that one or more of these associated device sensors 720 may be used by one or more subsystems of the vehicle system 200.

In FIG. 7B, a block diagram of an embodiment of exterior sensors 340 for a vehicle 104 is shown. The exterior sensors may include sensors that are identical, or substantially similar, to those previously disclosed in conjunction with the interior sensors of FIG. 7A. Optionally, the exterior sensors 340 may be configured to collect data relating to one or more conditions, objects, users 216, and other events that are external to the interior space 108 of the vehicle 104. For instance, the oxygen/air sensors 724 may measure a quality and/or composition of the air outside of a vehicle 104. As another example, the motion sensors 744 may detect motion outside of a vehicle 104.

The external environmental group 708E may comprise sensors configured to collect data relating to the external environment of a vehicle 104. In addition to including one or more of the sensors previously described, the external environmental group 708E may include additional sensors, such as, vehicle sensors 750, biological sensors, and wireless signal sensors 758. Vehicle sensors 750 can detect vehicles that are in an environment surrounding the vehicle 104. For example, the vehicle sensors 750 may detect vehicles in a first outside area 516, a second outside area 520, and/or combinations of the first and second outside areas 516, 520. Optionally, the vehicle sensors 750 may include one or more of RF sensors, IR sensors, image sensors, and the like to detect vehicles, people, hazards, etc. that are in an environment exterior to the vehicle 104. Additionally or alternatively, the vehicle sensors 750 can provide distance/directional information relating to a distance (e.g., distance from the vehicle 104 to the detected object) and/or a direction (e.g., direction of travel, etc.) associated with the detected object.

The biological sensors 754 may determine whether one or more biological entities (e.g., an animal, a person, a user 216, etc.) is in an external environment of the vehicle 104. Additionally or alternatively, the biological sensors 754 may provide distance information relating to a distance of the biological entity from the vehicle 104. Biological sensors 754 may include at least one of RF sensors, IR sensors, image sensors and the like that are configured to detect biological entities. For example, an IR sensor may be used to determine that an object, or biological entity, has a specific temperature, temperature pattern, or heat signature. Continuing this example, a comparison of the determined heat signature may be compared to known heat signatures associated with recognized biological entities (e.g., based on shape, locations of temperature, and combinations thereof, etc.) to determine whether the heat signature is associated with a biological entity or an inanimate, or non-biological, object.

The wireless signal sensors 758 may include one or more sensors configured to receive wireless signals from signal sources such as Wi-Fi™ hotspots, cell towers, roadside beacons, other electronic roadside devices, and satellite positioning systems. Optionally, the wireless signal sensors 758 may detect wireless signals from one or more of a mobile phone, mobile computer, keyless entry device, RFID device, near field communications (NFC) device, and the like.

The external safety group 716E may comprise sensors configured to collect data relating to the safety of a user 216 and/or one or more components of a vehicle 104. Examples of safety sensors associated with the external safety group 716E may include, but are not limited to, force sensors 768, mechanical motion sensors 772, orientation sensors 776, vehicle body sensors 782, and more. Optionally, the exterior safety sensors 716E may be configured to collect data relating to one or more conditions, objects, vehicle components, and other events that are external to the vehicle 104. For instance, the force sensors 768 in the external safety group 716E may detect and/or record force information associated with the outside of a vehicle 104. For instance, if an object strikes the exterior of the vehicle 104, the force sensors 768 from the exterior safety group 716E may determine a magnitude, location, and/or time associated with the strike.

The vehicle 104 may include a number of vehicle body sensors 782. The vehicle body sensors 782 may be configured to measure characteristics associated with the body (e.g., body panels, components, chassis, windows, etc.) of a vehicle 104. For example, two vehicle body sensors 782, including a first body sensor and a second body sensor, may be located at some distance apart. Continuing this example, the first body sensor may be configured to send an electrical signal across the body of the vehicle 104 to the second body sensor, or vice versa. Upon receiving the electrical signal from the first body sensor, the second body sensor may record a detected current, voltage, resistance, and/or combinations thereof associated with the received electrical signal. Values (e.g., current, voltage, resistance, etc.) for the sent and received electrical signal may be stored in a memory. These values can be compared to determine whether subsequent electrical signals sent and received between vehicle body sensors 782 deviate from the stored values. When the subsequent signal values deviate from the stored values, the difference may serve to indicate damage and/or loss of a body component. Additionally or alternatively, the deviation may indicate a problem with the vehicle body sensors 782. The vehicle body sensors 782 may communicate with each other, a vehicle control system 204, and/or systems of the vehicle system 200 via a communications channel 356. Although described using electrical signals, it should be appreciated that alternative embodiments of the vehicle body sensors 782 may use sound waves and/or light to perform a similar function.

Figure 8A:
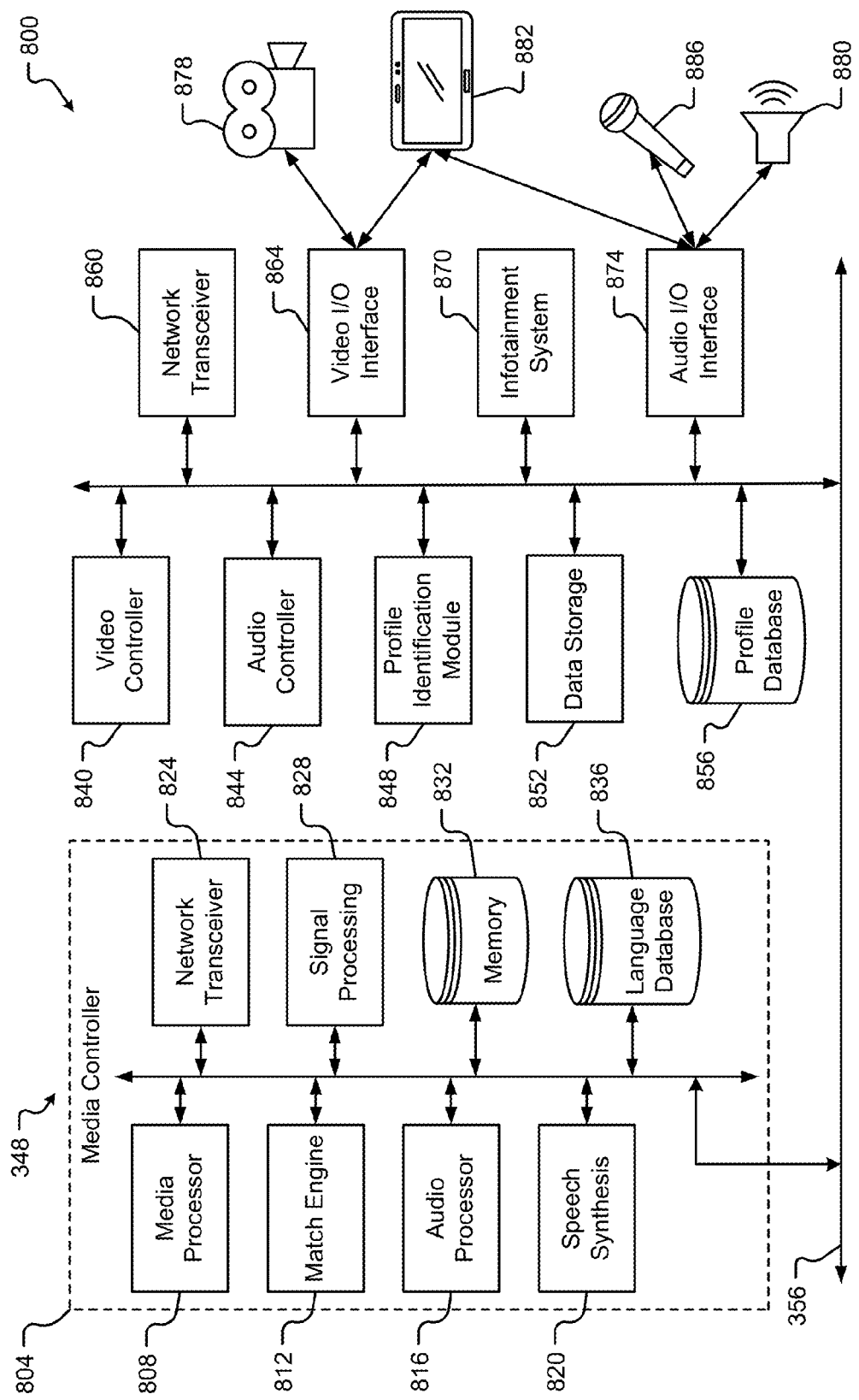
FIG. 8A is a block diagram of an embodiment of a media subsystem for a vehicle.

FIG. 8A is a block diagram of an embodiment of a media controller subsystem 348 for a vehicle 104. The media controller subsystem 348 may include, but is not limited to, a media controller 804, a media processor 808, a match engine 812, an audio processor 816, a speech synthesis module 820, a network transceiver 824, a signal processing module 828, memory 832, and a language database 836. Optionally, the media controller subsystem 348 may be configured as a dedicated blade that implements the media-related functionality of the system 200. Additionally or alternatively, the media controller subsystem 348 can provide voice input, voice output, library functions for multimedia, and display control for various areas 508 and/or zones 512 of the vehicle 104.

Optionally, the media controller subsystem 348 may include a local IP address (e.g., IPv4, IPv6, combinations thereof, etc.) and even a routable, global unicast address. The routable, global unicast address may allow for direct addressing of the media controller subsystem 348 for streaming data from Internet resources (e.g., cloud storage, user accounts, etc.). It is anticipated, that the media controller subsystem 348 can provide multimedia via at least one Internet connection, or wireless network communications module, associated with the vehicle 104. Moreover, the media controller subsystem 348 may be configured to service multiple independent clients simultaneously.

The media processor 808 may comprise a general purpose programmable processor or controller for executing application programming or instructions related to the media subsystem 348. The media processor 808 may include multiple processor cores, and/or implement multiple virtual processors. Optionally, the media processor 808 may include multiple physical processors. By way of example, the media processor 808 may comprise a specially configured application specific integrated circuit (ASIC) or other integrated circuit, a digital signal processor, a controller, a hardwired electronic or logic circuit, a programmable logic device or gate array, a special purpose computer, or the like. The media processor 808 generally functions to run programming code or instructions implementing various functions of the media controller 804.

The match engine 812 can receive input from one or more components of the vehicle system 800 and perform matching functions. Optionally, the match engine 812 may receive audio input provided via a microphone 886 of the system 800. The audio input may be provided to the media controller subsystem 348 where the audio input can be decoded and matched, via the match engine 812, to one or more functions available to the vehicle 104. Similar matching operations may be performed by the match engine 812 relating to video input received via one or more image sensors, cameras 878, and the like.

The media controller subsystem 348 may include a speech synthesis module 820 configured to provide audio output to one or more speakers 880, or audio output devices, associated with the vehicle 104. Optionally, the speech synthesis module 820 may be configured to provide audio output based at least partially on the matching functions performed by the match engine 812.

As can be appreciated, the coding/decoding, the analysis of audio input/output, and/or other operations associated with the match engine 812 and speech synthesis module 820, may be performed by the media processor 808 and/or a dedicated audio processor 816. The audio processor 816 may comprise a general purpose programmable processor or controller for executing application programming or instructions related to audio processing. Further, the audio processor 816 may be similar to the media processor 808 described herein.

The network transceiver 824 can include any device configured to transmit and receive analog and/or digital signals. Optionally, the media controller subsystem 348 may utilize a network transceiver 824 in one or more communication networks associated with the vehicle 104 to receive and transmit signals via the communications channel 356. Additionally or alternatively, the network transceiver 824 may accept requests from one or more devices 212, 248 to access the media controller subsystem 348. One example of the communication network is a local-area network (LAN). As can be appreciated, the functionality associated with the network transceiver 824 may be built into at least one other component of the vehicle 104 (e.g., a network interface card, communications module, etc.).

The signal processing module 828 may be configured to alter audio/multimedia signals received from one or more input sources (e.g., microphones 886, etc.) via the communications channel 356. Among other things, the signal processing module 828 may alter the signals received electrically, mathematically, combinations thereof, and the like.

The media controller 804 may also include memory 832 for use in connection with the execution of application programming or instructions by the media processor 808, and for the temporary or long term storage of program instructions and/or data. As examples, the memory 832 may comprise RAM, DRAM, SDRAM, or other solid state memory.

The language database 836 may include the data and/or libraries for one or more languages, as are used to provide the language functionality as provided herein. In one case, the language database 836 may be loaded on the media controller 804 at the point of manufacture. Optionally, the language database 836 can be modified, updated, and/or otherwise changed to alter the data stored therein. For instance, additional languages may be supported by adding the language data to the language database 836. In some cases, this addition of languages can be performed via accessing administrative functions on the media controller 804 and loading the new language modules via wired (e.g., USB, etc.) or wireless communication. In some cases, the administrative functions may be available via a vehicle console device 248, a user device 212, 248, and/or other mobile computing device that is authorized to access administrative functions (e.g., based at least partially on the device's address, identification, etc.).

One or more video controllers 840 may be provided for controlling the video operation of the devices 212, 248, 882 associated with the vehicle. Optionally, the video controller 840 may include a display controller for controlling the operation of touch sensitive screens, including input (touch sensing) and output (display) functions. Video data may include data received in a stream and unpacked by a processor and loaded into a display buffer. In this example, the processor and video controller 840 can optimize the display based on the characteristics of a screen of a display device 212, 248, 882. The functions of a touch screen controller may be incorporated into other components, such as a media processor 808 or display subsystem.

The audio controller 844 can provide control of the audio entertainment system (e.g., radio, subscription music service, multimedia entertainment, etc.), and other audio associated with the vehicle 104 (e.g., navigation systems, vehicle comfort systems, convenience systems, etc.). Optionally, the audio controller 844 may be configured to translate digital signals to analog signals and vice versa. As can be appreciated, the audio controller 844 may include device drivers that allow the audio controller 844 to communicate with other components of the system 800 (e.g., processors 816, 808, audio I/O 874, and the like).

The system 800 may include a profile identification module 848 to determine whether a user profile is associated with the vehicle 104. Among other things, the profile identification module 848 may receive requests from a user 216, or device 212, 228, 248, to access a profile stored in a profile database 856 or profile data 252. Additionally or alternatively, the profile identification module 848 may request profile information from a user 216 and/or a device 212, 228, 248, to access a profile stored in a profile database 856 or profile data 252. In any event, the profile identification module 848 may be configured to create, modify, retrieve, and/or store user profiles in the profile database 856 and/or profile data 252. The profile identification module 848 may include rules for profile identification, profile information retrieval, creation, modification, and/or control of components in the system 800.

By way of example, a user 216 may enter the vehicle 104 with a smart phone or other device 212. In response to determining that a user 216 is inside the vehicle 104, the profile identification module 848 may determine that a user profile is associated with the user's smart phone 212. As another example, the system 800 may receive information about a user 216 (e.g., from a camera 878, microphone 886, etc.), and, in response to receiving the user information, the profile identification module 848 may refer to the profile database 856 to determine whether the user information matches a user profile stored in the database 856. It is anticipated that the profile identification module 848 may communicate with the other components of the system to load one or more preferences, settings, and/or conditions based on the user profile. Further, the profile identification module 848 may be configured to control components of the system 800 based on user profile information.

Optionally, data storage 852 may be provided. Like the memory 832, the data storage 852 may comprise a solid state memory device or devices. Alternatively or in addition, the data storage 852 may comprise a hard disk drive or other random access memory. Similar to the data storage 852, the profile database 856 may comprise a solid state memory device or devices.

An input/output module 860 and associated ports may be included to support communications over wired networks or links, for example with other communication devices, server devices, and/or peripheral devices. Examples of an input/output module 860 include an Ethernet port, a Universal Serial Bus (USB) port, CAN Bus, Institute of Electrical and Electronics Engineers (IEEE) 1594, or other interface. Users may bring their own devices (e.g., Bring Your Own Device (BYOD), device 212, etc.) into the vehicle 104 for use with the various systems disclosed. Although most BYOD devices can connect to the vehicle systems (e.g., the media controller subsystem 348, etc.) via wireless communications protocols (e.g., Wi-Fi™, Bluetooth®, etc.) many devices may require a direct connection via USB, or similar. In any event, the input/output module 860 can provide the necessary connection of one or more devices to the vehicle systems described herein.

A video input/output interface 864 can be included to receive and transmit video signals between the various components in the system 800. Optionally, the video input/output interface 864 can operate with compressed and uncompressed video signals. The video input/output interface 864 can support high data rates associated with image capture devices. Additionally or alternatively, the video input/output interface 864 may convert analog video signals to digital signals.

The infotainment system 870 may include information media content and/or entertainment content, informational devices, entertainment devices, and the associated programming therefor. Optionally, the infotainment system 870 may be configured to handle the control of one or more components of the system 800 including, but in no way limited to, radio, streaming audio/video devices, audio devices 880, 882, 886, video devices 878, 882, travel devices (e.g., GPS, navigational systems, etc.), wireless communication devices, network devices, and the like. Further, the infotainment system 870 can provide the functionality associated with other infotainment features as provided herein.

An audio input/output interface 874 can be included to provide analog audio to an interconnected speaker 880 or other device, and to receive analog audio input from a connected microphone 886 or other device. As an example, the audio input/output interface 874 may comprise an associated amplifier and analog to digital converter. Alternatively or in addition, the devices 212, 248 can include integrated audio input/output devices 880, 886 and/or an audio jack for interconnecting an external speaker 880 or microphone 886. For example, an integrated speaker 880 and an integrated microphone 886 can be provided, to support near talk, voice commands, spoken information exchange, and/or speaker phone operations.

Among other things, the system 800 may include devices that are part of the vehicle 104 and/or part of a device 212, 248 that is associated with the vehicle 104. For instance, these devices may be configured to capture images, display images, capture sound, and present sound. Optionally, the system 800 may include at least one of image sensors/cameras 878, display devices 882, audio input devices/microphones 886, and audio output devices/speakers 880. The cameras 878 can be included for capturing still and/or video images. Alternatively or in addition, image sensors 878 can include a scanner or code reader. An image sensor/camera 878 can include or be associated with additional elements, such as a flash or other light source. In some cases, the display device 882 may include an audio input device and/or an audio output device in addition to providing video functions. For instance, the display device 882 may be a console, monitor, a tablet computing device, and/or some other mobile computing device.

Figure 8B:
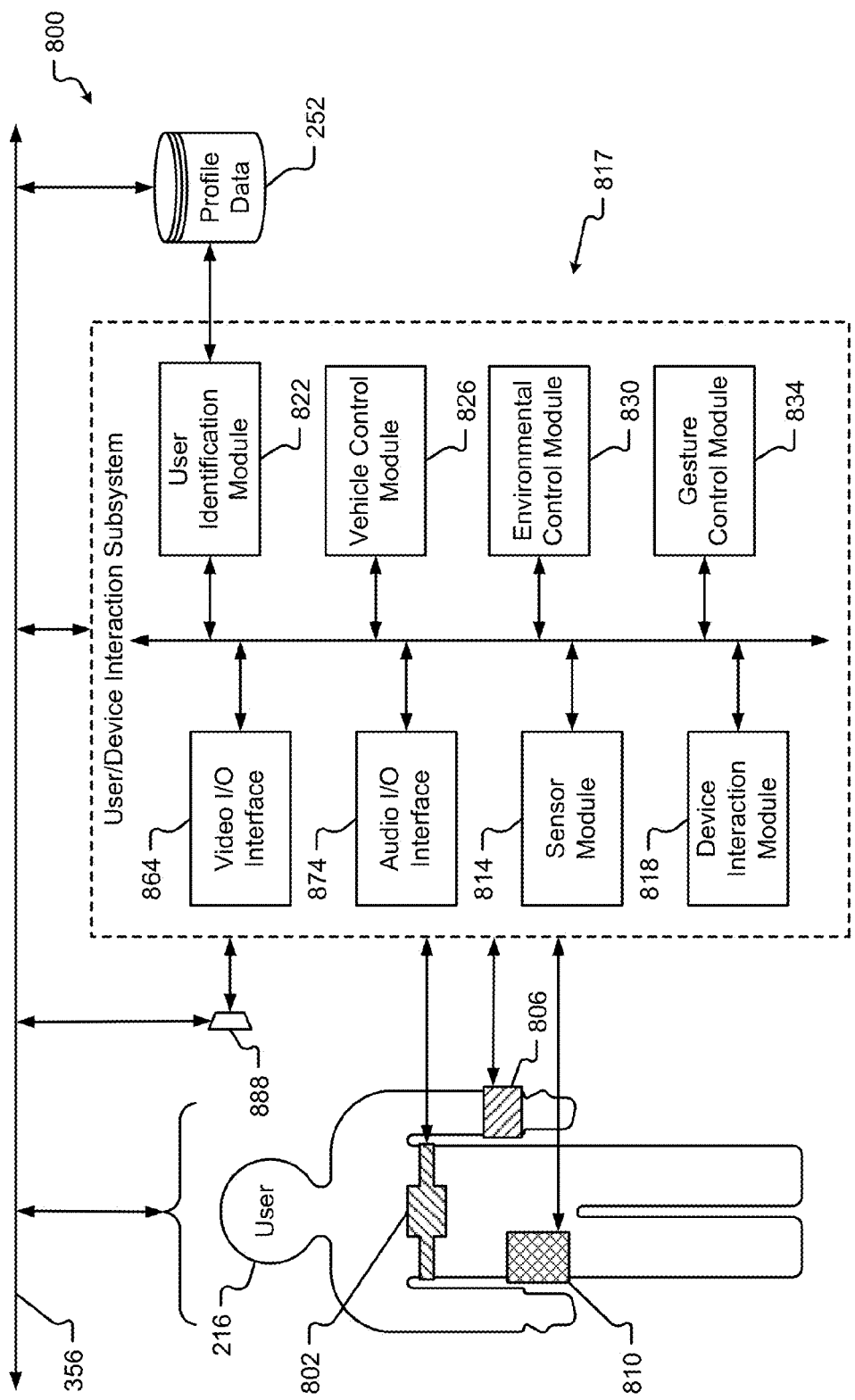
FIG. 8B is a block diagram of an embodiment of a user and device interaction subsystem for a vehicle.

FIG. 8B is a block diagram of an embodiment of a user/device interaction subsystem 817 in a vehicle system 800. The user/device interaction subsystem 817 may comprise hardware and/or software that conduct various operations for or with the vehicle 104. For instance, the user/device interaction subsystem 817 may include at least one user interaction subsystem 332 and device interaction subsystem 352 as previously described. These operations may include, but are not limited to, providing information to the user 216, receiving input from the user 216, and controlling the functions or operation of the vehicle 104, etc. Among other things, the user/device interaction subsystem 817 may include a computing system operable to conduct the operations as described herein.

Optionally, the user/device interaction subsystem 817 can include one or more of the components and modules provided herein. For instance, the user/device interaction subsystem 817 can include one or more of a video input/output interface 864, an audio input/output interface 874, a sensor module 814, a device interaction module 818, a user identification module 822, a vehicle control module 826, an environmental control module 830, and a gesture control module 834. The user/device interaction subsystem 817 may be in communication with other devices, modules, and components of the system 800 via the communications channel 356.

The user/device interaction subsystem 817 may be configured to receive input from a user 216 and/or device via one or more components of the system. By way of example, a user 216 may provide input to the user/device interaction subsystem 817 via wearable devices 802, 806, 810, video input (e.g., via at least one image sensor/camera 878, etc.) audio input (e.g., via the microphone, audio input source, etc.), gestures (e.g., via at least one image sensor 878, motion sensor 888, etc.), device input (e.g., via a device 212, 248 associated with the user, etc.), combinations thereof, and the like.

The wearable devices 802, 806, 810 can include heart rate monitors, blood pressure monitors, glucose monitors, pedometers, movement sensors, wearable computers, and the like. Examples of wearable computers may be worn by a user 216 and configured to measure user activity, determine energy spent based on the measured activity, track user sleep habits, determine user oxygen levels, monitor heart rate, provide alarm functions, and more. It is anticipated that the wearable devices 802, 806, 810 can communicate with the user/device interaction subsystem 817 via wireless communications channels or direct connection (e.g., where the device docks, or connects, with a USB port or similar interface of the vehicle 104).

A sensor module 814 may be configured to receive and/or interpret input provided by one or more sensors in the vehicle 104. In some cases, the sensors may be associated with one or more user devices (e.g., wearable devices 802, 806, 810, smart phones 212, mobile computing devices 212, 248, and the like). Optionally, the sensors may be associated with the vehicle 104, as described in conjunction with FIGS. 6A-7B.

The device interaction module 818 may communicate with the various devices as provided herein. Optionally, the device interaction module 818 can provide content, information, data, and/or media associated with the various subsystems of the vehicle system 800 to one or more devices 212, 248, 802, 806, 810, 882, etc. Additionally or alternatively, the device interaction module 818 may receive content, information, data, and/or media associated with the various devices provided herein.

The user identification module 822 may be configured to identify a user 216 associated with the vehicle 104. The identification may be based on user profile information that is stored in profile data 252. For instance, the user identification module 822 may receive characteristic information about a user 216 via a device, a camera, and/or some other input. The received characteristics may be compared to data stored in the profile data 252. Where the characteristics match, the user 216 is identified. As can be appreciated, where the characteristics do not match a user profile, the user identification module 822 may communicate with other subsystems in the vehicle 104 to obtain and/or record profile information about the user 216. This information may be stored in a memory and/or the profile data storage 252.

The vehicle control module 826 may be configured to control settings, features, and/or the functionality of a vehicle 104. In some cases, the vehicle control module 826 can communicate with the vehicle control system 204 to control critical functions (e.g., driving system controls, braking, accelerating, etc.) and/or noncritical functions (e.g., driving signals, indicator/hazard lights, mirror controls, window actuation, etc.) based at least partially on user/device input received by the user/device interaction subsystem 817.

The environmental control module 830 may be configured to control settings, features, and/or other conditions associated with the environment, especially the interior environment, of a vehicle 104. Optionally, the environmental control module 830 may communicate with the climate control system (e.g. changing cabin temperatures, fan speeds, air direction, etc.), oxygen and/or air quality control system (e.g., increase/decrease oxygen in the environment, etc.), interior lighting (e.g., changing intensity of lighting, color of lighting, etc.), an occupant seating system 648 (e.g., adjusting seat position, firmness, height, etc.), steering wheel 640 (e.g., position adjustment, etc.), infotainment/entertainment system (e.g., adjust volume levels, display intensity adjustment, change content, etc.), and/or other systems associated with the vehicle environment. Additionally or alternatively, these systems can provide input, set-points, and/or responses, to the environmental control module 830. As can be appreciated, the environmental control module 830 may control the environment based at least partially on user/device input received by the user/device interaction subsystem 817.

The gesture control module 834 is configured to interpret gestures provided by a user 216 in the vehicle 104. Optionally, the gesture control module 834 may provide control signals to one or more of the vehicle systems 300 disclosed herein. For example, a user 216 may provide gestures to control the environment, critical and/or noncritical vehicle functions, the infotainment system, communications, networking, and more. Optionally, gestures may be provided by a user 216 and detected via one or more of the sensors as described in conjunction with FIGS. 6B-7A. As another example, one or more motion sensors 888 may receive gesture input from a user 216 and provide the gesture input to the gesture control module 834. Continuing this example, the gesture input is interpreted by the gesture control module 834. This interpretation may include comparing the gesture input to gestures stored in a memory. The gestures stored in memory may include one or more functions and/or controls mapped to specific gestures. When a match is determined between the detected gesture input and the stored gesture information, the gesture control module 834 can provide a control signal to any of the systems/subsystems as disclosed herein.

FIG. 8C illustrates a GPS/Navigation subsystem(s) 336. The Navigation subsystem(s) 336 can be any present or future-built navigation system that may use location data, for example, from the Global Positioning System (GPS), to provide navigation information or control the vehicle 104. The Navigation subsystem(s) 336 can include several components or modules, such as, one or more of, but not limited to, a GPS Antenna/receiver 892, a location module 896, a maps database 8100, an automobile controller 8104, a vehicle systems transceiver 8108, a traffic controller 8112, a network traffic transceiver 8116, a vehicle-to-vehicle transceiver 8120, a traffic information database 8124, etc. Generally, the several components or modules 892-8124 may be hardware, software, firmware, computer readable media, or combinations thereof.

A GPS Antenna/receiver 892 can be any antenna, GPS puck, and/or receiver capable of receiving signals from a GPS satellite or other navigation system, as mentioned hereinbefore. The signals may be demodulated, converted, interpreted, etc. by the GPS Antenna/receiver 892 and provided to the location module 896. Thus, the GPS Antenna/receiver 892 may convert the time signals from the GPS system and provide a location (e.g., coordinates on a map) to the location module 896. Alternatively, the location module 896 can interpret the time signals into coordinates or other location information.

The location module 896 can be the controller of the satellite navigation system designed for use in automobiles. The location module 896 can acquire position data, as from the GPS Antenna/receiver 892, to locate the user or vehicle 104 on a road in the unit's map database 8100. Using the road database 8100, the location module 896 can give directions to other locations along roads also in the database 8100. When a GPS signal is not available, the location module 896 may apply dead reckoning to estimate distance data from sensors 242 including one or more of, but not limited to, a speed sensor attached to the drive train of the vehicle 104, a gyroscope, an accelerometer, etc. GPS signal loss and/or multipath can occur due to urban canyons, tunnels, and other obstructions. Additionally or alternatively, the location module 896 may use known locations of Wi-Fi hotspots, cell tower data, etc. to determine the position of the vehicle 104, such as by using time difference of arrival (TDOA) and/or frequency difference of arrival (FDOA) techniques.

The maps database 8100 can include any hardware and/or software to store information about maps, geographical information system information, location information, etc. The maps database 8100 can include any data definition or other structure to store the information. Generally, the maps database 8100 can include a road database that may include one or more vector maps of areas of interest. Street names, street numbers, house numbers, and other information can be encoded as geographic coordinates so that the user can find some desired destination by street address. Points of interest (waypoints) can also be stored with their geographic coordinates. For example, a point of interest may include speed cameras, fuel stations, public parking, and "parked here" (or "you parked here") information. The map database contents can be produced or updated by a server connected through a wireless system in communication with the Internet, even as the vehicle 104 is driven along existing streets, yielding an up-to-date map.

An automobile controller 8104 can be any hardware and/or software that can receive instructions from the location module 896 or the traffic controller 8112 and operate the vehicle 104. The automobile controller 8104 receives this information and data from the sensors 242 to operate the vehicle 104 without driver input. Thus, the automobile controller 8104 can drive the vehicle 104 along a route provided by the location module 896. The route may be adjusted by information sent from the traffic controller 8112. Discrete and real-time driving can occur with data from the sensors 242. To operate the vehicle 104, the automobile controller 8104 can communicate with a vehicle systems transceiver 8108.

The vehicle systems transceiver 8108 can be any present or future-developed device that can comprise a transmitter and/or a receiver, which may be combined and can share common circuitry or a single housing. The vehicle systems transceiver 8108 may communicate or instruct one or more of the vehicle control subsystems 328. For example, the vehicle systems transceiver 8108 may send steering commands, as received from the automobile controller 8104, to an electronic steering system, to adjust the steering of the vehicle 100 in real time. The automobile controller 8104 can determine the effect of the commands based on received sensor data 242 and can adjust the commands as need be. The vehicle systems transceiver 8108 can also communicate with the braking system, the engine and drive train to speed or slow the car, the signals (e.g., turn signals and brake lights), the headlights, the windshield wipers, etc. Any of these communications may occur over the components or function as described in conjunction with FIG. 4.

A traffic controller 8112 can be any hardware and/or software that can communicate with an automated traffic system and adjust the function of the vehicle 104 based on instructions from the automated traffic system. An automated traffic system is a system that manages the traffic in a given area. This automated traffic system can instruct cars to drive in certain lanes, instruct cars to raise or lower their speed, instruct a car to change their route of travel, instruct cars to communicate with other cars, etc. To perform these functions, the traffic controller 8112 may register the vehicle 104 with the automated traffic system and then provide other information including the route of travel. The automated traffic system can return registration information and any required instructions. The communications between the automated traffic system and the traffic controller 8112 may be received and sent through a network traffic transceiver 8116.

The network traffic transceiver 8116 can be any present or future-developed device that can comprise a transmitter and/or a receiver, which may be combined and can share common circuitry or a single housing. The network traffic transceiver 8116 may communicate with the automated traffic system using any known or future-developed, protocol, standard, frequency, bandwidth range, etc. The network traffic transceiver 8116 enables the sending of information between the traffic controller 8112 and the automated traffic system.

The traffic controller 8112 can also communicate with another vehicle, which may be in physical proximity (i.e., within range of a wireless signal), using the vehicle-to-vehicle transceiver 8120. As with the network traffic transceiver 8116, the vehicle-to-vehicle transceiver 8120 can be any present or future-developed device that can comprise a transmitter and/or a receiver, which may be combined and can share common circuitry or a single housing. Generally, the vehicle-to-vehicle transceiver 8120 enables communication between the vehicle 104 and any other vehicle. These communications allow the vehicle 104 to receive traffic or safety information, control or be controlled by another vehicle, establish an alternative communication path to communicate with the automated traffic system, establish a node including two or more vehicle that can function as a unit, etc. The vehicle-to-vehicle transceiver 8120 may communicate with the other vehicles using any known or future-developed, protocol standard, frequency, bandwidth range, etc.

The traffic controller 8112 can control functions of the automobile controller 8104 and communicate with the location module 896. The location module 896 can provide current location information and route information that the traffic controller 8112 may then provide to the automated traffic system. The traffic controller 8112 may receive route adjustments from the automated traffic system that are then sent to the location module 896 to change the route. Further, the traffic controller 8112 can also send driving instructions to the automobile controller 8104 to change the driving characteristics of the vehicle 104. For example, the traffic controller

8112 can instruct the automobile controller 8104 to accelerate or decelerate to a different speed, change lanes, or perform another driving maneuver. The traffic controller 8112 can also manage vehicle-to-vehicle communications and store information about the communications or other information in the traffic information database 8124.

The traffic information database 8124 can be any type of database, such as relational, hierarchical, object-oriented, and/or the like. The traffic information database 8124 may reside on a storage medium local to (and/or resident in) the vehicle control system 204 or in the vehicle 104. The traffic information database 8124 may be adapted to store, update, and retrieve information about communications with other vehicles or any active instructions from the automated traffic system. This information may be used by the traffic controller 8112 to instruct or adjust the performance of driving maneuvers.

Figure 9:
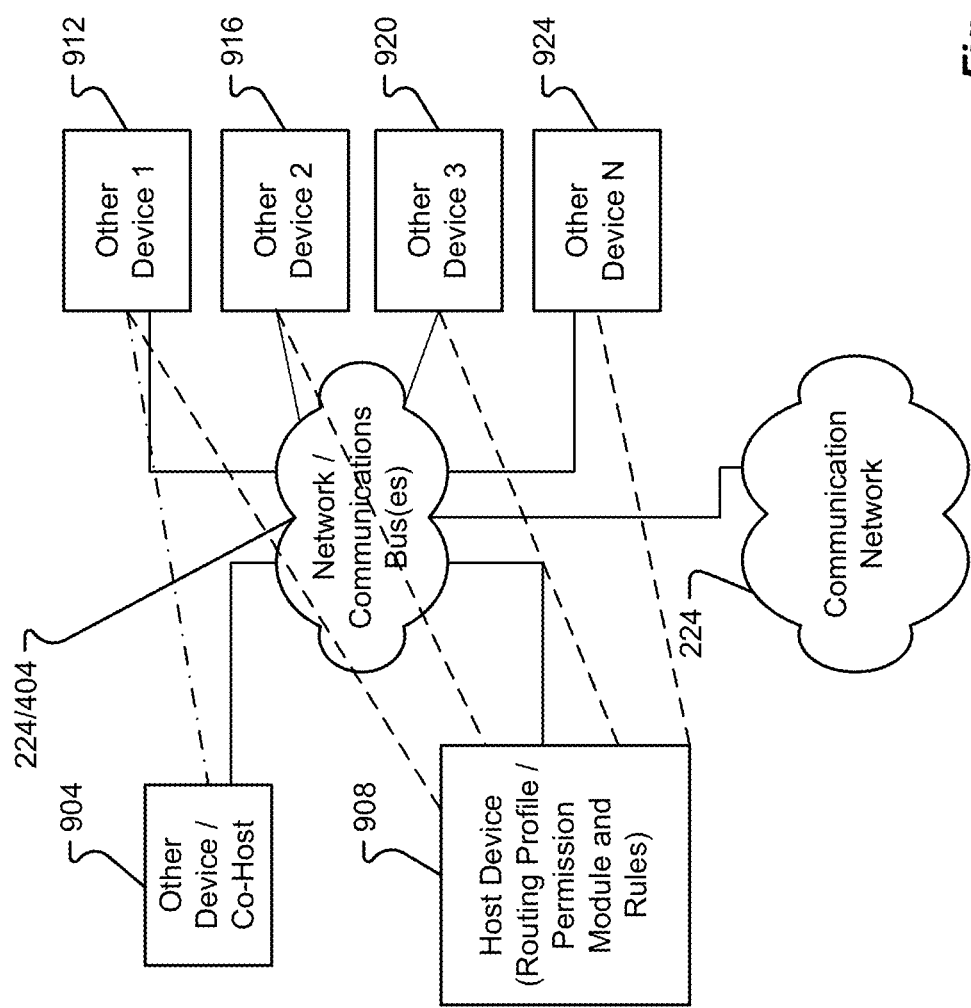
FIG. 9 is a block diagram of an embodiment of a communications subsystem for a vehicle.

FIG. 9 illustrates an optional communications architecture where, the host device 908 may include one more routing profiles, permission modules, and rules that control how communications within the vehicle 104 are to occur. This communications architecture can be used in conjunction with the routing tables, rules and permissions associated with access point 456 and optional firewall 484, or can be in lieu thereof. For example, the host device 908 acts as a mobile hot spot to one or more other devices within vehicle 104, such as, other device 1 912, other device 2 916, other device 3 920, and other device N 924. Optionally, one or more of the other devices 912 can communicate directly with the host device 908 which then provides Internet access to those devices 912 via the device 908. The host device 908 can act as a mobile hot spot for any one or more of the other devices 912, which may not need to communicate over the network/communications buses 224/404, but could instead connect directly to the host device 908 via, for example, NFC, Bluetooth®, WiFi, or the like. When the device 908 is acting as the host device, the device 908 can include one or more routing profiles, permissions, rules modules, and can also act as a firewall for the various inter and intra vehicle communications.

As will be appreciated, there could be alternative host devices, such as, host 904 which could also act as, for example, a co-host in association with device 908. Optionally, one or more of the routing profile, permission information, and rules could be shared between the co-host devices 904, 908, both of those devices being usable for Internet access for one or more of the other devices, 912-924. As will be appreciated, the other devices 912-924 need not necessarily connect to one or more of host device 908 and the other device 904 via a direct communications link, but could also interface with those devices 904, 908 utilizing the network/communications buses 224/404 associated with the vehicle 100. As previously discussed, one or more of the other devices can connect to the network/communications buses 224/404 utilizing the various networks and/or buses discussed herein which would therefore enable, for example, regulation of the various communications based on the Ethernet zone that the other device 912 is associated with.

An embodiment of one or more modules that may be associated with the vehicle control system 204 may be as shown in FIG. 10. The modules can include a communication subsystem interface 1008 in communication with an operating system 1004. The communications may pass through a firewall 1044. The firewall 1044 can be any software that can control the incoming and outgoing communications by analyzing the data packets and determining whether the packets should be allowed through the firewall, based on applied rule set. A firewall 1044 can establish a "barrier" between a trusted, secure internal network and another network (e.g., the Internet) that is not assumed to be secure and trusted.

In some situations, the firewall 1044 may establish security zones that are implemented by running system services and/or applications in restricted user groups and accounts. A set of configuration files and callbacks may then be linked to an IP table firewall. The IP table firewall can be configured to notify a custom filter application at any of the layers of the Ethernet packet. The different users/group rights to access the system may include: system users, which may have exclusive right over all device firewall rules and running software; a big-brother user, which may have access to on board device (OBD) control data and may be able to communicate with the vehicle subsystem 328 and may be able to alter the parameters in the vehicle control system 204; a dealer user, which can have rights to read OBD data for diagnostics and repairs; a dashboard user, which can have rights to launch dashboard applications and/or authenticate guest users and change their permissions to trusted/friend/family, and can read but cannot write into OBD diagnostic data; a world wide web (WWW) data user, which can have HTTP rights to respond to HTTP requests (the HTTP requests also can target different user data, but may be filtered by default user accounts); a guest user, which may have no rights; a family/friend user, which may have rights to play media from the media subsystem 348 and/or to stream media to the media subsystem 348.

The operating system 1004 can be a collection of software that manages computer hardware resources and provides common services for applications and other programs. The operating system 1004 may schedule time-sharing for efficient use of the system. For hardware functions, such as input, output, and memory allocation, the operating system 1004 can act as an intermediary between applications or programs and the computer hardware. Examples of operating systems that may be deployed as operating system 1004 include Android, BSD, iOS, Linux, OS X, QNX, Microsoft Windows, Windows Phone, IBM z/OS, etc.

The operating system 1004 can include one or more sub-modules. For example, a desktop manager 1012 can manage one or more graphical user interfaces (GUI) in a desktop environment. Desktop GUIs can help the user to easily access and edit files. A command-line interface (CLI) may be used if full control over the operating system (OS) 1004 is required. The desktop manager 1012 is described further hereinafter.

A kernel 1028 can be a computer program that manages input/output requests from software and translates them into data processing instructions for the processor 304 and other components of the vehicle control system 204. The kernel 1028 is the fundamental component of the operating system 1004 that can execute many of the functions associated with the OS 1004.

The kernel 1028 can include other software functions, including, but not limited to, driver(s) 1056, communication software 1052, and/or Internet Protocol software 1048. A driver 1056 can be any computer program that operates or controls a particular type of device that is attached to a vehicle control system 204. A driver 1056 can communicate with the device through the bus 356 or communications subsystem 1008 to which the hardware connects. When a calling program invokes a routine in the driver 1056, the driver 1056 may issue one or more commands to the device. Once the device sends data back to the driver 1056, the driver 1056 may invoke routines in the original calling program. Drivers can be hardware-dependent and operating-system-specific. Driver(s) 1056 can provide the interrupt handling required for any necessary asynchronous time-dependent hardware interface.

The IP module 1048 can conduct any IP addressing, which may include the assignment of IP addresses and associated parameters to host interfaces. The address space may include networks and sub-networks. The IP module 1048 can perform the designation of network or routing prefixes and may conduct IP routing, which transports packets across network boundaries. Thus, the IP module 1048 may perform all functions required for IP multicast operations.

The communications module 1052 may conduct all functions for communicating over other systems or using other protocols not serviced by the IP module 1048. Thus, the communications module 1052 can manage multicast operations over other busses or networks not serviced by the IP module 1048. Further, the communications module 1052 may perform or manage communications to one or more devices, systems, data stores, services, etc. that are in communication with the vehicle control system 204 or other subsystems through the firewall 1044. Thus, the communications module 1052 can conduct communications through the communication subsystem interface 1008.

A file system 1016 may be any data handling software that can control how data is stored and retrieved. The file system 1016 can separate the stored data into individual pieces, and giving each piece a name, can easily separate and identify the pieces of data. Each piece of data may be considered a "file". The file system 1016 can construct data structure and logic rules used to manage the information and the identifiers for the information. The structure and logic rules can be considered a "file system."

A device discovery daemon 1020 may be a computer program that runs as a background process that can discover new devices that connect with the network 356 or communication subsystem 1008 or devices that disconnect from the network 356 or communication subsystem 1008. The device discovery daemon 1020 can ping the network 356 (the local subnet) when the vehicle 104 starts, when a vehicle door opens or closes, or upon the occurrence of other events. Additionally or alternatively, the device discovery daemon 1020 may force Bluetooth®, USB, and/or wireless detection. For each device that responds to the ping, the device discovery daemon 1020 can populate the system data 208 with device information and capabilities, using any of one or more protocols, including one or more of, but not limited to, IPv6 Hop-by-Hop Option (HOPOPT), Internet Control Message Protocol (ICMP), Internet Group Management Protocol (IGMP), Gateway-to-Gateway Protocol (GGP), Internet Protocol (IP), Internet Stream Protocol (ST), Transmission Control Protocol (TCP), Exterior Gateway Protocol (EGP), CHAOS, User Datagram Protocol (UDP), etc.

For example, the device discovery daemon 1020 can determine device capabilities based on the opened ports the device exposes. If a camera exposes port 80, then the device discovery daemon 1020 can determine that the camera is using a Hypertext Transfer Protocol (HTTP). Alternatively, if a device is supporting Universal Plug and Play (UPnP), the system data 208 can include more information, for example, a camera control universal resource locator (URL), a camera zoom URL, etc. When a scan stops, the device discovery daemon 1020 can trigger a dashboard refresh to ensure the user interface reflects the new devices on the desktop.

A desktop manager 1012 may be a computer program that manages the user interface of the vehicle control system 204. The desktop environment may be designed to be customizable and allow the definition of the desktop configuration look-and-feel for a wide range of appliances or devices from computer desktops, mobile devices, computer tablets, etc. Launcher(s), panels, desktop areas, the desktop background, notifications, panes, etc., can be configured from a dashboard configuration file managed by the desktop manager 1012. The graphical elements in which the desktop manager 1012 controls can include launchers, the desktop, notification bars, etc.

The desktop may be an area of the display where the applications are running. The desktop can have a custom background. Further, the desktop may be divided into two or more areas. For example, the desktop may be divided into an upper half of a display and a lower half of the display. Each application can be configured to run in a portion of the desktop. Extended settings can be added to the desktop configuration file, such that, some objects may be displayed over the whole desktop or in custom size out of the context of the divided areas.

The notification bar may be a part of a bar display system, which may provide notifications by displaying, for example, icons and/or pop-up windows that may be associated with sound notifications. The notification mechanism can be designed for separate plug-ins, which run in separate processes and may subscribe to a system Intelligent Input Bus (IBUS)/D-BUS event service. The icons on the notifications bar can be accompanied with application short-cuts to associated applications, for example, a Bluetooth® manager, a USB manager, radio volume and or tone control, a security firewall, etc.

The desktop manager 1012 may include a windows manager 1032, an application launcher 1036, and/or a panel launcher 1040. Each of these components can control a different aspect of the user interface. The desktop manager 1012 can use a root window to create panels that can include functionality for one or more of, but not limited to: launching applications, managing applications, providing notifications, etc.

The windows manager 1032 may be software that controls the placement and appearance of windows within a graphical user interface presented to the user. Generally, the windows manager 1032 can provide the desktop environment used by the vehicle control system 204. The windows manager 1032 can communicate with the kernel 1028 to interface with the graphical system that provides the user interface(s) and supports the graphics hardware, pointing devices, keyboard, touch-sensitive screens, etc. The windows manager 1032 may be a tiling window manager (i.e., a window manager with an organization of the screen into mutually non-overlapping frames, as opposed to a coordinate-based stacking of overlapping objects (windows) that attempts to fully emulate the desktop metaphor). The windows manager 1032 may read and store configuration files, in the system data 208, which can control the position of the application windows at precise positions.

An application manager 1036 can control the function of any application over the lifetime of the process. The process or application can be launched from a panel launcher 1040 or from a remote console. The application manager 1036 can intercept the process name and may take appropriate action to manage that process. If the process is not running, the application manager 1036 can load the process and may bring the process to a foreground in a display. The application manager 1036 may also notify the windows manager 1032 to bring the associated window(s) to a top of a window stack for the display. When a process starts from a shell or a notification out of the context of the desktop, the application manager 1036 can scan files to match the process name with the entry name provided. When a match is found, the application manager 1036 can configure the process according to a settings file.

In some situations, the application manager 1036 may restrict an application as singleton (i.e., restricts the instantiation of a class to one object). If an application is already running and the application manager 1036 is asked to run the application again, the application manager 1036 can bring the running process to a foreground on a display. There can be a notification event exchange between the windows manager 1032 and the application manager 1036 for activating the appropriate window for the foreground process. Once an application is launched, the application may not be terminated or killed. The application can be sent to the background, except, possibly, for some applications (e.g., media player, Bluetooth®, notifications, etc.), which may be given a lowest process priority.

The panel launcher 1040 can be a widget configured to be placed along a portion of the display. The panel launcher 1040 may be built from desktop files from a desktop folder. The desktop folder location can be configured by a configuration file stored in system data 208. The panel launcher 1040 can allow for the launching or executing of applications or processes by receiving inputs from a user interface to launch programs.

A desktop plugin 1024 may be a software component that allows for customization of the desktop or software interface through the initiation of plug-in applications.

One or more gestures used to interface with the vehicle control system 204 may be as described in conjunction with FIG. 11A through 11K. FIGS. 11A through 11H depict various graphical representations of gesture inputs that may be recognized by the devices 212, 248. The gestures may be performed not only by a user's body part, such as a digit, but also by other devices, such as a stylus, that may be sensed by the contact sensing portion(s) of a screen associated with the device 212, 248. In general, gestures are interpreted differently, based on where the gestures are performed (either directly on a display or in a gesture capture region). For example, gestures in a display may be directed to a desktop or application, and gestures in a gesture capture region may be interpreted as for the system.

With reference to FIGS. 11A-11H, a first type of gesture, a touch gesture 1120, is substantially stationary on a portion (e.g., a screen, a display, etc.) of a device 212, 248 for a selected length of time. A circle 1128 represents a touch or other contact type received at particular location of a contact sensing portion of the screen. The circle 1128 may include a border 1132, the thickness of which indicates a length of time that the contact is held substantially stationary at the contact location. For instance, a tap 1120 (or short press) has a thinner border 1132A than the border 1132B for a long press 1124 (or for a normal press). The long press 1124 may involve a contact that remains substantially stationary on the screen for longer time period than that of a tap 1120. As will be appreciated, differently defined gestures may be registered depending upon the length of time that the touch remains stationary prior to contact cessation or movement on the screen.

Figure 11A:
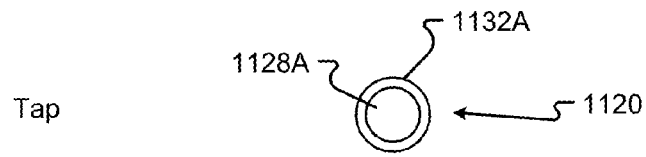
FIG. 11A is a graphical representation of an embodiment of a gesture that a user may perform to provide input to a vehicle control system.
Figure 11B:
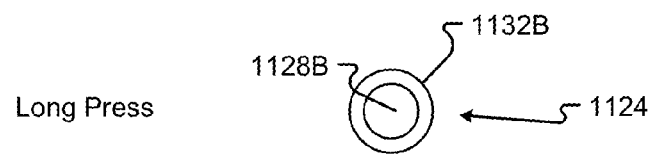
FIG. 11B is a graphical representation of an embodiment of a gesture that a user may perform to provide input to a vehicle control system.
Figure 11C:
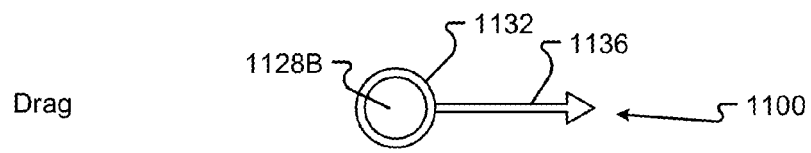
FIG. 11C is a graphical representation of an embodiment of a gesture that a user may perform to provide input to a vehicle control system.

With reference to FIG. 11C, a drag gesture 1100 on the screen is an initial contact (represented by circle 1128) with contact movement 1136 in a selected direction. The initial contact 1128 may remain stationary on the screen for a certain amount of time represented by the border 1132. The drag gesture typically requires the user to contact an icon, window, or other displayed image at a first location followed by movement of the contact in a drag direction to a new second location desired for the selected displayed image. The contact movement need not be in a straight line but have any path of movement so long as the contact is substantially continuous from the first to the second locations.

Figure 11D:
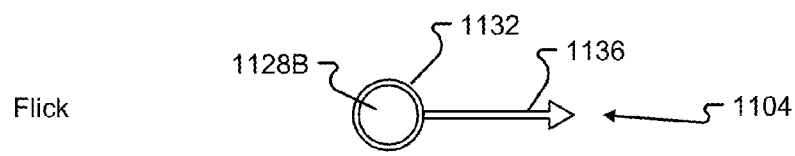
FIG. 11D is a graphical representation of an embodiment of a gesture that a user may perform to provide input to a vehicle control system.

With reference to FIG. 11D, a flick gesture 1104 on the screen is an initial contact (represented by circle 1128) with truncated contact movement 1136 (relative to a drag gesture) in a selected direction. A flick may have a higher exit velocity for the last movement in the gesture compared to the drag gesture. The flick gesture can, for instance, be a finger snap following initial contact. Compared to a drag gesture, a flick gesture generally does not require continual contact with the screen from the first location of a displayed image to a predetermined second location. The contacted displayed image is moved by the flick gesture in the direction of the flick gesture to the predetermined second location. Although both gestures commonly can move a displayed image from a first location to a second location, the temporal duration and distance of travel of the contact on the screen is generally less for a flick than for a drag gesture.

Figure 11E:
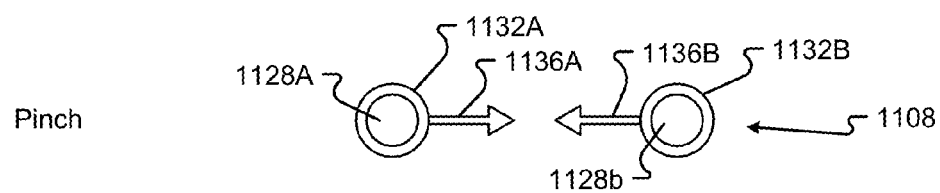
FIG. 11E is a graphical representation of an embodiment of a gesture that a user may perform to provide input to a vehicle control system.

With reference to FIG. 11E, a pinch gesture 1108 on the screen is depicted. The pinch gesture 1108 may be initiated by a first contact 1128A to the screen by, for example, a first digit and a second contact 1128B to the screen by, for example, a second digit. The first and second contacts 1128A,B may be detected by a common contact sensing portion of a common screen, by different contact sensing portions of a common screen, or by different contact sensing portions of different screens. The first contact 1128A is held for a first amount of time, as represented by the border 1132A, and the second contact 1128B is held for a second amount of time, as represented by the border 1132B. The first and second amounts of time are generally substantially the same, and the first and second contacts 1128A,B generally occur substantially simultaneously. The first and second contacts 1128A,B generally also include corresponding first and second contact movements 1136A,B, respectively. The first and second contact movements 1136A,B are generally in opposing directions. Stated another way, the first contact movement 1136A is towards the second contact 1136B, and the second contact movement 1136B is towards the first contact 1136A. More simply stated, the pinch gesture 1108 may be accomplished by a user's digits touching the screen in a pinching motion.

Figure 11F:
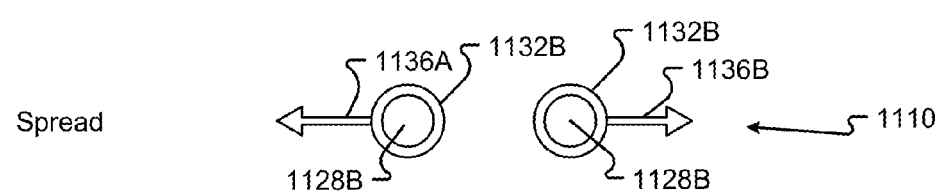
FIG. 11F is a graphical representation of an embodiment of a gesture that a user may perform to provide input to a vehicle control system.

With reference to FIG. 11F, a spread gesture 1110 on the screen is depicted. The spread gesture 1110 may be initiated by a first contact 1128A to the screen by, for example, a first digit, and a second contact 1128B to the screen by, for example, a second digit. The first and second contacts 1128A,B may be detected by a common contact sensing portion of a common screen, by different contact sensing portions of a common screen, or by different contact sensing portions of different screens. The first contact 1128A is held for a first amount of time, as represented by the border 1132A, and the second contact 1128B is held for a second amount of time, as represented by the border 1132B. The first and second amounts of time are generally substantially the same, and the first and second contacts 1128A,B generally occur substantially simultaneously. The first and second contacts 1128A,B generally also include corresponding first and second contact movements 1136A,B, respectively. The first and second contact movements 1136A,B are generally in an opposing direction. Stated another way, the first and second contact movements 1136A,B are away from the first and second contacts 1128A,B. More simply stated, the spread gesture 1110 may be accomplished by a user's digits touching the screen in a spreading motion.

Figure 11G:
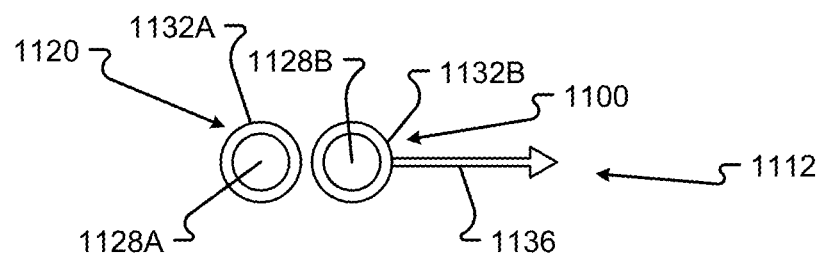
FIG. 11G is a graphical representation of an embodiment of a gesture that a user may perform to provide input to a vehicle control system.
Figure 11H:
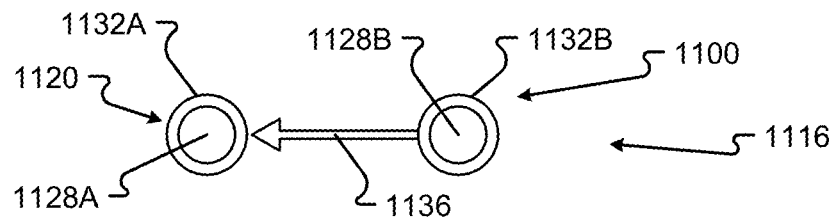
FIG. 11H is a graphical representation of an embodiment of a gesture that a user may perform to provide input to a vehicle control system.

The above gestures may be combined in any manner, such as those shown by FIGS. 11G and 11H, to produce a determined functional result. For example, in FIG. 11G a tap gesture 1120 is combined with a drag or flick gesture 1112 in a direction away from the tap gesture 1120. In FIG. 11H, a tap gesture 1120 is combined with a drag or flick gesture 1116 in a direction towards the tap gesture 1120.

The functional result of receiving a gesture can vary depending on a number of factors, including a state of the vehicle 104, display, or screen of a device, a context associated with the gesture, or sensed location of the gesture, etc. The state of the vehicle 104 commonly refers to one or more of a configuration of the vehicle 104, a display orientation, and user and other inputs received by the vehicle 104. Context commonly refers to one or more of the particular application(s) selected by the gesture and the portion(s) of the application currently executing, whether the application is a single- or multi-screen application, and whether the application is a multi-screen application displaying one or more windows. A sensed location of the gesture commonly refers to whether the sensed set(s) of gesture location coordinates are on a touch sensitive display or a gesture capture region of a device 212, 248, whether the sensed set(s) of gesture location coordinates are associated with a common or different display, or screen, or device 212, 248, and/or what portion of the gesture capture region contains the sensed set(s) of gesture location coordinates.

A tap, when received by a touch sensitive display of a device 212, 248, can be used, for instance, to select an icon to initiate or terminate execution of a corresponding application, to maximize or minimize a window, to reorder windows in a stack, and/or to provide user input such as by keyboard display or other displayed image. A drag, when received by a touch sensitive display of a device 212, 248, can be used, for instance, to relocate an icon or window to a desired location within a display, to reorder a stack on a display, or to span both displays (such that the selected window occupies a portion of each display simultaneously). A flick, when received by a touch sensitive display of a device 212, 248 or a gesture capture region, can be used to relocate a window from a first display to a second display or to span both displays (such that the selected window occupies a portion of each display simultaneously). Unlike the drag gesture, however, the flick gesture is generally not used to move the displayed image to a specific user-selected location but to a default location that is not configurable by the user.

The pinch gesture, when received by a touch sensitive display or a gesture capture region of a device 212, 248, can be used to minimize or otherwise increase the displayed area or size of a window (typically when received entirely by a common display), to switch windows displayed at the top of the stack on each display to the top of the stack of the other display (typically when received by different displays or screens), or to display an application manager (a "pop-up window" that displays the windows in the stack). The spread gesture, when received by a touch sensitive display or a gesture capture region of a device 212, 248, can be used to maximize or otherwise decrease the displayed area or size of a window, to switch windows displayed at the top of the stack on each display to the top of the stack of the other display (typically when received by different displays or screens), or to display an application manager (typically when received by an off-screen gesture capture region on the same or different screens).

The combined gestures of FIG. 11G, when received by a common display capture region in a common display or screen of a device 212, 248, can be used to hold a first window location constant for a display receiving the gesture while reordering a second window location to include a window in the display receiving the gesture. The combined gestures of FIG. 11H, when received by different display capture regions in a common display or screen of a device 212, 248 or in different displays or screens of one more devices 212, 248, can be used to hold a first window location for a display receiving the tap part of the gesture while reordering a second window location to include a window in the display receiving the flick or drag gesture. Although specific gestures and gesture capture regions in the preceding examples have been associated with corresponding sets of functional results, it is to be appreciated that these associations can be redefined in any manner to produce differing associations between gestures and/or gesture capture regions and/or functional results.

Figure 11I:
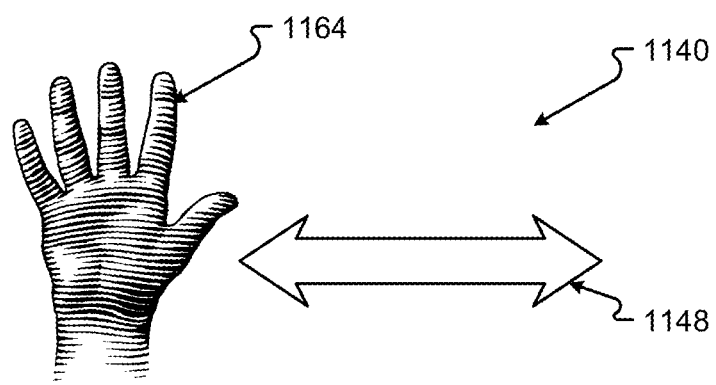
FIG. 11I is a graphical representation of an embodiment of a gesture that a user may perform to provide input to a vehicle control system.
Figure 11J:
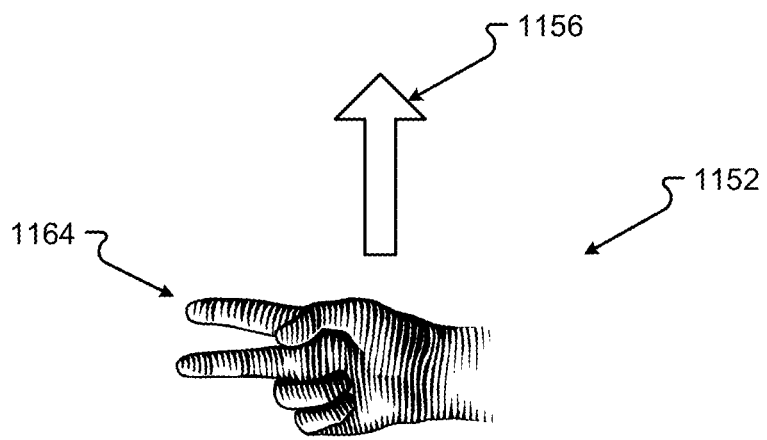
FIG. 11J is a graphical representation of an embodiment of a gesture that a user may perform to provide input to a vehicle control system.
Figure 11K:
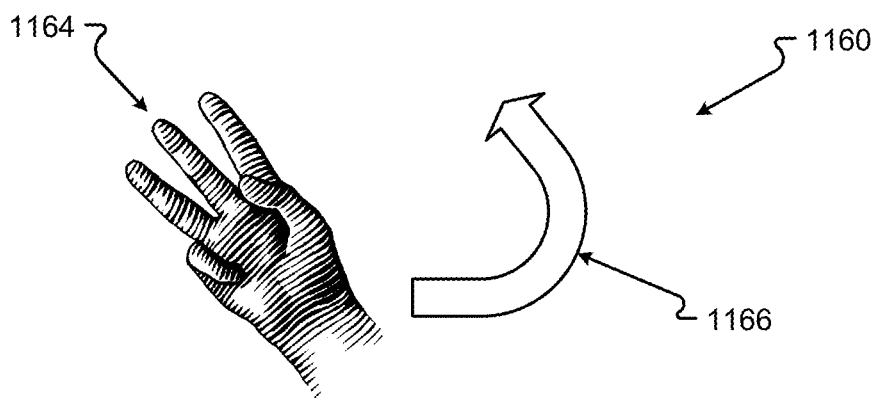
FIG. 11K is a graphical representation of an embodiment of a gesture that a user may perform to provide input to a vehicle control system.

Gestures that may be completed in three-dimensional space and not on a touch sensitive screen or gesture capture region of a device 212, 248 may be as shown in FIGS. 11I-11K. The gestures may be completed in an area where a sensor, such as an optical sensor, infrared sensor, or other type of sensor, may detect the gesture. For example, the gesture 1140 in FIG. 11I may be executed by a person when the person opens their hand 1164 and moves their hand in a back and forth direction 1148 as a gesture 1140 to complete some function with the vehicle 104. For example gesture 1140 may change the station of the radio in the vehicle 104. The sensors 242 may both determine the configuration of the hand 1164 and the vector of the movement. The vector and hand configuration can be interpreted to mean certain things to the vehicle control system 204 and produce different results.

In another example of a gesture 1152 in FIG. 11J, a user may configure their hand 1164 to extend two fingers and move the hand 1164 in an up and down operation 1156. This gesture 1152 may control the volume of the radio or some other function. For instance, this gesture 1152 may be configured to place the vehicle in a "valet" mode to, among other things, restrict access to certain features associated with the vehicle. Again, the sensors 242 may determine how the person has configured their hand 1164, and the vector of the movement. In another example of a gesture 1160 shown in FIG. 11K, a user may extend their middle three fingers at an angle that is substantially 45° for vertical from straight vertical and circle the hand in a counter-clockwise motion 1166. This gesture 1160 may cause the automobile to change the heat setting or do some other function. As can be understood by one skilled in the art, the configurations of the hand and the types of movement are variable. Thus, the user may configure the hand 1164 in any way imaginable and may also move that hand 1164 in any direction with any vector in three-dimensional space.

The gestures 1140, 1152, 1160, as shown in FIGS. 11I-11K, may occur in a predetermined volume of space within the vehicle 104. For example, a sensor may be configured to identify such gestures 1140, 1152, 1160 between the front passenger's and front driver's seats over a console area within the passenger compartment of the vehicle 104. The gestures 1140, 1152, 1160 may be made within area 1 508A between zones A 512A and B 512B. However, there may be other areas 508 where a user may use certain gestures, where sensors 242 may be able to determine a certain function is desired. Gestures that may be similar but used in different areas within the vehicle 104 may cause different functions to be performed. For example, the gesture 1140 in FIG. 11I, if used in zone E 512E, may change the heat provided in zone E 512E, but may change the station of a radio if used in zone A 512A and/or zone B 512B. Further, the gestures may be made with other body parts or, for example, different expressions of a person's face and may be used to control functions in the vehicle 104. Also, the user may use two hands in some circumstances or do other types of physical movements that can cause different reactions in the vehicle 104.

FIGS. 12A-12D show various embodiments of a data structure 1200 to store different settings. The data structure 1200 may include one or more of data files or data objects 1204, 1250, 1270, 1280. Thus, the data structure 1200 may represent different types of databases or data storage, for example, object-oriented data bases, flat file data structures, relational database, or other types of data storage arrangements. Embodiments of the data structure 1200 disclosed herein may be separate, combined, and/or distributed. As indicated in FIGS. 12A-12D, there may be more or fewer portions in the data structure 1200, as represented by ellipses 1244. Further, there may be more or fewer files in the data structure 1200, as represented by ellipses 1248.

Figure 12A:
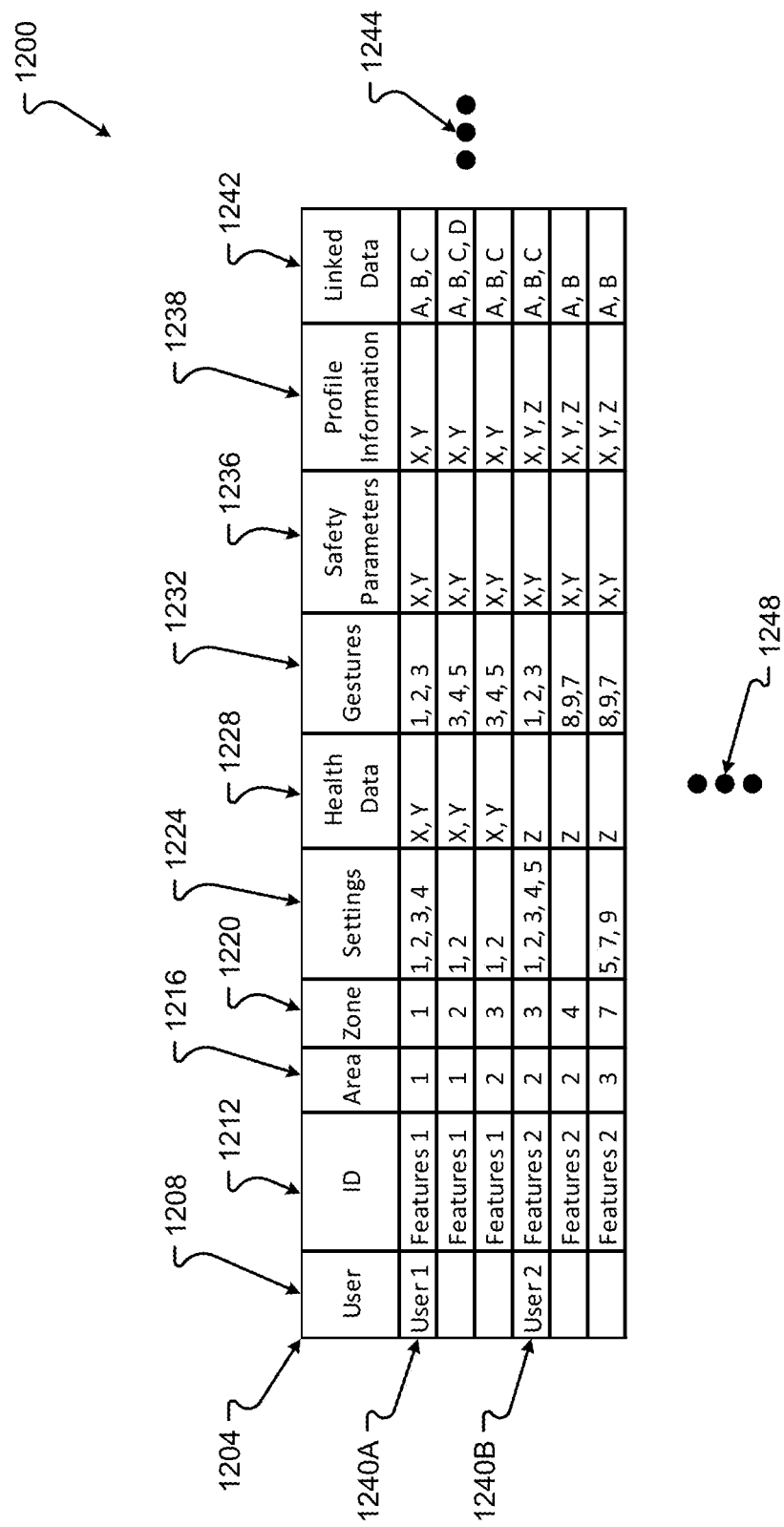
FIG. 12A is a diagram of an embodiment of a data structure for storing information about a user of a vehicle.

Referring to FIG. 12A, a first data structure is shown. The data file 1204 may include several portions 1208-1242 representing different types of data. Each of these types of data may be associated with a user, as shown in portion 1208.

There may be one or more user records 1240 and associated data stored within the data file 1204. As provided herein, the user can be any person that uses or rides within the vehicle or conveyance 104. The user may be identified in portion 1212. For the vehicle 104, the user may include a set of one or more features that may identify the user. These features may be the physical characteristics of the person that may be identified by facial recognition or some other type of system. In other situations, the user may provide a unique code to the vehicle control system 204 or provide some other type of data that allows the vehicle control system 204 to identify the user. The features or characteristics of the user are then stored in portion 1212.

Each user, identified in portion 1208, may have a different set of settings for each area 508 and/or each zone 512 within the vehicle 104. Thus, each set of settings may also be associated with a predetermined zone 512 or area 508. The zone 512 is stored in portion 1220, and the area 508 is stored in portion 1216.

One or more settings may be stored in portion 1224. These settings 1224 may be the configurations of different functions within the vehicle 104 that are specified by or for that user. For example, the settings 1224 may be the position of a seat, the position of a steering wheel, the position of accelerator and/or brake pedals, positions of mirrors, a heating/cooling setting, a radio setting, a cruise control setting, or some other type of setting associated with the vehicle 104. Further, in vehicles adapted to have a configurable console or a configurable dash or heads-up display, the settings 1224 may also provide for how that heads-up display, dash, or console are configured for this particular user.

Each setting 1224 may be associated with a different area 508 or zone 512. Thus, there may be more settings 1224 for when the user is the driver and in zone A 512A, 512A, of area 1, 508A. However, there may be similar settings 1224 among the different zones 512 or areas 508 as shown in portion 1224. For example, the heating or radio settings for the user may be similar in every zone 512.

The sensors 242 within the vehicle 104 may be able to either obtain or track health data in portion 1228. Health data 1228 may include any type of physical characteristic associated with the user. For example, a heart rate, a blood pressure, a temperature, or other types of heath data may be obtained and stored in portion 1228. The user may have this health data tracked over a period of time to allow for statistical analysis of the user's health while operating the vehicle 104. In this way, if some function of the user's health deviates from a norm (e.g., a baseline measurement, average measurements taken over time, and the like), the vehicle 104 may be able to determine there is a problem with the person and react to that data.

One or more gestures may be stored in portion 1232. Thus, the gestures used and described in conjunction FIG. 11A through 11K may be configurable. These gestures may be determined or created by the user and stored in portion 1132. A user may have different gestures for each zone 512 or area 508 within the vehicle. The gestures that do certain things while driving may do other things while in a different area 508 of the vehicle 104. Thus, the user may use a first set of gestures while driving and a second set while a passenger. Further, one or more users may share gestures as shown in portion 1232. Each driver may have a common set of gestures that they use in zone A 512A, 512A. Each of these gestures may be determined or captured and then stored with their characteristics (e.g., vector, position of gesture, etc.) in portion 1232.

One or more sets of safety parameters may be stored in portion 1236. Safety parameters 1236 may be common operating characteristics for this driver/passenger or for all drivers/passengers that if deviated from may determine there is a problem with the driver/passenger or the vehicle 104. For example, a certain route may be taken repeatedly and an average speed or mean speed may be determined. If the mean speed deviates by some number of standard deviations, a problem with the vehicle 104 or the user may be determined. In another example, the health characteristics or driving experience of the user may be determined. If the user drives in a certain position where their head occupies a certain portion of three-dimensional space within the vehicle 104, the vehicle control system 204 may determine that the safety parameter includes the users face or head being within this certain portion of the vehicle interior space. If the user's head deviates from that interior space for some amount of time, the vehicle control system 204 can determine that something is wrong with the driver and change the function or operation of the vehicle 104 to assist the driver. This may happen, for example, when a user falls asleep at the wheel. If the user's head droops and no longer occupies a certain three dimensional space, the vehicle control system 204 can determine that the driver has fallen asleep and may take control of the operation of the vehicle 204 and the automobile controller 8104 may steer the vehicle 204 to the side of the road. In other examples, if the user's reaction time is too slow or some other safety parameter is not nominal, the vehicle control system 204 may determine that the user is inebriated or having some other medical problem. The vehicle control system 204 may then assume control of the vehicle to ensure that the driver is safe.

Information corresponding to a user and/or a user profile may be stored in the profile information portion 1238. For example, the profile information 1238 may include data relating to at least one of current data, historical data, a user preference, user habit, user routine, observation, location data (e.g., programmed and/or requested destinations, locations of parking, routes traveled, average driving time, etc.), social media connections, contacts, brand recognition (e.g., determined via one or more sensors associated with the vehicle 104, a device 212, 248, etc.), audible recording data, text data, email data, political affiliation, preferred retail locations/sites (e.g., physical locations, web-based locations, etc.), recent purchases, behavior associated with the aforementioned data, and the like. The data in the profile information portion 1238 may be stored in one or more of the data structures 1200 provided herein. As can be appreciated, these one or more data structures may be stored in one or more memory locations. Examples of various memory locations are described in conjunction with FIG. 2.

One or more additional data fields may be stored in the linked data portion 1242 as data and/or locations of data. The linked data 1242 may include at least one of pointers, addresses, location identification, data source information, and other information corresponding to additional data associated with the data structure 1200. Optionally, the linked data portion 1242 may refer to data stored outside of a particular data structure 1200. For example, the linked data portion 1242 may include a link/locator to the external data. Continuing this example, the link/locator may be resolved (e.g., via one or more of the methods and/or systems provided herein, etc.) to access the data stored outside of the data structure 1200. Additionally or alternatively, the linked data portion 1242 may include information configured to link the data objects 1204 to other data files or data objects 1250, 1270, 1280. For instance, the data object 1204 relating to a user may be linked to at least one of a device data object 1250, a vehicle system data object 1270, and a vehicle data object 1280, to name a few.

Figure 12B:
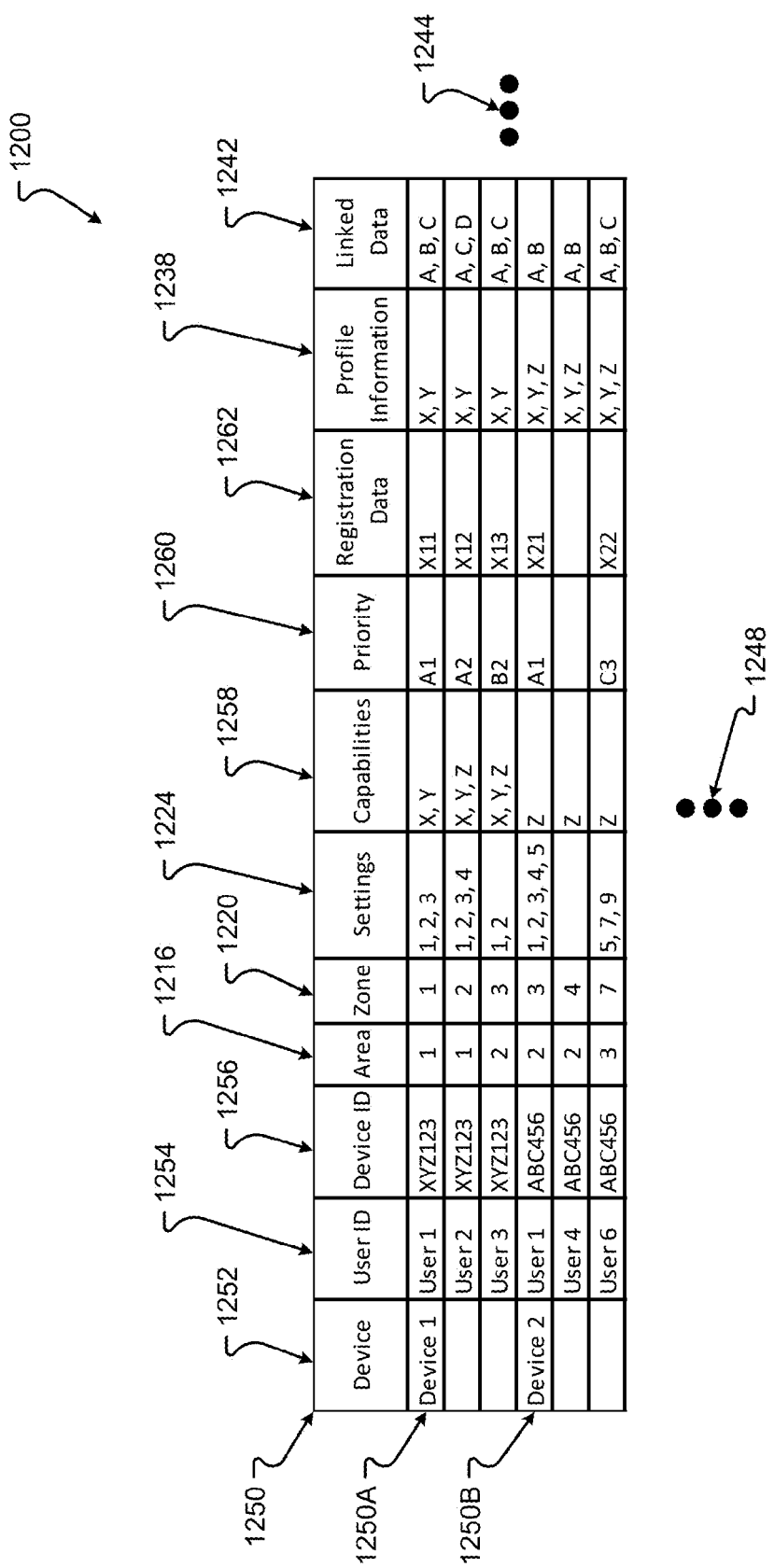
FIG. 12B is a diagram of an embodiment of a data structure for storing information about a device associated with or in a vehicle.

An embodiment of a data structure 1200 to store information associated with one or more devices is shown in FIG. 12B. The data file 1250 may include several portions 1216-1262 representing different types of data. Each of these types of data may be associated with a device, as shown in portion 1252.

There may be one or more device records 1250 and associated data stored within the data file 1250. As provided herein, the device may be any device that is associated with the vehicle 104. For example, a device may be associated with a vehicle 104 when that device is physically located within the interior space 108 of the vehicle 104. As another example, a device may be associated with a vehicle 104 when the device registers with the vehicle 104. Registration may include pairing the device with the vehicle 104 and/or one or more of the vehicle systems (e.g., as provided in FIG. 3). In some cases, the registration of a device with a vehicle 104 may be performed manually and/or automatically. An example of automatic registration may include detecting, via one or more of the vehicle systems, that a device is inside the vehicle 104. Upon detecting that the device is inside the vehicle 104, the vehicle system may identify the device and determine whether the device is or should be registered. Registration may be performed outside of a vehicle 104 via providing a unique code to the vehicle 104 and/or at least one of the vehicle systems.

The device may be identified in portion 1256. Among other things, the device identification may be based on the hardware associated with the device (e.g., Media Access Control (MAC) address, Burned-In Address (BIA), Ethernet Hardware Address (EHA), physical address, hardware address, and the like).

Optionally, a device may be associated with one or more users. For example, a tablet and/or graphical user interface (GUI) associated with the vehicle 104 may be used by multiple members of a family. For instance, the GUI may be located in a particular area 508 and/or zone 512 of the vehicle 104. Continuing this example, when a family member is located in the particular area 508 and/or zone 512, the device may include various settings, features, priorities, capabilities, and the like, based on an identification of the family member. The user may be identified in portion 1254. For the device, the user identification portion 1254 may include a set of one or more features that may identify a particular user. These features may be the physical characteristics of the person that may be identified by facial recognition, or some other type of system, associated with the device and/or the vehicle 104. Optionally, the user may provide a unique code to the device, or provide some other type of data, that allows the device to identify the user. The features or characteristics of the user are then stored in portion 1254.

Each device identified in the device identification portion 1256 may have a different set of settings for each area 508 and/or each zone 512, and/or each user of the device. Thus, each set of settings may also be associated with a predetermined zone 512, area 508, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a device is configured for a particular user. Each setting 1224 may be associated with a different area 508 or zone 512. Thus, there may be more restrictive settings 1224 (e.g., restricted multimedia, texting, limited access to device functions, and the like) for the device when the user is the driver and in zone A 512A, 512A, of area 1, 508A. However, when the user is in another zone 512 or area 508, for example, where the user is not operating a vehicle 104, the settings 1224 may provide unrestricted access to one or more features of the device (e.g., allowing texting, multimedia, etc.).

Optionally, the capabilities of a device may be stored in portion 1258. Examples of device capabilities may include, but are not limited to, a communications ability (e.g., via wireless network, EDGE, 3G, 4G, LTE, wired, Bluetooth®, Near Field Communications (NFC), Infrared (IR), etc.), hardware associated with the device (e.g., cameras, gyroscopes, accelerometers, touch interface, processor, memory, display, etc.), software (e.g., installed, available, revision, release date, etc.), firmware (e.g., type, revision, etc.), operating system, system status, and the like. Optionally, the various capabilities associated with a device may be controlled by one or more of the vehicle systems provided herein. Among other things, this control allows the vehicle 104 to leverage the power and features of various devices to collect, transmit, and/or receive data.

One or more priorities may be stored in portion 1260. The priority may correspond to a value, or combination of values, configured to determine how a device interacts with the vehicle 104 and/or its various systems. The priority may be based on a location of the device (e.g., as stored in portions 1216, 1220). A default priority can be associated with each area 508 and/or zone 512 of a vehicle 104. For example, the default priority associated with a device found in zone 1 512A of area 1 508A (e.g., a vehicle operator position) may be set higher than an (or the highest of any) alternative zone 512 or area 508 of the vehicle 104. Continuing this example, the vehicle 104 may determine that, although other devices are found in the vehicle, the device, having the highest priority, controls features associated with the vehicle 104. These features may include vehicle control features, critical and/or non-critical systems, communications, and the like. Additionally or alternatively, the priority may be based on a particular user associated with the device. Optionally, the priority may be used to determine which device will control a particular signal in the event of a conflict.

Registration data may be stored in portion 1262. As described above, when a particular device registers with a vehicle 104, data related to the registration may be stored in the registration data portion 1262. Such data may include, but is not limited to, registration information, registration codes, initial registration time, expiration of registration, registration timers, and the like. Optionally, one or more systems of the vehicle 104 may refer to the registration data portion 1262 to determine whether a device has been previously registered with the vehicle 104. As shown in FIG. 12B, User 4 of Device 2 has not been registered. In this case, the registration data field 1262, for this user, may be empty, contain a null value, or other information/indication that there is no current registration information associated with the user.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 12C:
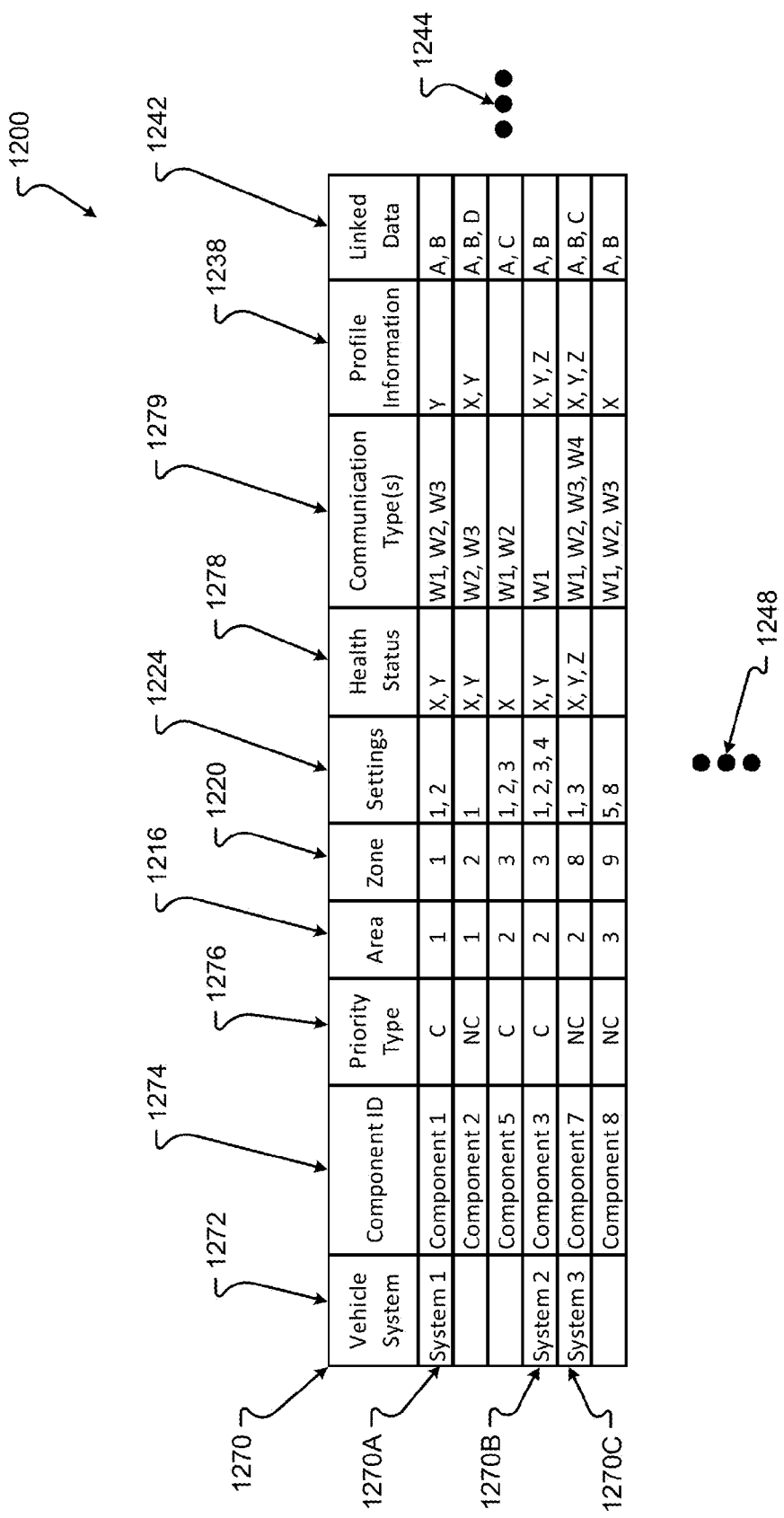
FIG. 12C is a diagram of an embodiment of a data structure for storing information about a system of a vehicle.

An embodiment of a data structure 1200 to store information associated with one or more vehicle systems is shown in FIG. 12C. The data file 1270 may include several portions 1216-1279 representing different types of data. Each of these types of data may be associated with a vehicle system, as shown in portion 1272.

There may be one or more system records 1270 and associated data stored within the data file 1270. As provided herein, the vehicle systems may be any system and/or subsystem that is associated with the vehicle 104. Examples of various systems are described in conjunction with FIG. 3 and other related figures (e.g., systems 324-352, etc.). One example of a system associated with the vehicle 104 is the vehicle control system 204. Other systems may include communications subsystems 344, vehicle subsystems 328, and media subsystems 348, to name a few. It should be appreciated that the various systems may be associated with the interior space 108 and/or the exterior of the vehicle 104.

Each system may include one or more components. The components may be identified in portion 1274. Identification of the one or more components may be based on hardware associated with the component. This identification may include hardware addresses similar to those described in conjunction with the devices of FIG. 12B. Additionally or alternatively, a component can be identified by one or more signals sent via the component. Such signals may include an Internet Protocol (IP), or similar, address as part of the signal. Optionally, the signal may identify the component sending the signal via one or more of a header, a footer, a payload, and/or an identifier associated with the signal (e.g., a packet of a signal, etc.).

Each system and/or component may include priority type information in portion 1276. Among other things, the priority type information stored in portion 1276 may be used by the various methods and systems provided herein to differentiate between critical and non-critical systems. Non-limiting examples of critical systems may correspond to those systems used to control the vehicle 104, such as, steering control, engine control, throttle control, braking control, and/or navigation informational control (e.g., speed measurement, fuel measurement, etc.) Non-critical systems may include other systems that are not directly related to the control of the vehicle 104. By way of example, non-critical systems may include media presentation, wireless communications, comfort settings systems (e.g., climate control, seat position, seat warmers, etc.), and the like. Although examples of critical and/or non-critical systems are provided above, it should be appreciated that the priority type of a system may change (e.g., from critical to non-critical, from non-critical to critical, etc.) depending on the scenario. For instance, although the interior climate control system may be classified as a non-critical system at a first point in time, it may be subsequently classified as a critical system when a temperature inside/outside of the vehicle 104 is measured at a dangerous level (e.g., sub-zero Fahrenheit, greater than 90-degrees Fahrenheit, etc.). As such, the priority type may be associated with temperature conditions, air quality, times of the day, condition of the vehicle 104, and the like.

Each system may be associated with a particular area 508 and/or zone 512 of a vehicle 104. Among other things, the location of a system may be used to assess a state of the system and/or provide how the system interacts with one or more users of the vehicle 104. As can be appreciated each system may have a different set of settings for each area 508 and/or each zone 512, and/or each user of the system. Thus, each set of settings may also be associated with a predetermined zone 512, area 508, system, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a system is configured for a particular user. Each setting 1224 may be associated with a different area 508 or zone 512. For instance, a climate control system may be associated with more than one area 508 and/or zone 512. As such, a first user seated in zone 1 512A of area 1 508A may store settings related to the climate control of that zone 512A that are different from other users and/or zones 512 of the vehicle 104. Optionally, the settings may not be dependent on a user. For instance, specific areas 508 and/or zones 512 of a vehicle 104 may include different, default, or the same settings based on the information stored in portion 1224.

The various systems and/or components may be able to obtain or track health status data of the systems and/or components in portion 1278. The health status 1278 may include any type of information related to a state of the systems. For instance, an operational condition, manufacturing date, update status, revision information, time in operation, fault status, state of damage detected, inaccurate data reporting, and other types of component/system health status data may be obtained and stored in portion 1278.

Each component and/or system may be configured to communicate with users, systems, servers, vehicles, third parties, and/or other endpoints via one or more communication type. At least one communication ability and/or type associated with a system may be stored in the communication type portion 1279. Optionally, the communication types contained in this portion 1279 may be ordered in a preferential order of communication types. For instance, a system may be configured to preferably communicate via a wired communication protocol over one or more wired communication channels (e.g., due to information transfer speeds, reliability, and the like). However, in this instance, if the one or more wired communication channels fail, the system may transfer information via an alternative communication protocol and channel (e.g., a wireless communication protocol and wireless communication channel, etc.). Among other things, the methods and systems provided herein may take advantage of the information stored in the communication type portion 1279 to open available communication channels in the event of a communication channel failure, listen on other ports for information transmitted from the systems, provide a reliability rating based on the number of redundant communication types for each component, and more. Optionally, a component or system may be restricted from communicating via a particular communication type (e.g., based on rules, traffic, critical/non-critical priority type, and the like). In this example, the component or system may be forced by the vehicle control system 204 to use an alternate communication type where available, cease communications, or store communications for later transfer.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 12D:
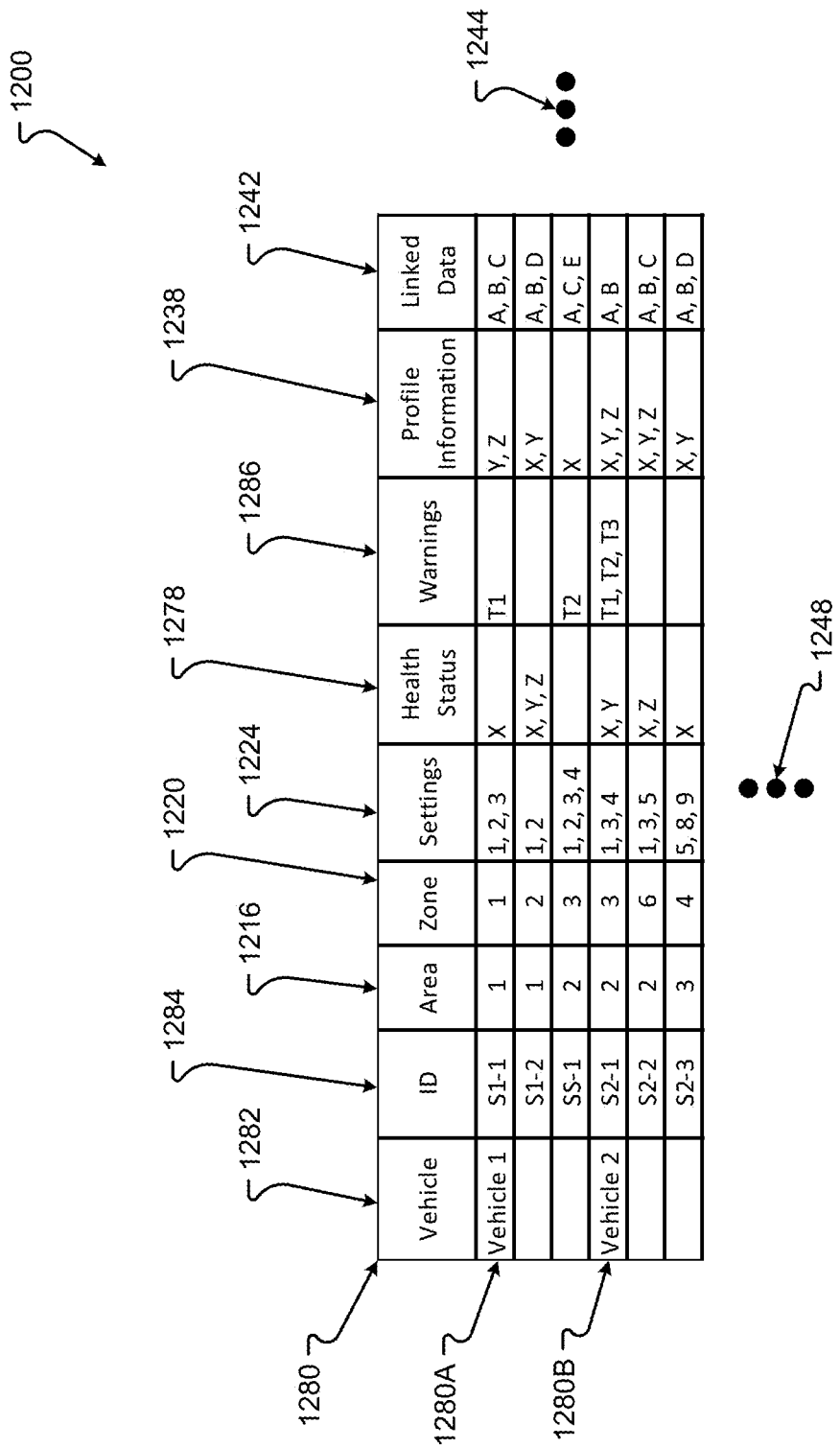
FIG. 12D is a diagram of an embodiment of a data structure for storing information about a vehicle.

Referring now to FIG. 12D, a data structure 1200 is shown optionally. The data file 1280 may include several portions 1216-1286 representing different types of data. Each of these types of data may be associated with a vehicle, as shown in portion 1282.

There may be one or more vehicle records 1280 and associated data stored within the data file 1282. As provided herein, the vehicle 104 can be any vehicle or conveyance 104 as provided herein. The vehicle 104 may be identified in portion 1282. Additionally or alternatively, the vehicle 104 may be identified by one or more systems and/or subsystems. The various systems of a vehicle 104 may be identified in portion 1284. For example, various features or characteristics of the vehicle 104 and/or its systems may be stored in portion 1284. Optionally, the vehicle 104 may be identified via a unique code or some other type of data that allows the vehicle 104 to be identified.

Each system may be associated with a particular area 508 and/or zone 512 of a vehicle 104. Among other things, the location of a system may be used to assess a state of the system and/or provide how the system interacts with one or more users of the vehicle 104. As can be appreciated each system may have a different set of settings for each area 508 and/or each zone 512, and/or each user of the system. Thus, each set of settings may also be associated with a predetermined zone 512, area 508, system, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a vehicle and/or its systems are configured for one or more users. Each setting 1224 may be associated with a different area 508 or zone 512. Optionally, the settings may not be dependent on a particular user. For instance, specific areas 508 and/or zones 512 of a vehicle 104 may include different, default, or the same settings based on the information stored in portion 1224.

The various systems and/or components may be able to obtain or track health status data of the systems and/or components in portion 1278. The health status 1278 may include any type of information related to a state of the systems. For instance, an operational condition, manufacturing date, update status, revision information, time in operation, fault status, state of damage detected, inaccurate data reporting, and other types of component/system health status data may be obtained and stored in portion 1278.

One or more warnings may be stored in portion 1286. The warnings data 1286 may include warning generated by the vehicle 104, systems of the vehicle 104, manufacturer of the vehicle, federal agency, third party, and/or a user associated with the vehicle. For example, several components of the vehicle may provide health status information (e.g., stored in portion 1278) that, when considered together, may suggest that the vehicle 104 has suffered some type of damage and/or failure. Recognition of this damage and/or failure may be stored in the warnings data portion 1286. The data in portion 1286 may be communicated to one or more parties (e.g., a manufacturer, maintenance facility, user, etc.). In another example, a manufacturer may issue a recall notification for a specific vehicle 104, system of a vehicle 104, and/or a component of a vehicle 104. It is anticipated that the recall notification may be stored in the warning data field 1286. Continuing this example, the recall notification may then be communicated to the user of the vehicle 104 notifying the user of the recall issued by the manufacturer.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 13:
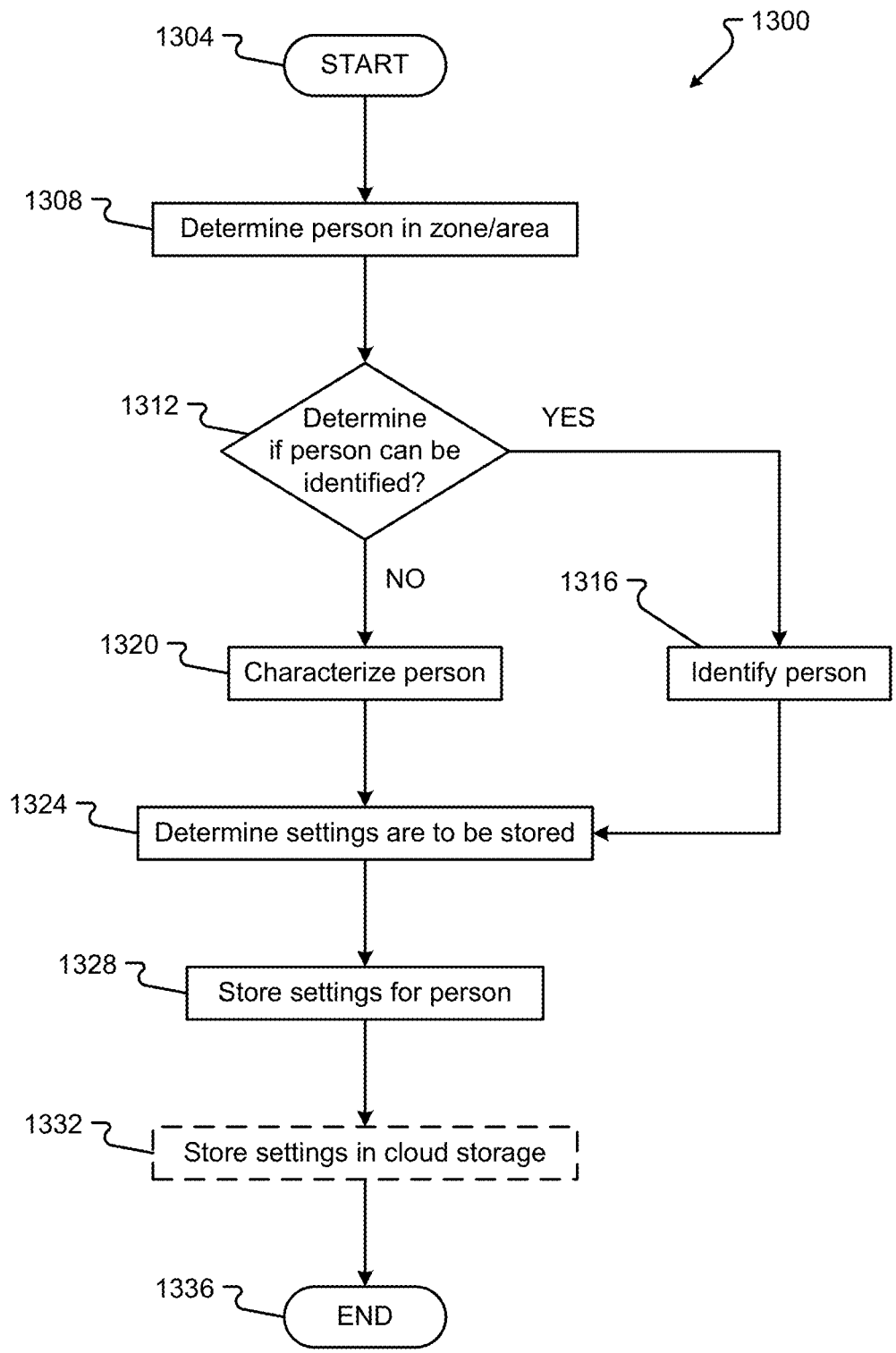
FIG. 13 is a flow or process diagram of a method for storing one or more settings associated with a user.

An embodiment of a method 1300 for storing settings for a user 216 associated with vehicle 104 is shown in FIG. 13. While a general order for the steps of the method 1300 is shown in FIG. 13, the method 1300 can include more or fewer steps or can arrange the order of the steps differently than those shown in FIG. 13. Generally, the method 1300 starts with a start operation 1304 and ends with an end operation 1336. The method 1300 can be executed as a set of computer-executable instructions executed by a computer system and encoded or stored on a computer readable medium. Hereinafter, the method 1300 shall be explained with reference to the systems, components, modules, software, data structures, user interfaces, etc. described in conjunction with FIGS. 1-12.

A person may enter the vehicle space 108. One or more sensors 242 may then identify that a person is sitting within the vehicle 104, in step 1308. For example, sensors 242 in a seat, may determine that some new amount of weight has been registered. The amount of weight may fall within predetermined parameters (e.g., over a threshold, in a specific range, etc.). This weight may then be determined to be a person by one or more optical or other sensors 242. The vehicle control system 204 may then determine that a person is in a certain zone 512 or area 508. For example, the sensors 242 may send signals to the vehicle controls system 204 that an event has occurred. This information may be sent to the vehicle control system processor 304 to determine the zone 512 and area 508 where the event occurred. Further, the vehicle control system 204 may then identify the person, in step 1312.

The vehicle control system 204 can receive the information from the sensors 242 and use that information to search the database 1200 that may be stored within the system data 208. The sensor data may be compared to ID characteristics 1212 to determine if the person has already been identified. The vehicle control system 204 may also send the characteristic data from the sensors to the communication network 224 to a server 228 to compare the sensor data to stored data 232 that may be stored in a cloud system. The person's features can be compared to stored features 1212 to determine if the person in the vehicle 104 can be identified.

If the person has been identified previously and their characteristics stored in portion 1212, the method 1300 proceeds YES to step 1316 where that person may be identified. In identifying a person, the information associated with that person 1240 may be retrieved and provided to the vehicle control system 204 for further action. If a person cannot be identified by finding their sensor characteristics in portion 1212, the method 1300 proceeds NO to step 1320. In step 1320, the vehicle control system 204, using an application, may create a new record in table 1200 for the user. This new record may store a user identifier and their characteristics 1212. It may also store the area 508 and zone 512 in data portions 1216 and 1220. The new record may then be capable of receiving new settings data for this particular user. In this way, the vehicle 104 can automatically identify or characterize a person so that settings may be established for the person in the vehicle 104.

The input module 312 may then determine if settings are to be stored, in step 1324. Settings might be any configuration of the vehicle 104 that may be associated with the user. The determination may be made after receiving a user input from the user. For example, the user may make a selection on a touch sensitive display indicating that settings currently made are to be stored. In other situations, a period of time may elapse after the user has made a configuration. After determining that the user is finished making changes to the settings, based on the length of the period of time since the setting was established, the vehicle control system 204 can save the setting. Thus, the vehicle control system 204 can make settings automatically based on reaching a steady state for settings for user.

The vehicle control system 204 may then store the settings for the person, in step 1328. The user interaction subsystem 332 can make a new entry for the user 1208 in data structure 1204. The new entry may be either a new user or a new settings listed in 1224. The settings may be stored based on the area 508 and zone 512. As explained previously, the settings can be any kind of configuration of the vehicle 104 that may be associated with the user in that area 508 and the zone 512.

The settings may also be stored in cloud storage, in step 1332. Thus, the vehicle control system 204 can send the new settings to the server 228 to be stored in storage 232. In this way, these new settings may be ported to other vehicles for the user. Further, the settings in storage system 232 may be retrieved, if local storage does not include the settings in storage system 208.

Additionally or alternatively, the settings may be stored in profile data 252. As provided herein, the profile data 252 may be associated with one or more devices 212, 248, servers 228, vehicle control systems 204, and the like. Optionally, the settings in profile data 252 may be retrieved in response to conditions. For instance, the settings may be retrieved from at least one source having the profile data if local storage does not include the settings in storage system 208. As another example, a user 216 may wish to transfer settings stored in profile data 252 to the system data 208. In any event, the retrieval and transfer of settings may be performed automatically via one or more devices 204, 212, 248, associated with the vehicle 104.

Figure 14:
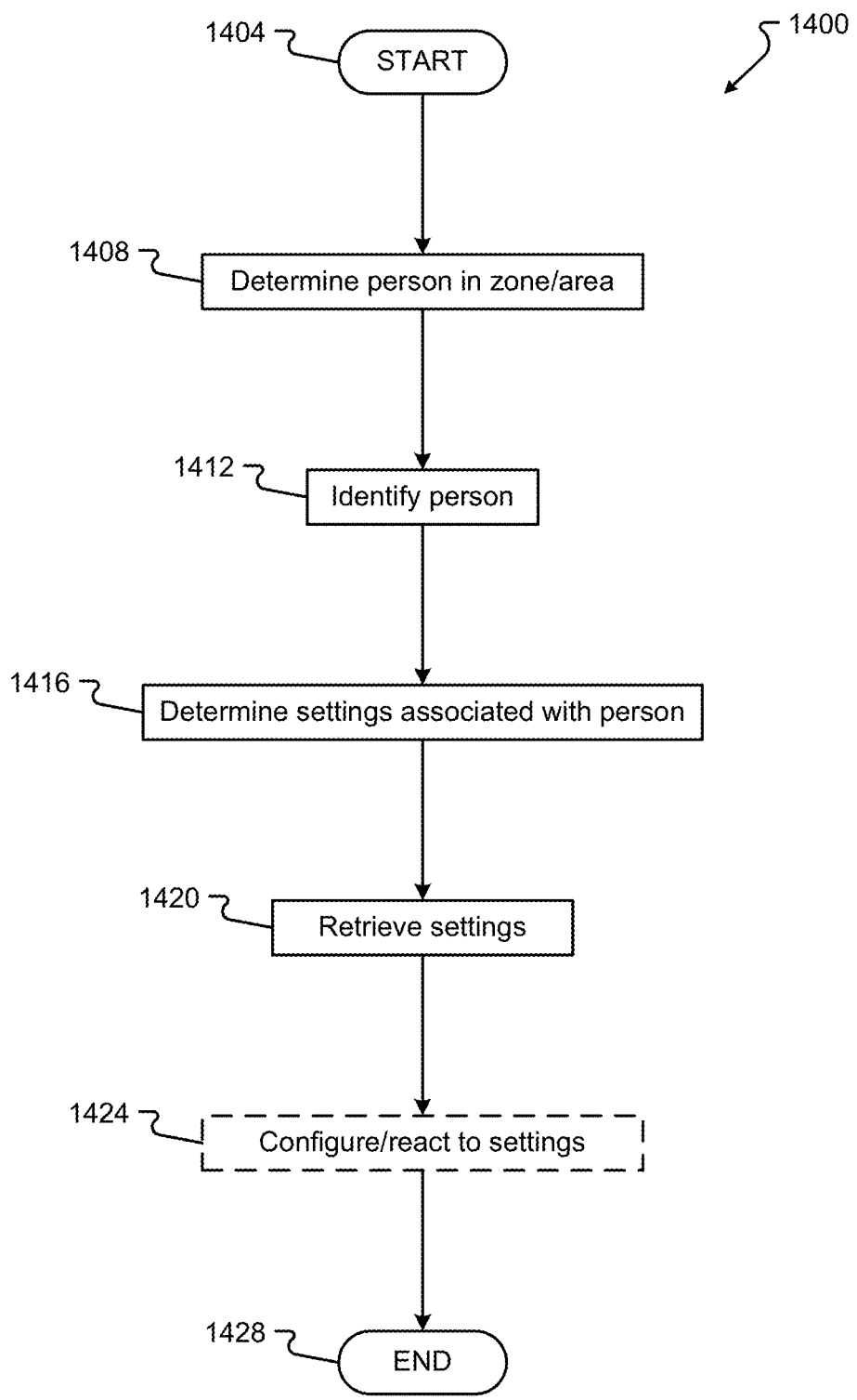
FIG. 14 is a flow or process diagram of a method for establishing one or more settings associated with a user.

An embodiment of a method 1400 to configure the vehicle 104 based on stored settings is shown in FIG. 14. A general order for the steps of the method 1400 is shown in FIG. 14. Generally, the method 1400 starts with a start operation 1404 and ends with an end operation 1428. The method 1400 can include more or fewer steps or can arrange the order of the steps differently than those shown in FIG. 14. The method 1400 can be executed as a set of computer-executable instructions executed by a computer system and encoded or stored on a computer readable medium. Hereinafter, the method 1400 shall be explained with reference to the systems, components, modules, software, data structures, user interfaces, etc. described in conjunction with FIGS. 1-13.

The vehicle control system 204 can determine if a person is in a zone 512 or area 508, in step 1408. This determination may be made by receiving data from one or more sensors 242. The vehicle 104 can use facial recognition, weight sensors, heat sensors, or other sensors to determine whether a person is occupying a certain zone 512.

Using the information from the sensors 242, the vehicle control system 204 can identify the person, in step 1412. The vehicle control system 204 can obtain characteristics for the user currently occupying the zone 512 and compare those characteristics to the identifying features in portion 1212 of data structure 1204. Thus, the settings in portion 1224 may be retrieved by identifying the correct zone 512, area 508, and characteristics for the user.

The vehicle control system 204 can first determine if there are settings associated with the identified person for that zone 512 and/or area 508, in step 1416. After identifying the user by matching characteristics with the features in portion 1212, the vehicle control system 204 can determine if there are settings for the user for the area 1216 and zone 1220 the user currently occupies. If there are settings, then the vehicle control system 204 can make the determination that there are settings in portion 1224, and the vehicle control system 204 may then read and retrieve those settings, in step 1420. The settings may be then used to configure or react to the presence of the user, in step 1424. Thus, these settings may be obtained to change the configuration of the vehicle 104, for example, how the position of the seats or mirrors are set, how the dash, console, or heads up display is configured, how the heat or cooling is configured, how the radio is configured, or how other different configurations are made.

Figure 15:
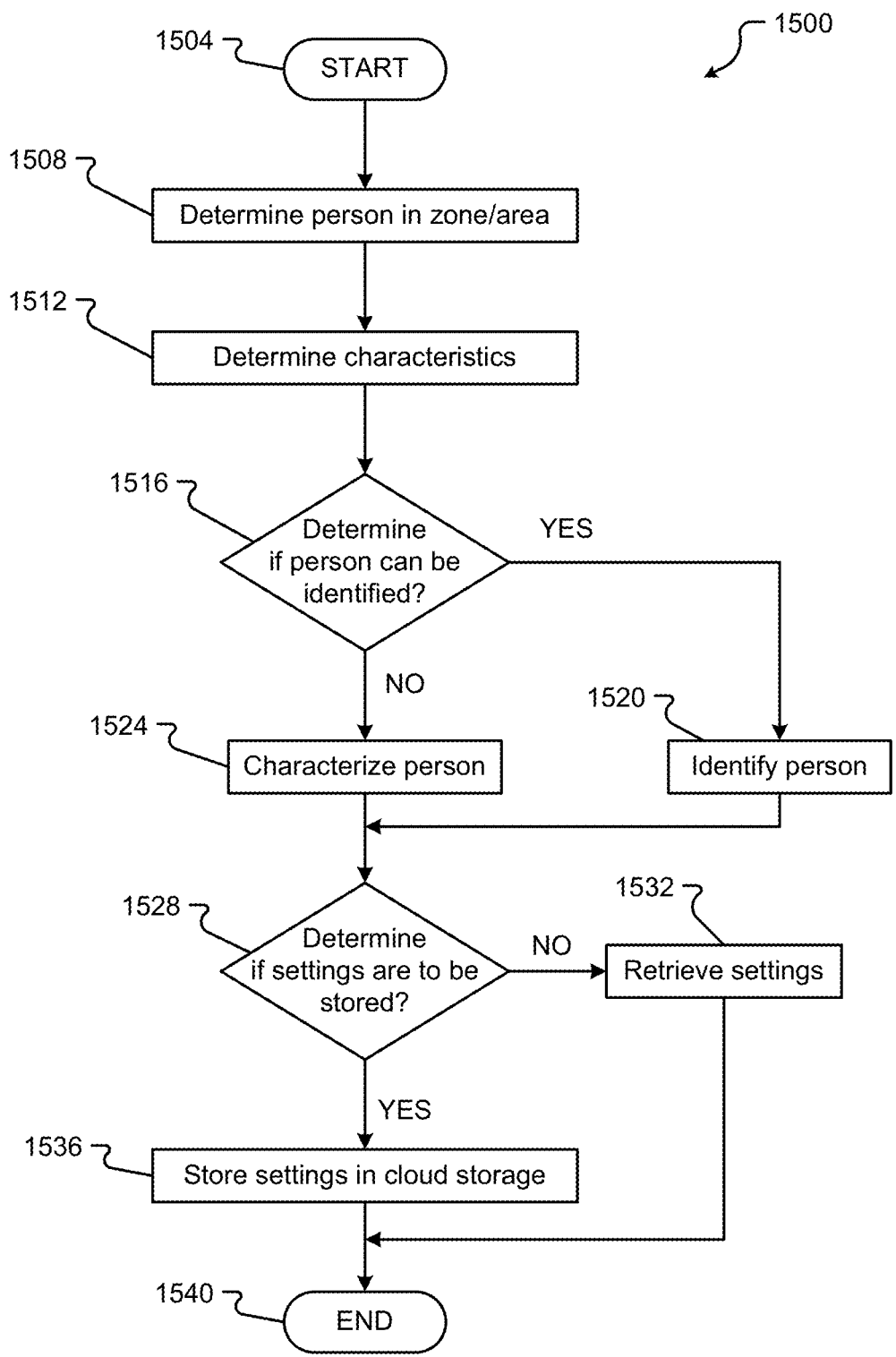
FIG. 15 is a flow or process diagram of a method for storing one or more settings associated with a user.

Embodiments of a method 1500 for storing settings in cloud storage are shown in FIG. 15. A general order for the steps of the method 1500 is shown in FIG. 15. Generally, the method 1500 starts with a start operation 1504 and ends with an end operation 1540. The method 1500 can include more or fewer steps or can arrange the order of the steps differently than those shown in FIG. 15. The method 1500 can be executed as a set of computer-executable instructions executed by a computer system and encoded or stored on a computer readable medium. Hereinafter, the method 1500 shall be explained with reference to the systems, components, modules, software, data structures, user interfaces, etc. described in conjunction with FIGS. 1-14.

The vehicle control system 204 can determine if a person is in a zone 512 or area 508, in step 1508. As explained previously, the vehicle control system 204 can receive vehicle sensor data from vehicle sensors 242 that show a person has occupied a zone 512 or an area 508 of the vehicle 104. Using the vehicle sensor data, the vehicle control system 204 can determine characteristics of the person, in step 1512. These characteristics are compared to the features in portion 1212 of the data structure 1204. From this comparison, the vehicle control system 204 can determine if the person is identified within the data structure 1204, in step 1516. If there is a comparison and the person can be identified, the method 1500 proceeds YES to step 1520. However, if the person cannot be identified, the method 1500 proceeds NO, to step 1524.

In step 1520, the person is identified in portion 1208 by the successful comparison of the characteristics and the features. It should be noted that there may be a degree of variability between the characteristics and the features in portion 1212. Thus, the comparison may not be an exact comparison but may use methods known in the art to make a statistically significant comparison between the characteristics received from the sensors 242 and the features stored in portion 1212. In step 1524, the characteristics received from sensors 242 are used to characterize the person. In this way, the received characteristics may be used as an ID, in portion 1212, for a new entry for a new user in portion 1208.

The user may make one or more settings for the vehicle 104. The vehicle control system 204 may determine if the settings are to be stored, in step 1528. If the settings are to be stored, the method 1500 proceeds YES to step 1536. If the settings are not to be stored or if there are no settings to be stored, the method 1500 proceeds NO to step 1532. In step 1532, the vehicle control system 204 can retrieve the settings in the portion 1224 of the data structure 1204. Retrieval of the settings may be as described in conjunction with FIG. 14. If settings are to be stored, the vehicle control system 204 can send those settings to server 228 to be stored in data storage 232, in step 1536. Data storage 232 acts as cloud storage that can be used to retrieve information on the settings from other vehicles or from other sources. Thus, the cloud storage 232 allows for permanent and more robust storage of user preferences for the settings of the vehicle 104.

Figure 16:
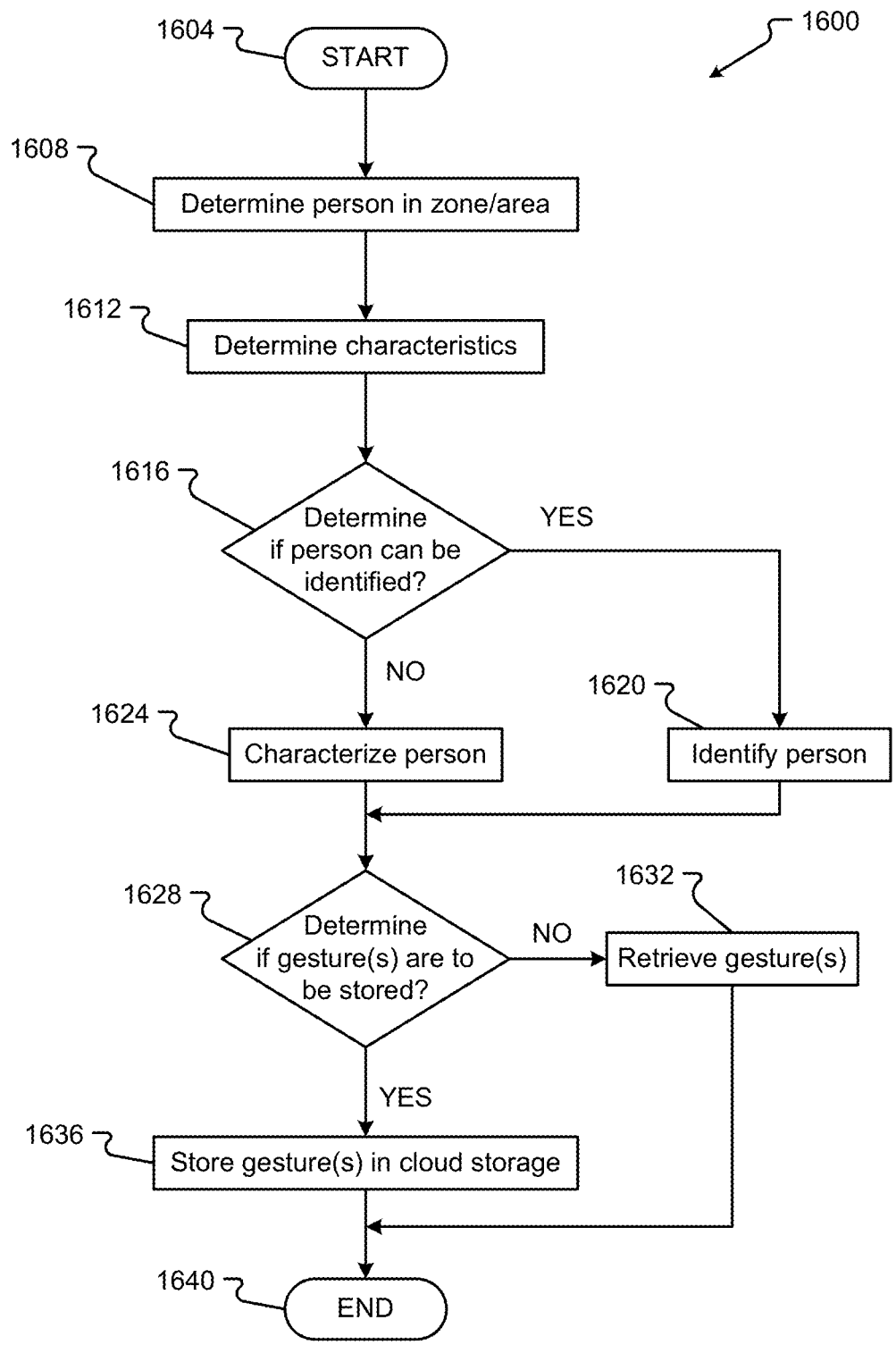
FIG. 16 is a flow or process diagram of a method for storing one or more gestures associated with a user.

An embodiment of a method 1600 for storing gestures associated with the user is shown in FIG. 16. A general order for the steps of the method 1600 is shown in FIG. 16. Generally, the method 1600 starts with a start operation 1604 and ends with an end operation 1640. The method 1600 can include more or fewer steps or can arrange the order of the steps differently than those shown in FIG. 16. The method 1600 can be executed as a set of computer-executable instructions executed by a computer system and encoded or stored on a computer readable medium. Hereinafter, the method 1600 shall be explained with reference to the systems, components, modules, software, data structures, user interfaces, etc. described in conjunction with FIGS. 1-15.

Vehicle control system 204 may receive sensor data from sensors 242 to determine a person is occupying a zone 512 in an area 508 of the vehicle 104, in step 1608. The sensor data may provide characteristics for the person, in step 1612. The vehicle control system 204 may then use the characteristics to determine if the person can be identified, in step 1616. The vehicle control system 204 may compare the characteristics to the features in portion 1212 for the people having been recognized and having data associated therewith. If a comparison is made between the characteristics and the features in portion 1212, the person can be identified, and the method 1600 proceeds YES to step 1620. If there is no comparison, the method 1600 may proceed NO to step 1624. In step 1620, the person may be identified by the vehicle control system 204. Thus, the person's features and associated data record 1240 may be determined and the user identified in portion 1208. If the person is not identified, the vehicle control system 204 can characterize the person in step 1624 by establishing a new record in data structure 1204 using the characteristics, received from the sensors 242, for the features in portion 1212.

Thereinafter, the vehicle control system 204 may determine if gestures are to be stored and associated with the user, in step 1628. The vehicle control system 204 may receive user input on a touch sensitive display or some other type of gesture capture region which acknowledges that the user wishes to store one or more gestures. Thus, the user may create their own gestures such as those described in conjunction with FIGS. 11A-11K. These gestures may then be characterized and stored in data structure 1204. If there are gestures to be stored, the method 1600 proceeds YES to step 1636. If gestures are not to be stored the method 1600 may proceed NO to step 1632.

In step 1632, the vehicle control system 204 can retrieve current gestures from portion 1232, which are associated with user 1240. These gestures may be used then to configure how the vehicle 104 will react if a gesture is received. If gestures are to be stored, the vehicle control system 204 may store characteristics, in step 1636, as received from sensor 242 or from one more user interface inputs. These characteristics may then be used to create the stored gestures 1232, in data structure 1204. The characteristics may include what the gesture looks like or appears and also what affect the gesture should have. This information may then be used to change the configuration or operation of the vehicle 104 based on the gesture if it is received at a later time.

Figure 17:
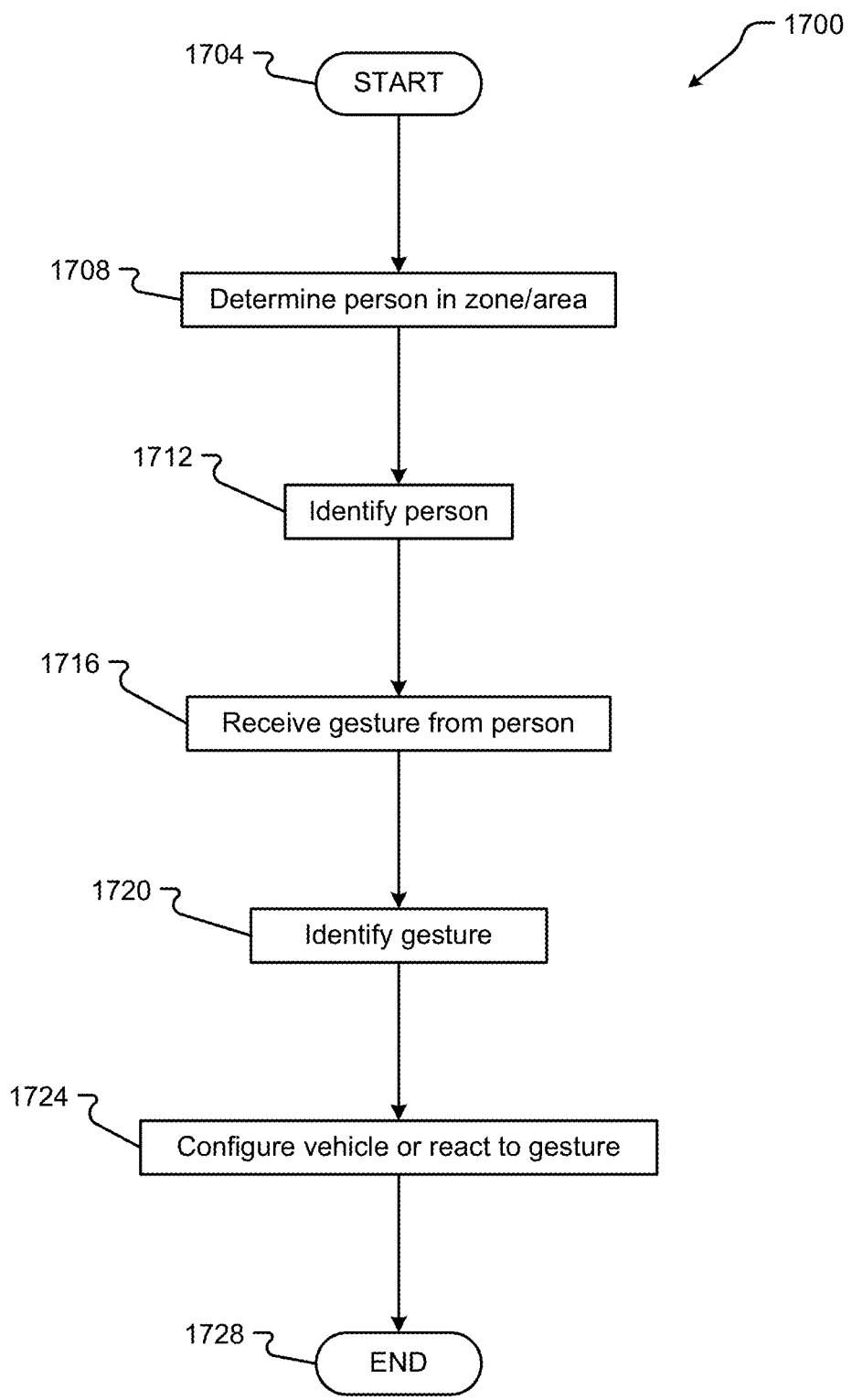
FIG. 17 is a flow or process diagram of a method for reacting to a gesture performed by a user.

An embodiment of a method 1700 for receiving a gesture and configuring the vehicle 104 based on the gesture may be as provided in FIG. 17. A general order for the steps of the method 1700 is shown in FIG. 17. Generally, the method 1700 starts with a start operation 1704 and ends with an end operation 1728. The method 1700 can include more or fewer steps or can arrange the order of the steps differently than those shown in FIG. 17. The method 1700 can be executed as a set of computer-executable instructions executed by a computer system and encoded or stored on a computer readable medium. Hereinafter, the method 1700 shall be explained with reference to the systems, components, modules, software, data structures, user interfaces, etc. described in conjunction with FIGS. 1-16.

A vehicle control system 204 can receive sensor data from vehicle sensors 242. The vehicle sensor data can be used by the vehicle control system 204 to determine that a person is in a zone 512 or area 508, in step 1708. The vehicle sensor data may then be used to compare against feature characteristics 1212 to identify a person, in step 1712. The vehicle control system 204 thereinafter may receive a gesture, in step 1716. The gesture may be perceived by vehicle sensors 242 or received in a gesture capture region. The gesture may be as described in conjunction with FIGS. 11A-11K. Upon receiving the gesture, the vehicle control system 204 can compare the gesture to gesture characteristics in portion 1232, in step 1720. The comparison may be made so that a statistically significant correlation between the sensor data or gesture data and the gesture characteristic 1232 is made. Upon identifying the gesture, the vehicle control system 204 can configure the vehicle 104 and/or react to the gesture, in step 1724. The configuration or reaction to the gesture may be as prescribed in the gesture characteristic 1232.

Figure 18:
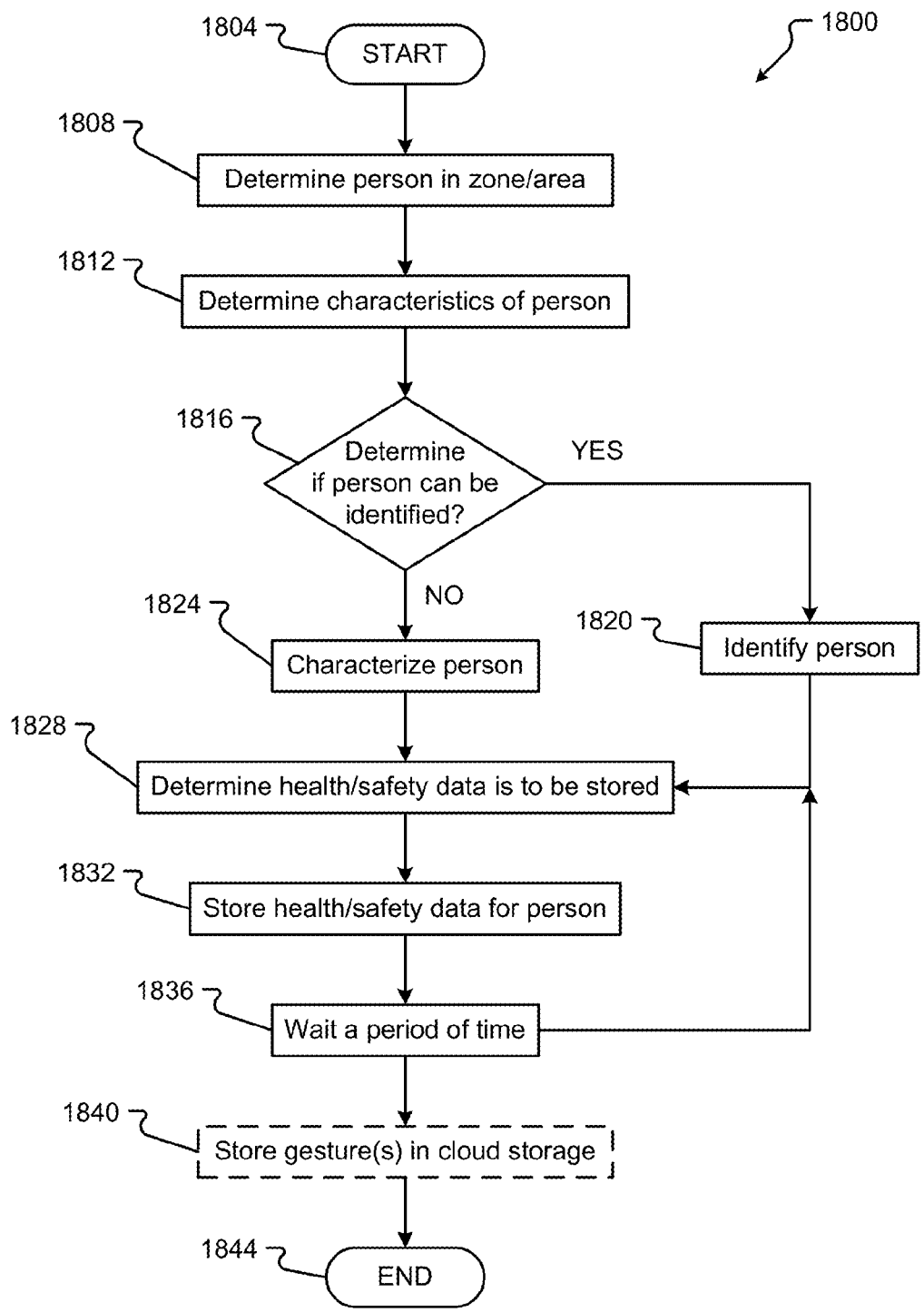
FIG. 18 is a flow or process diagram of a method for storing health data associated with a user.

An embodiment of a method 1800 for storing health data may be as shown in FIG. 18. A general order for the steps of the method 1800 is shown in FIG. 18. Generally, the method 1800 starts with a start operation 1804 and ends with an end operation 1844. The method 1800 can include more or fewer steps or can arrange the order of the steps differently than those shown in FIG. 18. The method 1800 can be executed as a set of computer-executable instructions executed by a computer system and encoded or stored on a computer readable medium. Hereinafter, the method 1800 shall be explained with reference to the systems, components, modules, software, data structures, user interfaces, etc. described in conjunction with FIGS. 1-17.

Vehicle control system 204 can receive sensor data from sensors 242. The sensor data may be used to determine that a person is in a zone 512 or area 508, in step 1808. The sensor data may then be used to determine characteristics of the person, in step 1812. From the characteristics, the vehicle control system 204 can determine if a person may be identified in data structure 1204, in step 1816. If it is determined that the person can be identified in step 1816, the method 1800 proceeds YES to step 1820. If the person cannot be identified, the method 1800 proceeds NO to step 1824. A person may be identified by matching the characteristics of a person from the sensor data to the features shown in portion 1212. If these comparisons are statistically significant, the person may be identified in portion 1208, in step 1820. However, if the person is not identified in portion 1208, the vehicle control system 204 can characterize the person using the vehicle sensor data, in step 1824. In this way, the vehicle control system 204 can create a new record for a new user in data structure 1204.

Thereinafter, the vehicle control system 204 may receive health and/or safety data from the vehicle sensors 242, in step 1828. The vehicle control system 204 can determine if the health or safety data is to be stored, in step 1832. The determination is made as to whether or not there is sufficient health data or safety parameters, in portion 1228 and 1236, to provide a reasonable baseline data pattern for the user 1240. If there is data to be received and stored, the vehicle control system 204 can store the data for the person in portions 1228 and 1236 of the data structure 1204, in step 1832.

The vehicle control system 204 may then wait a period of time, in step 1836. The period of time may be any amount of time from seconds to minutes to days. Thereinafter, the vehicle control system 204 can receive new data from vehicle sensors 242, in step 1828. Thus, the vehicle control system 204 can receive data periodically and update or continue to refine the health data and safety parameters in data structure 1204. Thereinafter, the vehicle control system 204 may optionally store the health and safety data in cloud storage 232 by sending it through the communication network 224 to the server 228, in step 1840.

Figure 19:
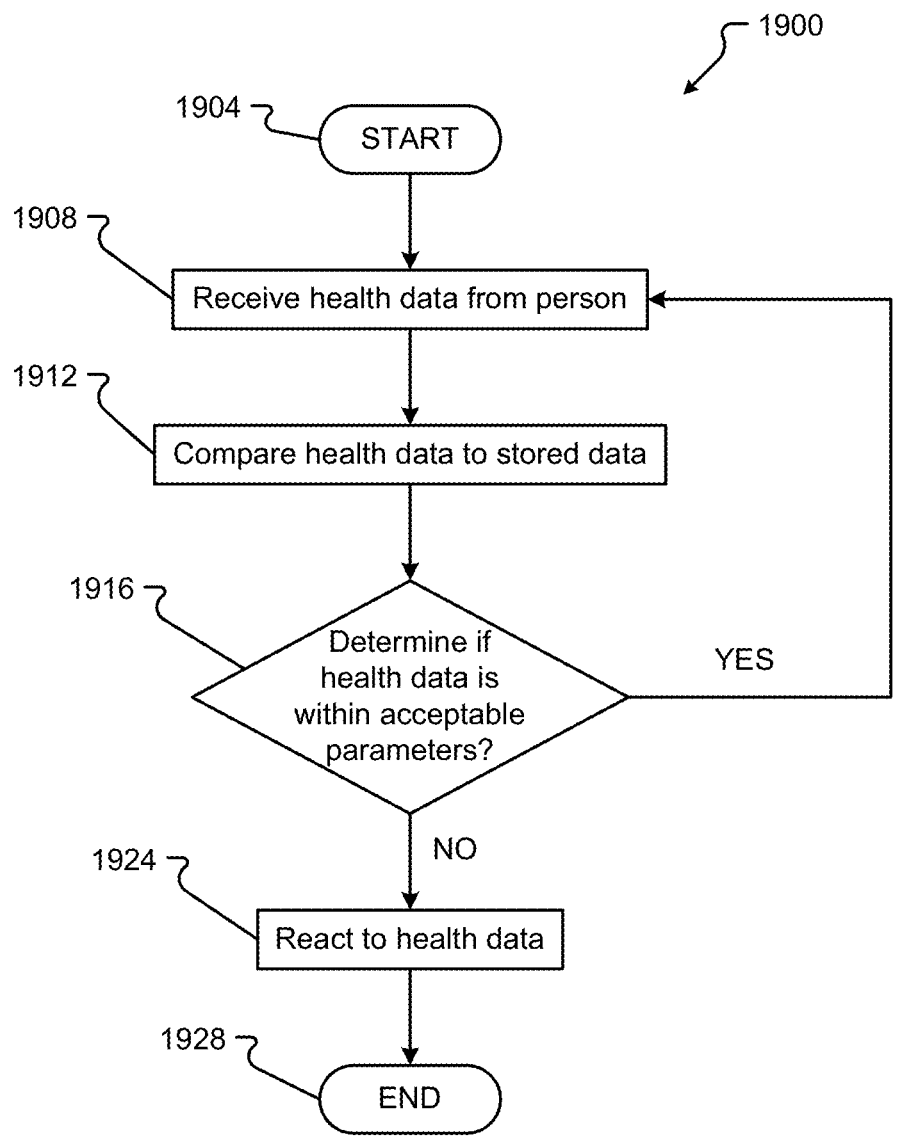
FIG. 19 is a flow or process diagram of a method for reacting to a gesture performed by a user.

An embodiment of a method 1900 for monitoring the health of a user may be as shown in FIG. 19. A general order for the steps of the method 1900 is shown in FIG. 19. Generally, the method 1900 starts with a start operation 1904 and ends with an end operation 1928. The method 1900 can include more or fewer steps or can arrange the order of the steps differently than those shown in FIG. 19. The method 1900 can be executed as a set of computer-executable instructions executed by a computer system and encoded or stored on a computer readable medium. Hereinafter, the method 1900 shall be explained with reference to the systems, components, modules, software, data structures, user interfaces, etc. described in conjunction with FIGS. 1-18.

The vehicle control system 204 can receive health data from sensors 242. The health data may be received in step 1908. The vehicle control system 204 may then compare the received health data to stored health parameters in portion 1228 or portion 1236, in step 1912. The comparison may check if there is statistically significant separation or disagreement between the received health data and the stored health data. Thus, the vehicle control system 204 can make a health comparison of the user based on a baseline of health data previously stored. A statistically significant comparison may include determining if there are any parameters more than three standard deviations from the average or norm, any parameter that is increasing or decreasing over a period of eight different measurements, a measurement that is more than two standard deviations from the norm more than three measurements consecutively, or other types of statistical comparisons.

If the vehicle control system 204 determines that measured health parameter does deviate from the norm, the vehicle control system 204 can determine whether the health data is within acceptable limits, in step 1916. If the health data is within acceptable limits, the method 1900 proceeds YES back to receiving new health data, in step 1908. In this way, the health data is periodically or continually monitored to ensure that the driver is in a healthy state and able to operate the vehicle. If the health data is not within acceptable parameters, the method 1900 may proceed NO to step 1924 where the vehicle control system 204 may react to the change in the health data. The reaction may include any measure to provide for the safety of the user, such as stopping the vehicle, beginning to drive the vehicle, driving the vehicle to a new location, such as a hospital, waking the driver with an alarm or other noise, or performing some other function that may help maintain the health or safety of the user.

The health data received may be a reaction from the driver. For example, the driver may call for help or ask the vehicle for assistance. For example, the driver or passenger may say that they are having a medical emergency and ask the car to perform some function to help. The function to help may include driving the person to a hospital or stopping the car and calling for emergency assistance.

Vehicle Network Security

Vehicle network security is a major obstacle to be overcome in making vehicles Internet capable. Firewall 484 can provide security but, due to the seriousness of the consequences to public safety of a security breach, additional security measures are desirable.

Network security can use a common computer to run simultaneously first and second operating systems, respectively, for critical and non-critical tasks, functions, and operations of each processing module of the vehicle control system 204, whereby, in the event of a security breach event, the second operating system is disabled or its execution discontinued.

Other vehicle network security algorithms will be discussed with reference to FIGS. 23-25. An effective approach to protecting the critical tasks, functions, and operations from attack is to have one computer that handles vehicle tasks, functions, and operations and a different computer that handles infotainment tasks, functions, and operations. The first and second computers (and the distributed processing networks of which each of the first and second computers are a part) are disconnected from one another and unable to communicate with one another either wirelessly or non-wirelessly (e.g., by a signal transmission line such as a bus). The first computer (and/or any component in the distributed processing component of which it is a part) is not discoverable by the vehicle wireless network access points 456 and/or the second computer and does not appear on any network topology (or management information base or MIB) stored in the second computer. The converse may or may not be true with respect to the second computer being discoverable by the first computer; that is, a network topology (or MIB) of a component in the network controlled by the first computer, including the first computer itself, may describe or include information regarding one or more components of the network controlled by the second computer or the second computer itself. Stated another way, the infotainment network (or the distributed processing network containing any component (such as one or more of the IP router 420, IP module 1048, communications module 1052, device discovery daemon 1020, media controller 492, media processor 808, access point 456, match engine 812, video controller 840, audio controller 844, speech synthesis module 820, network transceiver 824, signal processing module 828, device interaction module 818, and combo controller 460) participating in, providing, or handling infotainment content) can be prohibited from communicating with a vehicle non-infotainment control network containing any component participating in, providing, or handling signaling for controlling non-infotainment vehicle control tasks, functions, or operations, such as critical tasks, functions or operations (such as one or more of the vehicle control module 826, location module 896, automobile controller 8104, vehicle systems transceiver 8108, traffic controller 8112, network traffic transceiver 8116, and environmental control module 830). The first computer can have no contactable address (such as a local IP address or global unicast address) on any wireless or non-wireless network, including the infotainment network, and is not addressable, contactable, or otherwise able to communicate with the second computer, a component in the network controlled by the second computer, or any portable computational device (such as the device or user interface 212, 248, user interface (s)/input interface(s) 324 and/or I/O module 312).

Critical tasks, functions or operations can include one or more of (depending on the particular vehicle) monitoring, controlling, and/or operating the ECU, TCU, door settings, window settings, and/or blind spot monitor, monitoring, controlling, and/or operating the safety equipment (e.g., airbag deployment control unit, collision sensor, nearby object sensing system, seat belt control unit, sensors for setting the seat belt, etc.), monitoring and/or controlling certain critical sensors such as the power source controller and energy output sensor, engine temperature, oil pressure sensing, hydraulic pressure sensors, sensors for headlight and other lights (e.g., emergency light, brake light, parking light, fog light, interior or passenger compartment light, and/or tail light state (on or off)), vehicle control system sensors, and/or steering/torque sensor, controlling the operation of the engine (e.g., ignition), head light control unit, power steering, display panel, switch state control unit, power control unit, and/or brake control unit, and/or issuing alerts to a user and/or remote monitoring entity of potential problems with a vehicle operation.

Less critical tasks, functions or operations to vehicle operation (which are unrelated to infotainment) can, depending on the application, further include one or more of (depending on the particular vehicle) monitoring, controlling, and/or operating a wireless network sensor (e.g., Wi-Fi and/or Bluetooth sensor), cellular data sensor, emissions control, seating system controller and sensor, monitoring certain non-critical sensors such as ambient (outdoor) weather readings (e.g., temperature, precipitation, wind speed, and the like), odometer reading sensor, trip mileage reading sensor, road condition sensors (e.g., wet, icy, etc.), radar transmitter/receiver output, brake wear sensor, oxygen sensor, ambient lighting sensor, vision system sensor, ranging sensor, parking sensor, heating, venting, and air conditioning (HVAC) system and sensor, water sensor, air-fuel ratio meter, hall effect sensor, microphone, radio frequency (RF) sensor, and/or infrared (IR) sensor.

Infotainment tasks, functions, or operations can include one or more of monitoring, controlling, and/or operating a wireless network sensor (e.g., Wi-Fi and/or Bluetooth sensor), cellular data sensor, emissions control, entertainment system, receiving, processing, and/or providing media and/or multimedia content. Infotainment tasks, functions, or operations are typically performed by one or more of the IP router 420, IP module 1048, communications module 1052, device discovery daemon 1020, media controller 492, media processor 808, access point 456, match engine 812, video controller 840, audio controller 844, speech synthesis module 820, network transceiver 824, signal processing module 828, device interaction module 818, desktop manager 1012, windows manager 1032, application manager 1036, panel launcher 1040, desktop plugin 1024, and combo controller 460.

Figure 23:
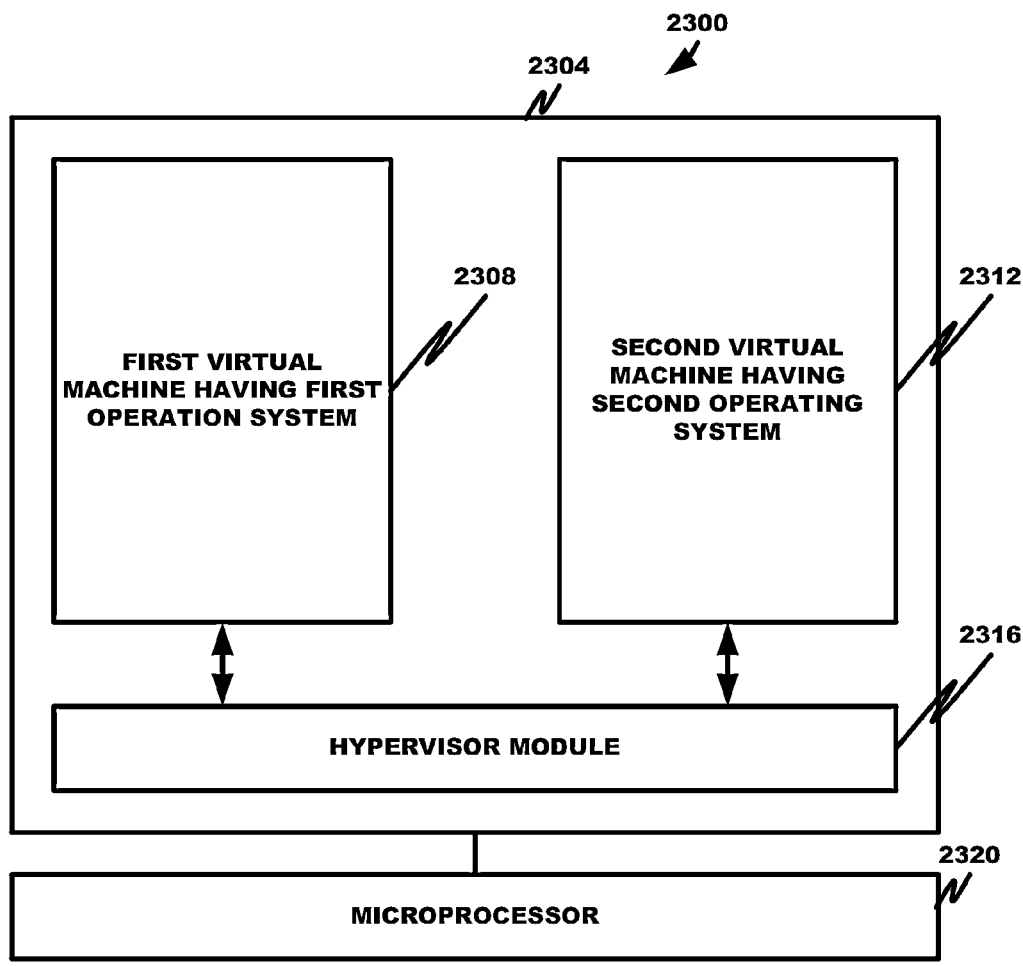
FIG. 23 depicts a flow diagram according to an embodiment.

Another approach is depicted in FIG. 23, which shows a common computer 2300 having a microprocessor 2320 executing first and second virtual machines 2308 and 2312. In common memory 2304, each of the first and second virtual machines is an isolated software container with its own operating system 1004 and executing one or more applications. By way of example and with reference to the first and second computers discussed above, the first virtual machine can simulate the first computer while the second virtual machine can simulate the second computer. Applications stored in each virtual machine would be those applications responsible for critical tasks, functions, and operations in the first virtual machine 2308 and non-critical tasks, functions, and operations in the second virtual machine 2312. Alternatively, the applications stored in the first virtual machine 2308 can be those controlling vehicle tasks, functions, and operations while those stored in the second virtual machine 2312 can be those controlling infotainment tasks, functions, and operations. For example, the first virtual machine 2308 can include one or more of vehicle control module 826, location module 896, automobile controller 8104, vehicle systems transceiver 8108, traffic controller 8112, network traffic transceiver 8116, and environmental control module 830 while the second virtual machine 2312 can include one or more of the IP module 1048, communications module 1052, device discovery daemon 1020, media controller 492, media processor 808, access point 456, match engine 812, video controller 840, audio controller 844, speech synthesis module 820, network transceiver 824, signal processing module 828, device interaction module 818, and combo controller 460. Because each of the first and second virtual machines is completely separate and independent, multiple virtual machines can run simultaneously on a common computer. A hypervisor module 2316 decouples the first and second virtual machines 2308 and 2312 from the host and dynamically allocates computing resources to each of the first and second virtual machine as needed. Computing resources includes, for example, interrupt requests, input/output memory locations, direct memory access, memory capacity allocated for each operating system, scheduling of central processing units, and the like.

Figure 24:
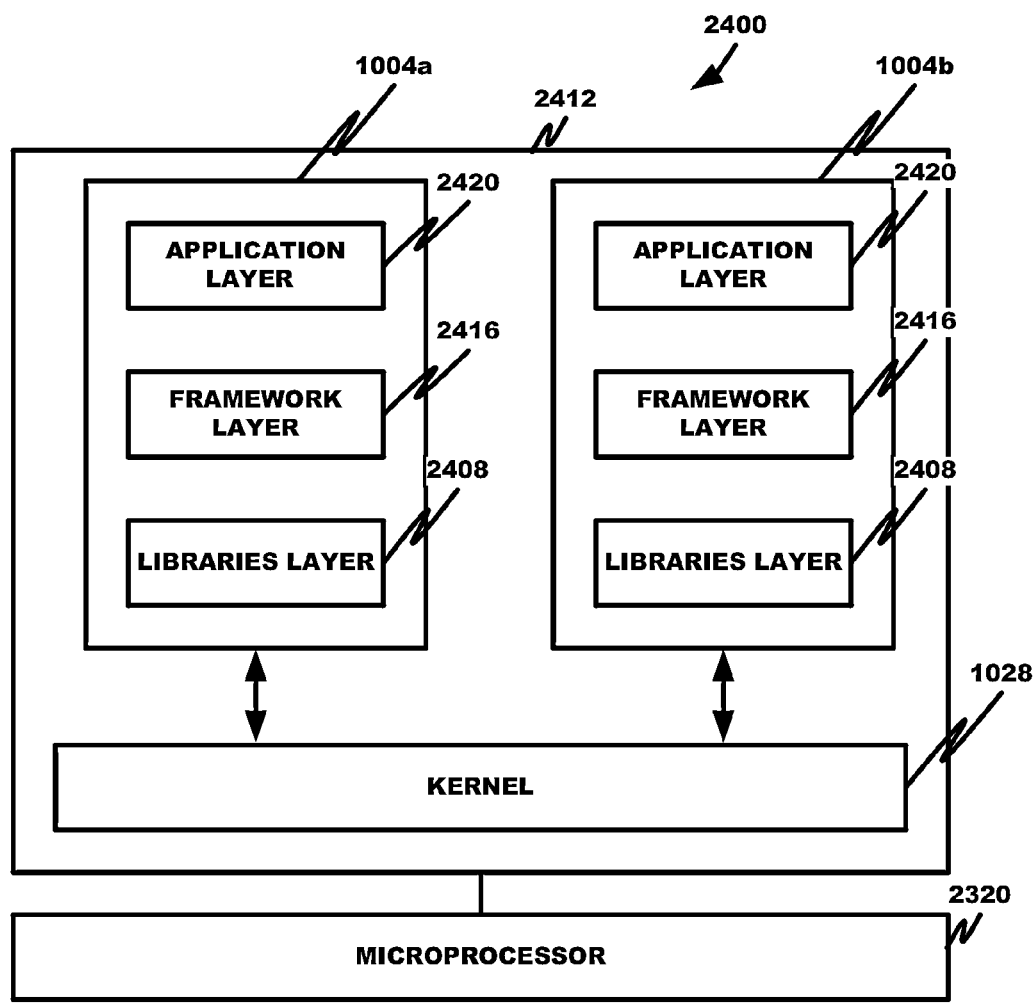
FIG. 24 depicts a computational system according to an embodiment.

Yet another approach is shown in FIG. 24. As illustrated in FIG. 24, a common computer 2400 includes first and second operating systems 1004a and 1004b stored in common memory 2412. Each of the first and second operating systems 1004a and 1004b executing by the microprocessor 2320, can have one or more of a libraries layer 2408, application framework layer 2416, and application layer 2420. Applications are executed in application layer supported by application framework layer of the respective operating system. For example in the case of infotainment, the application framework layer may include a window manager, activity manager, package manager, resource manager, telephony manager, gesture controller, and/or other managers and services. Each operating system can rely on a common kernel 1028 for process isolation, memory management, and threading support. Libraries layer includes user libraries that implement common functions with input/output and string manipulation, graphics libraries, database libraries, communication libraries, and/or other libraries.

By way of example and with reference to the prior paragraph, the first operating system and environment can simulate the first computer while the second operating system and environment can simulate the second computer. Applications executing in each operating system and environment would be those applications responsible for critical and non-critical tasks, functions, and operations. More specifically, the applications stored in the application framework layer of the first operating system 1004a can be those controlling vehicle tasks, functions, and operations while those stored in the second operating system 1004b can be those controlling infotainment tasks, functions, and operations. For example, the first operating system 1004a can include one or more of vehicle control module 826, location module 896, automobile controller 8104, vehicle systems transceiver 8108, traffic controller 8112, network traffic transceiver 8116, and environmental control module 830 while the second operating system 1004b can include one or more of the IP module 1048, communications module 1052, device discovery daemon 1020, media controller 492, media processor 808, access point 456, match engine 812, video controller 840, audio controller 844, speech synthesis module 820, network transceiver 824, signal processing module 828, device interaction module 818, and combo controller 460.

The first operating system 1004a can run in a separate execution environment from the second operating system 1004b. For example, one operating system (typically the first operating system 1004a) can run in a root execution environment while the other operating system (typically the first operating system 1004b) runs in a secondary execution environment established under the root execution environment. Processes and applications running on the second operating system, for instance, can access user libraries, manager(s), and service(s) in the secondary execution environment. Generally applications for one operating system do not run on the other operating system.

The kernel 1028 is shared such that the first and second operating systems run concurrently and independently on the shared kernel 1028. Specifically, both operating systems 1004a,b interface to the shared kernel 1028 through the same kernel interface, such as by making system calls to the shared kernel 1028. The shared kernel 1028 manages task scheduling for processes of both operating systems and resource management, such as CPU scheduling, memory access and input/output.

Other techniques exist for running multiple operating systems, including dual-boot, multiple operating systems loaded on a computing device one-at-a-time, hosted virtual machines, and operating system level virtualization.

Figure 25:
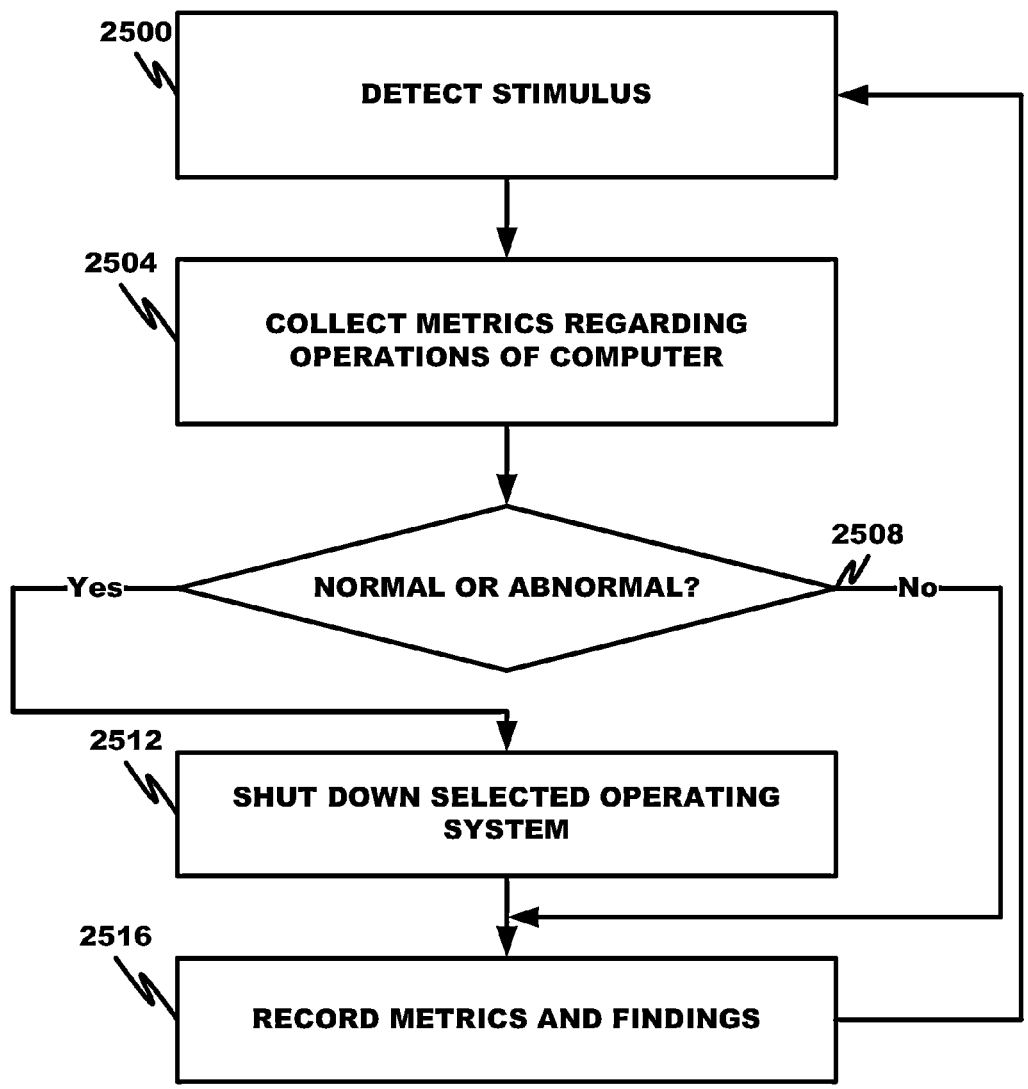
FIG. 25 depicts a computational system according to an embodiment.

FIG. 25 depicts an operation of the hypervisor module 2316 or common kernel 1028 (collectively "computer control module").

In step 2500, the computer control module detects a stimulus, such as a potential security breach, attack, or other intrusion or attempted intrusion notification, a clock signal, an interrupt and the like. Examples of breaches, attacks, and other intrusions include denial-of-service attacks, spoofing, man in the middle, ARP spoofing, smurf attack, buffer overflow, heap overflow, format string attack, SQL injection, and cyber attack.

In step 2504, the computer control module collects metrics regarding operations of the first and/or second operating system (e.g., of first or second virtual machine) and/or of the computer or associated therewith (e.g., of the network controlled by the first or second operating system). Metrics include network metrics, computational device metrics, and the like. Examples of network metrics include measuring link utilization, number of hops, speed of the path, packet loss, latency, path reliability, path bandwidth, network overhead, maximum transmission unit or MTU, throughput and the like and of computer metrics include load, transaction times, database access times, available memory, central processing unit ("CPU") usage, memory usage, and the like.

In decision diamond 2508, the computer control module determines whether or not the collected metrics indicate a normal or abnormal operating state of the computer and/or of the first or second operating system and/or associated therewith. A normal operating state is deemed to occur when the collected metrics are within normal operational ranges. An abnormal operating state is deemed to occur when one or more of the collected metrics are outside of normal operational ranges. The ranges are predetermined or preconfigured by the manufacturer. Where some metrics are normal and others abnormal, the metrics may be ranked or scored, with the cumulative score being the basis for the normal or abnormal operating state determination.

In one application, the computer control module acts differently depending on whether the abnormality impacts the first or second operating system. When the first operating system responsible for critical vehicle functions, tasks, or operations is behaving abnormally, the driver can be warned of the potential problem and asked to terminate operation of the vehicle. Execution of certain critical vehicle tasks, functions or operations can be discontinued in favor of manual control of the vehicle tasks, functions, or operations. Execution of certain critical vehicle tasks, functions, or operations can be discontinued while other more critical tasks, functions, or operations continue to be executed. For example, steering, brakes, headlights, wipers, and vehicle acceleration can continue to be executed while environmental or climate control operations are discontinued. When the second operating system responsible for infotainment functions, tasks, or operations behaves abnormally, the driver can be warned of the potential problem and execution of the second operating system terminated automatically.

The determination as to whether the first or second operating system is behaving abnormally can be different. The first operating system can require more metrics to be abnormal than the second operating system or vice versa. Because the second operating system is more likely to be subject to an attack from the Internet or a portable device, a lesser deviation from normal operational ranges can be considered to be abnormal operation of the second operating system compared to the deviation required for the first operating system to be considered to be operating abnormally. Stated another way, a lower threshold is required to find abnormal operation of the second operating system when compared to the first operating system.

When the operating state is abnormal, the computer control module, in step 2512, shuts down or disables the second virtual machine, operating system, or computer so that the first virtual machine, operating system, or computer continues to perform critical and/or automotive tasks, functions or operations while shutting down, terminating, or discontinuing execution of infotainment tasks, functions, or operations.

When the operating state of a network in communication with the computer control module is abnormal as determined by comparison of a network metric with one or more threshold values, the second, but not the first, operating system can be shut down, particularly when the second operating system (but not the first operating system) is controlling and/or receiving input from the network.

After step 2512 or when the operating state is normal, the computer control module, in step 2516, records the metrics and findings and returns to step 2500.

The above discussion can be applied to a vehicle having separate computers running the first and second operating systems, respectively. In other words, the computer controller would monitor the operations of each of the first and second computers and a corresponding network providing input to each and perform the steps of FIG. 25 with respect to each of the first and second operating systems in each of the first and second computers and their respective networks.

Critical tasks, functions, and operations can be performed by an application executing in the first operating system and less critical tasks, functions, and operations (and infotainment tasks, functions, and operations) can be performed by an application executing in the second operating system. For instance, vehicle controls (e.g., steering, braking, indicating, etc.) can be considered mission critical and performed in the first operating system environment, whereas environmental controls and radio stations and entertainment presentations can be considered as non-critical and performed in the second operating system environment. Among other things, the critical tasks, functions, and operations can be performed not only by the first operating system but also alternatively by a redundant operating system. The redundant operating system may be configured to run in tandem with the first operating system performing critical tasks, functions, and operations and replace, or receive a "hot" handoff from, the first operating system in the event of a failure or malfunction of the first operating system or an application executing in the first operating system. In a "hot" handoff, the redundant operating system may replace the mission critical operating system without interruption of operation. Additionally or alternatively, the first operating system may utilize one or more of error checking communication protocols, secure communication standards, encrypted communications, high speed communications protocols, and the like.

The Vehicle as an Artificially Intelligent Assistant

The vehicle control system 204 can act as an artificially intelligent assistant that, based on an awareness of a selected vehicle occupant's persona (e.g., his or her physical, psychological, mental and other characteristics, needs, desires, behavior, personality, goals, habits, biometric information, likes or interests, dislikes, preferences, and the like) and/or the persona of family and friends of the selected vehicle occupant, proactively (without a preceding request of the selected vehicle occupant) provides feedback, suggestions, reminders, recommendations, and/or other types of assistance to the selected vehicle occupant. For example, the vehicle control system 204 can characterize, define, and/or analyze a person's persona based on profile data 252 of the person, device data 220 associated with the person, stored data 232, system data 208, and information related to the person as collected by vehicle interior and exterior sensors. In other words, a vehicle occupant's persona can include the information in one or more of the profile data 252 of the person, device data 220 associated with the person, stored data 232, system data 208, and information related to the person as collected by vehicle interior and exterior sensors. Based on the persona of selected persona and vehicle-related information (such as vehicle context, state, external surroundings, location, past, current, and/or intended path of travel, waypoints, and destination of the vehicle) can proactively provide suggestions, reminders, recommendations and/or other types of assistance to the selected vehicle occupant.

The persona can include a user selected and/or configured avatar, which is provided to the user via any graphical user interface by which the vehicle control system provides suggestions, reminders, recommendations and/or other types of assistance to the selected user as a vehicle occupant. As will be appreciated, an "avatar" is the graphical and/or voice representation of an object that can be the user or the user's alter ego or character or of a person selected by the user. It may take either a three-dimensional form, as in games or virtual worlds, or a two-dimensional form as an icon in Internet forums and other online communities. It can have not only a visual image but also distinct voice, mannerisms, and/or other behavior. It is commonly an object selected and/or configured by the user. Avatars can be used as virtual embodiments of embodied agents, which are driven more or less by artificial intelligence rather than real people.

Each occupant of a vehicle can have a differently configured and/or appearing avatar at his or her display interacting with him or her. As set forth below, the avatar may accompany the user from vehicle-to-vehicle as part of the user's persona, which can be shared from vehicle to vehicle.

For example, the vehicle control system, based on an awareness of a selected person's persona and the vehicle-related information, can note vehicle related alarms, bring to a selected person's attention instant messages, emails, voice mails from, missed phone calls from, current activities of and/or locations of friends, and points of interest near the vehicle or its path of travel.

In a further illustration, the vehicle control system notes that a vehicle driver's anniversary is next week, that the driver's spouse has pinned a bracelet that she likes, that the bracelet is on sale at a specific store, and that the driver has an appointment near the store and, in response, alerts the driver to the sale and spousal interest in the bracelet and asks the driver, via any one of the user interfaces 212, 248, input/output module 312, and user interface/input interfaces 324, whether the vehicle control system can (i) add a stop to the driver's calendar and/or waypoint for the store to the driver's path of travel and/or (ii) make the purchase of the bracelet online for the driver.

In yet a further illustration, the vehicle control system notes that a vehicle warning has been triggered, such as an actual or potential engine or other vehicle malfunction (e.g., low battery charge voltage, low oil pressure, high engine pressure, low fuel level, low tire pressure, air bag initiator malfunction, etc.), identifies vehicle service facilities in proximity to the current vehicle position or path of travel that is capable of repairing or addressing the source of the warning (e.g., a service garage, fuel station, dealership, etc.), contacts the facility to provide details on the malfunction to determine service cost, determine possible appointment times, notifies the driver of the possible appointment times, service cost, and corresponding facility location, and, at the option of the driver, schedules an appointment at the facility and adds a stop to the driver's calendar and/or waypoint for the facility to the driver's path of travel.

In yet a further illustration, the vehicle control system notes that a friend or family member of a vehicle occupant is in spatial proximity to the current vehicle position or path of travel, notifies the vehicle occupant of the identity and current location of the friend or family member, and, at the option of the occupant, contacts the friend or family member to notify them of the vehicle occupant's current position and arrange a meeting at a specified location nearby the current vehicle location or path of travel and adds a stop to the driver's calendar and/or waypoint for the meeting location to the driver's path of travel. This is particularly useful where the friend of family member is mobile too, such as in a vehicle or on a bike.

In yet a further illustration, the vehicle control system notes that the vehicle is on a long distance trip (based on the driver's or other occupant's electronic calendar and/or current location relative to the driver's or other occupant's home location), identifies hotels or motels in proximity to the current vehicle position or path of travel, contacts the hotel or motel to determine possible room types (e.g., one or two beds, bed size, etc.), cost, and availabilities, notifies the driver of the accommodations available and cost, and, at the option of the driver, books an accommodation at a selected hotel or motel and adds a stop to the driver's calendar and/or waypoint for the hotel or motel to the driver's path of travel.

In yet a further illustration, the vehicle control system notes that the vehicle is on a long distance trip, identifies a point or location of interest based on a persona of a vehicle occupant in proximity to the current vehicle position or path of travel, collects and provides information about the point or location of interest to the vehicle occupant, optionally contacts the point or location of interest to determine business hours and costs to visit the point or location of interest, notifies the occupant of the business hours and cost, and, at the option of the driver, books an accommodation at the point or location of interest and adds a stop to the occupant's calendar and/or waypoint for the point or location of interest to the driver's path of travel. The point or location of interest can be a historical landmark, museum, library, church, store, restaurant, coffee shop, mall, healthcare facility, and the like.

In yet a further illustration, the vehicle control system notes, from the electronic calendar of the driver and/or historic driver behavior, that the destination of the vehicle is a meeting, place of employment, or other point of interest and the location thereof, determines that the path of travel of the vehicle will not arrive at the destination timely such as due to traffic, road construction, or other delays, determines a different route that will arrive timely at the destination, proposes the alternate route to the driver, and, at the driver's option, changes the on board navigation to redirect the driver along the alternate route. The vehicle control system can also send a message, such as an email or instant message, to one or more meeting participants or his or her place of employment to let them know that he or she will or may be late.

In a further illustration, an interior or exterior vehicle sensor 340 senses a condition or activity, such as of a vehicle passenger (e.g., a child passenger unbuckling a seat belt, children fighting in the back seat, an in appropriate gesture of a vehicle occupant, and the like) and notifies a selected vehicle occupant, such as the driver of the condition or activity.

In a further illustration, a vehicle control system based on information received from a sensor, such as a camera sensor 760, can identify and/or distinguish an occupant's actions, clothing, held objects or objects in the possession of the user, and the like and perform an action. For instance, the vehicle control system can direct the occupant to a current sale of an identified object worn by or in the possession of the occupant that is in spatial proximity to the current vehicle location. Information regarding objects associated with the user can also be identified by radio frequency identification readers and tags, barcode readers, quick response code readers and the like.

In a further illustration, the vehicle control system determines that the occupant is driving the vehicle to a specific store and provides an alternate store site based on a busyness of one or more store locations. Parking information (e.g., how many spaces are occupied or free based on parking sensors, metered parking information, etc.) may be used to help determine an optimal store or destination location. A user, for instance, may be driving down a street and pull into a Starbucks™ parking lot at where the user and five other vehicles cannot find a parking spot. In this case, the user may spend five minutes waiting for the five other vehicles to clear the lot so the user can travel to another location. However, the vehicle control system, knowing that the parking lot associated with that particular Starbucks™ was fully occupied, may cause the vehicle to alter the route (or suggest an alternate route) to go to another Starbucks™ location based on the traffic and/or lack of parking.

In a further illustration, the vehicle control system may use image sensors to translate signs (e.g., road signs, store signs, advertisements, billboards, etc.). The translation process may be provided via the processing power of the mobile device, via processing on the cloud, combinations thereof, etc., and provide the translated signage message to the occupant.

In a further illustration, the vehicle control system may present a translated availability and/or assistance to guide a user in finding products traditionally purchased on trips. This guidance may be based upon the past behavior associated with the user persona. For instance, when a user travels to a new place the user may always (or mostly) shop for toothpaste, water, and ibuprofen. As can be appreciated, some foreign countries may not offer all of the products at a single store, like North American supermarkets. Continuing this example, the vehicle may provide a translation for the purchasing behavior by at least providing one or more shopping outlets where a user can procure toothpaste, water, and ibuprofen. In this example, the vehicle control system may state in the user's own language "You can find toothpaste and ibuprofen at the Apotheke on Dipplestrasse in downtown Munich. For water you may wish to visit the Marktkauf on Maybach Gaenge two blocks south of Dipplestrasse."

In a further illustration, the user may query for translation and visual assistance, such as "What does Aspirin look like in Germany". In response, the system may provide a picture or image and a translation text, voice, etc. via the mobile device and/or the vehicle.

In a further illustration, the vehicle control system and/or the mobile device, based on vehicle location and/or path of travel, may present travel and tourism options based on popular sites and/or destinations and, if selected, add the selected option as a waypoint or destination. For instance, the vehicle control system may provide the popular sites and/or destinations with a message, such as "75% of travelers visit the following destinations." The vehicle control system may develop a "perfect itinerary" based on the destinations desired and the timeframe. In some cases the itinerary may be based on desired locations and/or locations to be avoided. For instance a user may not wish to visit an industrial neighborhood, and as such the itinerary may provide routes that avoid industrialization.

In a further illustration, the vehicle control system can use a vehicle location-based trigger to activate and/or deactivate features and/or settings at a waypoint or destination, such as a home, a garage, and the like. For instance, the user may be returning home from work (this determination may be predicted based on prior trips made at the same or similar time of day by the same user), at a certain distance from the home, the vehicle may send a signal to a home automation system to set appropriate levels of lighting, thermostat, and/or initiate/deactivate other devices and/or open a garage door or entrance gate. A user may be traveling home from work and the vehicle control system may send a message, such as a text message, phone call, email, etc. to a third party to indicate the user is coming home. In some cases, the message may be identified as being sent from the vehicle (e.g., a vehicle icon with the message). The third party may respond to the message, which is then relayed, visually and or audibly, to the user via the components of the vehicle (e.g., dashboard, head unit, speakers, combinations thereof, etc.). By way of example, a third party may state "Please pick up some eggs and fabric softener before you come home, thanks."

In a further illustration, the vehicle control system can learn which routes one or more users travels at any given time period (hours, days, weeks, months, etc.). This information may be used to adjust routes based on traffic, weather, mood, etc. For instance, a user may plan to travel (or is traveling) to work on a Monday morning where heavy traffic is detected ahead in the user's "usual" Monday morning route. Upon detecting the traffic along the usual route, the vehicle may present the user with alternate route selections, or automatically adjust a route presented to the user. Routes may be altered by the vehicle control system based on past purchases, patterns, preferences and the like associated with a user profile. For instance, if a user visits McDonalds every morning for a cup of coffee and an egg McMuffin, the route guidance may alter the route of the individual to pass along several McDonalds. The route alteration may be terminated once the user stops to purchase products at the McDonalds. As can be appreciated, businesses may pay for route alteration and suggestion as a form of advertising.

In a further illustration, the vehicle control system centers around interactions and learns from user preferences. For instance, the vehicle control system learns that the user tends to like it warmer in the morning than in the afternoon, and adjust temperature settings in the vehicle accordingly. Further, since there are cameras and facial recognition, it can know my preferences and put them in, no matter what seat the user is in. IN another instance, the user has been surfing the Internet looking for new bikes, and the vehicle control system informs the user that there is a bike shop around the corner and adds the bike shop as a waypoint or destination.

In a further illustration, the vehicle control system synchronizes with an electronic calendar of the user to create (i) smarter alarms and (ii) updates. Smart alarms mean that instead of a standard 15 minute warning before a meeting, if it is an offsite meeting with an address entered, the system can determine how much time it will take based upon traffic, previous driving habits, the amount of time it generally takes to exit the office and get to the car, etc., and change the warning accordingly. The updates can be triggered based upon the time of arrival determination from the GPS or as calculated above and send SMS notices to other attendees or prompt to call the meeting leader. Similarly, if the car determines the user is stopping into Starbucks, it could remotely ask the other meeting attendees if they want anything.

In a further illustration, The vehicle control system knows a child's curfew and also the distance from home. Given that information, it could inform the child driver that he or she must leave to make it home in time to avoid a curfew violation. Further, since it knows the occupants, it could potentially include time to deliver them home too.

In a further illustration, the user is training for a marathon. He has a wearable device attached to his clothing that uses his biometric data (e.g., heart rate, body temperature, energy levels, sleeping habits, etc.) throughout the day. It also has a GPS that tracks location and terrain and an MP3 player. On his way to work, the wearable device has synchronized with the vehicle control system. The user verbally checks off his breakfast from his marathon widget on the home page displayed on the on board console and confirms his goals to be realized that day as well as his calendar appointments. On his way to a meeting later that day, the vehicle control system notes that it is near lunch time, reviews the restaurants in spatial proximity to the vehicle, determines which restaurants have menu items consistent with the user's dietary goals that day, and recommends a nearby restaurant. The user accepts the recommendation, and the vehicle control system books an advanced reservation and adds the restaurant as a waypoint. On his way back to the office, the vehicle control system notes that the user's heart rate is too low, notifies the user, and, upon the user's confirmation, adjusts the oxygen levels in the vehicle, seat and lumbar settings, and temperature levels to inhibit drowsiness.

In a further illustration, a user and his child enter the vehicle while the child is watching programming (such as a movie on Netflix™) on a tablet computer. The vehicle control system recognizes the user, determines his role in the car or seating position (driver), and applies the user's personal settings. The user's phone is automatically paired with the multimedia controller via the local or on board wireless access point. The vehicle control system determines that the child is in the back seat and recognizes his identity. The vehicle control system asks the user if the programming is to be continued to be provided to the child on the child's rear seat display subsystem. After dropping the child off at school, the vehicle control system determines, based on the user's electronic calendar, that the user is behind schedule for a next appointment due to an accident on the current path of travel, recommends an alternate path of travel and sends a message to the meeting participants that the user will be late and providing an estimated arrival time and reason for the late arrival. The message may be automatically generated or dictated by the user via the vehicle infotainment system. After work is over, the user drives home during a baseball game. The persona of the user informs the vehicle control system that the user is a baseball fan and recommends to the user that he tune into the game on radio. At the user's request, the infotainment system tunes automatically into the game broadcast on the radio.

The occupant persona is not limited to information obtained and stored directly by the vehicle. It can include information obtained by the vehicle from other sources, such as from a server 228 over a communication network 228 such as the Internet and IP router 420. An example would be from a social network profile or page of a selected vehicle occupant, a web or home page of the selected vehicle occupant, a telecommunications presence server associated with the selected vehicle occupant, and the like. Another example would be from another vehicle driven or occupied by the selected vehicle occupant. Another example would be from a home computer network of the selected vehicle occupant. In the latter examples, the information can be obtained not only via the Internet but also directly via synchronization when the vehicles are parked in a common garage of the occupant's home even when the ignition of the vehicle(s) is/are turned off. Another example would be from a portable communication or computational device of an occupant, such as from a device or user interface 212, 248. As noted, a transceiver of the vehicle can provide a mobile hot spot functionality not only to any user device(s) therein but also to a computer of another vehicle located in proximity to the selected vehicle. Synchronization with another vehicle's computer or with a home computer can be done, for example, by the http server capabilities of the vehicles.

The persona can be stored as part of a template locally, remotely, or combinations thereof. The persona can be stored in the cloud, on a personal communication device (such as a phone or tablet computer), in a memory of the vehicle, on a local storage memory, key fob, and the like. It may be encrypted and accessed and/or modified by the user via authorization through a verification system, which may rely on credentials and/or biometric information. The template may be universally applied by all vehicle manufacturers to enable the persona to be portable among vehicles so that the intelligent capability of the vehicle appears to follow the associated user from vehicle to vehicle even when manufactured by different companies. The template can even follow the user from seat position to seat position within a vehicle, automatically populating vehicle settings, such as seat and console settings and features associated with a new seating position, when the user is identified as having moved to the new seat.

A console may not support multimedia entertainment, particularly video. Multimedia content is typically displayed on remote display subsystems dedicated to a specific seating position.

By way of illustration, user personas may be presented (or uploaded) to a vehicle in advance of a user reaching a vehicle (rental cars, etc.). For example, Hertz® car rental agency can maintain a persona for each customer and upload the persona onto the car rented to the customer at the time the leasing is consummated. While the user is walking from the rental desk to the car, the car is automatically adjusting all of the vehicle settings as set forth in the user persona. In this way, the user need not manually select any settings when he or she begins driving the car.

By way of further illustration, as part of a travel package, a rental car system may determine where a user is staying (e.g., hotel, motel, building, etc.), a mobile device number associated with the user, and the like. The system may send a text message, email, phone call, or other signal to the mobile device number to request access to the user's persona template. The template can be incorporated with the vehicle and settings associated with the vehicle may be updated prior to the user reaching the vehicle. Using this method, administrative assistants can reserve a vehicle on behalf of another individual and link the user template to the reservation based on the user's mobile device phone number. The mobile device can act as the key. For instance, a phone number may be embedded in the private key of the mobile device. The public key may be presented to the rental car. In some cases a combination of phone number and device ID (e.g., EIN, MAC address, etc.) may be used as part of the authentication.

The vehicle control system can apply rule sets or templates to trigger notifications and other actions of the vehicle control system and/or display artificial or computational intelligence based on observing the behavior of a selected person over time. In any of the embodiments disclosed herein, the vehicle control system and/or mobile device may determine patterns, such as, destinations, purchases, etc. to categorize data, advertising, and the like. The artificial or computational intelligence can, for example, have symbolic, sub-symbolic, or hybrid components and/or modules. Examples include neural networks (e.g., acyclic or feedforward neural networks and recurrent neural networks), fuzzy systems, and evolutionary computation.

Figure 30:
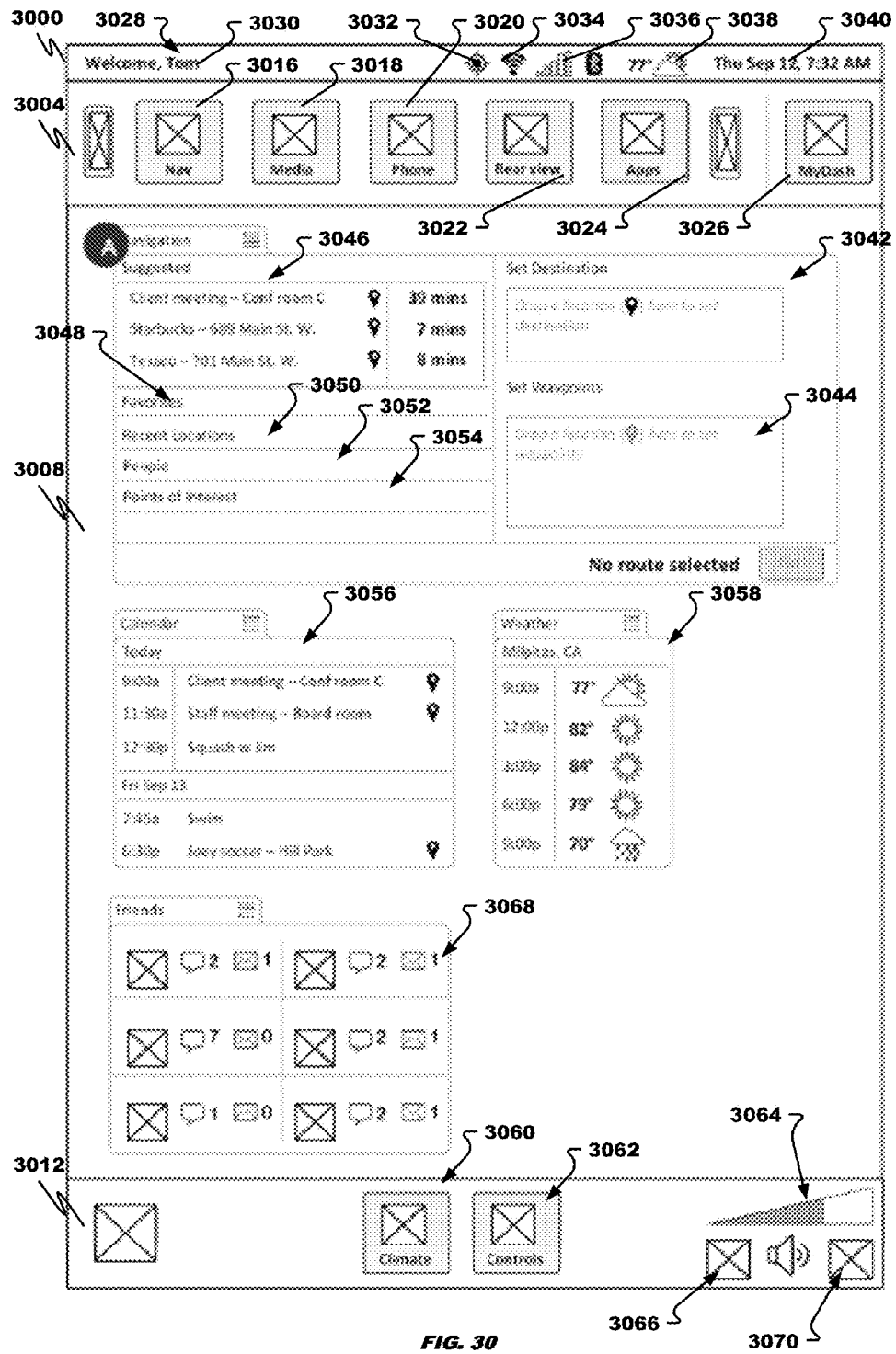
FIG. 30 depicts a screen shot according to an embodiment.

An example of a home page 3000 displayed by a device or user interface 212, 248, user interface (s)/input interface(s) 324 and/or I/O module 312 is shown in FIG. 30. The layout of the home page 3000 is defined by the user profile. When the user is signed as a guest user, a default layout is provided. The various objects in the layout can be configured as widgets or a lightweight version of an application or item of functionality.

The home page 3000 includes, in an upper area 3004 of the screen, user selectable icons for various applications (which if selected open or initiate or recall the application), such as navigation ("Nav" icon) 3016, media ("Media" icon) 3018, phone ("Phone" icon) 3020, rear view (to provide the driver with a video stream from a backup camera) ("Rear View" icon) 3022, other applications 3024, and "my dash" (to provide the user with a display having typical dash indicators, such as speedometer, tachometer, oil pressure, warning lights, battery charge indicator, fuel level, and the like) 3026; an upper information bar 3028 including a greeting to the identified driver 3030, satellite reception indicator 3032, WiFi connectivity indicator 3034, cellular connectivity indicator 3036, weather information 3038, and date 3040; in a central area 3008 of the screen, various types of information, such as navigation input fields 3042 (e.g., "set destination" field (which is a drop target into which location-enabled objects can be dragged and dropped) to provide guidance from the user's current user inputted or satellite-based location to the inputted destination), "set waypoints" field 3044 ((which is a drop target field into which any location-enabled object can be dragged and dropped) to set an ordering of waypoints along a selected or inputted route), suggested locations 3046 (based on upcoming events in the electronic calendar of the user and/or based on the user's preferences, likes, schedule, and observed habits and other persona information) (and therefore have location information, such as address information, inputted into the calendar entry and/or satellite-based coordinates based on prior driving history)) to be dragged and dropped into the "set destination" and/or "set waypoints" field, favorite locations 3048 (which is a list of user-defined favorite locations and which can also be dragged and dropped into the "set destination" and/or "set waypoints" field (and therefore have corresponding location information, such as satellite-based geographic coordinates or addresses entered in field(s) associated with the respective favorite locations (a home or work address is an example of a user selected favorite location))), recent locations 3050 (which refer to locations visited within a user-defined time interval of the present time and/or at least a predetermined number of times over a user-defined time interval and which can also be dragged and dropped into the "set destination" and/or "set waypoints" field (and therefore have corresponding location information, such as satellite-based geographic coordinates or addresses entered in field(s) associated with the respective recent locations)), "people" 3052 (which can be the contacts of the user or other list of friends and which provide names, contact information, and addresses for people having a corresponding contact profile, which profile can also be dragged and dropped into either the "set destination" or "set waypoints" field), points of interest 3054 (which are points of interest or potential interest to the operator such as food serving locations, fuel stations, lodging facilities, parking, attractions, health care facilities, historical landmarks, and the like and which can also be dragged and dropped into either the set destination or set waypoints field (and therefore have corresponding location information, such as satellite-based geographic coordinates or addresses entered in field(s) associated with the corresponding point of interest)), display of calendar appointments for a selected day 3056, weather information for a selected day (e.g., temperatures, precipitation, wind speed and direction, atmospheric condition (e.g., sunny, partially sunny, cloudy, partly cloudy, etc.), 3058 and received and/or sent messages (e.g., emails, voice mails, and/or texts) 3068 from friends (which dropdown menu can include family, business contacts, and other user defined category of contacts); and in a lower area 3012 of the screen, a climate control icon ("Climate" icon) for a climate control application 3060, controls icon ("Control" icon) to control vehicle tasks, functions or operations 3062, and speaker volume settings (shown by the speaker and triangle images) 3064 and controls to the left and right of the speaker image 3066 and 3070.

When a suggested, favorite, recent location, people, or points of interest object or object identifier is dragged and dropped by a sensed gesture or stylus or mouse into the "set destination" or "set waypoint" fields, the navigation subsystem 336, based on the current satellite-based location of the vehicle, automatically determines a route from the vehicle's current location to the stored location associated with the dragged and dropped object. As more objects are dragged and dropped into either the "set destination" or "set waypoint" fields, the route is altered to accommodate the various associated locations. A traceroute on a map and/or directions can be provided to the vehicle operator. The traceroute or directions can be updated to show the vehicle's current location. The traceroute or directions can be altered to reflect traffic and/or road conditions (when the user selects "quickest" route), surface street or highway preferences, roadside aesthetics (when the user selects "most scenic" route), and the like. This information can be displayed by the user selection of the "Nav" icon 3016.

The screen can provide a map on the background to assist navigation configuration. As the user configures the "set destination" and "set waypoint" fields, the traceroute can be updated on the background map. In other words, the various location-enabled objects and the "set destination" and "set waypoint" fields are overlays of the map.

As noted, the screen configuration and content, such as the arrangement of the various icons and displayed information, can be rearranged or reconfigured by the user to reflect his or her needs or desires.

Because the screen content is complex and/or content-heavy and can distract the operator when driving, the screen may be altered when the vehicle is in a driving mode relative to a parked mode. In a driving mode, the wheels are in motion and the gear shift is out of the "parked" position. In the parked mode, the wheels are not in motion and the gear shift is in the "parked" position. The home screen of FIG. 30 therefore can be closed automatically on the driver's console display and disabled when the vehicle is in the driving mode and opened automatically and enabled when the vehicle is in the parked mode.

Certain applications can be launched automatically when the vehicle is in the driving mode. An example would be the navigation application so that the console display shows the display for the navigation application instead of the home screen of FIG. 30. One or more other applications can be selected by the user as the display in driving mode.

Alternatively or additionally, when the vehicle is placed in reverse gear with the home screen active, the rear-view application can be launched automatically to display, in the rear view application display, live video from one or more rear cameras on the back of the vehicle. When the vehicle is placed in forward gear, the rear view application can be automatically closed to terminate the rear view application display and the navigation application automatically opened to provide the navigation display.

Figure 36:
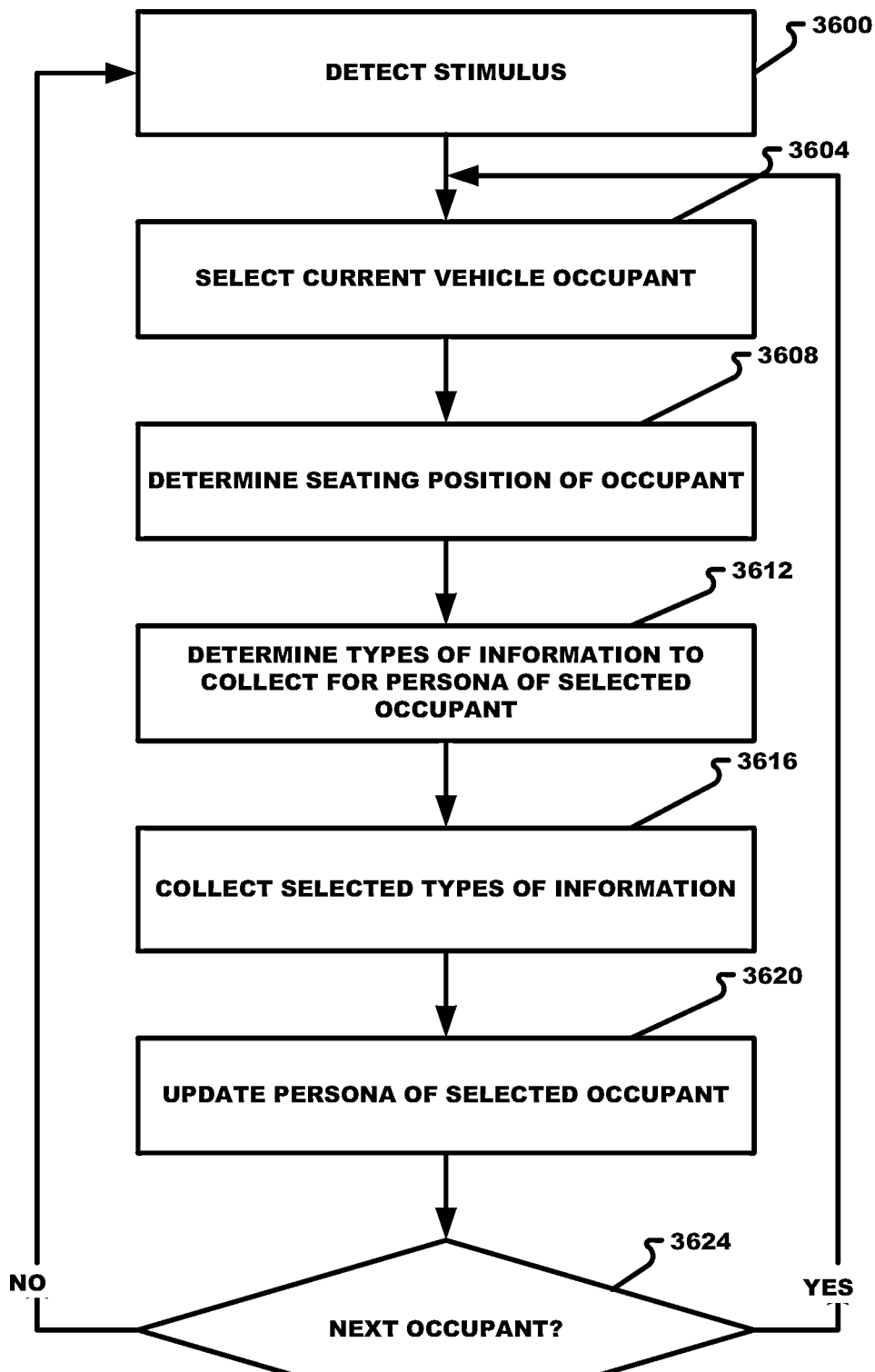
FIG. 36 depicts a flow diagram according to an embodiment.

The operation of the profile identification module 848 will be discussed with reference to FIG. 36.

In step 3600, the, the profile identification module 848 detects a stimulus, such as the vehicle changing operational state, expiration of a selected time period, a door opening or closing, and the like.

In step 3604, the profile identification module 848 selects a current vehicle occupant, which can be the driver or a passenger.

In step 3608, the profile identification module 848 determines a seating position of the selected vehicle occupant; that is, the module 848 determines which of the driver's seat, front passenger seat, driver's side rear passenger seat, middle rear passenger seat, and passenger's side rear passenger seat the selected vehicle occupant is occupying. This can be done by the user identification module 822.

In step 3612, the profile identification module 848 determines the types of information to collect for the persona of the selected occupant. The type of information to be collected can vary by occupant identity, age of occupant, an association of the occupant with the vehicle, and/or occupant seating position. For example, the driving history during the recent vehicle use may be collected for a driver but not a passenger. The driving history during the recent vehicle use may be collected for an adult passenger but not for a child passenger. The driving history during the recent vehicle use may be collected for a vehicle owner but not for a guest driver or driver having a default profile.

In step 3616, the profile identification module 848 collects the selected types of information.

In step 3620, the profile identification module 848 determines whether there is a next occupant to be selected. If so, the profile identification module 848 returns to step 3604. If not, the profile identification module 848 returns to step 3600 and awaits the next stimulus instance.

Figure 37A:
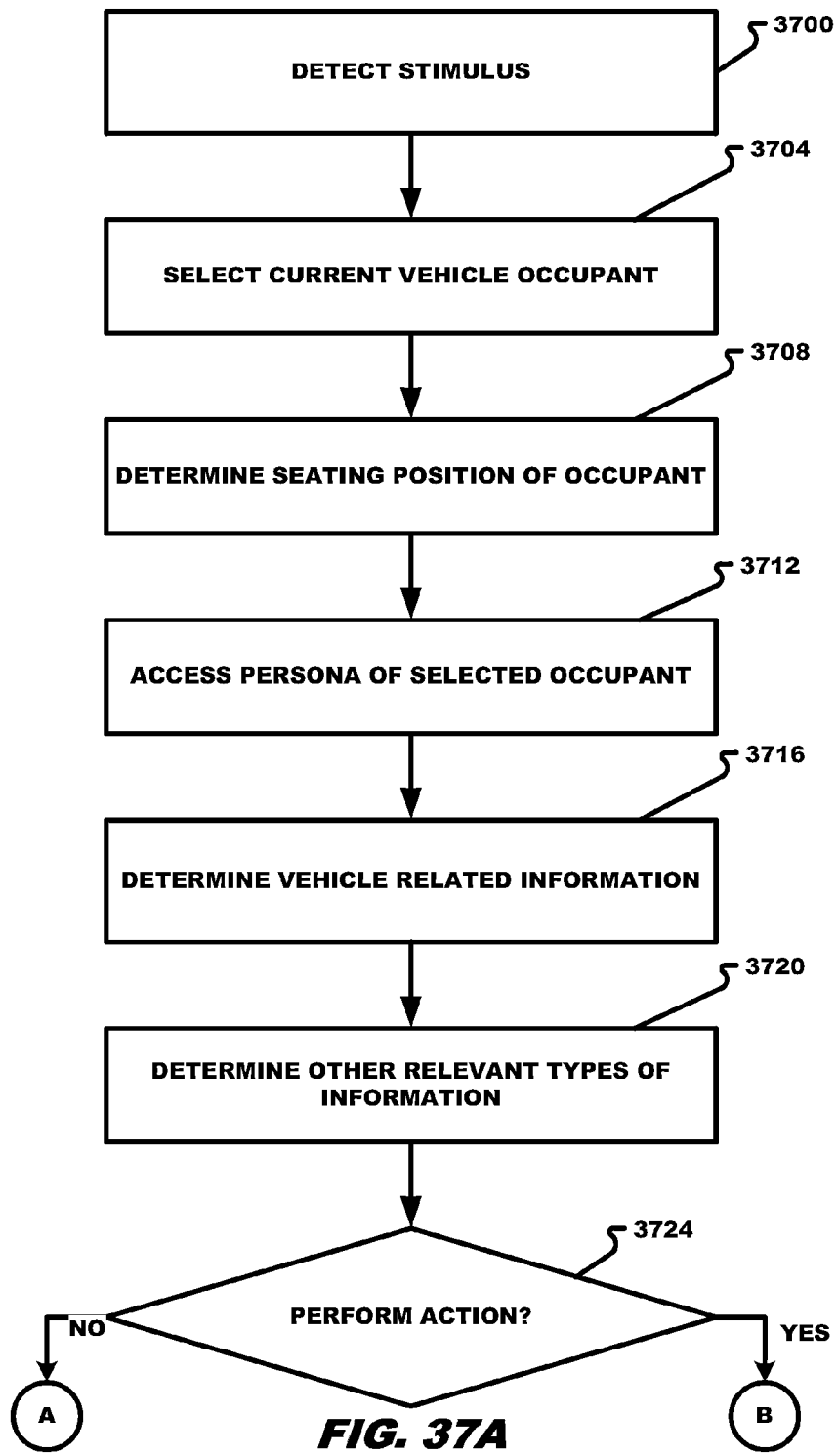
FIGS. 37A-B depict a flow diagram according to an embodiment.
Figure 37B:
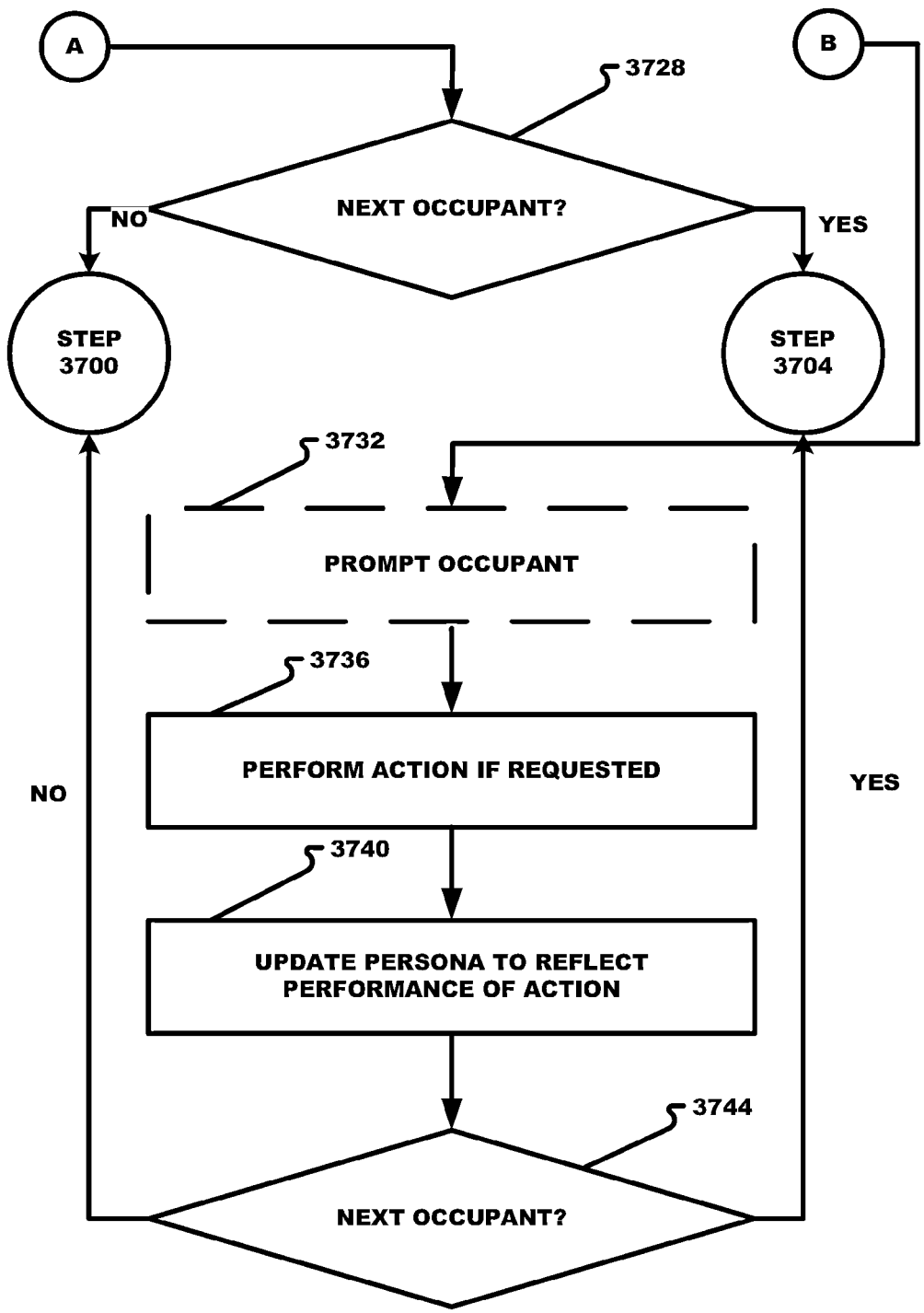

An operation of the vehicle control system 204 will be discussed with reference to FIGS. 37A-B.

In step 3700, the vehicle control system 204 detects a stimulus, such as the vehicle changing operational state, expiration of a selected time period, a door opening or closing, and the like.

In step 3704, the vehicle control system 204 selects a current vehicle occupant.

In step 3708, the vehicle control system 204 determines a seating position of the selected occupant.

In step 3712, the profile identification module 848 accesses, at the request of the vehicle control system 204, the persona of the selected occupant.

In step 3716, the vehicle control system 204 determines vehicle related information. This information includes typically any information collected by an interior or exterior vehicle sensor 104, 242, including a satellite navigation system, such as GPS 488.

In step 3720, the vehicle control system 204 determines other relevant types of information, such as the information referenced above in the examples and illustrations. The other relevant types of information can include, for instance, a persona of a selected person not currently in the vehicle, an instant message, email, voice mail from, missed phone call from, current activity of and/or current location of a friend and/or family member of the selected vehicle occupant, a location, hours of operation, and/or descriptive information about a point and/or location of interest near the vehicle and/or its path of travel, a location, hours of operation, and/or descriptive information about a vehicle service facility near the vehicle and/or its path of travel, a location, hours of operation, and descriptive information about a hotel and/or motel near the vehicle and/or its path of travel, a current location of the friend or family member near the vehicle and/or its path of travel, a road condition such as traffic, road construction, or other delay near the vehicle and/or its path of travel, and the like. This information can be collected from the server 228 via the communication network 224.

In decision diamond 3724, the vehicle control system 204 determines whether or not to perform an action. This determination can be based on a rule-based or template-based analysis of the persona of the selected occupant, vehicle related information, and other relevant types of information. The particular rules selected to apply to the collected information to determine whether or not to perform an action and what action to perform can depend on the identification of the selected vehicle occupant and/or seating position of the selected vehicle occupant. Actions that can be performed include those referenced above, including making an appointment or reservation, purchasing an item on line, adding a waypoint to a path of travel on a navigation system, adding an entry into the selected occupant's calendar, changing a destination or path of travel on a navigation system, warning or notifying the occupant, and sending a message to a person regarding an arrival time at a waypoint or destination.

When the vehicle control system 204 determines not to perform an action, the vehicle control system 204, in decision diamond 3728, determines if there is a next occupant to be selected in the vehicle. If not, the vehicle control system returns to step 3700 and, if so, to step 3704.

When an action is to be performed, the vehicle control system 204 in step 3732 optionally prompts the occupant whether or not the action is to be performed.

When instructed, the action is performed in step 3736.

In step 3740, the profile identification module 848 updates the persona of the selected vehicle occupant to reflect the action performed and the surrounding context. This can be important for the vehicle control system 204 creating new rules describing the likely behavior of the selected vehicle occupant.

In decision diamond 3728, the vehicle control system 204 determines if there is a next occupant to be selected in the vehicle. If not, the vehicle control system returns to step 3700 and, if so, to step 3704.

Operation of the Device Discovery Module 2080

The device discovery daemon 1020 can discover automatically computational devices within the vehicle that connect or attempt to connect to network 356 or communication subsystem 1008 or that disconnect or attempt to disconnect from the network 356 or communication subsystem 1008. The device discovery daemon 1020 discovers automatically computational devices, such as portable user communication devices, located within the vehicle and connects, wirelessly, the portable user communication device with the network 356 or communication subsystem 1008.

The device discovery daemon 1020 may intercept emitted signals from one or more devices in or about the vehicle to pair a device with the network 356 or communication subsystem 1008. Rather than requiring an active pair handshake, the network 356 or communication subsystem 1008 may utilize certain receivers to "listen" for cell tower registration signals, sent messages, sent packets (packet sniffing), etc. From this information, the device discovery daemon 1020 may isolate a MAC address, or other identifier, associated with a device and register the device with the vehicle, a vehicle zone, a user, etc. In some cases, and upon detecting a device signal, the device discovery daemon 1020 may request permission from a user before pairing the device. In one example, the pairing may be initiated by the device discovery daemon 1020 (upon a first registration) to a user's device. Subsequent pairings may be initiated by a user's device to the network 356 or communication subsystem 1008. One or more of Bluetooth, Near Field Communications (NFC), and other protocols may be used to pair a device with the network 356 or communication subsystem 1008.

Figure 20:
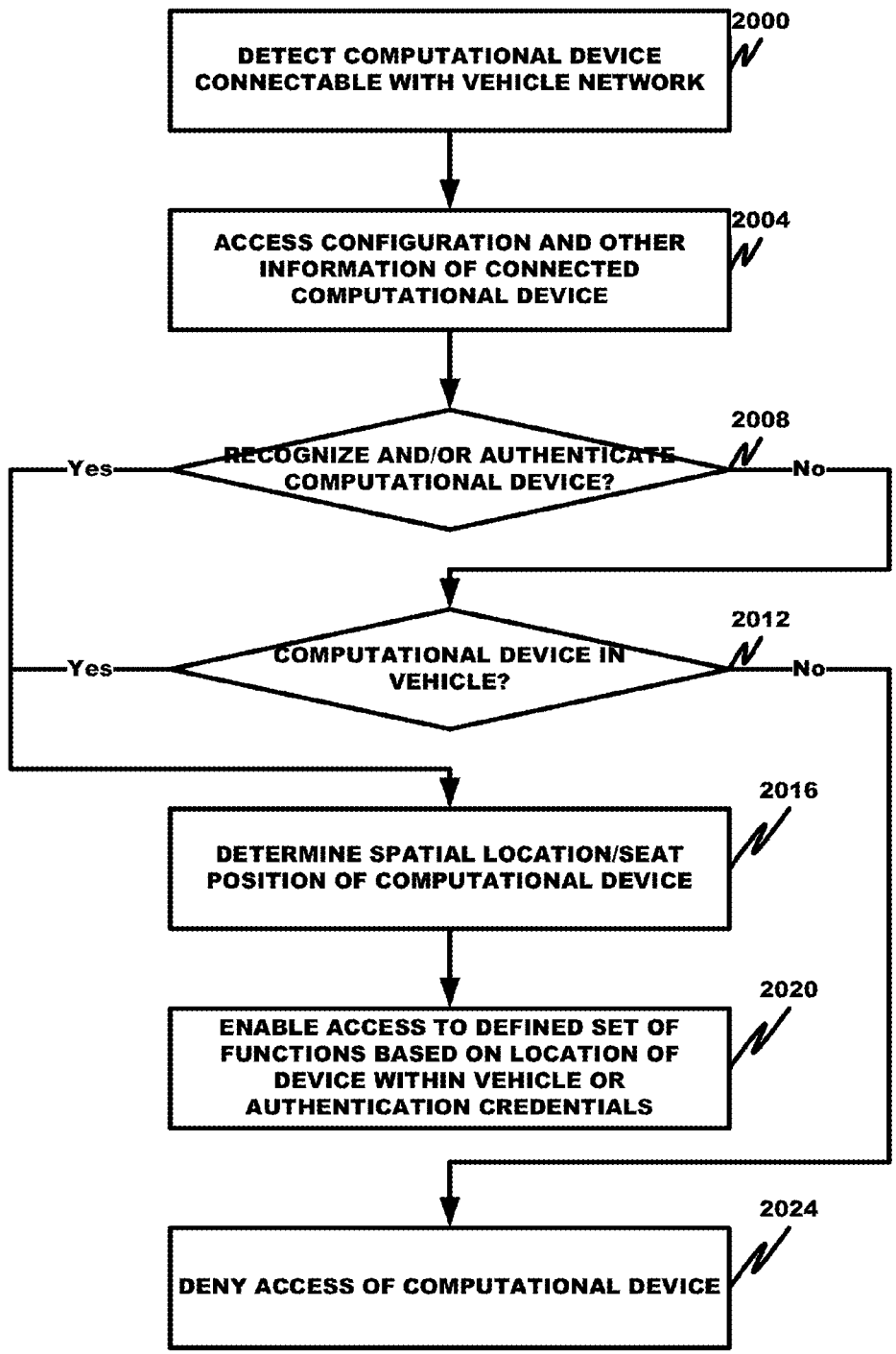
FIG. 20 depicts a flow diagram according to an embodiment.

FIG. 20 depicts an operation of the device discovery daemon 1020.

In this operation, the device discovery daemon 1020 detects a computational device attempting to connect to or otherwise connectable with the vehicle network 356 or communication subsystem 1008 and, applying rules, determines when it is appropriate to connect with the computational device. The computational device may be a module installed on a backplane, a vehicle component and/or module that is attempting to be installed, a portable user communication device, and the like. The daemon can ping the local communication network each time the vehicle starts or each time a vehicle door opens or closes. The daemon can perform a Bluetooth™ and WiFi™ device discovery too. For each communication device that responds to the ping, the daemon can use plural protocols, such as HPPOPT, ICMP, IGMP, GGP, IP, ST, TCP, EGP, CHAOS, and UDP to populate a device's folder in the device data with device capabilities. Device capabilities are determined by the opened port(s) the device exposes.

The device discovery daemon 1020, in conjunction with the combo controller can determine a spatial location of the computational device as a prerequisite to permitting the computational device, even if properly authenticated, to connect to the vehicle network 356 or communication subsystem 1008. The spatial location can be required to be in an area 508 or set of areas 508 and/or zone or set of zones. Depending on the type of computational device, the computational device, for example, may be required to be in the area two 508B for connection to be accepted. This can be the case for a portable personal communication device, such as a wireless or cellular phone, tablet computer, personal digital assistant, laptop, and the like. For other types of computational devices, the computational device, for example, may be required to be in area one 508A (such as the engine space) and/or area N 508n (such as the trunk). Thus, different types of computational devices can have different location requirements as a prerequisite for connectivity to be enabled or accepted. This can be the case for an engine control module, vehicle sensor, or other device that controls or senses a vehicle task, function or operation that, for instance, either connects wirelessly or by a wire-line connection, to the red zone 417, green zone 413, or I/O backplane on the network/bus 408.

In step 2000, the device discovery daemon 1020 detects a computational device connectable with the vehicle network 356 or communication subsystem 1008. "Connectable" can refer to the computational device being physically within the vehicle, the computational device having a threshold signal strength or connection quality with the vehicle network, the computational device being configured properly to connect with the vehicle network, and the like. "Connection" can be done either wirelessly or by wired connection.

Detection can be done by pinging the computational device and/or receiving a ping from the computational device. As an example, to connect to a Wi-Fi LAN a computational device must be equipped with a wireless network interface controller. The combination of a computer, such as the computer in the computational device, and interface controller is called a station. All stations share a single radio frequency communication channel. Transmissions on this channel are received by all stations within range. The hardware does not signal the user that the transmission was delivered and is therefore called a best-effort delivery mechanism. A carrier wave is used to transmit the data in packets, referred to as "Ethernet frames". Each station is constantly tuned in on the radio frequency communication channel to pick up available transmissions.

Device detection can be in response to or triggered by a sensed event other than receipt of a ping from the computational device. As noted, device detection can be receipt of information from one or more on board sensors that a new occupant has entered the vehicle. Exemplary information includes a door opening or closing, a successful authentication of an occupant or computational device, a sensed load in a seat, detection of movement within the vehicle, and detection of initiation of a vehicle task, function or operation, such as a key inserted in an ignition, engine start up, and the like.

In step 2004 and as noted above, the device discovery daemon 1020 accesses computational device accesses configuration and other information and capabilities of the connected computational device. This information can include device type and/or class, manufacturer name, product and/or device identifier or name, firmware identification, services running, device operating system, network address(es), capabilities, user credentials, and the like. The device discovery daemon 1020 can determine presence of the computational device on any input channel, such as Ethernet, USB, WiFi, Bluetooth, and the like.

In decision diamond 2008, the device discovery daemon 1020 determines whether or not the computational device is recognized and/or authenticated properly. Recognition can be based on any of the configuration and other information and is deemed to occur when selected fields of the information map to and are the same as similar fields previously encountered and/or recorded in system data 208 by the device discovery daemon 1020. Authentication is deemed to occur when the credentials match stored credentials for the recognized computational device.

When the computational device is not recognized and/or authenticated successfully, the device discovery daemon 1020, in decision diamond 2012, determines whether the computational device is in a predetermined area or zone of the vehicle for the type of computational device corresponding to the computational device. As will be appreciated, some wireless protocols, particularly WiFi™, use an access point (or hotspot) having a defined range, which can be commensurate with the area of the vehicle passenger cabin. The passenger cabin can be surrounded by walls that substantially block radio waves to prevent computational devices external to the passenger cabin from connecting to the network. Multiple overlapping access points can be used to cover larger passenger cabins, such as buses, trains, planes and the like. This determination can be based on received signal strength from the computational device, a satellite-based position of the computational device compared to a satellite-based position of the vehicle or sub-area of the passenger cabin, triangulation based on the relative received signal strengths of multiple access points, camera feedback or image processing of camera or video feed of the passenger compartment, occupant information received from other sensors such as occupant location or presence information received from an infrared sensor 740, motion sensor 744, weight sensor 748, biometric sensor 756, camera sensor 760, audio sensor 764, and associated device sensor 720, user input and the like. User input can be received by a screen pop-up on the computational device requesting the user to designate whether or not and what vehicle the user is currently in and/or what seat position the user has in that vehicle.

A level of confidence can be assigned by the device discovery daemon 1020 to the computational device indicating a likelihood or probability that the computational device is located within the passenger compartment. This level of confidence can be based on consideration and analysis of multiple of the factors identified above. When multiple factors indicate that the user is within the passenger compartment, a higher likelihood is assigned to that determination; likewise, when multiple factors indicate that the user is outside of the passenger compartment, a lower likelihood is assigned to the determination. When no or an unsatisfactory response is received from the user in response to a request for user input and/or the level of confidence is below a selected threshold, the user is deemed to be located outside of the predetermined area and/or zone.

A further spatial determination can be made by the device discovery daemon 1020 based on how the computational device connected to the automotive network. If the computational device is hard wire connected, or plugged in, to the automotive network (which can be determined by known techniques), the spatial location of the computational device can be assumed to be within the vehicle regardless of other location mechanisms employed by the device discovery module.

A further spatial determination can be made by the device discovery daemon 1020 based on whether or not the computational device has moved within a defined time interval. This indicates that the computational device may not be within the vehicle as movement of a computational device within the vehicle is less likely than a computational device located outside of the vehicle, where the person corresponding to the computational device is often moving relative to the position of the vehicle.

A further spatial determination can be made by the device discovery daemon 1020 based on whether the signal strength or signal-to-noise ratio associated with a ping or other signal from the computational device varies significantly over a selected time interval. The signal-to-noise ratio associated with signaling from a computational device located within the vehicle would remain relatively constant while the signal-to-noise ratio associated with signaling from a computational device located outside of the vehicle would likely vary significantly as the person associated with the computational device moves relative to the vehicle and/or network 356 or communication subsystem 1008.

A further spatial determination can be made by the device discovery daemon 1020 based on an analysis of signal characteristics. Signal characteristics can include one or more of, but is not limited to analyzing signal attenuation, where a signal with a shrinking strength or increasing strength may be determined to be moving in relative proximity or position to the vehicle, analyzing any Doppler shift in the frequency, which may indicate movement in reference to the vehicle and/or network 356 or communication subsystem 1008, analyzing any kind of delay between receiving the same signal at the various transceivers 260 and/or sensors 242A-N. A difference in the time of receipt can be used to triangulate where the location of the signal originated and if that location is outside the vehicle or inside the vehicle.

A further spatial determination can be made by the device discovery daemon 1020 based on an analysis of location information. Beyond the signal characteristics, the device discovery daemon 1020 may receive information from one or more sensors 242A-N to determine a location of the vehicle. If the location of the vehicle is in an area where there is not a likelihood of signal congestion, for example, in the driveway of someone's home, then all received signals may be determined to have been with inside the vehicle. Thus, as signals are received and if the location has changed, the device discovery daemon 1020 may determine whether the current location is an area where there may be more signals received that would be outside the vehicle or whether the signals received has changed.

Analysis of the person sending the signal may also be used by the device discovery daemon 1020. Thus, the device discovery daemon 1020 may access historical signal data (which is a record of devices that have previously been granted access to the vehicle communications network) to determine if the signals have been received from this device or from this person before. Thus, the signal may identify a person documented in the signal data, and the device discovery daemon 1020 may determine if that person has used or connected with the device discovery daemon 1020 previously. Further, the device discovery daemon 1020 can determine if there is movement of the vehicle. If a signal remains within the car after the vehicle moves, then that signal can be determined to be inside the vehicle. For example, if the signal is received at the beginning of a route and then at some time thereinafter the signal continues to be received, then it is determined that signal may be inside the vehicle.

Further, sensor data may be analyzed by the device discovery daemon 1020. Sensor data may include such things as determining if there are people and the number of people within a car. Thus, if there are three people in the vehicle and three signals are received, all three signals may be determined to be inside the vehicle. Further, it may be possible for the sensors 242 to determine if a device is currently being used inside the vehicle. For example, if an optical sensor can view a device within its field of vision and/or if an electromagnetic field sensor determines that there is EMF radiation emanating from a location in the vehicle, then the device discovery daemon 1020 can determine that that signal is originating inside a vehicle.

A further spatial determination can be made based on the type (or service) of computational device attempting to interact with the automotive network. If the computational device is not the type (or service) of device expected to be positioned within the passenger compartment, its attempt to connect to the automotive network can be disregarded completely. If the computational device is the type (or service) of device that can be connected to the vehicle network but is not the type (or service) of device expected to be associated with an occupant (such as a non-infotainment vehicle task, function, or operation control module, sensor module, a module plugged into a backplane (such as an XM radio module), or other type of device not permitted or expected to be associated with an occupant), the spatial determination may be deemed to be satisfied by the computational device being located somewhere within the vehicle even if outside of the passenger compartment. Conversely, if the computational device is the type (or service) of device that would normally be carried by a vehicle occupant, the spatial location query would be satisfied only when the computational device location were within the passenger compartment. This would prevent an unauthorized computational device, such as a cell phone or tablet computer, from connecting to the automotive network simply by being held above, beside, or beneath the vehicle. The mapping of type of computational device to permissible location (e.g., area and/or zone) within the vehicle can be effected in a look up table or other set of rules.

The device discovery daemon 1020 may receive one or more of these analyses and resolve the information. Thus, device discovery daemon 1020 can cross-correlate information from different analyses to determine if the signal is within the vehicle. Different weight may be given to different analyzes to make a determination about where the signal originates. In this way, a more robust decision is made as to whether or not the signal originates in the vehicle and should be allowed to connect to the universal bus or the routing system of the vehicle.

While this logic is described with respect to the location of the computational device, it is to be understood that this determination is optional. Whether or not a communication device is enabled to connect to the vehicle network 356 or communication subsystem 1008 can be based solely on successful authentication. In this way, the vehicle on board computer can connect automatically to the owner's home virtual private network to upload and/or download information, settings, and other information (such as user input into the vehicle computer, vehicle driving history (e.g., miles traveled, travel traceroutes, speeds traveled, and locations visited), vehicle service information (such as gas and fluid levels, engine problems, alarms or warnings activated, and the like), input received by on board applications from the user (such as scheduled appointments, notes, documents, and the like), applications downloaded, and the like. Synchronization of the on board vehicle and home computer can occur automatically whether the vehicle is turned on or off. This can be highly beneficial when the vehicle is parked in the garage.

When the computational device is recognized and/or authenticated and/or when the computational device is determined to be within a proper area and/or zone of the vehicle for the device type of the computational device, the device discovery daemon 1020, in optional step 2016 determines a spatial location and/or seat position of the computational device to determine appropriate rights and/or privileges and/or restrictions of the user of the computational device as defined by user account or profile associated with the user, the device type of the computational device, the seat position of the user, or area or zone in which the user and/or computational device is located.

In step 2020, the device discovery daemon 1020 permits or enables connection of the computational device with the vehicle network 356 or communication subsystem 1008 and optionally stipulates or defines what set of tasks, functions, and/or operations the user of the computational device can perform using the computational device, such as based on the location of the computational device within the vehicle and/or based on the authentication credentials (e.g., the identity of the computational device user).

When the computational device is determined to be outside of a defined area and/or zone of the vehicle (e.g., outside the passenger compartment or cabin) and the device discovery daemon 1020 does not recognize and/or authenticate the computational device successfully, the device discovery daemon 1020, in step 2024, denies access of the computational device to connect to or access the vehicle network 356 or communication subsystem 1008.

An example of the device discovery daemon 1020 operation will now be discussed. Assume that a vehicle owner purchases an XM radio module off the shelf from a vendor. The user then plugs in the module to the vehicle network. In attempting to enable the functionality of the XM radio, the device discovery daemon 1020 first attempts to recognize and/or authenticate the module. During the process, the XM radio module can be permitted to communicate through the vehicle network or an antenna internal to the module with a remote website to confirm that the XM radio was purchased by the vehicle owner and/or perform licensing validation checks. The vehicle owner's XM radio account is likely already associated with the XM radio module when purchased.

When the XM radio module is plugged into a backplane (FIG. 4) in the vehicle network 356 or communication subsystem 1008, the trigger event occurs, and the device discovery daemon 1020 and combo controller commence operation. After device discovery is completed successfully by the device discovery daemon 1020, the combo controller downloads, from the user's XM account, the user's XM preferences (e.g., favorites) and causes the XM functionality in the vehicle to be configured accordingly. During installation, the combo controller can provide an installation in process dialog the user and, upon successful completion, an installation complete dialog. After acknowledging that the installation is complete, a new application icon for the XM radio appears in the upper area of the screen of FIG. 30. The new application icon can have a different appearance than other previously installed application icons to inform the user that the new application is available. When the user launches the new application, the application screen is shown. The application screen of any application depends on the application and user preferences.

The environment 400 of FIG. 4 can interface with three different types of blade processors. A first type of blade processors is installed prior to sale by a manufacturer or vendor. These blade processors are in a manufacturer "crate" and not replaceable or upgradeable by the customer but only by a certified service facility. A second type of blade processors can be installed post-sale by or on behalf of the customer. These blade processors are in a customer "crate". A third type of blade processors interfaces with the first and second type of blade processors. These blade processors are in an accessory "crate". The blade processors generally refer to executable instructions executing on a microprocessor. Each blade typically includes a corresponding set of functions (such as 802.11 WiFi™ interface, Bluetooth™ radio, cellphone radio, storage unit, or satellite position system (such as GPS)), a flash memory, a microprocessor, and a network interface. Typically, the function is software or a combination of hardware and software. Examples include a media controller blade, video controller blade, audio controller blade, profile identification module blade, and the like. This configuration may also be used for a wide variety of other software, such as applications, drivers, and the like, and devices, such as an infotainment system, satellite receiving system, and the like and combinations thereof. For example, an aftermarket infotainment system upgrade or component and/or module can be installed by the customer. The infotainment system upgrade or component and/or module searches for, locates, and connects to a suitable antenna installed prior to sale. The output of the blade processor is an IP message framed into an Ethernet packet. The blade processor can be compatible with the Car Area Network ("CAN") protocol. The CAN control system, which was intended for sensor feedback and controller control signaling through a relatively slow, serial bus, can be integrated into the blade processor architecture by terminating CAN buses in one or more Ethernet bus controllers. The output is configured for a discrete Ethernet-based sensor or controller, with the translation to the CAN protocol being made at a CAN Ethernet controller subsystem.

A "crate" "commonly has a backplane connector and on-backplane Ethernet interfaces that enable blade processors to communicate with one another using Ethernet messages. The crate can be a USB hub have a series of ports to permit devices to connect to the USB hub; therefore, each "crate" generally has a corresponding USB hub and ports connected thereto.

A master blade processor can be provided. The master blade processor can be substantially the same as the other blade processors except for scheduling and control functionality. The master blade processor can include a service manager that inventories hardware and software capabilities of components and/or modules available (or connected) through hard wire connections within the vehicle and/or computational devices connected wirelessly to the vehicle local area network (e.g., through a wireless access point or local hot spot maintained by the vehicle control system). The output of the inventory step is a network topology comprising assigned network addresses, component and/or module description and capabilities, operational status, and "next hop" addresses to demonstrate positions of components and/or modules next to one another. An application resource table can be maintained that maps application identity, functional description, and/or application type against computational resource requirements and/or capabilities. Requests to the master blade processor allow various applications to access distributed services or automatically disable features not supported by the vehicle's computer system.

The master blade processor can coordinate a health check for the various components and/or modules in or connected wirelessly to the vehicle's computer system and be responsible for sending a keep alive messages (or status queries or interrogation messages sent at periodic intervals) to the various components and/or modules to evaluate health or identify malfunctions. If no response is received within a predetermined time period after keep alive message transmission, a malfunction is assumed to exist.

For components and/or modules requiring high availability, the master blade processor can create a high availability set with a required number of blade processors. This table controls the priority of which blades are capable of becoming master blade processors in the event of a malfunction of the current master blade processor. Shadow copies of each high availability component (e.g., device) and/or module (e.g., application) are created and maintained for backup purposes in the event of a malfunction of the corresponding active blade processor. High availability applications write all variables to a file created at application initiation residing in vehicle memory. In the event of a malfunction of a high availability application, the master blade processor reassigns the high availability application to a new blade processor. The application can be reinitiated or refreshed or synchronized (using the shadow file) on the newly assigned blade processor. In this manner, the master blade processor is able to redistribute applications to blade processors and/or stopping execution of applications to realize a selected level of performance for the entire vehicle computer system.

A table can be maintained mapping a network address (e.g., a MAC and/or IPv6 address) of each component and/or module against information about the corresponding component and/or module and/or a pointer to a variable file for the component and/or module in memory. Entries on the table may have a corresponding state of health or be added when the corresponding component and/or module passes a health check or removed when the corresponding component and/or module fails to pass a health check.

Upon start up, the master blade processor checks the application resource requirement entries in an application resource table and assigns each application to a blade processor having the most applicable and/or available resources. If an application has specific requirements for execution (e.g., a multimedia infotainment application), the application is assigned to and locked to a specific blade processor (such as a multimedia controller).

Figure 38:
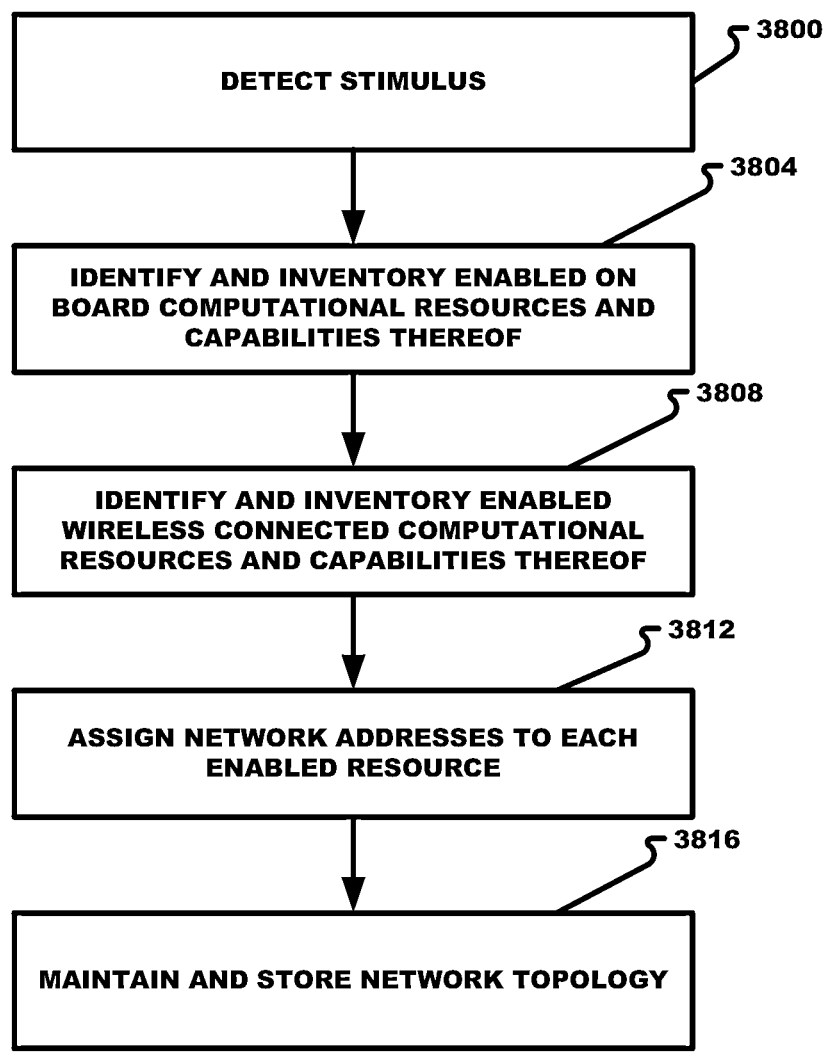
FIG. 38 depicts a flow diagram according to an embodiment.

An operation of the master blade processor will be discussed with reference to FIG. 38.

In step 3800, the blade processor detects a stimulus. The stimulus can be system boot sequence.

In step 3804, the master blade processor identifies and inventories enabled on board computational resources (such as each blade processor, IP router, vehicle sensors, database management systems, and the like, and the capabilities thereof. On board components and/or modules are typically physically connected to a network bus.

In step 3808, the master blade processor identifies and inventories enabled portable computational resources and the capabilities thereof. Portable components, such as tablet computers and smart phones, are typically wirelessly connected, via a wireless access point, to a network bus.

In step 3812, the master blade processor assigns a network address to each enabled resource.

In step 3816, the master blade processor maintains and stores the resulting network topology in system data 208.

In one configuration, a blade processor is not identified as the "master" blade processor prior to system booting. An application executes on a designated blade processor (such as a blade processor handling multimedia system or media subsystem functions) at boot time to detect the presence of a blade processor having specific capabilities. When the blade processor having the specific capabilities is identified, a variable associated with the designated blade processor is changed from "master" to "slave" and the system reboots, thereby transferring system control to the identified master blade processor. A table can be created controlling a priority of which blade processors are capable of becoming master blade processors in the event of master blade processor malfunction. When a master blade processor malfunctions, a next in priority blade processor is selected as the new master blade processor.

Figure 39:
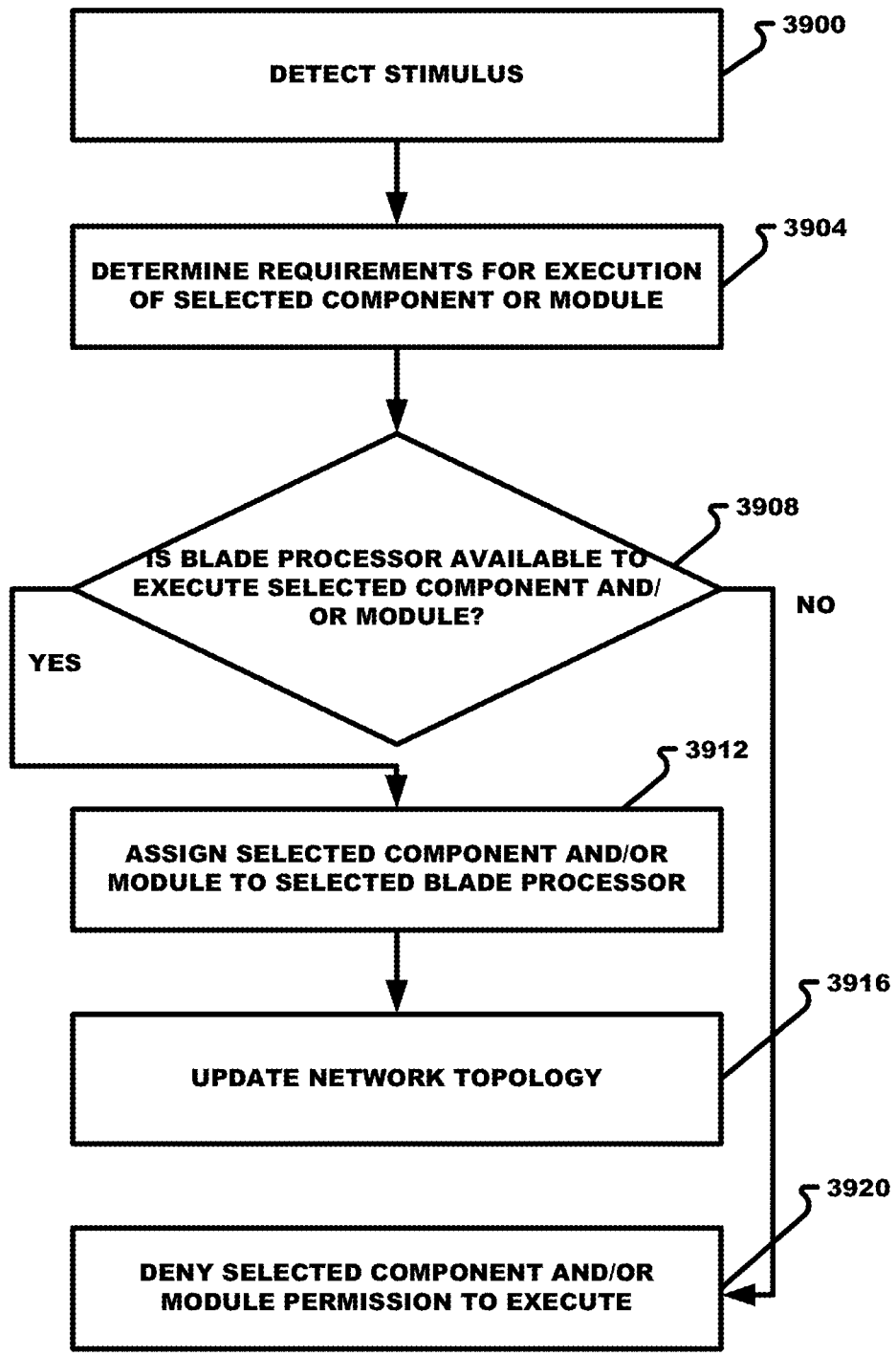
FIG. 39 depicts a flow diagram according to an embodiment.

An operation of the master blade processor will be discussed with reference to FIG. 39.

In step 3900, the master blade processor detects a stimulus. Exemplary stimuli include determining that a component and/or module has failed a health check, receipt of a request for a component and/or module for blade processor resources to execute, and the like.

In step 3904, the master blade processor determines the requirements for execution of a selected component and/or module, such as set forth in the application resource requirement table. The selected component and/or module can, for example, be a blade processor, software, such as an application, a component, such as a sensor, a satellite receiving system, and the like, and/or a combination thereof.

In decision diamond 3908, the master blade processor, based on the resource inventory output in step 3808, determines whether a blade processor is available to execute the selected component and/or module. This determination can be done by any number of techniques. It can be based on one or more of a degree of compatibility of the selected component and/or module with each of the blade processor, a current availability of a blade processor to execute the selected component and/or module (e.g., whether the blade processor is currently executing another component and/or module), a relative importance or priority of the selected component and/or module relative to a relative importance of a currently executing component and/or module on a blade processor, whether the blade processor can satisfy the requirements of the selected component and/or module, a current available bandwidth of a blade processor which may be executing another component and/or module, and the like.

In step 3912, which is performed when a blade processor is available to execute the selected component and/or module, the master blade processor assigns the selected component and/or module to a blade processor for execution. The assignment is recorded in a resource allocation table which maps application identity and/or description against an identifier of the assigned blade processor. If an application has specific requirements for execution (e.g., a multimedia infotainment application or firewall application), the master blade processor may permanently assign the application (or lock the assignment) to a specific blade processor. The master blade processor can, for unlocked assignments, redistribute or reassign components or modules to blade processors or stop components or modules from executing to realize a maximum performance level for the system and/or ensure that critical vehicle, less critical vehicle, or infotainment tasks, functions, or operations are performed.

By way of example, the master blade processor can stop a lower importance or priority component and/or module from executing in favor of a higher importance or priority component and/or module requiring a blade processor to execute. For example, a critical task, function or operation has a higher level of importance or priority than a less critical vehicle task, function or operation. A less critical vehicle task, function or operation can have a higher level of importance or priority than an infotainment task, function or operation or vice versa.

The master blade processor, in next step 3916, updates the network topology.

In step 3920, which is performed when a blade processor is unavailable to execute the selected component and/or module, the master blade processor denies the selected component and/or module permission to execute.

When the master blade processor determines that a minimum set of blade processor resources and/or capabilities is not operational, it will send a system reset message to clear operator warning circuitry within an allocated timeframe.

Streaming of Media

An integrated circuit board configuration can be provided to enable media streaming to computational devices wirelessly connected to the vehicle network via an access point 456 of the vehicle. In this manner, different media can be provided simultaneously to different user interfaces (e.g., on board display subsystems) of different vehicle occupants.

Figure 21:
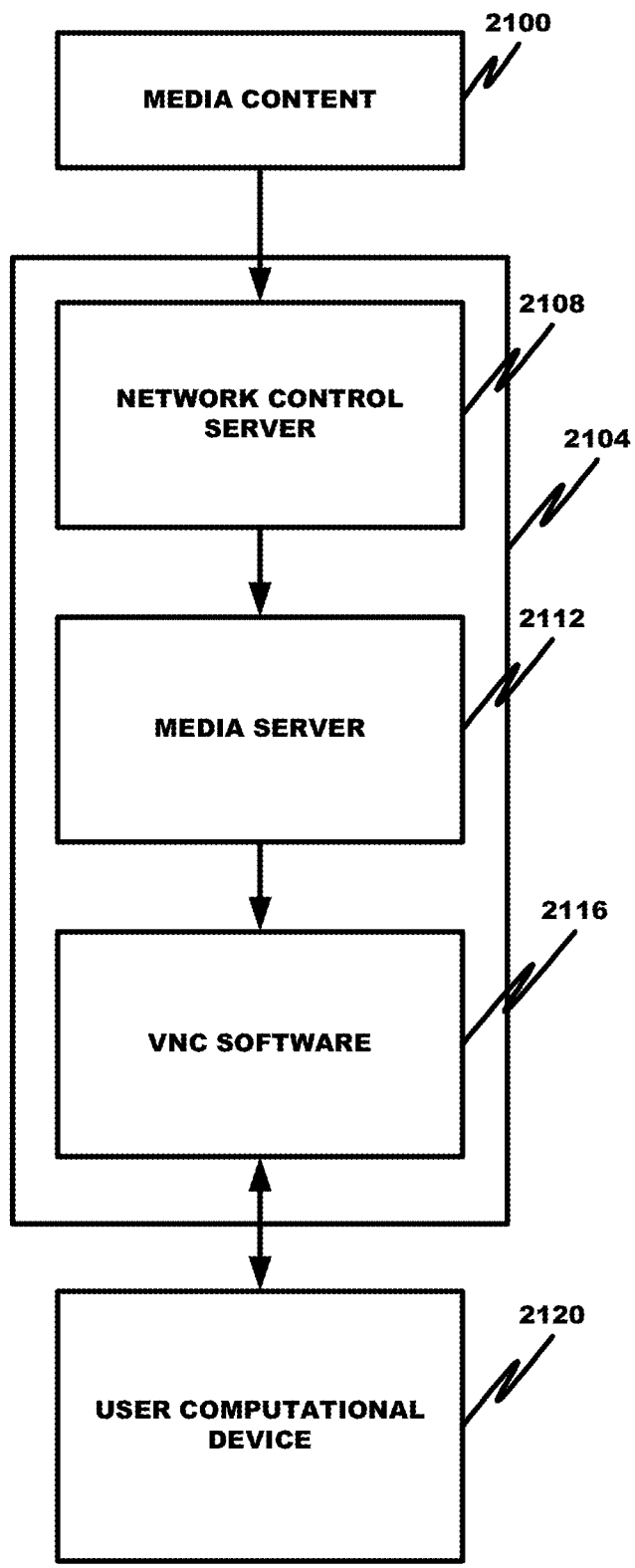
FIG. 21 depicts an on board media system according to an embodiment.

FIG. 21 depicts a configuration of the media controller subsystem 348 for simultaneously streaming multiple channels of media (e.g., multimedia or infotainment content). Media content 2100, such as audio, video, picture, and/or text media, is received by the network transceiver 824 and provided to a common media processing board 2104. The processing board 2104 comprises a network control server 2108, such as a distributed network control ("DNC") server, a media server 2112, such as a digital living network alliance ("DLNA") server, and virtual network console ("VNC") software 2116. The network control server 2108 has an IP address and/or a routable, global unicast address while the media server has a contactable electronic address (such as a media access control or MAC address) on the vehicle network 356 or communication subsystem 1008.

As will be appreciated, each of the network control and media servers 2108 and 2112 comprise a microprocessor and memory to buffer media content, execution of application programming, long term storage of program instructions and/or data, and the like. In one application, the media server 2112 comprises functionality of the media controller 804, media processor 808, and signal processing module 828.

A user portable (remote) or Bring Your Own Device (BYOD) computational device 2120 is in wireless or wired communication with the board 2104, such as via a wireless protocol (e.g., Bluetooth™, WiFi™ and the like). The VNC software 2116 effectively provides the remote computational device 2120 (e.g., portable communication device) with remote access to the board 2104, which is typically part of the vehicle on board computer (e.g., the console computer). As will be appreciated, the VNC software can operate in accordance with the RFB (Remote Frame Buffer) protocol on top of the TCP/IP suite of protocols. The result is that the remote computational device appears to the on board computer as if it were part of the on board vehicle computer or vehicle control system 204. This enables the remote computational device to provide commands to the media controller subsystem 348 for desired multimedia content and media presentation features and settings (such as volume, contrast, resolution, channel selection, and the like). In some applications, the remote computational device must download an application from the vehicle to enable multimedia requests from the remote computational device to pull information from the multimedia controller, where the media can be streamed to its final destination. The commands are provided, by the VNC software 2116 indirectly to the media server 2112 for delivery to the network control server 2108 or directly to the network control server 2108, which retrieves the requested content from an external network (e.g., an Internet or radio network) accessible source. The media may then be provided to a display at the seat position of the user and/or to the BYOD computational device 2120 (via the wireless access point). When the requested media content is available locally (already stored in vehicle memory), the media content is provided from local storage in preference to accessing the media content via the Internet. When the requested media is not available locally, it is obtained via the Internet and is cached in local storage in parallel with streaming to the user's display and/or BYOD computational device 2120. Each display at each seat position can independently provide a corresponding user with a playlist of audio or video from independent sources.

Figure 22:
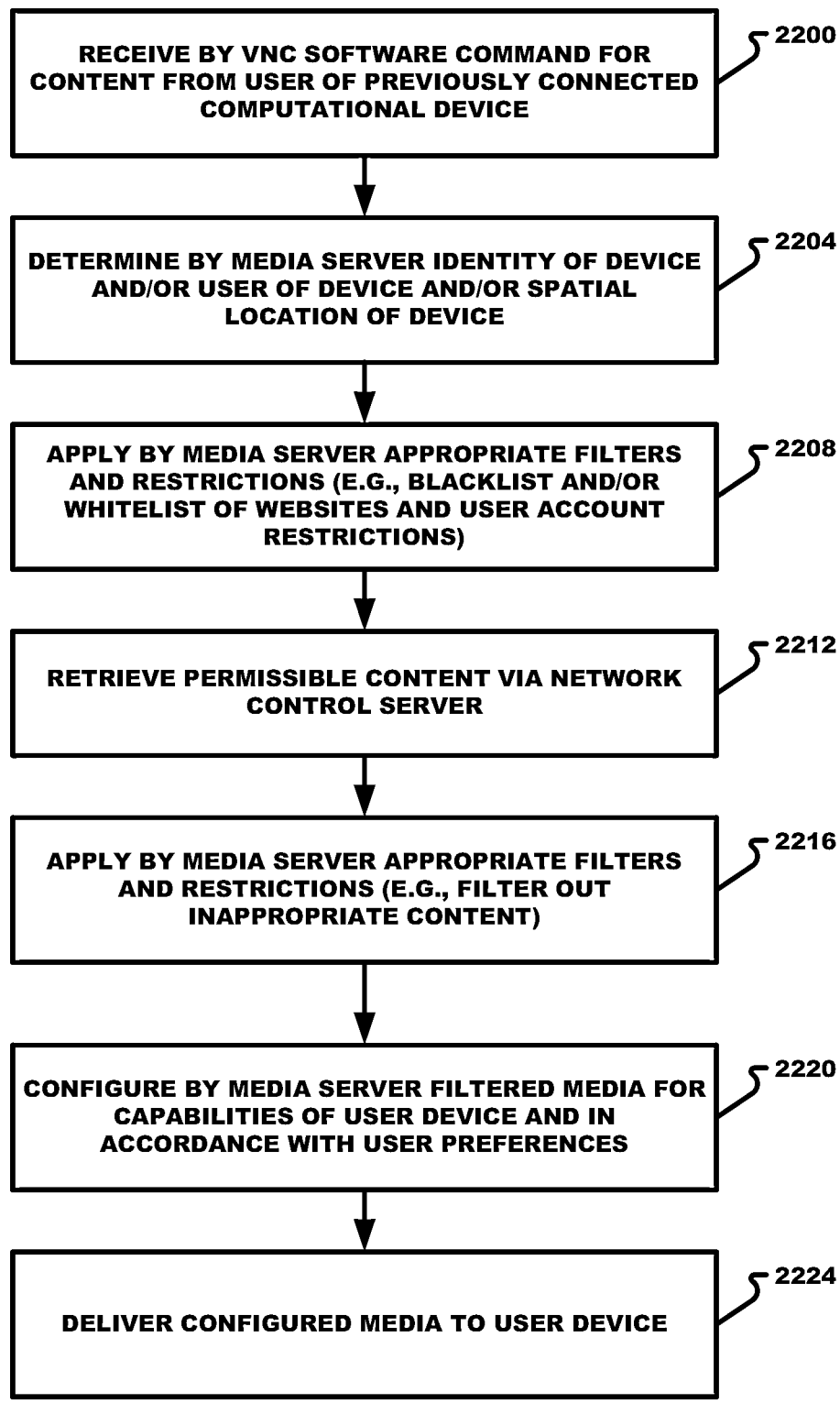
FIG. 22 depicts a flow diagram according to an embodiment.

With reference to FIG. 22, the operation of the media controller subsystem 348 will be discussed. In step 2200, the VNC software 2116 receives a command or request for content from the user of the BYOD computational device. The device has been previously connected successfully by the device discovery daemon or combo controller to the vehicle network 356 or communication subsystem 1008.

Typically, the combo controller has ports in the crate, implements certain device discovery functions, and packetizes information for transmission via IP over Ethernet. The combo controller commonly installs the correct driver for the discovered device. It then maps the device (e.g., USB) address to a local TCP/IP address for interaction with one of the blade processors.

In step 2204, the media server determines, from the system data 208, portable computational device information and capabilities, the identity of the user of the device, an identity of the portable computational device associated with the user, and/or the spatial location of the device (e.g., area and/or zone in which the device is located). This information has been previously determined by the device discovery daemon or combo controller but may be updated by the media server using the location techniques discussed above.

In step 2208, the media server applies appropriate filters and restrictions based on the identity of the user (e.g., user account) and/or spatial location of the device (e.g., user context). The filters or restrictions can include, for example, age-related content filters and/or restrictions, seating location filters and/or restrictions, and privacy filters and/or restrictions. The filters and/or restrictions can ban the type of content requested or the source of the content (e.g., a blacklist of web sites), redirect the request to a different source of the content, and/or limit the user to content from approved sources, such as permitted by a whitelist. Other user account restrictions can be applied by the media server before the content request is passed to the network control server 2108.

The owner of the vehicle can configure the multimedia controller menus. Initially, the menu allows for all seat positions to access any media that is available through the multimedia controller. The owner can create profiles for different potential vehicle occupants. By creating the profiles, the owner is able to allow or disallow access to media from selected seat positions, including access to media menus (e.g., audio or video playlists, software applications (such as Internet browsers, applications to control passenger compartment climate control functions, games, and the like). The owner can also limit media and/or media menu access based on a MAC address of a computational device 2120 of an occupant. Only devices having a permitted MAC address can access media and/or menus while those not having a permitted MAC address cannot. This can ensure that control is not only position-based but also device-based.

In step 2212 and if permitted by the media server, the network control server 2108 accesses the filtered content request (which may be altered to reflect user account restrictions) and retrieves the permissible content via the public network. The network control server 2108, for example, can access the media content 2100 from a media source accessed through an external network, such as a radio network or other type of untrusted public network (such as the Internet). The filtered content request may, for example, be for different content than that originally requested, differently formatted content than that originally requested, differently sourced content (e.g., from a different web server or site) than that originally requested, and the like.

In step 2216, the network control server 2108 receives the permissible content from a publicly networked source (e.g., web server or site) and passes the retrieved content to the media server 2112. Based on user account restrictions and/or user context, the media server applies appropriate filters and restrictions to remove or filter out inappropriate content. The filters or restrictions can include, for example, age-related content filters and/or restrictions, seating location filters and/or restrictions, and privacy filters and/or restrictions.

In one application, the combo controller connects via IP over Ethernet and assigns a local IP address to the BYOD device connected to a port in the consumer crate. The USB layer of the combo controller packetizes information from the BYOD device and communicates with a USB access program that executes on a multimedia blade processor. The USB access program de-packetizes the information and connects to the USB I/O subsystem of the multimedia blade processor to transfer the information to either local storage or directly to one of the output devices associated with the appropriate seating position.

Other user account restrictions can be applied by the media server before the content is passed by the media server to the user. For example, when the user is driving the vehicle video can be removed automatically from the content to avoid distracting the driver so that only the audio channel accompanying the video channel is provided to the user. In another example and in response to determining that the requesting user or user is driving the vehicle rather than being a (non-driving) passenger, screen magnification can be applied automatically to the visual content to assist the driver of the vehicle; that is, the user is the driver and larger font is easier to see than smaller font. In other examples, the visual content, in response to determining that the requesting user or user is driving the vehicle rather than being a (non-driving) passenger, is presented or rendered automatically in a large font and/or icon size (e.g., without changing screen resolution) compared to the font and/or icon size for the content displayed to a (non-driving) passenger to reduce driver distraction. In yet another example, the media server 2112 determines that the user is driving the car rather than being a (non-driving) passenger and enables or disables automatically removal of all unnecessary animations from the content to be displayed. In yet another example, the media server 2112 determines that the user is driving the car rather than being a (non-driving) passenger and enables automatic removal of background images from, while leaving one or more displayed foreground images in, the content to be displayed. In yet another example, the media server 2112 determines that the user is driving the car rather than being a (non-driving) passenger and automatically enables or renders high contrast (e.g., between text and background colors) to make the displayed content more visible to the user. The feature and/or setting and/or filters could be applied to the displayed content only when the vehicle is in motion or in forward or reverse gear and not parked even when the user is the driver.

Rather than automatic detection, any of the above features and/or settings and/or filters can be a standard feature and/or setting and/or filter and can be applied to the on board vehicle display for the driver but not to the on board vehicle displays of other (non-driving) passengers. In other words, the feature or setting or filter would not be applied to the on board vehicle display of a (non-driving) passenger. Alternatively, the feature and/or setting and/or filter would be applied to the on board vehicle display for the driver only when the vehicle is in motion or in forward or reverse gear but not when the vehicle is parked.

In step 2220, the media server 2112 configures the filtered media for the capabilities of the user device and/or on board vehicle display and in accordance with user preferences. The media server 2112 directly provides, or streams, the media stream or indirectly provides, or streams, the media stream via the VNC software 2116 to the user computational device 2120 and/or on board vehicle display for presentation to the user. Stated another way, the network control server 2108 provides the media content 2100 while the media server 2112 provides the channel for the media content 2100 to be provided to the user computational device 2120.

The media controller subsystem 348 can handle multiple (e.g., eight or more) media and/or multimedia streams simultaneously by differing channels. The streams of information may be separated and served on different channels via one or more of WiFi, Bluetooth, NFC, and other communications protocols. Multiple BYOD computational devices can be served simultaneously and can mix and match or otherwise control what is streamed and where it is streamed.

Assisted Driver Display

The device or user interface 212, 248, user interface (s)/input interface(s) 324 and/or I/O module 312 (such as the on board display for the driver) can be reconfigured when the vehicle changes state from parked or substantially motionless to be in motion or in forward or reverse gear to facilitate the driver's ability to view visual content and avoid driver distractions. Other devices or user interfaces 212, 248, user interface (s)/input interface(s) 324 and/or I/O modules 312 of other vehicle occupants or passengers typically are not reconfigured even when the vehicle is in gear or motion. When the state of the vehicle changes to parked (or not in motion), the device or user interface 212, 248, user interface (s)/input interface(s) 324 and/or I/O module 312 of the driver returns to a different configuration, which is typically the same configuration as the devices or user interfaces 212, 248, user interface (s)/input interface(s) 324 and/or I/O modules 312 of other vehicle occupants or passengers.

There are a number of reconfigurations that may be implemented for the unimpaired driver's device or user interface 212, 248, user interface (s)/input interface(s) 324 and/or I/O module 312 in response to a change of state of the vehicle, particularly from parked or stationary to be in motion or in forward or reverse gear.

For example, the media controller subsystem 348 can remove video automatically from the content to be displayed by the device or user interface 212, 248, user interface (s)/input interface(s) 324 and/or I/O module 312 of the driver to avoid distracting the driver so that only the audio channel accompanying the video channel is provided to the user. A still image derived from one or more frames of the video content can replace the video component in the displayed content.

In another example, the media controller subsystem 348 applies screen magnification automatically to the visual content to assist the driver of the vehicle; that is, the user is the driver and larger font is easier to see than smaller font. The screen magnifier is software that interfaces with a computer's graphical output to present enlarged screen content. The simplest form of magnification presents an enlarged portion of the original screen content, the focus, so that it covers some or all of the full screen. This enlarged portion should include the content of interest to the user and the pointer or cursor, also suitably enlarged. As the user moves the pointer or cursor the screen magnifier should track with it and show the new enlarged portion.

In another example, the media controller subsystem 348 presents or renders the automatically in a large font and/or icon size (e.g., without changing screen resolution) to reduce driver distraction. The large font and/or icon size, unlike screen magnification, applies to all, and not simply a portion of, displayed content.

In yet another example, the media controller subsystem 348 initiates automatically a screen reader (or other text-to-speech program) to audibly provide the visual content to the user. A screen reader is a software application that attempts to identify and interpret what is being displayed on the screen (or, more accurately, sent to standard output, whether a video monitor is present or not). This interpretation is then represented to the user with text-to-speech and/or sound icons. Screen readers can be used in combination with the screen magnifier to read the content within the enlarged portion of the screen content.

More specifically, screen narration in vehicle can describe the layout of a current display, including a current position, page, functionality, etc., of displayed content and the position of a digit of the user and/or cursor relative to displayed objects. The names of the displayed objects in proximity to the current digit and/or cursor location can be audibly identified. In another example, a user can identify a displayed object to be located and the media controller subsystem 348 can use "hotter", "hot", "colder", and cold" game to inform the user where his or her digit and digit movement is relative to the identified object. For example, the media controller subsystem 348 can tell the user that "you're getting warmer" as the user's digit moves closer to the identified object.

In yet another example, the media controller subsystem 348 determines that the user is driving the car rather than being a (non-driving) passenger and enables or disables automatically remove all unnecessary animation effects such as fading effects (e.g., fade windows), from the displayed content.

In yet another example, the media controller subsystem 348 automatically removes background images from the displayed content while leaving one or more displayed foreground images. The removed background image can be replaced with a uniform background, such as a commonly colored or white background.

In yet another example, the media controller subsystem 348 enables automatically a longer (than normal) period for notification dialog boxes to stay open on the display.

In yet another example, the media controller subsystem 348 automatically disables automatic arrangement of windows when the mouse cursor is moved to the edge of the screen.

In yet another example, the media controller subsystem 348 automatically enables activate a window by hovering over it with the mouse cursor.

In yet another example, the media controller subsystem 348 automatically enables keyboard web page navigation.

In yet another example, the media controller subsystem 348 automatically enables or renders high contrast (e.g., between text and background colors) to make the displayed content more visible to the user.

In yet another example, the media controller subsystem 348 automatically changes the color and transparency of window borders (making the borders easier to see).

In yet another example, the media controller subsystem 348 automatically changes the thickness of focus rectangle (around the currently selected item in a dialog box).

In yet another example, the media controller subsystem 348 automatically changes the color, size, and/or thickness of the on-screen mouse pointer.

In yet another example, the media controller subsystem 348 automatically changes the keyboard settings (e.g., select how long you need to press a key before the keyboard character starts repeating, the speed at which keyboard characters repeat, and the rate at which the cursor blinks, etc.).

In yet another example, the media controller subsystem 348 automatically ignores colors, font styles and font sizes used on web pages, or formats web pages using a user specified or default style sheet.

In yet another example, the media controller subsystem 348 automatically enables or renders in the content an increased size of a mouse-selectable screen element or object to provide a larger target.

In yet another example, the media controller subsystem 348 automatically enables mouse keys to move the mouse pointer or cursor.

In yet another example, the media controller subsystem 348 automatically enables one or more of sticky keys (which allow the user to enter a combination of multiple keys without having to hold a first key down when he or she depresses a second key), toggle keys (which play an alert each time the user presses Caps Lock, Num Lock, or Scroll Lock keys), and filter keys (which causes the computer to ignore keystrokes that occur in rapid succession or keystrokes held down for several seconds unintentionally).

In yet another example, the media controller subsystem 348 automatically causes the driver's device or user interface 212, 248, user interface (s)/input interface(s) 324 and/or I/O module 312 to be configured to enable blind typing. In blind typing, the driver can write naturally with a finger on the interface and the interface can determine, from the natural written script, a command or request of the driver. This configuration typically requires the interface to be configured as a touchpad. While other systems require the driver to focus away from the road—either by selecting letters from menus or on a displayed keyboard—blind typing permits the driver to input commands or requests to the vehicle control system without having to visually focus on any screen.

Although many of the above display changes or reconfigurations have been used to enable impaired users to access a computer, the driver is typically not disabled or impaired (e.g., not visually impaired or disabled). These changes or reconfigurations can however be highly beneficial in enabling a driver to interact with the computer in a manner that substantially avoids or inhibits driver distraction.

Rather than automatic detection, any of the above features and/or settings and/or filters can be a standard feature and/or setting and/or filter and can be applied to the on board vehicle display for the driver but not to the on board vehicle displays of other (non-driving) passengers. In other words, the feature or setting or filter would not be applied to the on board vehicle display of a (non-driving) passenger. Alternatively, the feature and/or setting and/or filter would be applied to the on board vehicle display for the driver only when the vehicle is in motion or in forward or reverse gear and not when the vehicle is parked.

A user interface (UI), such as the driver's device or user interface 212, 248, user interface (s)/input interface(s) 324 and/or I/O module 312, may be provided that includes an area for navigation by a user. As a user navigates the UI area, the user may be provided with one or more of sounds, audio narration, haptic/tactile feedback, visual indicator (e.g., not associated with the UI), and the like. For example, a location in the UI area may represent a button and/or other icon. When the user makes contact with the location having the button, a sound and/or tactile feedback may be presented to the user to indicate where the user's pointer (e.g., one or more finger, hand, etc.) is located. As one example, as a user reaches a location in the UI area associated with a "call" button, the sound presented may be a ring (e.g., a bell), and a vibration may be provided to the UI. Alternatively, screen narration by a screen reader can be provided, which informs conversationally the user where his or her digit is located. For example, the narration can be to recite the name corresponding to the button. In another example, as a user moves a pointer about the UI area, a frequency of sound may change to indicate a position in the UI area (e.g., the low left portion of the UI area may provide a low pitch and/or frequency sound, while a position in the upper right portion of the UI area may have a higher pitch and/or frequency sound, and portions in between can have different pitches and/or frequencies, etc.—similar to the Theremin musical instrument).

By way of example, a graphical UI or GUI may allow a user to interact with certain displayed buttons, features, and/or menus while a vehicle is stationary, but may restrict access and/or interaction when the vehicle is moving. One example of this restricted interaction involves greying-out buttons associated with an associated phone feature when the vehicle moves. In the embodiments provided herein, the display can be completely turned off or blanked out when moving and a user may still be able to interact with features. Because the user will not be distracted by the visual presentation of elements the user is free to drive while interacting.

In some embodiments a GUI may be used where a display of the GUI is turned off to provide the above described functionality.

A display navigation mode can be selectively triggered by the user to implement any of the above configurations and/or features. When the user wishes to enter display navigation mode, the user can provide a command, such as by voice or gesture, to enter that mode. In that mode, any of the above assistive configurations or features can be implemented. For example, voice navigation is activated and the residence time of the user's touch on the touch screen required to select a contacted icon is lengthened to avoid incidental or accidental icon selection as the user moves his or her hand/digit around the touch screen. When the user arrives at a desired location, the icon will be activated after touch contact for the longer residence time. When the icon is selected, the touch screen can return to normal operating mode with a shorter residence time for icon activation.

The user can alternatively use a roller or track ball and selector to effect narrated screen navigation.

In another embodiment, the user contacts an arbitrary and substantially planar or flat control surface, such as an arm rest, dash, steering wheel, glove box door, center or rear center console, window (e.g., windshield), passenger compartment roof, seat surface, door panel, or other electrically, magnetically, electromagnetically, and optically nonreactive surface to activate icons on the activated or deactivated vehicle computer center or rear center display. The control surface can be any arbitrary surface selected by the user. This can be done by optically or visually separating the surface into segments, each segment corresponding to a segment on the display. The movement of the user's hand or digit is tracked optically over the surface with reference to the segments. As the user moves his or her hand, the user can be audibly told where his or her hand is relative to the display. When the user's hand/digit is at a selected location, the user can leave his or her hand/digit at that location for a selected residence time to cause the icon in the corresponding segment of the display to be activated.

The activated or deactivated vehicle computer center or rear center display can be any of the driver's device or user interface 212, 248, user interface (s)/input interface(s) 324 and/or I/O module 312, may be provided that includes an area for navigation by a user.

Figure 33:
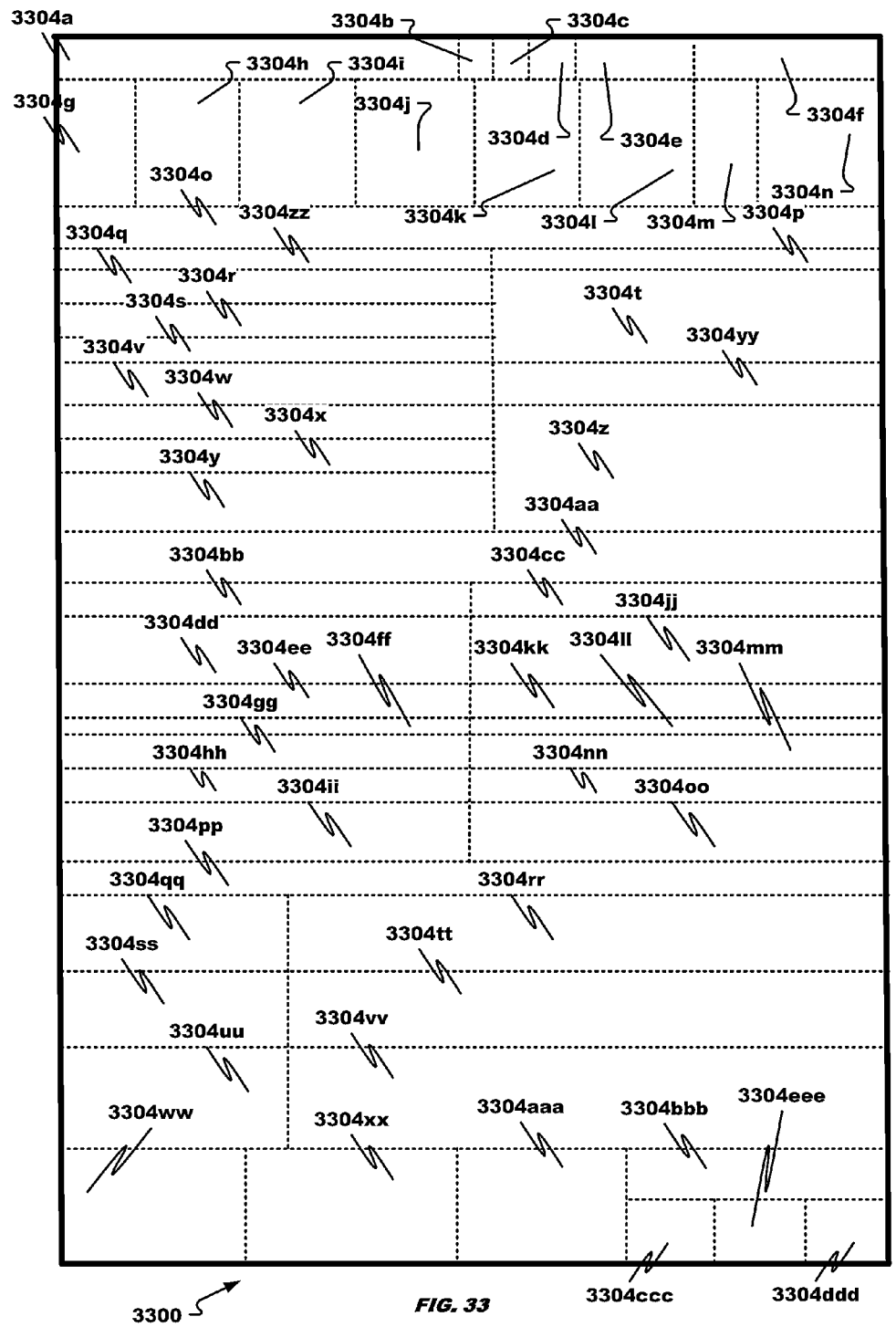
FIG. 33 depicts a segmented control surface according to an embodiment.
Figure 34:
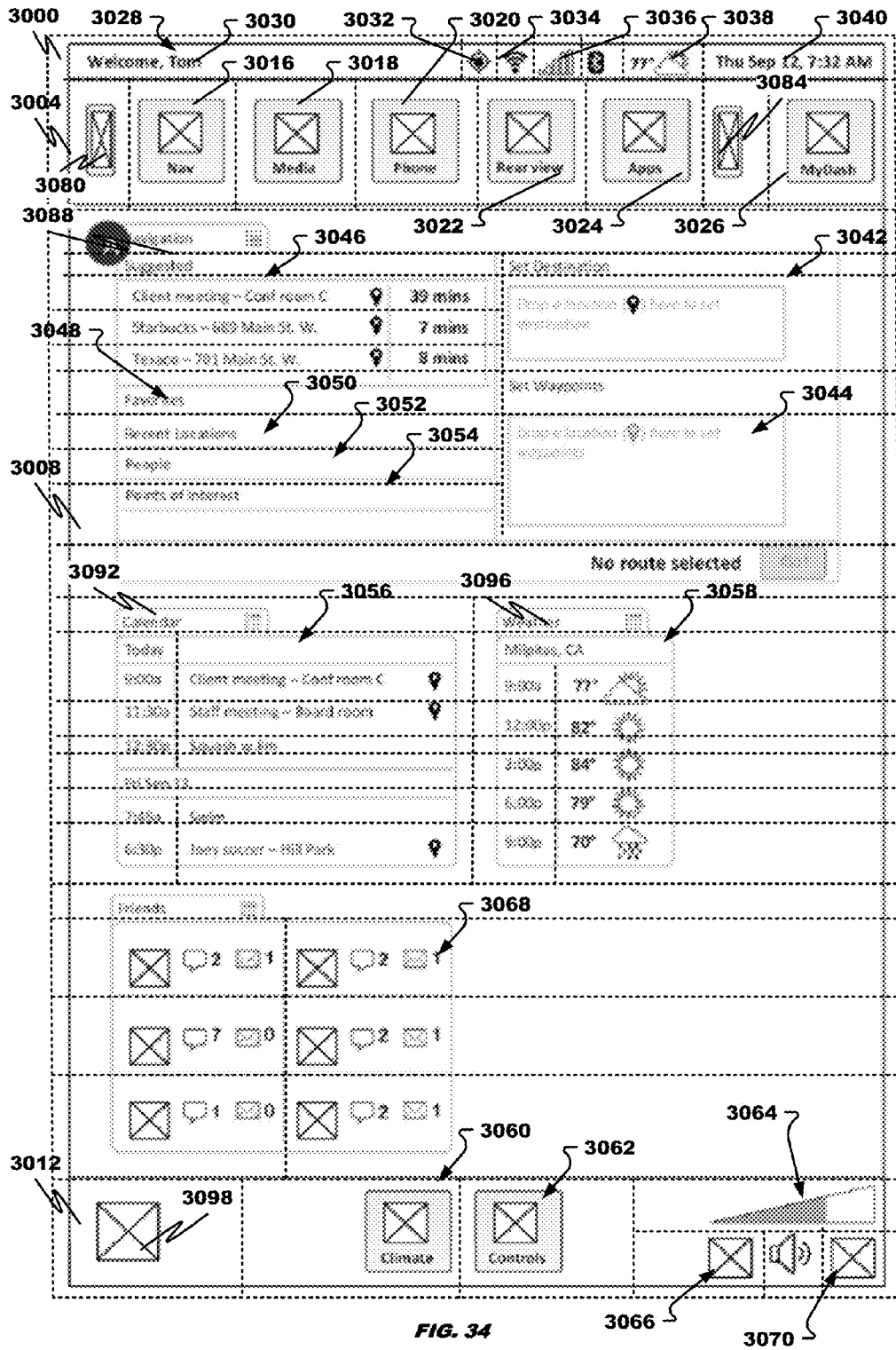
FIG. 34 depicts a mapped display according to an embodiment.

An example is described with reference to FIGS. 33-34. FIG. 34 depicts the display of FIG. 30 with defined segments overlaid on the display. This is done to show the process of mapping the control surface to the displayed objects. FIG. 33 shows the same defined segments positioned on the control surface 3300. Each segment of the control surface 3300 corresponds to an information-containing and/or activatable or selectable object of the current display. As the display changes in response to user input or otherwise, the type, identity, and/or arrangement of displayed information and objects changes requiring the display to be remapped to the control surface 3300. Remapping typically requires the defined segments to be redefined and reconfigured to reflect the new display configuration.

As shown by FIG. 33, the dividing lines define various cells, each of which corresponds to displayed content on the display of FIG. 34. Specifically, cell 3304a corresponds to display field comprising driver name 3028, cell 3304b to satellite reception indicator 3032, cell 3304c to WiFi connectivity indicator 3034, cell 3304d to cellular connectivity indicator 3036, cell 3304e to display field comprising weather information 3038, cell 3304f to display field comprising date 3040, cell 3304g to icon 3380, cell 3304h to navigation ("Nav" icon) 3016, cell 3304i to media ("Media" icon) 3018, cell 3304j to phone ("Phone" icon) 3020, cell 3304k to rear view ("Rear View" icon) 3022, cell 3304l to other applications icon 3024, cell 3304m to icon 3384, cell 3304n to "my dash" icon 3026, cell 3304o to navigation display field 3088, cell 3304zz to suggested icon, cell 3304p to set destination icon, cell 3304q to display field containing destination, cell 3304r to display field containing suggested waypoint, cell 3304s to display field containing suggested waypoint, cell 3304t to set destination icon, cell 3304u to set destination box, cell 3304v to favorites icon, cell 3304w to recent locations, cell 3304x to people icon, cell 3304y to points of interest icon, cell 3304yy to set waypoints, cell 3304z to set waypoints box, cell 3304aa to go icon, cell 3304bb to calendar icon 3092, cell 3304 cc to weather icon 3096, cell 3304dd to display field containing appointment, cell 3304ee to display field containing appointment, cell 3304ff to display field containing appointment, cell 3304gg to display field containing appointment, cell 3304hh to display field containing appointment, cell 3304ii to display field containing appointment, cell 3304jj to display field containing weather information, cell 3304kk to display field containing weather information, cell 3304ll to display field containing weather information, cell 3304mm to display field containing weather information, cell 3304nn to display field containing weather information, cell 3304oo to display field containing weather information, cell 3304 pp to friends icon, cell 3304qq to received and/or sent messages 3068, cell 3304rr to received and/or sent messages 3068, cell 3304ss to received and/or sent messages 3068, cell 3304tt to received and/or sent messages 3068, cell 3304uu to received and/or sent messages 3068, cell 3304vv to received and/or sent messages 3068, cell 3304ww to icon 3098, cell 3304xx to a climate control icon ("Climate" icon), cell 3304aaa to a controls icon ("Control" icon) to control vehicle tasks, functions or operations 3062, cell 3304bbb to speaker volume setting 3064, cells 3304ccc and 3304ddd to controls to the left and right of the speaker image 3066 and 3070, respectively, and cell 3304eee to speaker icon.

By way of example, the user's digit points at 3304h, which corresponds to the navigation icon 3016 of the home page 3000 of FIG. 30. By leaving the user's digit stationary in that location for a selected period of time, the media controller subsystem 348 determines that the user desires to activate the navigation icon 3016, which causes a different display to be rendered. The new display is remapped to the control surface so that the dividing lines on the control surface mirror the dividing lines overlain on the new display. By way of further example, the user's digit points at 3304f, which corresponds to the display field for date and time of the home page 3000 of FIG. 30. A screen reader reads the date and time to the user. By way of further example, the user's digit points at 3304dd, which corresponds to the display field for appointment of the home page 3000 of FIG. 30. A screen reader reads the displayed appointment information to the user.

Optical tracking of the user's digit enables the location of the digit. Optical tracking typically determines in real-time the position of the digit by tracking the positions of either active or passive infrared markers attached to the object. The position of the point of reflection is determined using the camera sensors 760, motion sensors 744, and/or infrared sensors 740. In one configuration, the user's digit is equipped with Markers can be light reflectors ("passive markers", e.g. retroreflectors) or light emitters ("active markers", e.g. LEDs). To also measure the orientation of a body, several (greater than or equal to 3) of these markers have to be arranged at a known geometry. The camera sensors 760 scan a certain volume and detect the light that comes from the markers. These images are processed to identify and calculate potential marker positions (in image coordinates). The result of each measurement are coordinates that describe the position of the markers, and hence the position and orientation of the body carrying the markers.

Other techniques can be employed. The cell dividing lines can be projected onto the control surface by the camera sensors 760. The position of a selected digit of the user can be tracked using image processing of images of the control surface with the cell boundary or dividing lines in the images. Examples of other techniques include video tracking, such as blob tracking, kernel-based tracking, contour tracking, visual feature matching, match moving, motion capture, motion estimation, Swistrack, and single particle tracking.

Figure 35:
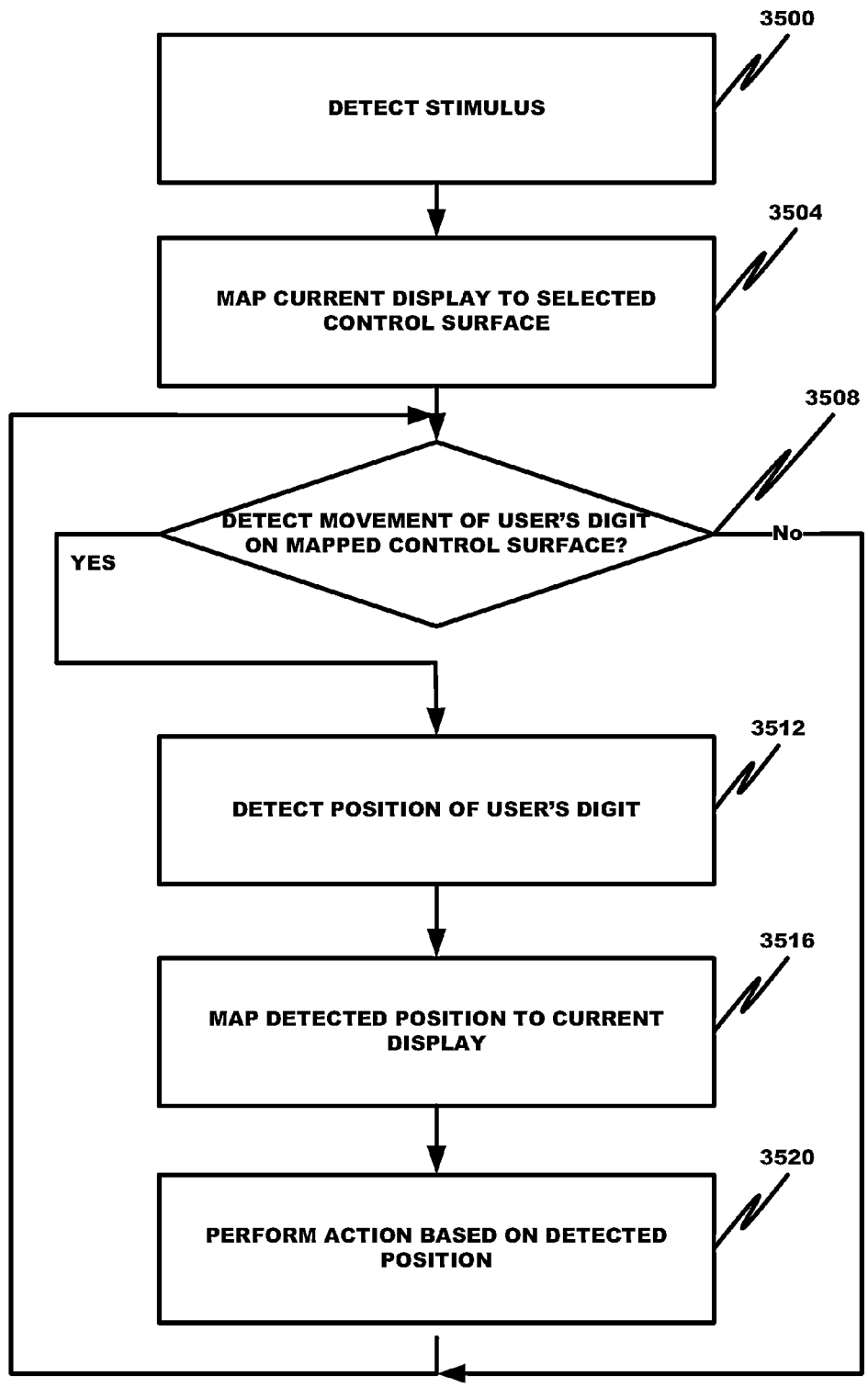
FIG. 35 depicts a flow diagram according to an embodiment.

The operation of the control surface will be discussed with reference to FIG. 35.

In step 3500, the media controller subsystem 348 detects a stimulus, such as ignition of the engine, motion of the vehicle, the vehicle being placed in gear, a gesture or other activation command from the user, and the like.

In response, the media controller subsystem 348, in step 3504, maps the current display of a selected one of the driver's device or user interface 212, 248, user interface (s)/input interface(s) 324 and/or I/O module 312 to a selected control surface. This can include proportional sizing the control surface to the display and determining cell and cell boundary locations. The sizes of the cells are commonly proportional to the corresponding displayed content.

In step 3508, the media controller subsystem 348 determines, by one or more of the motion sensors 744, infrared sensors 740, and camera sensors 760, whether a user's digit has moved relative to the stationary cell boundaries and cells on the mapped control surface.

When movement is detected, the media controller subsystem 348, in step 3512, detects or determines, by one or more of the motion sensors 744, infrared sensors 740, and camera sensors 760, the position of the digit on the control surface relative to the cells and cell boundaries.

In step 3516, the detected position of the digit is mapped to the currently displayed content. This is done by mapping the cell where the tip of the digit is positioned to the corresponding displayed content on the display.

In step 3520, the media controller subsystem 348 performs an action based on the detected digit position. The action depends on the type of displayed content corresponding to the digit position. When the displayed content is activatable or selectable, the media controller subsystem 348 activates the corresponding task, function or operation. When the displayed content is not activatable or selectable, a screen reader in the media controller subsystem 348 reads the displayed content to the user. Some operations are drag-and-drop operations where content is moved by the user's digit from one location to another, such as a destination or waypoint being dragged from one location and dropped into a set destination or wet waypoint box. This can be done by detecting the user's digit in a first location, determining that the displayed content can be dragged and dropped to another location, waiting for the digit to move to a second location, and, when in the second location, dropping the content into displayed content corresponding to the second location when the displayed content permits this operation to be performed.

As noted, when the task, function or operation causes the display to change the control surface is remapped to the display.

In another embodiment, the UI may not include any display at all. Because any surface can receive input, as provided herein, a display is not needed. Examples of this type of display-less UI can be implemented on any surface that has a substantially flat or planar area or surface. In one embodiment, the UI area may include a capacitive and/or resistive touch interface region. In another embodiment, the UI area may be a surface that includes an area visible from at least one image sensor (e.g., camera, etc.). Other examples of a display-less UI may include a volume of space in which a user can move a pointer.

In the examples provided above, a user may navigate the non-displayed UI elements (e.g., icons, buttons, etc.) using sound, haptic feedback, etc.

Figure 26:
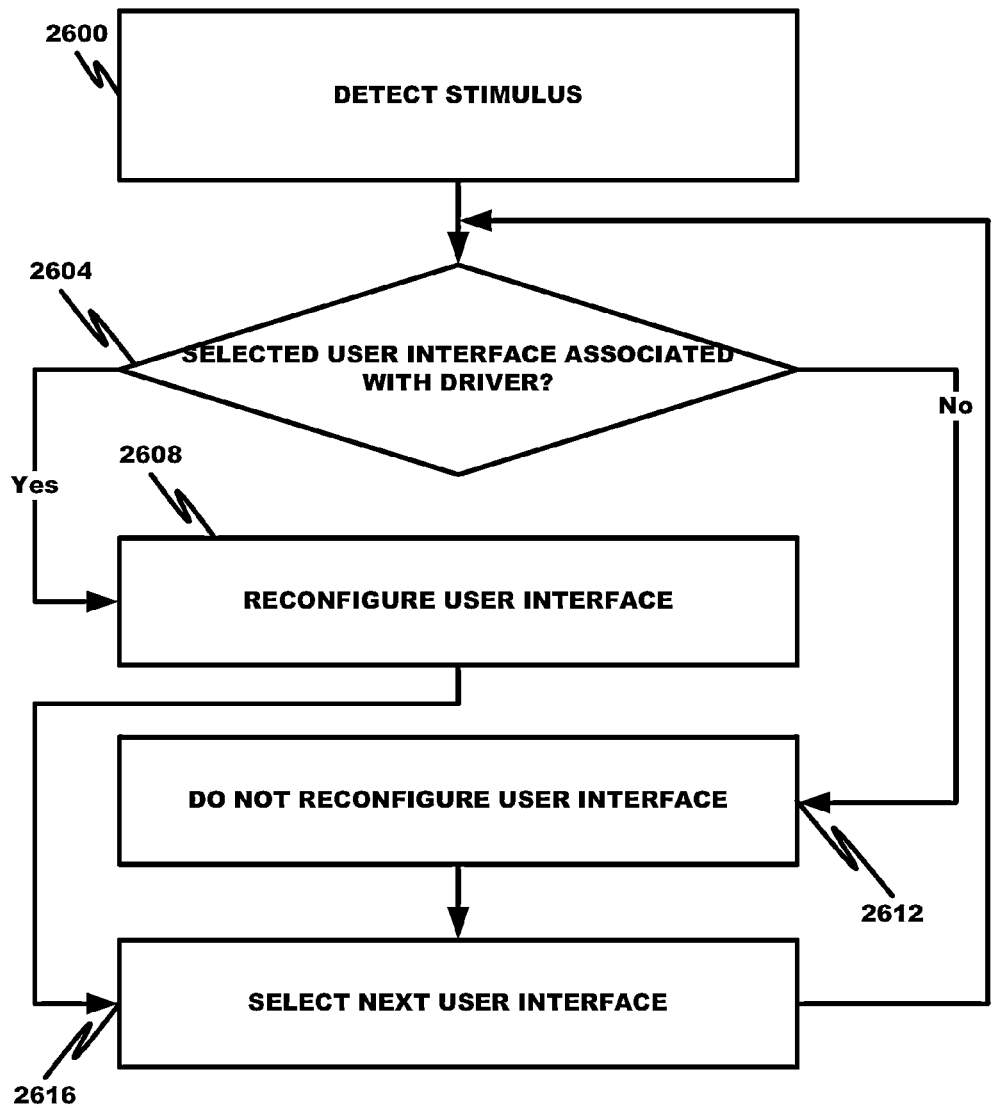
FIG. 26 depicts a flow diagram according to an embodiment.

An operation of the media controller subsystem 348 will now be described with reference to FIG. 26.

In step 2600, a stimulus is detected by the media controller subsystem 348 based on input from one or more vehicle sensors. An exemplary stimulus includes a change in vehicle operating state. Common changes in vehicle operating state include a change from "parked" to "forward gear" and vice versa, from "parked" to "reverse gear" and vice versa, from "forward gear" to "reverse gear" and vice versa, and from stationary to in motion and vice versa.

In decision diamond 2604, the media controller subsystem 348 selects a device or user interface 212, 248, user interface (s)/input interface(s) 324 and/or I/O module 312 and determines whether or not it is associated with the driver. This is typically determined by determining whether or not the selected device or user interface 212, 248, user interface (s)/input interface(s) 324 and/or I/O module 312 is located in an area and/or zone occupied by the driver. Location of the device or user interface 212, 248, user interface (s)/input interface(s) 324 and/or I/O module 312 can be determined using the techniques noted above.

When the device or user interface 212, 248, user interface (s)/input interface(s) 324 and/or I/O module 312 is located in the area and/or zone of the driver, the media controller subsystem 348, in step 2608, reconfigures the user interface to enable or disable (depending on the initial and final states) one of the features, settings, or filters discussed above.

When the device or user interface 212, 248, user interface (s)/input interface(s) 324 and/or I/O module 312 is not located in the area and/or zone of the driver, the media controller subsystem 348, in step 2608, does not reconfigure the user interface to enable or disable (depending on the initial and final states) one of the features, settings, or filters discussed above.

After performing either of steps 2608 or 2612, the media controller subsystem 348 selects a next device or user interface 212, 248, user interface (s)/input interface(s) 324 and/or I/O module 312 and returns to decision diamond 2604.

This process is continued until all devices or user interfaces 212, 248, user interface (s)/input interface(s) 324 and/or I/O modules 312 have been considered.

In other embodiments, the media controller subsystem 348 can audibly warn of or describe an image detected via an infrared sensor, motion sensor or camera sensor that is in the path of the vehicle. Known image processing and image recognition techniques can be used to identify the object image and compare the image to a projected path of the vehicle. An exemplary technique acquires the image, pre-processes the acquired image, performs feature extraction from the pre-processed image, performs detection and/or segmentation using the extracted features, and performs high level processing and decision making. The path of the vehicle, as determined by a steering wheel setting and a projected path of the center line of the vehicle for that setting along with a width of the vehicle can be compared against the position of the object. When the projected path causes any portion of the vehicle to contact the object or be within an unsafe distance of the object, appropriate instructions or warnings can be issued. Thus, not only can a warning containing the object description be provided to the driver but also directions can be audibly provided to enable the driver to miss the object. For example, the driver can be instructed by one or more of the following: "Watch Out!"; "Turn the wheel left, a little more, a little more, perfect, straighten out"; "Turn the wheel right, a little more, a little more, perfect, straighten out"; and the like. This can provide invaluable assistance to driver's who struggle, for example, with backing up the vehicle due to depth perception and/or orientation issues.

User Account Management and Occupant Control of Vehicle Tasks, Functions and Operations The vehicle control system 204 can manage user accounts that stipulate, control, and define rights and privileges of each user of the vehicle and vehicle network. Different users and/or devices may include different accounts. In some cases these accounts may include user and/or device-specific privileges.

For example, a system user has exclusive rights and privileges over all communication device firewall rules and running software. The system user can control selected vehicle tasks, functions and operations and infotainment via predetermined or preconfigured gestures. A manufacturer or vendor user can have local or remote access to on board control system data and alter the parameters and settings in the vehicle control system and to perform diagnosis and repair. A dashboard user can have rights to launch a dashboard application and authenticate guest or default users and change permissions to trusted friends or family members. Dashboard users can read on board diagnostic system data but cannot overwrite or change it. A user can be both a system and dashboard user. An Internet source interacting with the vehicle has only http rights to respond to http requests received from the vehicle. The requests can target different user data but these are filtered by default user accounts. Guest users have no rights. Family and friend users have rights to play media from the media controller and to stream its media to the controller. They may or may not have rights to control vehicle tasks, functions and operations, whether or not by gesture. The back seat displays are part of this group of users. The back seat displays can be smart WiFi removable communication devices that can be removed from the vehicle in WiFi range of the communication network.

In one example, a child user may wish to change the temperature in his zone of the vehicle. Continuing the example, the child may have an account that allows access to this feature (but not other more critical features). As such the child may change the temperature via the device or other control. The child, however, may not be entitled to change the feature for an area or zone other than that in which he or she is currently located. Additionally or alternatively, a driver may have a broader account and privileges. In this case, the driver may control critical features, and even tasks, operations, and functions, of a vehicle. Remote control of a vehicle or infotainment task, operation, or function through the on board vehicle computer and by a portable or handheld computational device, such as a cellular phone or tablet computer, interconnected with the vehicle computer, can be permitted for some users but not others. For example, a privileged user can control an infotainment or climate control function on the dashboard from the back seat of the vehicle. The control of the vehicle or infotainment task, function, or operation may be made via a device or user interface 212, 248, user interface (s)/input interface(s) 324 and/or I/O module 312. Accordingly, occupant control of a (typically non- or less critical) vehicle task, function, or operation (such as an infotainment task, function or operation) can be done using an on board (or vehicle mounted) computational device or a portable computational device discrete from and not mounted on the vehicle.

In another example, a user in the rear passenger seat of a vehicle may wish to take control of specific features that are allowed in that zone. Such features may include controlling the climate, changing a radio station or infotainment presentation, opening a window, setting a volume level, setting a screen contrast and/or resolution, and/or adjusting a seat position. The control of these features may be provided to the user in the rear passenger seat via a display, gesture control region, or other device associated with the zone in which the rear passenger is seated. Associated devices may include the user's smart-phone, tablet, computer, and/or other device.

In yet another example, a vehicle occupant can perform a first set of vehicle tasks, functions and operations when in a first area and/or zone and a different set of vehicle tasks, functions, and operations when in a different second area and/or zone. For instance, a vehicle occupant can drive the car or perform another critical vehicle task, function or operation when seated in the driver's seat but not when seated in a different seat. When the vehicle occupant is in the back seat, he is unable to be a back seat driver of the vehicle or perform another critical vehicle task, function or operation.

In yet another example, a vehicle occupant can perform a first set of vehicle tasks, functions and operations when the vehicle is in a first operating state and a different set of vehicle tasks, functions, and operations when the vehicle is in a second operating state. The vehicle occupant, for instance, can watch a video on the driver's center console or display subsystem when parked and/or the vehicle is stationary (not in motion) but cannot watch the video on the driver's center console or display subsystem when the vehicle is in gear and/or motion.

In yet another example, a different authentication procedure is used for the vehicle occupant when requesting a first set of vehicle tasks, operations, and functions than when requesting a second set of vehicle tasks, operations, and functions. When the vehicle occupant is entitled to drive the vehicle or perform another critical vehicle task, function or operation, a different and higher or more stringent set of authentication requirements can be required than when the vehicle occupant is not entitled to drive the vehicle. For instance, multiple authentication techniques may be used in the former case but only one in the latter case.

As noted, the vehicle control system 204 manages user accounts, which contain user credentials, such as user identifiers, passwords, user biometric data (e.g., fingerprints, retina images, facial characteristics, user weight, and other physical characteristics), and rights and privileges of the user in performing vehicle tasks, functions, and operations, both critical and non-critical. In addition to the rights and privileges defined in the user account, the vehicle control system 204 can consider additional gating or filtering factors, such as current user position (e.g., what area and/or zone the user is located or seated in), in determining what rights and privileges apply currently to the user.

The vehicle control system 204 can manage and enforce accounts for authenticated and non-authenticated users. Each account specifies rights and privileges for the corresponding user and/or security/authentication requirements and/or personal settings of the user (such as seat and lumbar settings, climate control settings, lighting settings, configuration of instrument cluster, rear view mirror settings, driving modes (such as fuel economy, sport, city, and the like), media channel settings or presets, media delivery preferences, music genre preferences, scheduled programs, playlists, synchronization with cloud-based data associated with the user (such as iCloud™ of Apple™, Outlook™, and the like with examples of cloud-based data being electronic calendar, email, contacts, media content, texts, voice mail messages, and the like), application-specific personalization and selections, display settings and configurations, and the like) and other information noted above with respect to the profile data 252 and device data 220. These will be henceforth encompassed by any reference to a user's account.

For example, an owner of the vehicle would have the right and privilege not only to access infotainment media but also to access and control critical and non- or less critical vehicle tasks, functions, and operations. Because he is entitled to the highest level of rights and privileges, his or her authentication requirements may be more demanding than another vehicle occupant not having such rights and privileges. A child of the vehicle owner on the other hand would have a very restricted or no right to access and control vehicle tasks, functions, and operations (except for climate control, seat, and/or window settings) and restricted rights to access infotainment media. As noted above, a child filter could be configured by the vehicle owner to prevent the child from accessing age-restricted media.

A guest of the vehicle owner having no corresponding account would be provided with a default account having default and restricted rights and privileges to access vehicle and infotainment tasks, functions, and operations, and settings and configurations, which could be expanded based on input from the owner. This could be done in response to a query by the vehicle control system 204 that the vehicle occupant is not recognized (or authenticated). The vehicle control system 204 could provide the owner with multiple default accounts, one for an adult with driving privileges, one for an adult without driving privileges, and one for a child, and request the owner select the appropriate default account for the occupant. An identifier of the occupant and optionally authentication credentials would be inputted by the owner, and the vehicle control system 204 could store image processing information of the occupant's facial or other image, biometric information, and/or occupant weight for purposes of authentication. The owner could define, in an account created or modified by the owner, the rights and privileges of the person associated with the account.

Figure 27:
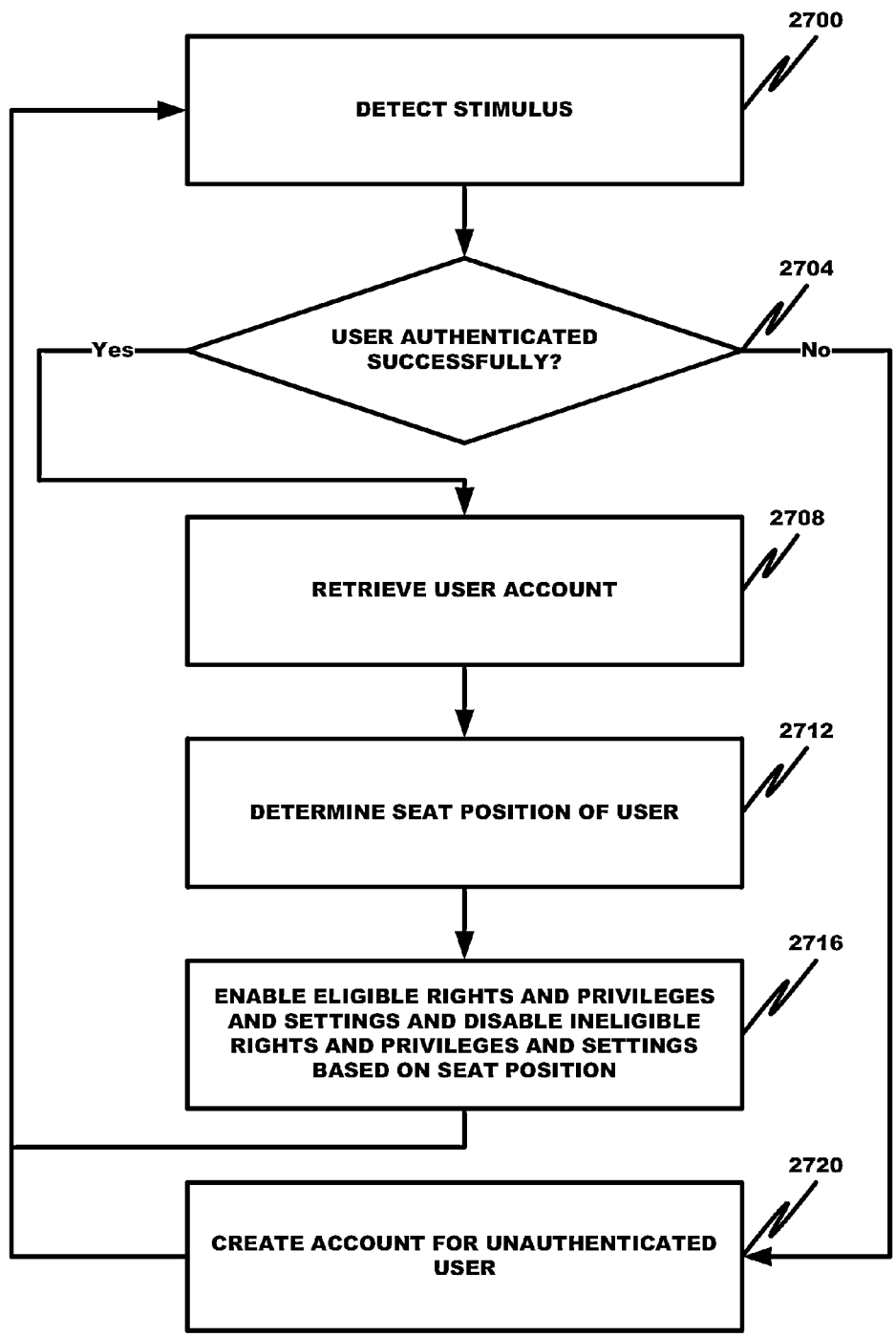
FIG. 27 depicts a flow diagram according to an embodiment.

An operation of the vehicle control system 204 is shown in FIG. 27.

In step 2700, the vehicle control system 204 detects a stimulus, such as a driver prompt, presence of an occupant, and the like. As noted above, the presence of an occupant can be sensed by seat weight sensors, image processing analysis, motion detection, proximity of a key fob, and/or biometric information.

In decision diamond 2704, the vehicle control system 204 determines whether or not each of the vehicle occupants has been authenticated successfully. Authentication can be performed by any suitable technique and using any suitable input, such as by one or more of receiving and validating user credentials, sensing an occupant's weight in a seat (with the weight being different from weight ranges predefined for each known occupant), image processing performed on the facial characteristics of the various vehicle occupants (and comparing the sensed facial characteristics against those for known occupants), biometrics (such as a fingerprint image of the occupant sensed by the occupant touching a touchscreen display, retinal scan, heart rhythm as received by conductive elements on a vehicle component such as the steering wheel or gear shift) (which are compared against corresponding stored biometrics for known occupants), and the like. An unauthenticated occupant could be recognized by sensing an occupant's weight in a seat (with the weight being different from weight ranges predefined for each known occupant), image processing performed on the facial characteristics of the various vehicle occupants (with the sensed facial characteristics failing to match stored facial characteristics for known occupants), unrecognized biometrics (which do not correspond to biometrics for known occupants), and the like.

Authentication using image processing applied to video images of occupants in the vehicle can be performed by any suitable technique. In one technique, facial recognition occurs in two stages, namely face detection and recognition. The face detection stage attempts to obtain an acceptable image from the video stream of the vehicle occupants to use in the face recognition stage. The face recognition process uses the image obtained from the detection stage and compares it with a database of known faces. When the facial image obtained from the detection stage matches a known stored facial image, authentication is successful. When the facial image obtained from the detection stage fails to match a known stored facial image, authentication is unsuccessful. As noted, image processing can be augmented by other security mechanisms for higher level privileges, such as authentication by user credentials (e.g., pattern lock, PIN, or other password).

When the user is authenticated successfully, the vehicle control system 204, in step 2708, retrieves the corresponding account for the successfully authenticated user.

In step 2712, the vehicle control system 204 next determines the area and/or zone (e.g., seat position) occupied by the authenticated user, such as by using any of the techniques discussed herein, including without limitation image processing information of the various occupants, sensed seat weight, user input, location coordinates received from a portable computational device, such as a cell phone, tablet computer, or personal digital assistant associated with the user, and the like. The vehicle control system 204 may also determine an operating state of the vehicle, e.g., in motion, parked, in gear, in neutral, and the like.

In step 2716, based on location (e.g., seat position) of the corresponding authenticated user and/or the operating state of the vehicle, the vehicle control system 204 enables eligible rights, privileges, settings and configurations set forth in the corresponding account and disables ineligible right or privileges or alters settings and configurations.

When the user is not authenticated successfully, the vehicle control system 204, in step 2720, creates an account for the unauthenticated user as set forth above. As noted, the account can be a default account.

Figure 28:
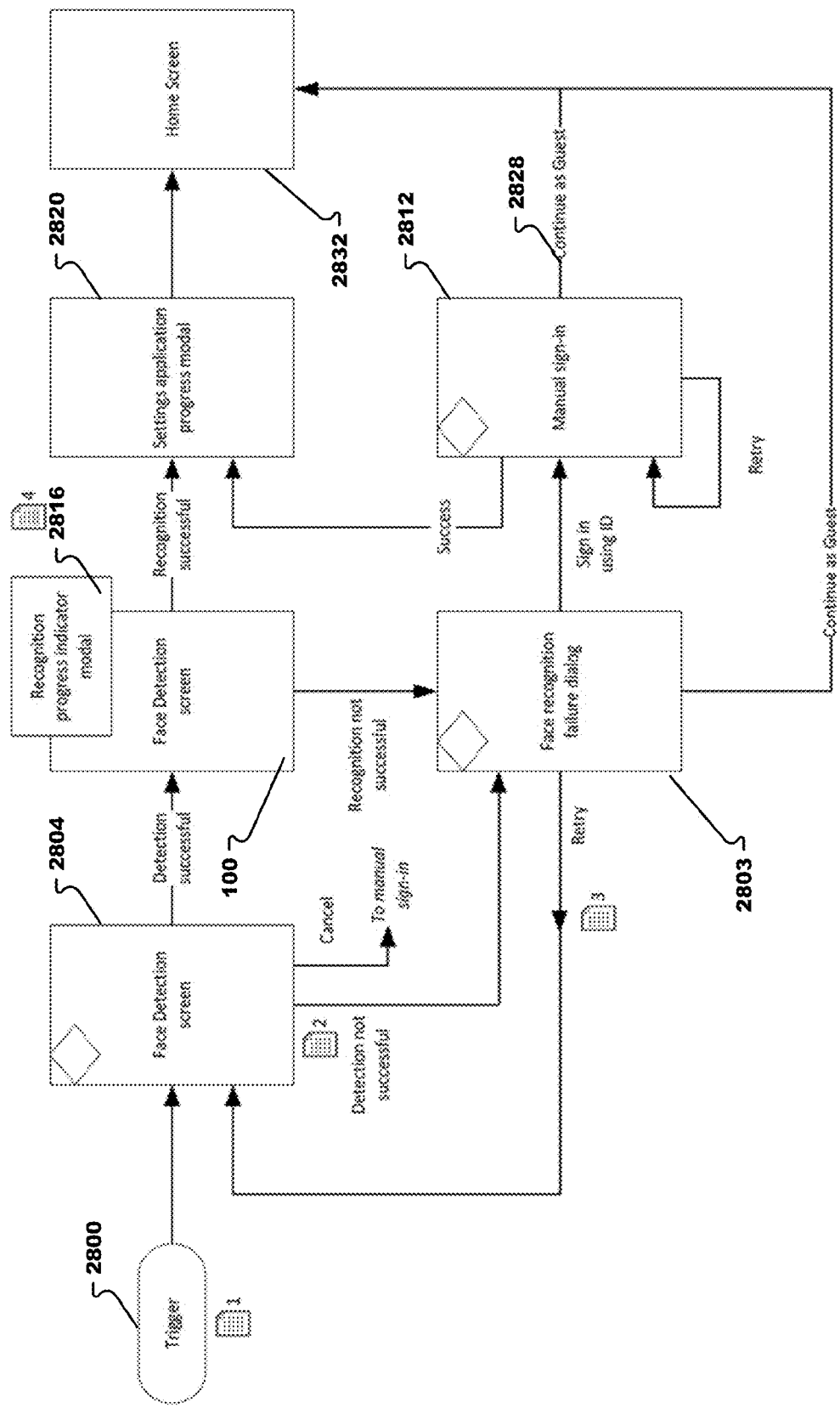
FIG. 28 depicts a screen shot according to an embodiment.
Figure 29:
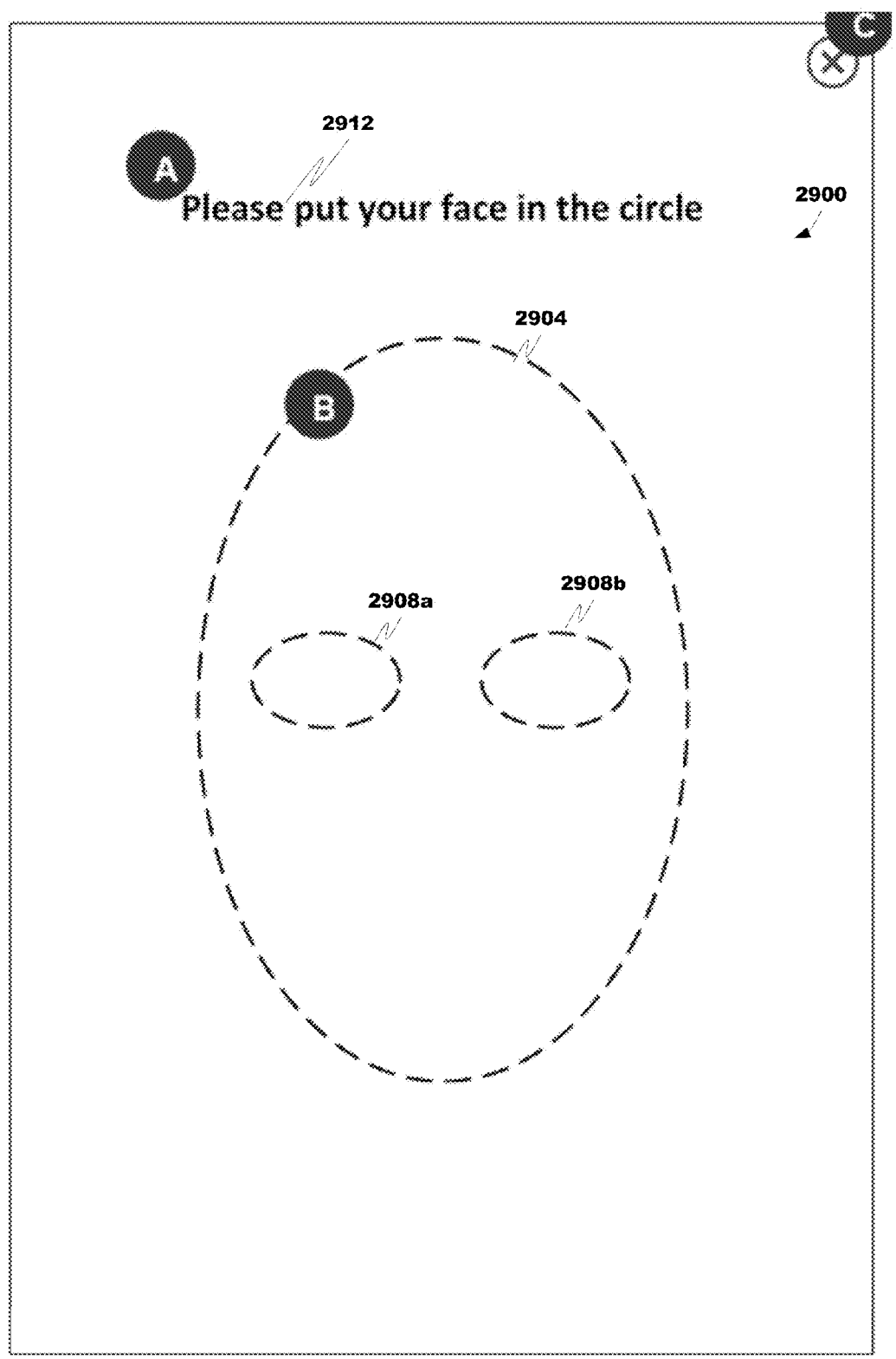
FIG. 29 depicts a screen shot according to an embodiment.

Another application of the vehicle control system 204 for authentication by facial recognition is shown in FIGS. 28-29.

In step 2800, the vehicle control system 204 detects a stimulus or trigger event.

In step 2804, the vehicle control system 204 provides, via the device or user interface 212, 248, user interface (s)/input interface(s) 324 and/or I/O module 312, the user with a face detection screen, such as that shown in FIG. 29. As shown in FIG. 29, the face detection screen 2900 is a dashed outline 2904 of a human face having eye holes 2908a and b to enable the user to align his or her face with the screen for a higher quality video image of the user's face. This screen 2900 prompts the user to align his or her face such that the facial recognition camera can obtain a good image. The screen can show the video feed from the facial recognition camera with the dashed outline as an overlay. The dashed outline is intended to assist users situate his or her image properly in the camera's field of view. An instruction line 2912 can appear at the top of the screen 2900.

When an acceptable facial image is not obtained so that facial recognition cannot be performed, the vehicle control system 204 proceeds 2803 to a manual sign-in step (discussed below) and provides the user with a face recognition failure notification dialog over the screen 2900 of the device or user interface 212, 248, user interface (s)/input interface(s) 324 and/or I/O module 312 in step 2812. If a proper facial image is obtained, the vehicle control system 204, in step 2816, searches through a repository of stored facial images to find a match and, during the mapping, provides the user with a recognition progress indicator modal on the screen 2900.

When recognition is not successful or no match is found, the vehicle control system 204 proceeds to step 2812 and the manual sign-in step discussed below.

When recognition is successful and a match is found, the vehicle control system 204 proceeds to step 2820 and applies the personal settings of the user, such as any or all of the settings referenced above. A settings application progress modal can be displayed over the displayed screen.

In step 2812, the vehicle control system 204 provides the user with a manual sign-in screen (not shown) requesting input of the user's credentials. The manual sign-in screen, for example, can include fields for user identifier and password and options to sign in or continue as a guest.

When the credentials are not received within a time out period or are incorrect or at the request of the user in step 2812, the vehicle control system 204 can create 2828 a guest or default account for the user as discussed above and applies default settings.

When the credentials are received and successfully authenticated, the vehicle control system 204 in step 2820 applies the personal settings of the user.

The vehicle control system 204, after steps 2820, 2824, or 2828 proceeds to step 2832 and provides a home screen page, such as home page 3000, configured in accordance with the applicable settings.

Configuration of Haptic Feedback and Visual Preferences in Vehicle User Interfaces The profile data 252 can include, for each occupant in a corresponding user profile, physical impairment information, such as information regarding a disability. The physical impairments include vision impairments (e.g., low vision, blindness, night and color blindness, and light sensitivity), hearing impairments (such as hearing loss, hard-of-hearing, and deafness), dexterity and mobility impairments (such as caused by arthritis, cerebral palsy, multiple sclerosis, loss of limb or digit, spinal cord injury, and repetitive stress injury), and language and/or communication impairments (such as aphasia, delayed speech, dyslexia, and other conditions resulting in difficulties remembering, solving problems, and/or perceiving sensory information).

System data 208 can include rules to implement by the vehicle control system 204 an accessibility or assistive technology. This can include reconfiguring, for example, the driver's device or user interface 212, 248, user interface (s)/input interface(s) 324 and/or I/O module 312. Once the user having the impairment is located in the vehicle or correlated with a particular seat position and/or device or user interface 212, 248, user interface (s)/input interface(s) 324 and/or I/O module 312, the accessibility or assistive technology can be applied to the corresponding device or user interface 212, 248, user interface (s)/input interface(s) 324 and/or I/O module 312. The type of accessibility or assistive technology employed can depend not only on the type and capabilities of the device or user interface 212, 248, user interface (s)/input interface(s) 324 and/or I/O module 312 but also on the seat position of the impaired user. Specifically, when the impaired user is a driver of the vehicle, he or she may receive different accessibility or assistive technology compared to when he or she is a non-driving vehicle occupant or passenger.

The type of assistance provided by the vehicle control system 204 depends on the particular impairment and/or disability involved. For example, if the vehicle control system 204 were to determine that the user has a particular impairment and/or disability, the vehicle control system 204 can recommend and/or implement automatically other feature or device settings and/or accessible technology that may provide improved access for the user. By way of illustration, information, commands, warnings, and requests provided by way of the driver's device or user interface 212, 248, user interface (s)/input interface(s) 324 and/or I/O module 312 to users with vision impairments can be one or more of the use of screen magnification, high contrast (e.g., between text and background colors such as white text on a black background, large font size and/or icon size (e.g., without changing screen resolution), color changes on the screen, a screen reader (or other text-to-speech program), speech recognition software (such as to operate the computer and/or software), enablement of a read mode, keyboard web page navigation, and the like. Information, commands, warnings, and requests provided by way of the driver's device or user interface 212, 248, user interface (s)/input interface(s) 324 and/or I/O module 312 to users with a hearing impairment can be one or more of the use of text or visual alternatives for sounds, high volume levels, changed computer sounds, sign language interpretation or translation (e.g., by image processing and acquisition based on visual images captured by one or more camera sensors), a text phone application, and the like. Information, commands, warnings, and requests provided by way of the driver's device or user interface 212, 248, user interface (s)/input interface(s) 324 and/or I/O module 312 to users with a dexterity and/or mobility impairment can be one or more of the use of particular mouse settings (e.g., mouse button configuration and timing (such as double-click speed), to make the mouse pointer more visible, and to alter the scroll speed of the mouse wheel or how quickly the mouse pointer responds to movements of the mouse), an increased size of a mouse-selectable screen element to provide a larger target, mouse keys to move the mouse pointer, sticky keys, toggle keys, filter keys, keyboard shortcuts, access keys, keyboard settings, an on-screen keyboard, speech recognition software (such as to dictate into almost any application (e.g., the user can dictate documents and email, surf the web, and control selected vehicle tasks, functions, and operations by voice command)), disablement of the automatic arrangement of windows when the mouse cursor is moved to the edge of the screen, enablement of activate a window by hovering over it with the mouse cursor, keyboard web page navigation, a disability assistive keyboard (such as an alternative keyboard) displayed on the screen, a keyboard filter, and the like. Information, commands, warnings, and requests provided by way of the driver's device or user interface 212, 248, user interface (s)/input interface(s) 324 and/or I/O module 312 to users with a language and/or communication impairment can be one or more of the use of sticky keys, toggle keys, filter keys, enablement of remove background images, disablement of all unnecessary animations, long period for notification dialog boxes to stay open, a keyboard filter, speech recognition software, enablement of a read mode, a screen reader, keyboard web page navigation, and a speech synthesizer, and the like. Information, commands, warnings, and requests provided by way of the driver's device or user interface 212, 248, user interface (s)/input interface(s) 324 and/or I/O module 312 to users with a learning impairment can be one or more of the use of a word prediction program, a reading tool, a learning disability program, a speech synthesizer, and speech recognition programs.

For users with an impairment, an assistive technology can use haptic feedback to provide information to a user. Haptic technology, or haptics, is a tactile feedback technology which takes advantage of the sense of touch by applying forces, vibrations, or motions to the user. Haptic feedback commonly uses the sense of touch in a user interface to provide information to an end user. The user interface can be any device with which a body part of the user is in contact and through which haptic feedback can be transmitted. Examples include a steering wheel, tactile electronic display, seat, seat belt, foot pedal, gear shift, center or rear center console, arm rest, other contact surface, and the like. In one configuration, the assistive technology is a system where at least two actuators are positioned beneath a user interface to provide vibratory feedback when a user makes contact with the unit. One actuator can induce a feedback vibration while one or more other actuator creates a second vibration to suppress the first from propagating to unwanted regions of the interface, thereby "localizing" the haptic experience. To minimize driver's attention away from the road or for a visually impaired occupant, tactile (or haptic or aural) feedback can be used to help a user identify which button/icon they are touching or pressing, without drawing their visual attention away from the road. It can also be used, for the hearing impaired, haptic feedback can be used to identify external sounds, such as sirens of an emergency vehicle, and/or a vehicle horn and/or information about a vehicle task, function or operation, such as an engine-related warning being activated, vehicle speed, vehicle gear currently engaged, and the like. Each type of information to be provided by haptic feedback to the user can have a correspondingly different haptic feedback response to enable the user to distinguish between types of information. For example, a police siren can have a different haptic feedback than an ambulance siren, both of which can have a different haptic feedback from an engine-related warning.

The external sound can be detected by one or more sound sensors positioned interiorly and/or exteriorly to the vehicle. Each sensor generates an analog or digital representation of the sound detected over a selected frequency range. The vehicle control system uses template matching to associate the profile of the sound detected with a corresponding matching profile of type of sound. In other words, the sound profile is the template and the sensed sound profile of a police siren is matched to the template sound profile.

Sensed sound template matching can be used to generate an alert or sound in a different frequency range to a user. All or part of the sensed sound profile can be frequency shifted to provide a corresponding output sound profile covering a different frequency range. The matching type of sound can have a unique corresponding output sound profile. The output sound profile can be played to the vehicle occupants over the sound system of the vehicle. The output sound profile may be suited to a user's particular frequency and/or hearing disability such that the output sound profile contains a set of frequencies that the user can hear. The sound may even adjust an audible signal presented to a user (e.g., statically, dynamically, and/or combinations thereof) to provide a differently shaped or phase-shifted sound profile. The sound profile over certain frequency ranges can be exaggerated in magnitude and/or the sound profile over certain frequency ranges can be decreased in magnitude or eliminated altogether. The output sound profile is played over the vehicle's sound system in temporal proximity to the detection of the corresponding external sound profile to alarm the occupant. In one configuration, the output sound profile is played over the spatially dispersed speakers in the passenger compartment with sound delays (or phase shifts) and/or magnitude levels at each speaker simulating the sound delays and/or magnitude levels of the various portions of the sound sensed by the various sound detectors positioned inside and/or outside of the vehicle. This can indicate to the user spatially where the origin or source of the sound is located relative to the vehicle.

Alternative to or in addition to playing the output sound profile, visual signals and/or alerts to a user (e.g., flashing lights, increasing intensity associated with a visual signal, animated icons, etc.) can be provided visually to the user. The color, brightness, duration, and/or intensity of the light emitted and/or appearance of the animated icon can vary by the matching type of sound profile such that each type of sound profile has a unique set of visual signals and/or alerts to the user.

The general interfaces of a vehicle, including but not limited to, at least one of the infotainment system, interfaces, graphical user interfaces, and the like, can be configured to display color-blind friendly colors so that the interface is meaningful and usable for a color-blind user. Colors, contrast, brightness, etc. may be configured to provide an optimum user experience based on the type of color-blindness.

The vehicle control system can adjust or modify settings on manual controls to account for a user impairment or medical condition, age, physical condition or characteristics, and/or driving history. This information can be recorded in a corresponding user profile, obtained over the Internet from a remote source (such as driving history from a law enforcement agency), and/or sensed by observing the user's behavior over time. For instance, the user may not respond quickly to a vehicle sensed obstacle in the path of the vehicle, may move, shake or jitter the steering wheel slightly during vehicle operation. The user response time, pedal displacement of the user, force applied to a pedal by the user, steering wheel displacement during straight-line driving, and the like can be monitored by the vehicle control system and the monitored behavior analyzed and stored in the corresponding user profile. Analysis can by matching the observed behavior against various templates. The closest template is associated with a corresponding set of configuration rules regarding what settings to use for manual controls of the vehicle. The abilities can be based on driving or responsiveness tests and/or driver profiles maintained by a law enforcement or driver regulating agency.

Based on impairment, medical condition, age, and/or abilities, for example, the steering wheel, pedals, and/or other systems can be adjusted for play and/or responsiveness. For example, an individual who suffers from one or more of Parkinsons, old age, shaking, etc. may require more "play" in the steering wheel such that any shaking and/or small movements of the individual do not adversely affect the steering sensitivity of the vehicle. Upon detecting the user impairment, the vehicle control system may alter the characteristics of the steering wheel, for example, by reducing the sensitivity associated with movement. In one case, the sensitivity may be changed by modifying the electrical output in response to receiving a certain mechanical angular movement of the steering wheel. For instance, an angular movement of 10 degrees at the steering wheel may be the minimum default angular movement to cause the wheels on a vehicle to begin to turn. Upon detecting a user's disability, this minimum default angular movement may be increased to 30 degrees, as an example. Therefore, small movements (e.g., under 30 degrees) will not affect the steering. The changes to be implemented are typically based on rule sets in the system data 208 which map a set of user-related descriptors to recommended or required changes. The descriptors typically describe one or more of user impairment, medical condition, age, and/or abilities.

As can be appreciated, the sensitivity associated with a steering wheel and/or other manual vehicle control systems may be increased based on a user's abilities. Using the example provided above, an angular movement of 10 degrees at the steering wheel may be the minimum default angular movement to cause the wheels on a vehicle to begin to turn. Upon detecting a user's ability (e.g., quick reactions, steady hands, past driving history, past vehicle history, etc.) this minimum default angular movement may be decreased to 5 degrees, as an example. Therefore, smaller movements (e.g., of 5 degrees applied at the wheel) will cause the vehicle to begin turning (similar to racing vehicles and/or high-end cars, etc.).

In other examples, (brake, emergency brake, accelerator and/or clutch) pedal movement range can be adjusted; that is, the vehicle control system can automatically adjust one or more of pedal stroke length, sensitivity, etc., based at least partially on user profile data and abilities.

The adjustment based on user profile and abilities can be extended to adjust settings and configurations of automated vehicle response systems. A collision avoidance system is an automobile safety system designed to reduce the severity of an accident. Also known as precrash system, forward collision warning system or collision mitigating system, it uses radar and sometimes laser and camera sensors to detect an imminent crash. Once the detection is done, these systems either provide a warning to the driver when there is an imminent collision or take action autonomously without any driver input (by braking or steering or both). In one approach, the collision avoidance system works in multiple phases. In a first phase, the collision avoidance system provides warning of an impending accident, while the hazard warning lights are activated, the side windows and sunroof are closed and the front seat belts are tensioned. In a second phase, the warning is followed by light braking, strong enough to win the driver's attention. In a third phase, the collision avoidance system initiates autonomous partial braking. In a fourth phase, the collision avoidance system decelerates the car followed by automatic deceleration at full braking power, roughly half a second before projected impact. In another approach, the collision avoidance system provides a warning to the driver through a Heads Up Display that visually resembles brake lamps. If the driver does not react, the system pre-charges the brakes and increases the brake assist sensitivity to maximize driver braking performance. In another approach, the collision avoidance system comprises radar and camera-based crash imminent braking in which radar technology detects a possible crash threat and alerts the driver. If the driver does not appear to react quickly enough or does not react at all, the system intervenes to apply the brakes in an effort to avoid the crash. In another approach, the collision avoidance system has three warning stages. In the first warning stage, the collision avoidance system includes audible and visual warnings to brake. If ignored, the collision avoidance system in the second stage tugs on the shoulder portion of the seat belt two to three times as an additional tactile warning to the driver to take action. In a third stage, the collision avoidance system predicts that a collision is unavoidable and includes full seat belt slack takeup for more effective seat belt protection and automatic application of the brakes to lessen the severity of the predicted crash. In another approach, the collision avoidance system highlights pedestrians in front of the vehicle at night by alerting the driver with an audible chime and visually displaying them via a Heads Up Display. In another approach, the collision avoidance system uses electronic stability control sensors to measure steering angle, vehicle yaw and lateral acceleration of the vehicle and brake assist (BAS) sensors to detect emergency braking. The collision avoidance system can tighten the seat belts, adjust seat positions including rear seats (if installed), raise folded rear headrests (if installed) and close the sunroof and windows if it detects a possible collision (including rollover). The collision avoidance system can use radar to monitor the traffic situation ahead and provide automatic partial braking if the driver does not react to the warnings and the system detects a severe danger of an accident. The disclosure can be applied to other automated response systems besides collision avoidance systems.

The vehicle can adjust the settings of the automotive response systems, such as a collision avoidance system, to reflect a driver's unique abilities and/or impairments. The settings for instance can be for instance the time at which a warning of a potential collision is provided to the driver, the duration of the driver response or reaction time interval from a warning of a collision is provided to the driver and the initiation of automated braking, the braking force or deceleration of automated braking, and the time over which automated braking occurs. For example, a driver with particularly quick responses can have less fault tolerant triggers than a driver with slow responses; that is, the collision avoidance system for the former driver will trigger automated braking later than the collision avoidance system for the latter driver.

Figure 31:
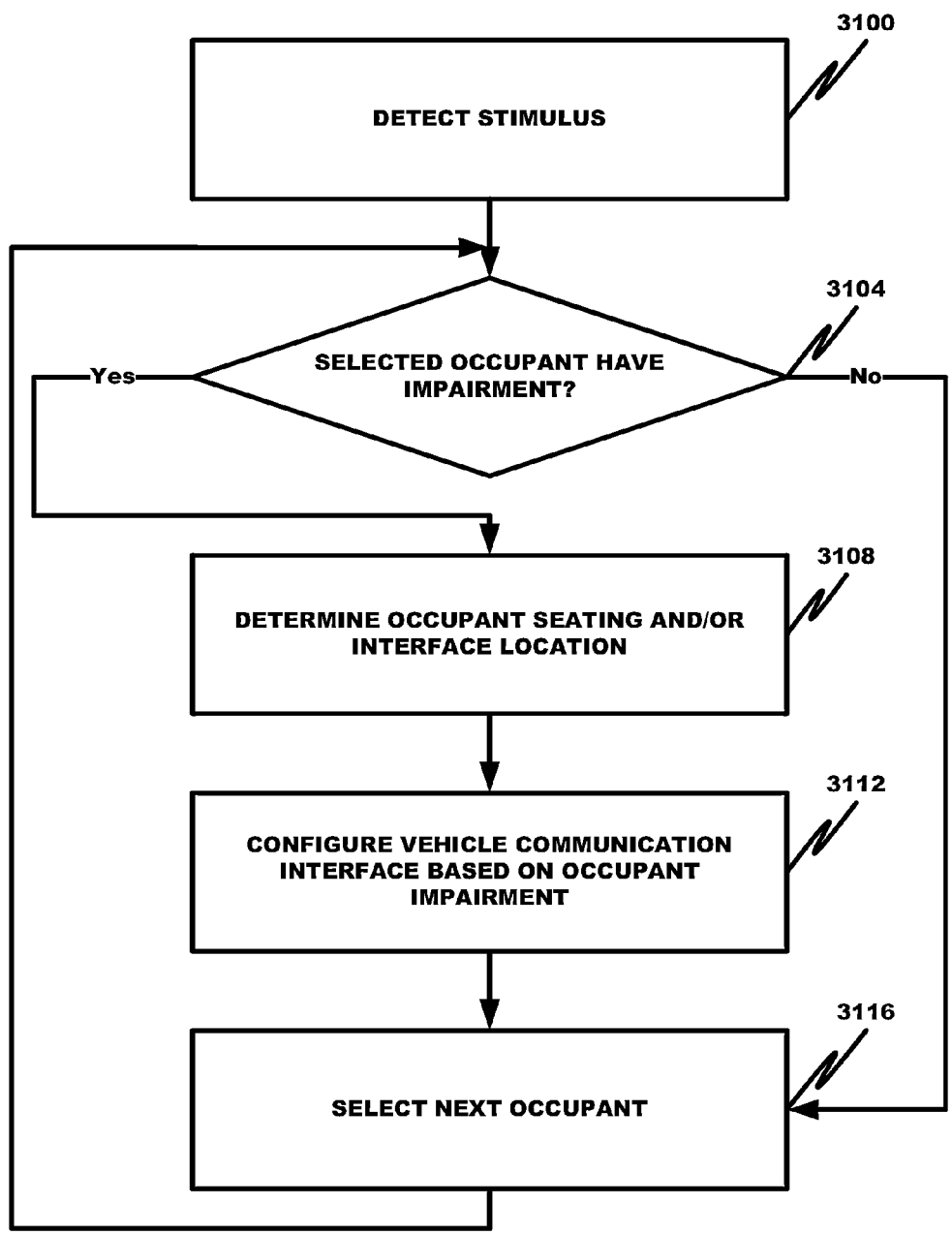
FIG. 31 depicts a flow diagram according to an embodiment.

An operation of the vehicle control system will be discussed with reference to FIG. 31.

In step 3100, the vehicle control system senses a stimulus, such as ignition of the vehicle, the vehicle being placed in gear, a door opening or closing to permit a person to enter or exit the vehicle, activation of a graphical user interface, and the like.

In step 3104, the vehicle control system determines an identity of each occupant and, based on the occupant's user profile, whether or not the occupant has an impairment. The occupant may be identified by any suitable technique, including authentication, electronic address information of a portable communication device associated with the user, image recognition, seat sensor feedback (e.g., weight of occupant), seat and lumbar settings selected by the occupant, and the like.

When the occupant has an impairment, the vehicle control system determines, in step 3108, occupant seating and/or interface location. The interface can be, for example, a graphical user interface, steering wheel, brake, clutch, or accelerator pedal, gear shift, or other communication interface by which the occupant is provided or provides information to the vehicle control system.

In step 3112, the vehicle control system configures the vehicle communication interface based on the type and/or severity of the occupant impairment(s), seating position of the occupant, and/or type of interface.

In step 3116, the vehicle control system selects a next occupant of the vehicle and returns to decision diamond 3104.

Figure 32:
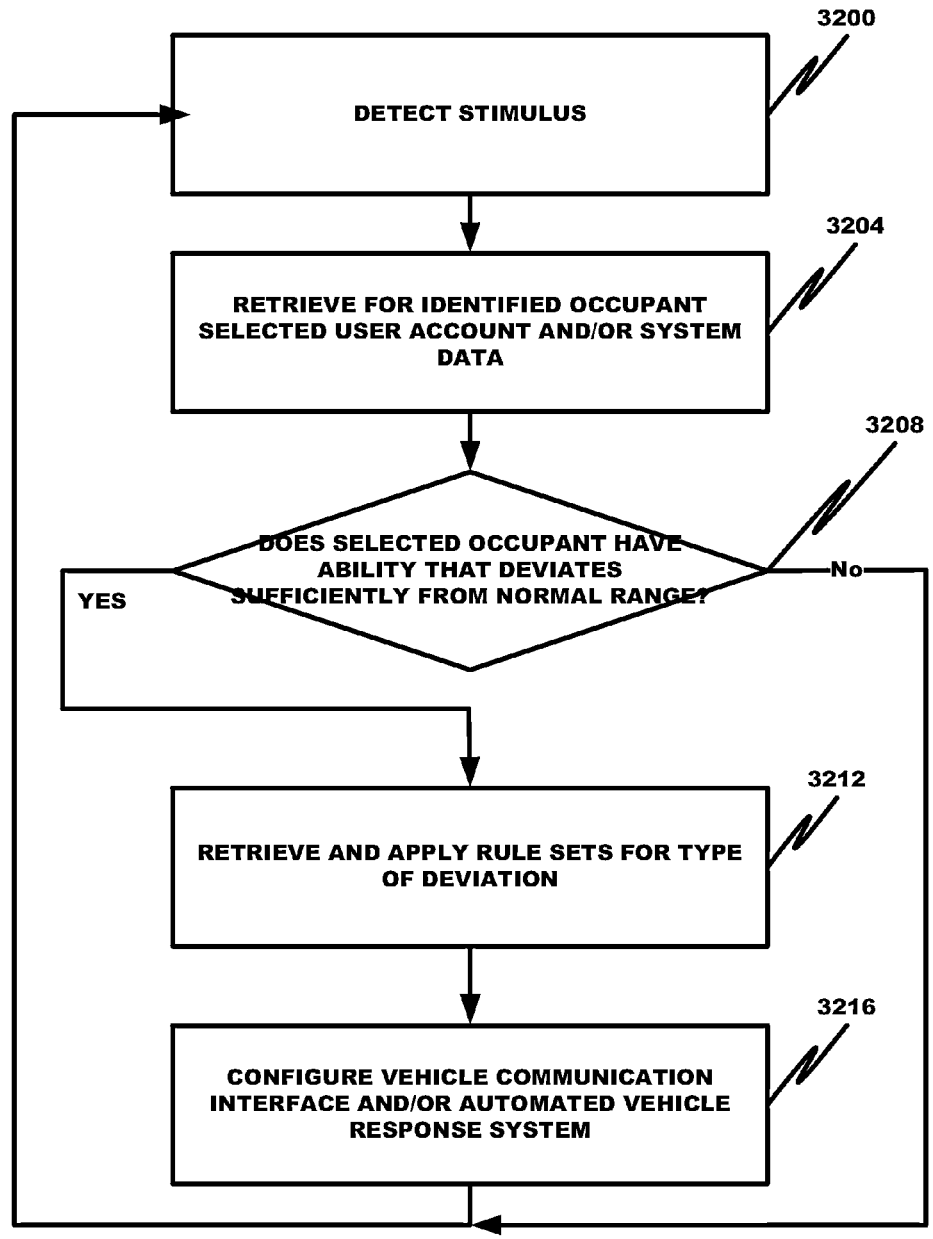
FIG. 32 depicts a flow diagram according to an embodiment.

An operation of the vehicle control system will be discussed with reference to FIG. 32.

In step 3200, the vehicle control system senses a stimulus, such as ignition of the vehicle, the vehicle being placed in gear, a door opening or closing to permit a person to enter or exit the vehicle, activation of a graphical user interface, and the like.

In step 3204, the vehicle control system determines an identity of each occupant, retrieves the corresponding user profile and relevant system data. The occupant may be identified by any suitable technique, including authentication, electronic address information of a portable communication device associated with the user, image recognition, seat sensor feedback (e.g., weight of occupant), seat and lumbar settings selected by the occupant, and the like.

In decision diamond 3208, the vehicle control system, based on the occupant's user profile and/or relevant system data, determines whether or not the occupant has an ability that deviates sufficiently from a normal range for the subject vehicle communication interface and/or automated vehicle response system. The normal range is defined for each type of activity and for each type of interface and/or automated control system. As will be appreciated, different types of activities, different types of interfaces, and/or different types of automated control systems have differing normal ranges.

When the occupant has an activity that deviates sufficiently from a normal range, the vehicle control system retrieves and applies rule sets, in step 3212, to determine what settings of the vehicle communication interface and/or automated vehicle response system require alteration.

In step 3216, the vehicle control system configures the vehicle communication interface and/or automated vehicle response system based on the rule set application.

The vehicle control system then returns to step 3200.

The exemplary systems and methods of this disclosure have been described in relation to configurable vehicle center or rear center consoles and associated devices. However, to avoid unnecessarily obscuring the present disclosure, the preceding description omits a number of known structures and devices. This omission is not to be construed as a limitation of the scopes of the claims. Specific details are set forth to provide an understanding of the present disclosure. It should however be appreciated that the present disclosure may be practiced in a variety of ways beyond the specific detail set forth herein.

Furthermore, while the exemplary aspects, embodiments, options, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a Personal Computer (PC), laptop, netbook, smart phone, Personal Digital Assistant (PDA), tablet, etc., or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

It should be appreciated that the various processing modules (e.g., processors, vehicle systems, vehicle subsystems, modules, etc.), for example, can perform, monitor, and/or control critical and non-critical tasks, functions, and operations, such as interaction with and/or monitoring and/or control of critical and non-critical on board sensors and vehicle operations (e.g., engine, transmission, throttle, brake power assist/brake lock-up, electronic suspension, traction and stability control, parallel parking assistance, occupant protection systems, power steering assistance, self-diagnostics, event data recorders, steer-by-wire and/or brake-by-wire operations, vehicle-to-vehicle interactions, vehicle-to-infrastructure interactions, partial and/or full automation, telematics, navigation/SPS, multimedia systems, audio systems, rear seat entertainment systems, game center or rear center consoles, tuners (SDR), heads-up display, night vision, lane departure warning, adaptive cruise control, adaptive headlights, collision warning, blind spot sensors, park/reverse assistance, tire pressure monitoring, traffic signal recognition, vehicle tracking (e.g., LoJack™), dashboard/instrument cluster, lights, seats, climate control, voice recognition, remote keyless entry, security alarm systems, and wiper/window control). Processing modules can be enclosed in an advanced EMI-shielded enclosure containing multiple expansion modules. Processing modules can have a "black box" or flight data recorder technology, containing an event (or driving history) recorder (containing operational information collected from vehicle on board sensors and provided by nearby or roadside signal transmitters), a crash survivable memory unit, an integrated controller and circuitry board, and network interfaces.

Critical system controller(s) can control, monitor, and/or operate critical systems. Critical systems may include one or more of (depending on the particular vehicle) monitoring, controlling, operating the ECU, TCU, door settings, window settings, blind spot monitor, monitoring, controlling, operating the safety equipment (e.g., airbag deployment control unit, collision sensor, nearby object sensing system, seat belt control unit, sensors for setting the seat belt, etc.), monitoring and/or controlling certain critical sensors such as the power source controller and energy output sensor, engine temperature, oil pressure sensing, hydraulic pressure sensors, sensors for headlight and other lights (e.g., emergency light, brake light, parking light, fog light, interior or passenger compartment light, and/or tail light state (on or off)), vehicle control system sensors, wireless network sensor (e.g., Wi-Fi and/or Bluetooth sensors, etc.), cellular data sensor, and/or steering/torque sensor, controlling the operation of the engine (e.g., ignition, etc.), head light control unit, power steering, display panel, switch state control unit, power control unit, and/or brake control unit, and/or issuing alerts to a user and/or remote monitoring entity of potential problems with a vehicle operation.

Non-critical system controller(s) can control, monitor, and/or operate non-critical systems. Non-critical systems may include one or more of (depending on the particular vehicle) monitoring, controlling, operating a non-critical system, emissions control, seating system controller and sensor, infotainment/entertainment system, monitoring certain non-critical sensors such as ambient (outdoor) weather readings (e.g., temperature, precipitation, wind speed, and the like), odometer reading sensor, trip mileage reading sensor, road condition sensors (e.g., wet, icy, etc.), radar transmitter/receiver output, brake wear sensor, oxygen sensor, ambient lighting sensor, vision system sensor, ranging sensor, parking sensor, heating, venting, and air conditioning (HVAC) system and sensor, water sensor, air-fuel ratio meter, hall effect sensor, microphone, radio frequency (RF) sensor, and/or infrared (IR) sensor.

It is an aspect of the present disclosure that one or more of the non-critical components and/or systems provided herein may become critical components and/or systems, and/or vice versa, depending on a context associated with the vehicle.

Optionally, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A media controller subsystem comprising:
   a microprocessor;
   a microprocessor executable distributed network control server that, when executed by the microprocessor, accesses selected content on a public network external to a vehicle comprising a media controller subsystem, the microprocessor executable distributed network control server having at least one of an assigned Internet Protocol ("IP") address and global unicast address;
   a microprocessor executable media server that, when executed by the microprocessor, receives requests for content from a vehicle occupant by a portable computational device associated with the vehicle occupant and provides requested content to the portable computational device associated with the vehicle occupant, the microprocessor executable media server having a contactable electronic address on a local area network maintained by the vehicle;
   a microprocessor readable memory to store content; and
   a microprocessor executable virtual network console that, when executed by the microprocessor, provides provide the portable computational device with remote access to the media server, wherein the media server simultaneously provides, via different wireless channels, different requested content to different portable computational devices and/or on board displays associated with different vehicle occupants.

2. The media controller subsystem of claim 1, wherein the distributed network control server, media server, and virtual network console are on a common media processing board mounted on the vehicle, wherein the virtual network console operates in accordance with the Remote Frame Buffer protocol on top of the Transport Control Protocol ("TCP")/IP suite of protocols, thereby causing the portable computational device to appear to a computer mounted in the vehicle as if the portable computational device is part of the on board vehicle control system comprising the computer, wherein requested content is provided to different portable computational devices and/or on board displays associated with different vehicle occupants on different channels via one or more of WiFi, Bluetooth, and NFC, wherein each different portable computational device and/or on board display of different vehicle occupants are provided with corresponding requested content simultaneously and control what requested content is provided to the associated vehicle occupant and to what on board display and/or portable computational device of the associated vehicle occupant the requested content is provided, and wherein the portable computational device is discrete from, remote from, and in wireless communication with the media processing board.

3. The media controller subsystem of claim 1, further comprising a combo controller having one or more ports to implement one or more device discovery functions and/or packetize information for transmission via the Internet Protocol over an Ethernet network, wherein the combo controller installs a correct driver for a discovered portable computational device and maps the discovered portable computational device address to an assigned IP address for interaction with a corresponding blade processor, and further comprising a plurality of blade processors, each blade processor including a microprocessor, a memory, and a network interface and performing a different set of functions.

4. The media controller of claim 1, wherein the vehicle occupant, through the portable computational device, can control one or more of the following media presentation features of a screen and sound system mounted on the vehicle: volume, contrast, resolution, and channel selection, wherein a device discovery daemon determines a device capability based on an opened port the portable communication device exposes, wherein the media server determines, from one or more of system data comprising portable computational device information and/or ca s abilities an identity of the vehicle occupant, an identity of the portable computational device, and spatial location of the computational device, one or more of a filter and restriction to be applied to the requested content and provides one or more of filtered and restricted content to the portable computational device.

5. A method, comprising:
providing, by a microprocessor executing a microprocessor executable virtual network console, a portable computational device associated with a vehicle occupant with remote access to a microprocessor executable media server;
receiving, by the microprocessor executing the microprocessor executable virtual network console, a request for media content;
determining, by the microprocessor executable media server, at least one of an identity of the vehicle occupant requesting, by the portable computational device associated with the vehicle occupant, the media content, an identity of the portable computational device associated with the vehicle occupant, and a spatial location of the vehicle occupant and/or portable computational device;
based on the at least one of the identity of the vehicle occupant requesting media content, the identity of a portable computational device associated with the vehicle occupant, and the spatial location of the vehicle occupant and/or the portable computational device, applying, by the microprocessor executable media server, at least one of a filter and restriction to the requested media content to form filtered and/or permitted media content to be provided to the portable computational device and/or on board display associated with the vehicle occupant; and
providing, by the microprocessor executable media server, the filtered and/or permitted media content to the portable computational device and/or on board display associated with the vehicle occupant, wherein the media server simultaneously provides, via different wireless channels, different filtered and/or permitted media content to different portable computational devices and/or on board displays associated with different vehicle occupants.

6. The method of claim 5, wherein the portable computational device is discrete from, remote from, and in wireless communication with the media processing board, wherein the at least one of a filter and restriction is applied to a media request of the vehicle occupant before the requested media content is accessed and wherein the at least one of a filter and restriction is one or more of an age-related content filter and/or restriction and a privacy filter and/or restriction.

7. The method of claim 6, wherein the microprocessor executable media server applies the at least one of a filter and restriction based on the at least one of the identity of the vehicle occupant requesting media content and the identity of a portable computational device associated with the vehicle occupant, wherein the at least one of a filter and restriction bans a type of content requested, bans a source of the content, redirects the request to a different source of the content, and/or limits the vehicle occupant to content from an approved source.

8. The method of claim 5, wherein the portable computational device is discrete from, remote from, and in wireless communication with the media processing board, wherein the at least one of a filter and restriction is applied after the requested media content is accessed and wherein the at least one of a filter and restriction is one or more of an age-related content filter and/or restriction and a privacy filter and/or restriction.

9. The method of claim 5, wherein a menu displayed to each occupant enables access to media content and wherein the at least one of a filter and restriction determines a content and/or configuration of the menu presented to each occupant.

10. The method of claim 5, wherein application of the at least one of a filter and restriction is based on an electronic address of the portable computational device on a network of the vehicle.

11. The method of claim 5, wherein the microprocessor executable media server operable to receive requests for content from a vehicle occupant by a portable computational device associated with the vehicle occupant and provide requested content to the portable computational device associated with the vehicle occupant, the media server having a contactable electronic address on a local area network maintained by the vehicle and further comprising:
a microprocessor executable distributed network control server operable to access selected content on a public network external to a vehicle comprising the media controller subsystem, the distributed network control server having at least one of an assigned Internet Protocol ("IP") address and global unicast address;
the microprocessor executable media server operable to receive requests for content from a vehicle occupant by a portable computational device associated with the vehicle occupant and provide requested content to the portable computational device associated with the vehicle occupant, the media server having a contactable electronic address on a local area network maintained by the vehicle; and a microprocessor readable memory to store content.

12. The method of claim 11, wherein the distributed network control server, media server, and virtual network console are on a common media processing board mounted on the vehicle, wherein the virtual network console operates in accordance with the Remote Frame Buffer protocol on top of the Transport Control Protocol ("TCP")/IP suite of protocols, thereby causing the portable computational device to appear to a computer mounted in the vehicle as if the portable computational device is part of the on board vehicle control system comprising the computer, wherein requested content is provided to different portable computational devices and/or on board displays associated with different vehicle occupants on different channels via one or more of WiFi, Bluetooth, and NFC, wherein each different portable computational device and/or on board display of different vehicle occupants are provided with corresponding requested content simultaneously and control what requested content is provided to the associated vehicle occupant and to what on board display and/or portable computational device of the associated vehicle occupant the requested content is provided, and wherein the portable computational device is discrete from, remote from, and in wireless communication with the media processing board.

13. The method of claim 11, further comprising a combo controller having one or more ports to implement one or more device discovery functions and/or packetize information for transmission via the Internet Protocol over an Ethernet network, wherein a device discovery daemon determines a device capability based on an opened port the portable communication device exposes, and wherein the combo controller installs a correct driver for a discovered portable computational device and maps the discovered portable computational device address to an assigned IP address for interaction with a corresponding blade processor of a plurality of blade processors, each blade processor including a microprocessor, a memory, and a network interface and performing a different set of functions.

14. The method of claim 11, wherein the vehicle occupant, through the portable computational device, can control one or more of the following media presentation features of a screen and sound system mounted on the vehicle: volume, contrast, resolution, and channel selection, wherein the media server determines, from one or more of system data, portable computational device information and capabilities, an identity of the vehicle occupant, an identity of the portable computational device, and spatial location of the computational device, one or more of a filter and restriction to be applied to the requested content and provides one or more of filtered and restricted content to the portable computational device.

15. A vehicle, comprising:
a microprocessor;
a microprocessor executable virtual network console that provides a portable computational device associated with a vehicle occupant with remote access to a microprocessor executable media server and receives a request for media content from the portable computational device; and
the microprocessor executable media server:
determines, at least one of an identity of the vehicle occupant requesting the media content, an identity of the portable computational device associated with the vehicle occupant, and a spatial location of the vehicle occupant and/or the portable computational device associated with the vehicle occupant;

based on the at least one of the identity of the vehicle occupant requesting media content, the identity of the portable computational device associated with the vehicle occupant, and the spatial location of the vehicle occupant and/or portable computational device, applies at least one of a filter and restriction to the media content requested by the vehicle occupant to form filtered and/or permitted media content to be provided to the portable computational device and/or on board display associated with the vehicle occupant; and provides the filtered and/or permitted media content to the portable computational device and/or on board display associated with the vehicle occupant, wherein the media server simultaneously provides, via different wireless channels, different filtered and/or permitted media content to different portable computational devices and/or on board displays associated with different vehicle occupants.

16. The vehicle of claim 15, wherein the portable computational device is discrete from, remote from, and in wireless communication with a media processing board, wherein the at least one of a filter and restriction is applied to a media request of the vehicle occupant before the requested media content is accessed and wherein the at least one of a filter and restriction is one or more of an age-related content filter and/or restriction and a privacy filter and/or restriction.

17. The vehicle of claim 16, wherein the microprocessor executable media server applies the at least one of a filter and restriction based on the at least one of the identity of the vehicle occupant requesting media content and the identity of a portable computational device associated with the vehicle occupant, wherein the at least one of a filter and restriction bans a type of content requested, bans a source of the content, redirects the request to a different source of the content, and/or limits the vehicle occupant to content from an approved source.

18. The vehicle of claim 15, wherein the portable computational device is discrete from, remote from, and in wireless communication with the media processing board, wherein the at least one of a filter and restriction is applied after the requested media content is accessed and wherein the at least one of a filter and restriction is one or more of an age-related content filter and/or restriction and a privacy filter and/or restriction.

19. The vehicle of claim 15, wherein a menu displayed to each occupant enables access to media content and wherein the at least one of a filter and restriction determines a content and/or configuration of the menu presented to each occupant.

20. The vehicle of claim 15, wherein application of the at least one of a filter and restriction is based on an electronic address of the portable computational device on a network of the vehicle.

21. The vehicle of claim 15, wherein the microprocessor executable media server is operable to receive requests for content from a vehicle occupant by a portable computational device associated with the vehicle occupant and provide requested content to the portable computational device associated with the vehicle occupant, the media server having a contactable electronic address on a local area network maintained by the vehicle and further comprising:

a microprocessor executable distributed network control server operable to access selected content on a public network external to a vehicle comprising the media controller subsystem, the distributed network control server having at least one of an assigned Internet Protocol ("IP") address and global unicast address;

the microprocessor executable media server operable to receive requests for content from a vehicle occupant by a portable computational device associated with the vehicle occupant and provide requested content to the portable computational device associated with the vehicle occupant, the media server having a contactable electronic address on a local area network maintained by the vehicle; and a microprocessor readable memory to store content.

22. The vehicle of claim 15, wherein the distributed network control server, media server, and virtual network console are on a common media processing board mounted on the vehicle, wherein the virtual network console operates in accordance with the Remote Frame Buffer protocol on top of the Transport Control Protocol ("TCP")/IP suite of protocols, thereby causing the portable computational device to appear to a computer mounted in the vehicle as if the portable computational device is part of the on board vehicle control system comprising the computer, wherein requested content is provided to different portable computational devices and/or on board displays associated with different vehicle occupants on different channels via one or more of WiFi, Bluetooth, and NFC, wherein each different portable computational device and/or on board display of different vehicle occupants are provided with corresponding requested content simultaneously and control what requested content is provided to the associated vehicle occupant and to what on board display and/or portable computational device of the associated vehicle occupant the requested content is provided, and wherein the portable computational device is discrete from, remote from, and in wireless communication with the media processing board.

23. The vehicle of claim 15, further comprising a combo controller having one or more ports to implement one or more device discovery functions and/or packetize information for transmission via the Internet Protocol over an Ethernet network, wherein a device discovery daemon determines a device capability based on an opened port the portable communication device exposes, and wherein the combo controller installs a correct driver for a discovered portable computational device and maps the discovered portable computational device address to an assigned IP address for interaction with a corresponding blade processor of a plurality of blade processors, each blade processor including a microprocessor, a memory, and a network interface and performing a different set of functions.

24. The vehicle of claim 15, wherein the vehicle occupant, through the remote computational device, can control one or more of the following media presentation features of a screen and sound system mounted on the vehicle: volume, contrast, resolution, and channel selection, wherein the media server determines, from one or more of system data, portable computational device information and capabilities, an identity of the vehicle occupant, an identity of the portable computational device, and spatial location of the computational device, one or more of a filter and restriction to be applied to the requested content and provides one or more of filtered and restricted content to the portable computational device.

25. A tangible and non-transitory computer readable medium comprising microprocessor executable distributed network control server instructions that, when executed by a microprocessor, perform functions comprising:

one or more instructions to provide, by a virtual network console, a portable computational device associated with a vehicle occupant with remote access to a microprocessor executable media server;

one or more instructions to receive a request, by the virtual network console, for media content;

one or more instructions to determine at least one of an identity of the vehicle occupant requesting media content, an identity of the portable computational device associated with the vehicle occupant, and a spatial location of the vehicle occupant and/or the portable computational device;

one or more instructions, based on the at least one of the identity of the vehicle occupant requesting media content, the identity of a portable computational device associated with the vehicle occupant, and the spatial location of the vehicle occupant and/or the portable computational device, to apply at least one of a filter and restriction to the requested media content to form filtered and/or permitted media content to be provided to the portable computational device and/or on board display associated with the vehicle occupant; and one or more instructions to provide the filtered and/or permitted media content to the portable computational device and/or on board display associated with the vehicle occupant, wherein the media server simultaneously provides, via different wireless channels, different filtered and/or permitted media content to different portable computational devices and/or on board displays associated with different vehicle occupants.

26. The computer readable medium of claim 25, wherein the portable computational device is discrete from, remote from, and in wireless communication with a media processing board, wherein the at least one of a filter and restriction is applied to a media request of the vehicle occupant before the requested media content is accessed and wherein the at least one of a filter and restriction is one or more of an age-related content filter and/or restriction and a privacy filter and/or restriction.

27. The computer readable medium of claim 26, wherein the one or more instructions applies the at least one of a filter and restriction based on the at least one of the identity of the vehicle occupant requesting media content and the identity of a portable computational device associated with the vehicle occupant, wherein the at least one of a filter and restriction bans a type of content requested, bans a source of the content, redirects the request to a different source of the content, and/or limits the vehicle occupant to content from an approved source.

28. The computer readable medium of claim 25, wherein the portable computational device is discrete from, remote from, and in wireless communication with the media processing board, wherein the at least one of a filter and restriction is applied after the requested media content is accessed and wherein the at least one of a filter and restriction is one or more of an age-related content filter and/or restriction and a privacy filter and/or restriction.

29. The computer readable medium of claim 25, wherein a menu displayed to each occupant enables access to media content and wherein the at least one of a filter and restriction determines a content and/or configuration of the menu presented to each occupant.

30. The computer readable medium of claim 25, wherein application of the at least one of a filter and restriction is based on an electronic address of the portable computational device on a network of the vehicle.

* * * * *

UNITED STATES PATENT AND TRADEMARK OFFICE
CERTIFICATE OF CORRECTION

| | | |
|---|---|---|
| PATENT NO. | : 9,235,941 B2 | Page 1 of 1 |
| APPLICATION NO. | : 14/253334 | |
| DATED | : January 12, 2016 | |
| INVENTOR(S) | : Christopher P. Ricci, Octavian Chincisan and Alisher Yusupov | |

It is certified that error appears in the above-identified patent and that said Letters Patent is hereby corrected as shown below:

Claims
Claim 1, column 124, line 59, delete "provide" therein.
Claim 4, column 125, line 43, delete "ca s abilities" and insert --capabilities-- therein.
Claim 15, column 127, line 65, after "server" insert --that-- therein.
Claim 21, column 129, line 12, delete "a" and insert --the-- therein.

Signed and Sealed this
Twenty-sixth Day of April, 2016

Michelle K. Lee
*Director of the United States Patent and Trademark Office*